US012584107B2

(12) United States Patent
Sibener et al.

(10) Patent No.: US 12,584,107 B2
(45) Date of Patent: Mar. 24, 2026

(54) T CELL RECEPTOR (TCR) COMPOSITIONS AND METHODS FOR OPTIMIZING ANTIGEN REACTIVE T-CELLS

(71) Applicant: 3T BIOSCIENCES, INC., South San Francisco, CA (US)

(72) Inventors: Leah Sibener, San Francisco, CA (US); John Leonard, South San Francisco, CA (US); Alejandro Ramirez, South San Francisco, CA (US); Marvin Gee, San Francisco, CA (US)

(73) Assignee: 3T BIOSCIENCES, INC., South San Francisco, CA (US)

( * ) Notice: Subject to any disclaimer, the term of this patent is extended or adjusted under 35 U.S.C. 154(b) by 678 days.

(21) Appl. No.: 18/157,598

(22) Filed: Jan. 20, 2023

(65) Prior Publication Data

US 2023/0287346 A1 Sep. 14, 2023

Related U.S. Application Data

(60) Provisional application No. 63/321,485, filed on Mar. 18, 2022, provisional application No. 63/301,485, filed on Jan. 20, 2022, provisional application No. 63/301,407, filed on Jan. 20, 2022, provisional application No. 63/301,401, filed on Jan. 20, 2022, provisional application No. 63/301,394, filed on Jan. 20, 2022, provisional application No. 63/301,413, filed on Jan. 20, 2022, provisional application No. 63/301,408, filed on Jan. 20, 2022, provisional application No. 63/301,410, filed on Jan. 20, 2022.

(51) Int. Cl.
*C12N 5/0783* (2010.01)
*C12N 5/0784* (2010.01)

(52) U.S. Cl.
CPC ......... *C12N 5/0636* (2013.01); *C12N 5/0639* (2013.01); *C12N 2501/2321* (2013.01); *C12N 2501/24* (2013.01)

(58) Field of Classification Search
CPC ............................ C12N 5/0636; C12N 5/0639
See application file for complete search history.

(56) References Cited

U.S. PATENT DOCUMENTS

| | | | |
|---|---|---|---|
| 5,750,341 A | 5/1998 | Macevicz | |
| 5,969,119 A | 10/1999 | Macevicz | |
| 6,306,597 B1 | 10/2001 | Macevicz | |
| 7,170,050 B2 | 1/2007 | Turner et al. | |
| 7,183,076 B2 | 2/2007 | Arathoon et al. | |
| 7,211,390 B2 | 5/2007 | Rothberg et al. | |
| 7,244,559 B2 | 7/2007 | Rothberg et al. | |
| 7,244,567 B2 | 7/2007 | Chen et al. | |
| 7,264,929 B2 | 9/2007 | Rothberg et al. | |
| 7,276,720 B2 | 10/2007 | Ulmer | |
| 7,302,146 B2 | 11/2007 | Turner et al. | |
| 7,313,308 B2 | 12/2007 | Turner et al. | |
| 7,315,019 B2 | 1/2008 | Turner et al. | |
| 7,323,305 B2 | 1/2008 | Leamon et al. | |
| 7,335,762 B2 | 2/2008 | Rothberg et al. | |
| 7,405,281 B2 | 7/2008 | Xu et al. | |
| 7,462,452 B2 | 12/2008 | Williams et al. | |
| 7,462,468 B1 | 12/2008 | Williams et al. | |
| 7,476,503 B2 | 1/2009 | Turner et al. | |
| 7,476,504 B2 | 1/2009 | Turner | |
| 7,491,498 B2 | 2/2009 | Lapidus et al. | |
| 7,501,245 B2 | 3/2009 | Quake et al. | |
| 7,951,917 B1 | 5/2011 | Arathoon et al. | |
| 8,642,745 B2 | 2/2014 | Arathoon et al. | |
| 8,765,412 B2 | 7/2014 | Arathoon et al. | |
| 8,969,526 B2 | 3/2015 | Baehner et al. | |
| 9,409,989 B2 | 8/2016 | Arathoon et al. | |
| 9,504,717 B2 | 11/2016 | Strober et al. | |
| 9,561,253 B2 | 2/2017 | Strober et al. | |
| 10,093,714 B1 | 10/2018 | Rueger et al. | |
| 10,731,128 B2 | 8/2020 | Borriello | |

(Continued)

FOREIGN PATENT DOCUMENTS

| | | |
|---|---|---|
| WO | 2018/213803 A1 | 11/2018 |
| WO | 2021/144020 A1 | 7/2021 |

OTHER PUBLICATIONS

Baker et al. (2001) "Expansion of cytolytic CD8+ natural killer T cells with limited capacity for graft-versus-host disease induction due to interferon γ production" Blood, The Journal of the American Society of Hematology, 97(10), 2923-2931. (Year: 2001).*

(Continued)

*Primary Examiner* — James Joseph Graber

(74) *Attorney, Agent, or Firm* — Brown Rudnick LLP; Adam M. Schoen

(57) ABSTRACT

Provided are methods for isolating T-cells with T cell receptors (TCRs) optimized for reactivity to specific peptides and decreased cross-reactivity to non-target peptides. Advantageously, TCRs of the invention can be optimized to target cancer antigens and peptides while having reducing reactivity to healthy cells. Methods of the invention utilize a novel combination of culturing conditions that increase T-cell activation and allow for validation of TCR activity. Culturing conditions of the invention further reduce culturing times generally needed to achieve expanded reactive T-cells. Because of the robust nature of the activation and validation conditions of the present invention, variants of identified TCRs can also be optimized and validated for their response to peptides, including cancer peptides.

27 Claims, 40 Drawing Sheets

Specification includes a Sequence Listing.

(56)  References Cited

U.S. PATENT DOCUMENTS

| | | | |
|---|---|---|---|
| 11,046,776 B2 | 6/2021 | Lazar et al. | |
| 2006/0024678 A1 | 2/2006 | Buzby | |
| 2006/0024711 A1 | 2/2006 | Apidus et al. | |
| 2006/0286566 A1 | 12/2006 | Lapidus et al. | |
| 2008/0087826 A1 | 4/2008 | Harris et al. | |
| 2008/0103058 A1 | 5/2008 | Siddiqi | |
| 2008/0206764 A1 | 8/2008 | Williams et al. | |
| 2008/0213770 A1 | 9/2008 | Williams et al. | |
| 2009/0029385 A1 | 1/2009 | Christians et al. | |
| 2009/0061439 A1 | 3/2009 | Buzby | |
| 2009/0068655 A1 | 3/2009 | Williams | |
| 2009/0137485 A1* | 5/2009 | Dilorenzo et al. | A61K 38/08 |
| | | | 514/15 |
| 2018/0193384 A1 | 7/2018 | Reisner et al. | |
| 2021/0102169 A1* | 4/2021 | Tjoa et al. | C12N 5/0639 |
| 2021/0338725 A1* | 11/2021 | McNeil et al. | A61K 35/17 |
| 2021/0403527 A1 | 12/2021 | Babb et al. | |

OTHER PUBLICATIONS

International Search Report and Written Opinion issued in International Application No. PCT/US2023/061019, date of mailing: Jul. 25, 2023, 19 pages.
Wittrup, 2015, Knocking down disease: a progress report on siRNA therapeutics, Nat Rev Genet, 16(9):543-552.

* cited by examiner

FIG. 8

| TCR | Cross-Reactivity Score | Critical Peptide Positions |
|---|---|---|
| Benchmark 1 | 7.75 | 1 |
| Benchmark 2 | 9.66 | 1 |
| EQ2ACU | 15.53 | 2 |
| NY7JSY | 0.58 | 3 |
| UQK4VX | 0.28 | 3 |
| C27CD8 | 0.46 | 3 |

Cross-Reactivity Score = 100 x (mean_off-target$_{\text{harm}}$/ NYESO$_{\text{harm}}$)

| TCR(s) | Peptide | Protein | Healthy Tissues of Concern |
|---|---|---|---|
| Benchmark 1 & 2 | Sequence A | PIGQ | kidney, pancreas, lung, others |
| Benchmark 1 | Sequence B | SFI1 | brain, GI, retina, skin, others |
| Benchmark 2 | Sequence C | FAM214B | brain, lung, heart, GI, others |
| 3T-EQ2 | Sequence D | PSMD13 | heart, liver, GI, others |
| 3T-EQ2 | Sequence E | FA8 | liver |

Top Activating Off-Target Peptides

SLLMWITQC  NY-ESO-1

(SEQ ID NO: 260)

FIG. 34

T CELL RECEPTOR (TCR) COMPOSITIONS AND METHODS FOR OPTIMIZING ANTIGEN REACTIVE T-CELLS

FIELD OF THE DISCLOSURE

The disclosure relates to T cell receptor (TCR) compositions and methods for optimizing antigen reactive T-cells.

SEQUENCE LISTING

This application contains a sequence listing in electronic form as an extensible Markup Language (XML) form via the Patent Center and is hereby incorporated by reference in its entirety. The XML-formatted sequence listing, created on Nov. 11, 2025, is named 3TBI-007-01US-ST26-2.xml, and is 359 KB in size.

BACKGROUND

Cancers are attributed to nearly 10 million deaths globally each year. Although recent advances in drug therapies have improved patient outcomes in some cancers, due to the complexity and heterogeneity of cancer cells there is no guarantee that any particular drug therapy will successfully result in remission and control of a patient's cancer. Moreover, remission and control can be fleeting, with drug targets changing as cancer cells continue to mutate and develop resistances to previously effective therapies.

Engineered immune cells have been proposed as potential treatment for cancers and other antigen presenting maladies. However, these immune cells, whether chimeric antigen receptor (CAR)-engineered cells or T-cell receptor (TCR)-engineered cells, often only show efficacious results in vitro. In vivo, these results are rarely duplicated. Moreover, increasing the affinity of TCRs in engineered T-cells to cancer antigens frequently increases the affinity of the cells to non-cancer-specific peptides, resulting in severe and intolerable side effects. Unfortunately, dangerous cross-reactivity of engineered T-cells has halted development of therapeutics products even where cross-reactivity for the TCR was not predicted. Thus, despite decades of consistent research, engineered T-cell specific therapies have struggled to find regulatory approval.

SUMMARY

Provided are T cell receptor (TCR) compositions and methods for isolating T-cells with TCRs optimized for reactivity to specific peptides and decreased cross-reactivity to non-target peptides. Advantageously, TCRs of the invention can be optimized to target cancer antigens and peptides while having reduced reactivity to healthy cells. Methods of the invention utilize a novel combination of culturing conditions that increase T-cell activation and allow for validation of TCR activity. Culturing conditions of the invention further reduce culturing times generally needed to achieve expanded reactive T-cells. Because of the robust nature of the activation and validation conditions of the present invention, variants of identified TCRs can also be optimized and validated for their response to peptides, including cancer peptides. The methods of the invention as described herein were used to produce the TCR compositions described herein.

TCR Expansion

In an aspect of the invention, provided is a method for isolating T-cells reactive to a target peptide. The methods comprise obtaining peripheral mononuclear blood cells (PMBCs) from a subject, differentiating monocytes from a first portion of the PBMCs into dendritic cells and maturing these dendritic cells in a culture comprising the target peptide. Naïve CD8+ T-cells from a second portion of the PMBCs are then cocultured with the mature dendritic cells, and T-cells reactive to the peptide isolated from the co-culture.

The dendritic cells may be obtained by in vitro differentiation of peripheral blood monocytes. The step of monocyte differentiation into dendritic cells may comprise culturing monocytes in the presence of IL-4 and GM-CSF. The step of maturing the dendritic cells may comprise maturing the dendritic cells in a culture comprising IFN-γ. The step of co-culturing the CD8+ T-cells with the mature dendritic cells may comprise adding IL-21 to the culture.

In aspects of the invention, the method further comprises the step of re-stimulating the cultured T cells with autologous PMBCs that have been depleted of T cells and natural killer cells and then incubated with the target peptide. Advantageously, the step of re-stimulating the cultured T cells with autologous PBMCs may be performed and completed between 5 and 15 days after co-culturing the CD8+ T-cells with the mature dendritic cells. Methods of the invention may further comprise the step of re-stimulating the cultured T cells with T2 cells that have been inactivated by mitomycin C and incubated with the target peptide, which may be performed and completed between 5 and 15 days after re-stimulating the cultured T cells with autologous PBMCs.

The step of isolating T-cells reactive to a target peptide may comprise the step of sorting for IFN-γ secreting cells and expanding the cells with phytohemagglutinin. Advantageously, the step of isolating T-cells reactive to a target peptide may comprise the step of sorting for IFN-γ secreting cells between 0 and 5 days after re-stimulating the culture with T2 cells.

The step of isolating T-cells reactive to a target peptide may further comprise binding the TCR of the T-cell to an epitope of the target peptide. The step of isolating T-cells reactive to a target peptide may comprise tetramer binding. Advantageously, the step of isolating T-cells reactive to a target peptide may further comprise binding the T-cell receptor (TCR) of the T-cell to an epitope of the target peptide between 5 and 15 days after sorting for IFN-γ secreting cells.

Surprisingly, it has been discovered by the present invention, that all of the steps of the method may be completed between 15 and 40 days.

Further advantageously, the step of obtaining PMBCs may comprise obtaining PMBCs from a subject with a cancer. The step of obtaining PMBCs comprises obtaining PMBCs from a subject previously treated with a checkpoint inhibitor. The step of obtaining PMBCs may comprise obtaining PMBCs from a subject without cancer. By the above methods, the target peptide may be a cancer peptide, for example NY-ESO-1.

Aspects of the invention provide for a method for identifying T-cell receptors (TCRs) reactive to a target peptide. The method comprises obtaining peripheral mononuclear blood cells (PMBCs) from a subject, differentiating and maturing dendritic cells from a first portion of the PMBCs in a culture comprising the target peptide and isolating naïve CD8+ T-cells from a second portion of the PMBCs. The CD8+ T-cells are then co-cultured with the mature dendritic cells and T-cells reactive to the peptide isolated from the co-culture. After isolating the T-cells, TCRs of the isolated T-cells can be sequenced and identified.

The step of sequencing the TCRs may comprise next generation sequencing.

In an aspect of the invention, the dendritic cells may be matured from monocytes. The step of maturing the dendritic cells may comprise maturing the dendritic cells in a culture comprising IFN-γ. The step of co-culturing the CD8+ T-cells with the mature dendritic cells may comprise adding IL-21 to the culture.

In aspects of the invention, the method further comprises the step of re-stimulating the cultured T cells with autologous PMBCs that have been depleted of T cells and natural killer cells and then incubated with the target peptide. Advantageously, the step of re-stimulating the cultured T cells with autologous PBMCs may be performed and completed between 5 and 15 days after co-culturing the CD8+ T-cells with the mature dendritic cells. Methods of the invention may further comprise the step of re-stimulating the cultured T cells with T2 cells that have been inactivated by mitomycin C and incubated with the target peptide, which may be performed and completed between 5 and 15 days after re-stimulating the cultured T cells with autologous PBMCs.

The step of isolating T-cells reactive to a target peptide may comprise the step of sorting for IFN-γ secreting cells. Advantageously, the step of isolating T-cells reactive to a target peptide may comprise the step of sorting for IFN-γ secreting cells between 0 and 5 days after re-stimulating the culture with T2 cells.

The step of isolating T-cells reactive to a target peptide may further comprise binding the TCR of the T-cell to an epitope of the target peptide. The step of isolating T-cells reactive to a target peptide may comprise tetramer binding. Advantageously, the step of isolating T-cells reactive to a target peptide may further comprise binding the T-cell receptor (TCR) of the T-cell to an epitope of the target peptide between 5 and 15 days after sorting for IFN-γ secreting cells.

Surprisingly, it has been discovered by the present invention, that all of the steps of the method may be completed between 15 and 40 days.

Further advantageously, the step of obtaining PMBCs may comprise obtaining PMBCs from a subject with a cancer. The step of obtaining PMBCs comprises obtaining PMBCs from a subject previously treated with a checkpoint inhibitor. By the above methods, the target peptide may be a cancer peptide, for example NY-ESO-1.

TCR Validation

Aspects of the invention further provide a method for analyzing T-cell receptor (TCR) activation by a target peptide. Methods of the invention comprise transfecting T-cells with a plasmid encoding, in order:

—a TCRβ—a 2A peptide—a TCRα—an internal ribosome entry site (IRES)—a low-affinity nerve growth factor receptor (LNGFR)—

The LNGFR may be a truncated LNGFR. Methods may comprise culturing the T-cells with T2 cells and the target peptide and analyzing CD69 activation by the T-cells. Advantageously, the step of culturing the T-cells may comprise culturing the T-cells for between 16 and 30 hours.

In aspects of the invention, the T-cells are Jurkat T-cells. In aspects of the invention, the Jurkat T-cells may be Jurkat T-cells in which the alpha and/or beta chains have been knocked out. The Jurkat T-cells may have been transduced with a vector encoding the human CD8 co-receptor (CD8 alpha-2A-CD8 beta).

The step of transfecting the T-cells may comprise any known method, for example the step may comprise electroporating the T-cell. The methods may further comprise the step of analyzing LNGFR expression prior to analyzing CD69 activation. The step of analyzing CD69 activation may comprise flow cytometry. Advantageously, the target peptide may be a peptide associated with cancer, for example the target peptide may be an NY-ESO-1.

Aspects of the invention disclose a method for analyzing T-cell receptor (TCR) activation to a target peptide. The method comprises introducing into T-cells an mRNA encoding, in order:

—a TCRβ—a 2A peptide—a TCRα—

In aspects of the invention, the mRNA is introduced into the T-cells via electroporation. In aspects of the invention, the DNA template is operably linked to a promoter to enable mRNA synthesis from the DNA template, for example a T7 promoter. Methods may comprise culturing the T-cells with T2 cells—the target peptide and analyzing CD69 expression by the T-cells. Advantageously, the step of culturing the T-cells may comprise culturing the T-cells for between 20 and 72 hours.

In aspects of the invention, the T-cells are Jurkat T-cells. In aspects of the invention, the Jurkat T-cells may be Jurkat T-cells in which the alpha and/or beta chains have been knocked out. The Jurkat T-cells may have been transduced with a vector encoding the human CD8 co-receptor (CD8 alpha-2A-CD8 beta).

The step of introducing the mRNA to the T-cells may comprise any known methods for introducing nucleic acids to cells, for example the step of introducing into T-cells an mRNA may comprise electroporating the T-cells.

The step of analyzing CD69 activation may comprise flow cytometry. Advantageously, the target peptide may be a peptide associated with cancer, for example the target peptide may be an NY-ESO-1.

Methods of the invention may comprise transducing T-cells with a vector encoding, in order:

—a TCRβ—a 2A peptide—a TCRα—an internal ribosome entry site (IRES)—a low-affinity nerve growth factor receptor (LNGFR)—

The LNGFR may be a truncated LNGFR. Methods may comprise culturing the T-cells with T2 cells and the target peptide and analyzing CD69 activation by the T-cells. Advantageously, the step of culturing the T-cells may comprise culturing the T-cells for between 20 and 72 hours.

In aspects of the invention, the T-cells are Jurkat T-cells. In aspects of the invention, the Jurkat T-cells may be Jurkat T-cells in which the alpha and/or beta chains have been knocked out. The Jurkat T-cells may have been transduced with a vector encoding the human CD8 co-receptor (CD8 alpha-2A-CD8 beta).

The step of transducing T-cells with a vector may comprise any known method, for example the step may comprise the use of a viral vector. The viral vector may be a lentiviral vector or a adeno viral vector. The methods may further comprise the step of analyzing LNGFR expression prior to analyzing CD69 activation. The step of analyzing CD69 activation may comprise flow cytometry. Advantageously, the target peptide may be a peptide associated with cancer, for example the target peptide may be an NY-ESO-1.

For example, aspects of the invention may provide a method that comprises transfecting a plurality of T-cells with plurality of viral vectors comprising a nucleic acid encoding, in order:

—a TCRβ—a 2A peptide—a TCRα—an internal ribosome entry site (IRES)—a low-affinity nerve growth factor receptor (LNGFR)— followed by culturing the T-cells with T2 cells and the target peptide and analyzing CD69 activation by the T-cells.

It is further understood that in any of the methods of the invention comprising the editing of a T-cell, any known method of genomic editing may be used. For example, methods of the invention may comprise the use of a targeted nuclease such as Cas endonucleases. Accordingly, aspects of the invention for TCR validation may comprise the step of editing T-cells to transcribe a nucleic acid encoding, in order:

a TCRβ;

a 2A peptide;

a low-affinity nerve growth factor receptor (LNGFR);

a 2A peptide;

a TCRα, followed by culturing the T-cells with T2 cells and the target peptide and analyzing CD69 activation by the T-cells.

TCR Cross-Reactivity

Aspects of the invention provided a method for analyzing T-cell receptor (TCR) cross-reactivity. The method comprises transfecting T-cells with a plasmid encoding, in order:

—a TCRβ—a 2A peptide—a TCRα—an internal ribosome entry site (IRES)—a low-affinity nerve growth factor reception (LNGFR)—

The LNGFR may be a truncated LNGFR. The method comprises culturing a first portion of the T-cells with T2 cells and the target peptide and culturing a second portion of the T-cells with T2 cells and may also be cultured with a control, for example dimethyl sulfoxide (DMSO). The method further comprises analyzing TCR activation by the T-cells in response to the target peptide and/or control.

Advantageously, the step of culturing the T-cells may comprise culturing the T-cells for a period of 16 and 72 hours.

In aspects of the invention, the T-cells are Jurkat T-cells. In aspects of the invention, the Jurkat T-cells may be Jurkat T-cells in which the alpha and/or beta chains have been knocked out. The Jurkat T-cells may have been transduced with a vector encoding the human CD8 co-receptor (CD8 alpha-2A-CD8 beta).

The step of transfecting the T-cells may comprise any known method, for example the step may comprise electroporating the T-cell.

The methods may further comprise the step of analyzing LNGFR expression prior to analyzing TCR activation. The step of analyzing TCR activation may comprise analyzing CD69 activation. Analyzing CD69 activation may comprise flow cytometry.

In an aspect of the invention, the T-cells may comprise a luciferase gene under the control of one or multiple nuclear factor of activated T-cell (NFAT) response elements. The step of analyzing TCR activation may comprise analyzing luminescence by the T cells.

Advantageously, the target peptide may be a peptide associated with cancer, for example the target peptide may be an NY-ESO-1.

Aspects of the invention provide a method for analyzing T-cell receptor (TCR) cross-reactivity. The method comprises introducing into T-cells a plurality of mRNA molecules encoding, in order:

—a TCRβ—a 2A peptide—a TCRα—

In aspects of the invention, the mRNA is introduced into the T-cells using a DNA template. In aspects of the invention, the DNA template is operably linked to a promoter to enable mRNA synthesis from the DNA template, for example a T7 promoter. Methods further comprise culturing the T-cells with T2 cells and one or more peptides corresponding to the TCRβ and/or TCRα chains expressed by the plurality of mRNA molecules introduced to the T-cells and one or more peptides that do not correspond to the TCRβ and/or TCRα chains expressed by the plurality of mRNA molecules introduced to the T-cells. TCR activation is then analyzed for a T-cell in response to the one or more peptides that do not correspond to the TCRβ and/or TCRα chains expressed by the T-cell.

Advantageously, the step of culturing the T-cells comprises culturing the T-cells in a period of 20 and 72 hours.

In aspects of the invention, the T-cells are Jurkat T-cells. In aspects of the invention, the Jurkat T-cells may be Jurkat T-cells in which the alpha and/or beta chains have been knocked out. The Jurkat T-cells may have been transduced with a vector encoding the human CD8 co-receptor (CD8 alpha-2A-CD8 beta).

The step of introducing into T-cells the plurality of mRNA may comprise electroporating the T-cells. The T-cells may comprise a luciferase gene under the control of a nuclear factor of activated T-cell (NFAT) reporter. The step of analyzing TCR activation may comprise analyzing luminescence by the T cells.

In aspects of the invention, the plurality of mRNA molecules may comprise mRNA molecules encoding a TCRβ and TCRα corresponding to an NY-ESO-1 peptide. The step of culturing the T-cells with a plurality of peptides may comprise culturing the T-cells with NY-ESO-1 peptides.

Aspects of the invention provided a method for analyzing T-cell receptor (TCR) cross-reactivity. The method comprises transducing T-cells with a vector encoding, in order:

—a TCRβ—a 2A peptide—a TCRα—an internal ribosome entry site (IRES)—a low—affinity nerve growth factor reception (LNGFR)—

The LNGFR may be a truncated LNGFR. The method comprises culturing a first portion of the T-cells with T2 cells and the target peptide and culturing a second portion of the T-cells with T2 cells and may also be cultured with a control, for example DMSO. The method further comprises analyzing TCR activation by the T-cells in response to the target peptide and/or control.

Advantageously, the step of culturing the T-cells may comprise culturing the T-cells for a period of 16 and 72 hours.

In aspects of the invention, the T-cells are Jurkat T-cells. In aspects of the invention, the Jurkat T-cells may be Jurkat T-cells in which the alpha and/or beta chains have been knocked out. The Jurkat T-cells may have been transduced with a vector encoding the human CD8 co-receptor (CD8 alpha-2A-CD8 beta).

The step of transducing T-cells with a vector may comprise any known method, for example the step may comprise the use of a viral vector. The viral vector may be a lentiviral vector or an adeno viral vector. The methods may further comprise the step of analyzing LNGFR expression prior to analyzing TCR activation. The step of analyzing TCR activation may comprise analyzing CD69 activation. Analyzing CD69 activation may comprise flow cytometry.

In an aspect of the invention, the T-cells may comprise a luciferase gene under the control of one or multiple nuclear factor of activated T-cell (NFAT) response elements. The step of analyzing TCR activation may comprise analyzing luminescence by the T cells.

Advantageously, the target peptide may be a peptide associated with cancer, for example the target peptide may be an NY-ESO-1.

For example, aspects of the invention may provide a method that comprises transfecting a plurality of T-cells with a virus comprising a nucleic acid encoding, in order:

—a TCRβ—a 2A peptide—a TCRα—an internal ribosome entry site (IRES)—a low—affinity nerve growth factor receptor (LNGFR)— followed by culturing a first portion of the T-cells with T2 cells and the target peptide and culturing a second portion of the T-cells with T2 cells and may also be cultured with a control, for example DMSO. The method further comprises analyzing TCR activation by the T-cells in response to the target peptide and/or in response to the control.

As discussed above, it is further understood that in any of the methods of the invention comprising the editing of a T-cell, any known method of genomic editing may be used. Accordingly, aspects of the invention for TCR cross-reactivity assays may comprise the step of editing T-cells to transcribe a nucleic acid encoding, in order:

a TCRβ;
a 2A peptide;
a TCRα;
an internal ribosome entry site (IRES); and
a low-affinity nerve growth factor receptor (LNGFR),
followed by culturing a first portion of the T-cells with T2 cells and the target peptide and culturing a second portion of the T-cells with T2 cells and may also be cultured with a control, for example DMSO. The method further comprises analyzing TCR activation by the T-cells in response to the target peptide and/or in response to the control.

TCR Optimization I

Aspects of the invention provide a method for identifying activated T-cells reactive to a target peptide. The methods comprise transducing a plurality of T-cells with a plurality of nucleic acid molecules encoding a T-cell receptor (TCR) specific for the target peptide or a TCR comprising one or more amino acid substitutions at a CDR position of the TCR specific for the target peptide. The methods comprise co-culturing the T-cells with antigen presenting cells presenting an epitope of the target peptide and sorting for T-cells with activated TCRs.

Aspects of the invention may further comprise the step of sequencing T-cells with active TCRs. Advantageously, each of the nucleic acid molecules may comprise a barcode unique to the TCR encoded by the nucleic acid molecule.

The step of sorting may comprise fluorescence-activated cell sorting. The methods may further comprise the step of comparing the activation levels of the substituted TCRs. Comparing the activation levels of the substituted TCRs may comprise comparing Mean Fluorescent Intensity (MFI). Aspects of the invention may further comprise the step of identifying the amino acid substitutions of the TCRs of activated T-cells.

Advantageously, the target peptide may be associated with cancer, for example the target peptide may be an NY-ESO-1 peptide.

In aspects of the invention, the amino acid substitution may be in only one of the CDR1, CDR2, or CDR3 of the alpha or beta chain of the TCR. The amino acid substitution may be in only one of the CDR1 or CDR3 of the alpha or beta chain of the TCR. The amino acid substitution may be in only one of the CDR1 or CDR2 of the alpha or beta chain of the TCR.

Aspects of the invention provide a method for identifying activated T-cells reactive to a target peptide. The method may comprise transducing a plurality of T-cells with a plurality of nucleic acid molecules encoding a T-cell receptor (TCR) specific for the target peptide or a TCR comprising one or more amino acid substitutions at a CDR position of the TCR. The methods comprise co-culturing the T-cells with antigen presenting cells presenting an epitope of the target peptide, sorting for T-cells with activated TCRs, and comparing the activation levels of the substituted TCRs.

Aspects of the invention may further comprise the step of sequencing T-cells with active TCRs. Each of the nucleic acid molecules may comprise a barcode unique to the TCR encoded by the nucleic acid molecule. The step of sorting may comprise fluorescence-activated cell sorting. Comparing the activation levels of the substituted TCRs may comprise comparing Mean Fluorescent Intensity (MFI).

Aspects of the invention may further comprise the step of identifying the amino acid substitutions of the TCRs of activated T-cells.

Advantageously, the target peptide may be associated with cancer, for example the target peptide may be an NY-ESO-1 peptide.

In aspects of the invention, the amino acid substitution may be in only one of the CDR1 or CDR3 of the alpha or beta chain of the TCR.

As discussed above, it is further understood that in any of the methods of the invention comprising the editing of a T-cell, any known method of genomic editing may be used.

For example, aspects of the invention may comprise transfecting a plurality of T-cells with a plurality of viral vectors comprising nucleic acid molecules encoding a T-cell receptor (TCR) specific for the target peptide or a TCR comprising one or more amino acid substitutions at a CDR position of the TCR specific for the target peptide. The transfected T-cells may then be co-cultured with antigen presenting cells presenting an epitope of the target peptide and the cultured T-cells may be sorted for T-cells with activated TCRs.

Aspects of the invention may comprise editing a plurality of T-cells to express either a T-cell receptor (TCR) specific for the target peptide or a TCR comprising one or more amino acid substitutions at a CDR position of the TCR specific for the target peptide. Once edited, the T-cells may be co-cultured with antigen presenting cells presenting an epitope of the target peptide and the T-cells may be sorted for T-cells with activated TCRs.

TCR Optimization II

Aspects of the invention provide a method of optimizing the TCR of a T-cell reactive to a target peptide. The methods comprise transducing a plurality of T-cells with a plurality of nucleic acids encoding a T-cell receptor (TCR) specific for the target peptide and at least one TCR comprising one or more amino acid substitutions at a CDR1 and/or CDR3 position of the TCR. The T-cells may then be co-cultured with T2 cells pulsed with the target peptide and one or more non-target peptide.

Methods may further comprise the step of sorting for T-cells with activated TCRs. The sorting step may comprise fluorescence-activated cell sorting. Sorting may comprise sorting for T-cells expressing CD69. The methods may comprise the further step of comparing the activation levels of the substituted TCRs. Comparing activation levels of the substituted TCRs may comprise comparing Mean Fluorescent Intensity (MFI).

In aspects of the invention, the T-cells are Jurkat T-cells.

In aspects of the invention, the at least one amino acid substitution is not cysteine. In an aspect of the invention, the peptide is not MART-1. In aspects of the invention, the T2 cells are pulsed with the target peptide and MART-1. Advantageously, the target peptide may be a peptide associated with cancer, for example the target peptide may be an NY-ESO-1 peptide.

Aspects of the invention provide a method of optimizing the TCR of a T-cell reactive to a target peptide. The method comprises transducing a plurality of T-cells with a plurality of nucleic acids encoding a T-cell receptor (TCR) specific for the target peptide and at least one TCR comprising one or more amino acid substitutions at a CDR1 and/or CDR3 position of the TCR. The T-cells are co-cultured with T2 cells pulsed with the target peptide and a plurality of non-target peptides. Activated T-cells are sorted and the activation levels of the substituted TCRs compared.

The sorting step may comprise fluorescence-activated cell sorting. The sorting step may further comprise sorting for T-cells expressing CD69.

In aspects of the invention, the T-cells are Jurkat T-cells.

In aspects of the invention, the at least one amino acid substitution is not cysteine. In an aspect of the invention, the peptide is not MART-1. In an aspect of the invention, the T2 cells are pulsed with the target peptide and MART-1.

Advantageously, the target peptide may be a peptide associated with cancer, for example the target peptide may be an NY-ESO-1 peptide. Advantageously, the target peptide may be a peptide associated with cancer, for example the target peptide may be an NY-ESO-1 peptide.

As discussed above, it is further understood that in any of the methods of the invention comprising the editing of a T-cell, any known method of genomic editing may be used. Accordingly, aspects of the invention for TCR optimization may comprise editing a plurality of T-cells to express a T-cell receptor specific for the target peptide and at least one TCR comprising one or more amino acid substitutions at a CDR1 and/or CDR3 position of the TCR. The T-cells are co-cultured with T2 cells pulsed with the target peptide and a plurality of non-target peptides. Activated T-cells are sorted and the activation levels of the substituted TCRs compared.

NY7 TCR Variants

Aspects of the invention provide TCRs optimized against cancer peptides. Aspects of the invention provide a T-cell receptor (TCR), wherein the TCR comprises no more than four amino acid substitutions in the alpha chain or the beta chain of the TCR, wherein the unsubstituted TCR comprises:

an alpha chain CDR1 comprising the sequence DRGSQS (SEQ ID NO: 1);

an alpha chain CDR2 comprising the sequence IYSNGD (SEQ ID NO: 2);

an alpha chain CDR3 comprising the sequence CAVM-RAGGFKTI (SEQ ID NO: 3);

a beta chain CDR1 comprising the sequence SGDLS (SEQ ID NO: 4);

a beta chain CDR2 comprising the sequence YYNGEE (SEQ ID NO: 5);

a beta chain CDR3 comprising the sequence CASSVVDGEQY (SEQ ID NO: 6).

In an aspect of the invention, the amino acid substitution or substitutions may be in the CDR1 or CDR3 of the alpha chain. The amino acid substitution or substitutions may be in the CDR1 or CDR3 of the beta chain. In aspects of the invention, the substitution or substitutions are not cysteine.

The substitution or substitutions may not be in the first amino acid of the alpha chain CDR1, alpha chain CD3, beta chain CDR1, or beta chain CDR3. The substitution or substitutions may not be in the last amino acid of the alpha chain CD3, beta chain CDR1, or beta chain CDR3. The substitution or substitutions may not be in the fifth amino acid of the beta chain CDR1.

In aspects of the invention, the TCR comprises only one substitution in the alpha chain, with the one substitution is in the alpha chain CDR1. The alpha chain CDR1 may comprise the sequence DRGVQS (SEQ ID NO: 7), DRESQS (SEQ ID NO: 8), DRGIQS (SEQ ID NO: 9), DRGSQA (SEQ ID NO: 10), DRWSQS (SEQ ID NO: 11), FRGSQS (SEQ ID NO: 12), RRGSQS (SEQ ID NO: 13), DRYSQS (SEQ ID NO: 14), DRGSGS (SEQ ID NO: 15), DRGLQS (SEQ ID NO: 16), QRGSQS (SEQ ID NO: 17), DRGNQS (SEQ ID NO: 18), DRGSQG (SEQ ID NO: 19), WRGSQS (SEQ ID NO: 20), DRGAQS (SEQ ID NO: 21), DWGSQS (SEQ ID NO: 22), DGGSQS (SEQ ID NO: 23), DRPSQS (SEQ ID NO: 24), HRGSQS (SEQ ID NO: 25), DRSSQS (SEQ ID NO: 26), or DRGFQS (SEQ ID NO: 27).

The substitution or substitutions may be in the alpha chain, with at least one substitution in the alpha chain CDR3. The alpha chain CDR3 may comprise the sequence CAVM-RAMGFKTI (SEQ ID NO: 28), CAVVRAGGFKTI (SEQ ID NO: 29), CAVLRAGGFKTI (SEQ ID NO: 30), CAYM-RAGGFKTI (SEQ ID NO: 31), CAVMRAGYFKTI (SEQ ID NO: 32), CAVMRAGGFKEI (SEQ ID NO: 33), CAVM-RAFGFKTI (SEQ ID NO: 34), CATMRAGGFKTI (SEQ ID NO: 35), CAVWRAGGFKTI (SEQ ID NO: 36), CAYM-RAGGFKEI (SEQ ID NO: 37), CAVMRAGGFKTS (SEQ ID NO: 38), CAAMRAGGFKTI (SEQ ID NO: 39), CAVQRAGGFKTI (SEQ ID NO: 40), CAVMRIGGFKTI (SEQ ID NO: 41), CAVMRMGGFKTI (SEQ ID NO: 42), CAVMRATGFKTI (SEQ ID NO:43), CAVMRAHGFKTI (SEQ ID NO: 44), CANMRAGGFKTI (SEQ ID NO: 45), CAVMRAQGFKTI (SEQ ID NO: 46), CAVMRAAGFKTI (SEQ ID NO: 47), CAVMFAGGFKTI (SEQ ID NO: 48), CAVMRAGGFKTA (SEQ ID NO: 49), CAVMRAVGFKTI (SEQ ID NO: 50), CAVMRAYGFKTI (SEQ ID NO: 51), CAVMRASGFKTI (SEQ ID NO: 52), CAVMRALGFKTI (SEQ ID NO: 53), CAVMRAGGFKTF (SEQ ID NO: 54), CAVMRAGGFKTQ (SEQ ID NO: 55), CASMRAGGFKTI (SEQ ID NO: 56), or CLVMRAGGFKTI (SEQ ID NO: 57).

The substitution or substitutions may be in the beta chain. The TCR may comprise a substitution in the beta chain CDR1. The beta chain CDR1 may comprise the sequence SGNLS (SEQ ID NO: 58), AGDLS (SEQ ID NO: 59), SGDLI (SEQ ID NO: 60), SGWLS (SEQ ID NO: 61), SGLLS (SEQ ID NO: 62), SGSLS (SEQ ID NO: 63), TGDLS (SEQ ID NO: 64), MGDLS (SEQ ID NO: 65), GGDLS (SEQ ID NO: 66), WGDLS (SEQ ID NO: 67), IGDLS (SEQ ID NO: 68), or QGDLS (SEQ ID NO: 69).

At least one substitution may be in the beta chain CDR3. The beta chain CDR3 may comprise the sequence CASSVVDGEQT (SEQ ID NO: 70), CASLVVDGEQY (SEQ ID NO: 71), CASSVQDGEQY (SEQ ID NO: 72), CASSVVDGEQF (SEQ ID NO: 73), CASSVVDIEQY (SEQ ID NO: 74), CASSVVDDEQY (SEQ ID NO: 75), CASSVVDYEQY (SEQ ID NO: 76), CASSVVDGEDY (SEQ ID NO: 77), CASAVVDGEQY (SEQ ID NO: 78), CASSNVDGEQY (SEQ ID NO: 79), CAWSVVDGEQY (SEQ ID NO: 80), CASLVVDGEQT (SEQ ID NO: 81), CASSVVDGEMY (SEQ ID NO: 82), CASSVVDGEGY (SEQ ID NO: 83), CASSVVDGEEY (SEQ ID NO: 84), CASSVVDGENY (SEQ ID NO: 85), CASSVVDGEQV (SEQ ID NO: 86).

The alpha chain and beta chain of the TCRs may be selected from the chains of Table A:

TABLE A

| TCR ID | Alpha Chain | Beta Chain |
| --- | --- | --- |
| 1 | QKEVEQNSGPLSVPEGAIASLNCTYS DRGVQSFFWYRQYSGKSPELIMFIYS NGDKEDGRFTAQLNKASQYVSLLIR DSQPSDSATYLCAVMRAGGFKTIFGA GTRLFVKANIQNPDPAVYQLRDSKSS DKSVCLFTDFDSQTNVSQSKDSDVYI TDKCVLDMRSMDFKSNSAVAWSNK SDFACANAFNNSIIPEDTFFPSPESSCD VKLVEKSFETDTNLNFQNLSVIGFRIL LLKVAGFNLLMTLRLWSS (SEQ ID NO: 87) | DSGVTQTPKHLITATGQRVTLRCSPRSGD LSVYWYQQSLDQGLQFLIQYYNGEERA KGNILERFSAQQFPDLHSELNLSSLELGD SALYFCASSVVDGEQYFGPGTRLTVTED LKNVFPPEVAVFEPSEAEISHTQKATLVC LATGFYPDHVELSWWVNGKEVHSGVCT DPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 88) |
| 2 | QKEVEQNSGPLSVPEGAIASLNCTYS DRFSQSFFWYRQYSGKSPELIMFIYSN GDKEDGRFTAQLNKASQYVSLLIRDS QPSDSATYLCAVMRAGGFKTIFGAG TRLFVKANIQNPDPAVYQLRDSKSSD KSVCLFTDFDSQTNVSQSKDSDVYIT DKCVLDMRSMDFKSNSAVAWSNKS DFACANAFNNSIIPEDTFFPSPESSCD VKLVEKSFETDTNLNFQNLSVIGFRIL LLKVAGFNLLMTLRLWSS (SEQ ID NO: 89) | DSGVTQTPKHLITATGQRVTLRCSPRSGD LSVYWYQQSLDQGLQFLIQYYNGEERA KGNILERFSAQQFPDLHSELNLSSLELGD SALYFCASSVVDGEQYFGPGTRLTVTED LKNVFPPEVAVFEPSEAEISHTQKATLVC LATGFYPDHVELSWWVNGKEVHSGVCT DPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 90) |
| 3 | QKEVEQNSGPLSVPEGAIASLNCTYS DRGIQSFFWYRQYSGKSPELIMFIYSN GDKEDGRFTAQLNKASQYVSLLIRDS QPSDSATYLCAVMRAGGFKTIFGAG TRLFVKANIQNPDPAVYQLRDSKSSD KSVCLFTDFDSQTNVSQSKDSDVYIT DKCVLDMRSMDFKSNSAVAWSNKS DFACANAFNNSIIPEDTFFPSPESSCD VKLVEKSFETDTNLNFQNLSVIGFRIL LLKVAGFNLLMTLRLWSS (SEQ ID NO: 91) | DSGVTQTPKHLITATGQRVTLRCSPRSGD LSVYWYQQSLDQGLQFLIQYYNGEERA KGNILERFSAQQFPDLHSELNLSSLELGD SALYFCASSVVDGEQYFGPGTRLTVTED LKNVFPPEVAVFEPSEAEISHTQKATLVC LATGFYPDHVELSWWVNGKEVHSGVCT DPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 92) |
| 4 | QKEVEQNSGPLSVPEGAIASLNCTYS DRGSQAFFWYRQYSGKSPELIMFIYS NGDKEDGRFTAQLNKASQYVSLLIR DSQPSDSATYLCAVMRAGGFKTIFGA GTRLFVKANIQNPDPAVYQLRDSKSS DKSVCLFTDFDSQTNVSQSKDSDVYI TDKCVLDMRSMDFKSNSAVAWSNK SDFACANAFNNSIIPEDTFFPSPESSCD VKLVEKSFETDTNLNFQNLSVIGFRIL LLKVAGFNLLMTLRLWSS (SEQ ID NO: 93) | DSGVTQTPKHLITATGQRVTLRCSPRSGD LSVYWYQQSLDQGLQFLIQYYNGEERA KGNILERFSAQQFPDLHSELNLSSLELGD SALYFCASSVVDGEQYFGPGTRLTVTED LKNVFPPEVAVFEPSEAEISHTQKATLVC LATGFYPDHVELSWWVNGKEVHSGVCT DPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 94) |
| 5 | QKEVEQNSGPLSVPEGAIASLNCTYS DRWSQSFFWYRQYSGKSPELIMFIYS NGDKEDGRFTAQLNKASQYVSLLIR DSQPSDSATYLCAVMRAGGFKTIFGA GTRLFVKANIQNPDPAVYQLRDSKSS DKSVCLFTDFDSQTNVSQSKDSDVYI TDKCVLDMRSMDFKSNSAVAWSNK SDFACANAFNNSIIPEDTFFPSPESSCD VKLVEKSFETDTNLNFQNLSVIGFRIL LLKVAGFNLLMTLRLWSS (SEQ ID NO: 95) | DSGVTQTPKHLITATGQRVTLRCSPRSGD LSVYWYQQSLDQGLQFLIQYYNGEERA KGNILERFSAQQFPDLHSELNLSSLELGD SALYFCASSVVDGEQYFGPGTRLTVTED LKNVFPPEVAVFEPSEAEISHTQKATLVC LATGFYPDHVELSWWVNGKEVHSGVCT DPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 96) |
| 6 | QKEVEQNSGPLSVPEGAIASLNCTYS FRGSQSFFWYRQYSGKSPELIMFIYSN GDKEDGRFTAQLNKASQYVSLLIRDS QPSDSATYLCAVMRAGGFKTIFGAG TRLFVKANIQNPDPAVYQLRDSKSSD KSVCLFTDFDSQTNVSQSKDSDVYIT DKCVLDMRSMDFKSNSAVAWSNKS DFACANAFNNSIIPEDTFFPSPESSCD VKLVEKSFETDTNLNFQNLSVIGFRIL LLKVAGFNLLMTLRLWSS (SEQ ID NO: 97) | DSGVTQTPKHLITATGQRVTLRCSPRSGD LSVYWYQQSLDQGLQFLIQYYNGEERA KGNILERFSAQQFPDLHSELNLSSLELGD SALYFCASSVVDGEQYFGPGTRLTVTED LKNVFPPEVAVFEPSEAEISHTQKATLVC LATGFYPDHVELSWWVNGKEVHSGVCT DPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 98) |
| 7 | QKEVEQNSGPLSVPEGAIASLNCTYS DRYSQSFFWYRQYSGKSPELIMFIYS NGDKEDGRFTAQLNKASQYVSLLIR | DSGVTQTPKHLITATGQRVTLRCSPRSGD LSVYWYQQSLDQGLQFLIQYYNGEERA KGNILERFSAQQFPDLHSELNLSSLELGD |

TABLE A-continued

| TCR ID | Alpha Chain | Beta Chain |
|---|---|---|
| | DSQPSDSATYLCAVMRAGGFKTIFGA<br>GTRLFVKANIQNPDPAVYQLRDSKSS<br>DKSVCLFTDFDSQTNVSQSKDSDVYI<br>TDKCVLDMRSMDFKSNSAVAWSNK<br>SDFACANAFNNSIIPEDTFFPSPESSCD<br>VKLVEKSFETDTNLNFQNLSVIGFRIL<br>LLKVAGFNLLMTLRLWSS (SEQ ID<br>NO: 99) | SALYFCASSVVDGEQYFGPGTRLTVTED<br>LKNVFPPEVAVFEPSEAEISHTQKATLVC<br>LATGFYPDHVELSWWVNGKEVHSGVCT<br>DPQPLKEQPALNDSRYCLSSRLRVSATF<br>WQNPRNHFRCQVQFYGLSENDEWTQDR<br>AKPVTQIVSAEAWGRADCGFTSESYQQG<br>VLSATILYEILLGKATLYAVLVSALVLM<br>AMVKRKDSR (SEQ ID NO: 100) |
| 8 | QKEVEQNSGPLSVPEGAIASLNCTYS<br>DRGSGSFFWYRQYSGKSPELIMFIYS<br>NGDKEDGRFTAQLNKASQYVSLLIR<br>DSQPSDSATYLCAVMRAGGFKTIFGA<br>GTRLFVKANIQNPDPAVYQLRDSKSS<br>DKSVCLFTDFDSQTNVSQSKDSDVYI<br>TDKCVLDMRSMDFKSNSAVAWSNK<br>SDFACANAFNNSIIPEDTFFPSPESSCD<br>VKLVEKSFETDTNLNFQNLSVIGFRIL<br>LLKVAGFNLLMTLRLWSS (SEQ ID<br>NO: 101) | DSGVTQTPKHLITATGQRVTLRCSPRSGD<br>LSVYWYQQSLDQGLQFLIQYYNGEERA<br>KGNILERFSAQQFPDLHSELNLSSLELGD<br>SALYFCASSVVDGEQYFGPGTRLTVTED<br>LKNVFPPEVAVFEPSEAEISHTQKATLVC<br>LATGFYPDHVELSWWVNGKEVHSGVCT<br>DPQPLKEQPALNDSRYCLSSRLRVSATF<br>WQNPRNHFRCQVQFYGLSENDEWTQDR<br>AKPVTQIVSAEAWGRADCGFTSESYQQG<br>VLSATILYEILLGKATLYAVLVSALVLM<br>AMVKRKDSR (SEQ ID NO: 102) |
| 9 | QKEVEQNSGPLSVPEGAIASLNCTYS<br>DRGSQSFFWYRQYSGKSPELIMFIYS<br>NGDKEDGRFTAQLNKASQYVSLLIR<br>DSQPSDSATYLCAVMRAHGFKTIFGA<br>GTRLFVKANIQNPDPAVYQLRDSKSS<br>DKSVCLFTDFDSQTNVSQSKDSDVYI<br>TDKCVLDMRSMDFKSNSAVAWSNK<br>SDFACANAFNNSIIPEDTFFPSPESSCD<br>VKLVEKSFETDTNLNFQNLSVIGFRIL<br>LLKVAGFNLLMTLRLWSS (SEQ ID<br>NO: 103) | DSGVTQTPKHLITATGQRVTLRCSPRSGD<br>LSVYWYQQSLDQGLQFLIQYYNGEERA<br>KGNILERFSAQQFPDLHSELNLSSLELGD<br>SALYFCASSVVDGEQYFGPGTRLTVTED<br>LKNVFPPEVAVFEPSEAEISHTQKATLVC<br>LATGFYPDHVELSWWVNGKEVHSGVCT<br>DPQPLKEQPALNDSRYCLSSRLRVSATF<br>WQNPRNHFRCQVQFYGLSENDEWTQDR<br>AKPVTQIVSAEAWGRADCGFTSESYQQG<br>VLSATILYEILLGKATLYAVLVSALVLM<br>AMVKRKDSR (SEQ ID NO: 104) |
| 10 | QKEVEQNSGPLSVPEGAIASLNCTYS<br>DRGSQSFFWYRQYSGKSPELIMFIYS<br>NGDKEDGRFTAQLNKASQYVSLLIR<br>DSQPSDSATYLCAVVRAGGFKTIFGA<br>GTRLFVKANIQNPDPAVYQLRDSKSS<br>DKSVCLFTDFDSQTNVSQSKDSDVYI<br>TDKCVLDMRSMDFKSNSAVAWSNK<br>SDFACANAFNNSIIPEDTFFPSPESSCD<br>VKLVEKSFETDTNLNFQNLSVIGFRIL<br>LLKVAGFNLLMTLRLWSS (SEQ ID<br>NO: 105) | DSGVTQTPKHLITATGQRVTLRCSPRSGD<br>LSVYWYQQSLDQGLQFLIQYYNGEERA<br>KGNILERFSAQQFPDLHSELNLSSLELGD<br>SALYFCASSVVDGEQYFGPGTRLTVTED<br>LKNVFPPEVAVFEPSEAEISHTQKATLVC<br>LATGFYPDHVELSWWVNGKEVHSGVCT<br>DPQPLKEQPALNDSRYCLSSRLRVSATF<br>WQNPRNHFRCQVQFYGLSENDEWTQDR<br>AKPVTQIVSAEAWGRADCGFTSESYQQG<br>VLSATILYEILLGKATLYAVLVSALVLM<br>AMVKRKDSR (SEQ ID NO: 106) |
| 11 | QKEVEQNSGPLSVPEGAIASLNCTYS<br>DRGSQSFFWYRQYSGKSPELIMFIYS<br>NGDKEDGRFTAQLNKASQYVSLLIR<br>DSQPSDSATYLCAVLRAGGFKTIFGA<br>GTRLFVKANIQNPDPAVYQLRDSKSS<br>DKSVCLFTDFDSQTNVSQSKDSDVYI<br>TDKCVLDMRSMDFKSNSAVAWSNK<br>SDFACANAFNNSIIPEDTFFPSPESSCD<br>VKLVEKSFETDTNLNFQNLSVIGFRIL<br>LLKVAGFNLLMTLRLWSS (SEQ ID<br>NO: 107) | DSGVTQTPKHLITATGQRVTLRCSPRSGD<br>LSVYWYQQSLDQGLQFLIQYYNGEERA<br>KGNILERFSAQQFPDLHSELNLSSLELGD<br>SALYFCASSVVDGEQYFGPGTRLTVTED<br>LKNVFPPEVAVFEPSEAEISHTQKATLVC<br>LATGFYPDHVELSWWVNGKEVHSGVCT<br>DPQPLKEQPALNDSRYCLSSRLRVSATF<br>WQNPRNHFRCQVQFYGLSENDEWTQDR<br>AKPVTQIVSAEAWGRADCGFTSESYQQG<br>VLSATILYEILLGKATLYAVLVSALVLM<br>AMVKRKDSR (SEQ ID NO: 108) |
| 12 | QKEVEQNSGPLSVPEGAIASLNCTYS<br>DRGSQSFFWYRQYSGKSPELIMFIYS<br>NGDKEDGRFTAQLNKASQYVSLLIR<br>DSQPSDSATYLCAYMRAGGFKTIFGA<br>GTRLFVKANIQNPDPAVYQLRDSKSS<br>DKSVCLFTDFDSQTNVSQSKDSDVYI<br>TDKCVLDMRSMDFKSNSAVAWSNK<br>SDFACANAFNNSIIPEDTFFPSPESSCD<br>VKLVEKSFETDTNLNFQNLSVIGFRIL<br>LLKVAGFNLLMTLRLWSS (SEQ ID<br>NO: 109) | DSGVTQTPKHLITATGQRVTLRCSPRSGD<br>LSVYWYQQSLDQGLQFLIQYYNGEERA<br>KGNILERFSAQQFPDLHSELNLSSLELGD<br>SALYFCASSVVDGEQYFGPGTRLTVTED<br>LKNVFPPEVAVFEPSEAEISHTQKATLVC<br>LATGFYPDHVELSWWVNGKEVHSGVCT<br>DPQPLKEQPALNDSRYCLSSRLRVSATF<br>WQNPRNHFRCQVQFYGLSENDEWTQDR<br>AKPVTQIVSAEAWGRADCGFTSESYQQG<br>VLSATILYEILLGKATLYAVLVSALVLM<br>AMVKRKDSR (SEQ ID NO: 110) |
| 13 | QKEVEQNSGPLSVPEGAIASLNCTYS<br>DRGSQSFFWYRQYSGKSPELIMFIYS<br>NGDKEDGRFTAQLNKASQYVSLLIR<br>DSQPSDSATYLCAVMRAGYFKTIFGA<br>GTRLFVKANIQNPDPAVYQLRDSKSS<br>DKSVCLFTDFDSQTNVSQSKDSDVYI<br>TDKCVLDMRSMDFKSNSAVAWSNK | DSGVTQTPKHLITATGQRVTLRCSPRSGD<br>LSVYWYQQSLDQGLQFLIQYYNGEERA<br>KGNILERFSAQQFPDLHSELNLSSLELGD<br>SALYFCASSVVDGEQYFGPGTRLTVTED<br>LKNVFPPEVAVFEPSEAEISHTQKATLVC<br>LATGFYPDHVELSWWVNGKEVHSGVCT<br>DPQPLKEQPALNDSRYCLSSRLRVSATF |

TABLE A-continued

| TCR ID | Alpha Chain | Beta Chain |
|---|---|---|
|  | SDFACANAFNNSIIPEDTFFPSPESSCD VKLVEKSFETDTNLNFQNLSVIGFRIL LLKVAGFNLLMTLRLWSS (SEQ ID NO: 111) | WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 112) |
| 14 | QKEVEQNSGPLSVPEGAIASLNCTYS DRGSQSFFWYRQYSGKSPELIMFIYS NGDKEDGRFTAQLNKASQYVSLLIR DSQPSDSATYLCAVMRAGGFKEIFGA GTRLFVKANIQNPDPAVYQLRDSKSS DKSVCLFTDFDSQTNVSQSKDSDVYI TDKCVLDMRSMDFKSNSAVAWSNK SDFACANAFNNSIIPEDTFFPSPESSCD VKLVEKSFETDTNLNFQNLSVIGFRIL LLKVAGFNLLMTLRLWSS (SEQ ID NO: 113) | DSGVTQTPKHLITATGQRVTLRCSPRSGD LSVYWYQQSLDQGLQFLIQYYNGEERA KGNILERFSAQQFPDLHSELNLSSLELGD SALYFCASSVVDGEQYFGPGTRLTVTED LKNVFPPEVAVFEPSEAEISHTQKATLVC LATGFYPDHVELSWWVNGKEVHSGVCT DPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 114) |
| 15 | QKEVEQNSGPLSVPEGAIASLNCTYS DRGSQSFFWYRQYSGKSPELIMFIYS NGDKEDGRFTAQLNKASQYVSLLIR DSQPSDSATYLCAVMRMGGFKTIFG AGTRLFVKANIQNPDPAVYQLRDSKS SDKSVCLFTDFDSQTNVSQSKDSDVY ITDKCVLDMRSMDFKSNSAVAWSNK SDFACANAFNNSIIPEDTFFPSPESSCD VKLVEKSFETDTNLNFQNLSVIGFRIL LLKVAGFNLLMTLRLWSS (SEQ ID NO: 115) | DSGVTQTPKHLITATGQRVTLRCSPRSGD LSVYWYQQSLDQGLQFLIQYYNGEERA KGNILERFSAQQFPDLHSELNLSSLELGD SALYFCASSVVDGEQYFGPGTRLTVTED LKNVFPPEVAVFEPSEAEISHTQKATLVC LATGFYPDHVELSWWVNGKEVHSGVCT DPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 116) |
| 16 | QKEVEQNSGPLSVPEGAIASLNCTYS DRGSQSFFWYRQYSGKSPELIMFIYS NGDKEDGRFTAQLNKASQYVSLLIR DSQPSDSATYLCAVMRAFGFKTIFGA GTRLFVKANIQNPDPAVYQLRDSKSS DKSVCLFTDFDSQTNVSQSKDSDVYI TDKCVLDMRSMDFKSNSAVAWSNK SDFACANAFNNSIIPEDTFFPSPESSCD VKLVEKSFETDTNLNFQNLSVIGFRIL LLKVAGFNLLMTLRLWSS (SEQ ID NO: 117) | DSGVTQTPKHLITATGQRVTLRCSPRSGD LSVYWYQQSLDQGLQFLIQYYNGEERA KGNILERFSAQQFPDLHSELNLSSLELGD SALYFCASSVVDGEQYFGPGTRLTVTED LKNVFPPEVAVFEPSEAEISHTQKATLVC LATGFYPDHVELSWWVNGKEVHSGVCT DPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR(SEQ ID NO: 118) |
| 17 | QKEVEQNSGPLSVPEGAIASLNCTYS DRGSQSFFWYRQYSGKSPELIMFIYS NGDKEDGRFTAQLNKASQYVSLLIR DSQPSDSATYLCAVMRATGFKTIFGA GTRLFVKANIQNPDPAVYQLRDSKSS DKSVCLFTDFDSQTNVSQSKDSDVYI TDKCVLDMRSMDFKSNSAVAWSNK SDFACANAFNNSIIPEDTFFPSPESSCD VKLVEKSFETDTNLNFQNLSVIGFRIL LLKVAGENLLMTLRLWSS (SEQ ID NO: 119) | DSGVTQTPKHLITATGQRVTLRCSPRSGD LSVYWYQQSLDQGLQFLIQYYNGEERA KGNILERFSAQQFPDLHSELNLSSLELGD SALYFCASSVVDGEQYFGPGTRLTVTED LKNVFPPEVAVFEPSEAEISHTQKATLVC LATGFYPDHVELSWWVNGKEVHSGVCT DPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 120) |
| 18 | QKEVEQNSGPLSVPEGAIASLNCTYS DRGSQSFFWYRQYSGKSPELIMFIYS NGDKEDGRFTAQLNKASQYVSLLIR DSQPSDSATYLCATMRAGGFKTIFGA GTRLFVKANIQNPDPAVYQLRDSKSS DKSVCLFTDFDSQTNVSQSKDSDVYI TDKCVLDMRSMDFKSNSAVAWSNK SDFACANAFNNSIIPEDTFFPSPESSCD VKLVEKSFETDTNLNFQNLSVIGFRIL LLKVAGFNLLMTLRLWSS (SEQ ID NO: 121) | DSGVTQTPKHLITATGQRVTLRCSPRSGD LSVYWYQQSLDQGLQFLIQYYNGEERA KGNILERFSAQQFPDLHSELNLSSLELGD SALYFCASSVVDGEQYFGPGTRLTVTED LKNVFPPEVAVFEPSEAEISHTQKATLVC LATGFYPDHVELSWWVNGKEVHSGVCT DPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 122) |
| 19 | QKEVEQNSGPLSVPEGAIASLNCTYS DRGSQSFFWYRQYSGKSPELIMFIYS NGDKEDGRFTAQLNKASQYVSLLIR DSQPSDSATYLCAVWRAGGFKTIFG AGTRLFVKANIQNPDPAVYQLRDSKS SDKSVCLFTDFDSQTNVSQSKDSDVY ITDKCVLDMRSMDFKSNSAVAWSNK SDFACANAFNNSIIPEDTFFPSPESSCD VKLVEKSFETDTNLNFQNLSVIGFRIL LLKVAGFNLLMTLRLWSS (SEQ ID NO: 123) | DSGVTQTPKHLITATGQRVTLRCSPRSGD LSVYWYQQSLDQGLQFLIQYYNGEERA KGNILERFSAQQFPDLHSELNLSSLELGD SALYFCASSVVDGEQYFGPGTRLTVTED LKNVFPPEVAVFEPSEAEISHTQKATLVC LATGFYPDHVELSWWVNGKEVHSGVCT DPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 124) |

TABLE A-continued

| TCR ID | Alpha Chain | Beta Chain |
|---|---|---|
| 20 | QKEVEQNSGPLSVPEGAIASLNCTYS DRGSQSFFWYRQYSGKSPELIMFIYS NGDKEDGRFTAQLNKASQYVSLLIR DSQPSDSATYLCAYMRAGGFKEIFGA GTRLFVKANIQNPDPAVYQLRDSKSS DKSVCLFTDFDSQTNVSQSKDSDVYI TDKCVLDMRSMDFKSNSAVAWSNK SDFACANAFNNSIIPEDTFFPSPESSCD VKLVEKSFETDTNLNFQNLSVIGFRIL LLKVAGFNLLMTLRLWSS (SEQ ID NO: 125) | DSGVTQTPKHLITATGQRVTLRCSPRSGD LSVYWYQQSLDQGLQFLIQYYNGEERA KGNILERFSAQQFPDLHSELNLSSLELGD SALYFCASSVVDGEQYFGPGTRLTVTED LKNVFPPEVAVFEPSEAEISHTQKATLVC LATGFYPDHVELSWWVNGKEVHSGVCT DPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 126) |
| 40 | QKEVEQNSGPLSVPEGAIASLNCTYS DRGSQSFFWYRQYSGKSPELIMFIYS NGDKEDGRFTAQLNKASQYVSLLIR DSQPSDSATYLCAVMRAGGFKTSFG AGTRLFVKANIQNPDPAVYQLRDSKS SDKSVCLFTDFDSQTNVSQSKDSDVY ITDKCVLDMRSMDFKSNSAVAWSNK SDFACANAFNNSIIPEDTFFPSPESSCD VKLVEKSFETDTNLNFQNLSVIGFRIL LLKVAGFNLLMTLRLWSS (SEQ ID NO: 127) | DSGVTQTPKHLITATGQRVTLRCSPRSGD LSVYWYQQSLDQGLQFLIQYYNGEERA KGNILERFSAQQFPDLHSELNLSSLELGD SALYFCASSVVDGEQYFGPGTRLTVTED LKNVFPPEVAVFEPSEAEISHTQKATLVC LATGFYPDHVELSWWVNGKEVHSGVCT DPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 128) |
| 41 | QKEVEQNSGPLSVPEGAIASLNCTYS DRGSQSFFWYRQYSGKSPELIMFIYS NGDKEDGRFTAQLNKASQYVSLLIR DSQPSDSATYLCAAMRAGGFKTIFGA GTRLFVKANIQNPDPAVYQLRDSKSS DKSVCLFTDFDSQTNVSQSKDSDVYI TDKCVLDMRSMDFKSNSAVAWSNK SDFACANAFNNSIIPEDTFFPSPESSCD VKLVEKSFETDTNLNFQNLSVIGFRIL LLKVAGFNLLMTLRLWSS (SEQ ID NO: 129) | DSGVTQTPKHLITATGQRVTLRCSPRSGD LSVYWYQQSLDQGLQFLIQYYNGEERA KGNILERFSAQQFPDLHSELNLSSLELGD SALYFCASSVVDGEQYFGPGTRLTVTED LKNVFPPEVAVFEPSEAEISHTQKATLVC LATGFYPDHVELSWWVNGKEVHSGVCT DPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 130) |
| 42 | QKEVEQNSGPLSVPEGAIASLNCTYS DRGSQSFFWYRQYSGKSPELIMFIYS NGDKEDGRFTAQLNKASQYVSLLIR DSQPSDSATYLCAVQRAGGFKTIFGA GTRLFVKANIQNPDPAVYQLRDSKSS DKSVCLFTDFDSQTNVSQSKDSDVYI TDKCVLDMRSMDFKSNSAVAWSNK SDFACANAFNNSIIPEDTFFPSPESSCD VKLVEKSFETDTNLNFQNLSVIGFRIL LLKVAGFNLLMTLRLWSS (SEQ ID NO: 131) | DSGVTQTPKHLITATGQRVTLRCSPRSGD LSVYWYQQSLDQGLQFLIQYYNGEERA KGNILERFSAQQFPDLHSELNLSSLELGD SALYFCASSVVDGEQYFGPGTRLTVTED LKNVFPPEVAVFEPSEAEISHTQKATLVC LATGFYPDHVELSWWVNGKEVHSGVCT DPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 132) |
| 43 | QKEVEQNSGPLSVPEGAIASLNCTYS RRGSQSFFWYRQYSGKSPELIMFIYS NGDKEDGRFTAQLNKASQYVSLLIR DSQPSDSATYLCAVMRAGGFKTIFGA GTRLFVKANIQNPDPAVYQLRDSKSS DKSVCLFTDFDSQTNVSQSKDSDVYI TDKCVLDMRSMDFKSNSAVAWSNK SDFACANAFNNSIIPEDTFFPSPESSCD VKLVEKSFETDTNLNFQNLSVIGFRIL LLKVAGFNLLMTLRLWSS (SEQ ID NO: 133) | DSGVTQTPKHLITATGQRVTLRCSPRSGD LSVYWYQQSLDQGLQFLIQYYNGEERA KGNILERFSAQQFPDLHSELNLSSLELGD SALYFCASSVVDGEQYFGPGTRLTVTED LKNVFPPEVAVFEPSEAEISHTQKATLVC LATGFYPDHVELSWWVNGKEVHSGVCT DPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 134) |
| 44 | QKEVEQNSGPLSVPEGAIASLNCTYS DRGLQSFFWYRQYSGKSPELIMFIYS NGDKEDGRFTAQLNKASQYVSLLIR DSQPSDSATYLCAVMRAGGFKTIFGA GTRLFVKANIQNPDPAVYQLRDSKSS DKSVCLFTDFDSQTNVSQSKDSDVYI TDKCVLDMRSMDFKSNSAVAWSNK SDFACANAFNNSIIPEDTFFPSPESSCD VKLVEKSFETDTNLNFQNLSVIGFRIL LLKVAGFNLLMTLRLWSS (SEQ ID NO: 135) | DSGVTQTPKHLITATGQRVTLRCSPRSGD LSVYWYQQSLDQGLQFLIQYYNGEERA KGNILERFSAQQFPDLHSELNLSSLELGD SALYFCASSVVDGEQYFGPGTRLTVTED LKNVFPPEVAVFEPSEAEISHTQKATLVC LATGFYPDHVELSWWVNGKEVHSGVCT DPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 136) |
| 45 | QKEVEQNSGPLSVPEGAIASLNCTYS DRGSQSFFWYRQYSGKSPELIMFIYS NGDKEDGRFTAQLNKASQYVSLLIR DSQPSDSATYLCAVMRIGGFKTIFGA GTRLFVKANIQNPDPAVYQLRDSKSS | DSGVTQTPKHLITATGQRVTLRCSPRSGD LSVYWYQQSLDQGLQFLIQYYNGEERA KGNILERFSAQQFPDLHSELNLSSLELGD SALYFCASSVVDGEQYFGPGTRLTVTED LKNVFPPEVAVFEPSEAEISHTQKATLVC |

TABLE A-continued

| TCR ID | Alpha Chain | Beta Chain |
|---|---|---|
|  | DKSVCLFTDFDSQTNVSQSKDSDVYI<br>TDKCVLDMRSMDFKSNSAVAWSNK<br>SDFACANAFNNSIIPEDTFFPSPESSCD<br>VKLVEKSFETDTNLNFQNLSVIGFRIL<br>LLKVAGFNLLMTLRLWSS (SEQ ID<br>NO: 137) | LATGFYPDHVELSWWVNGKEVHSGVCT<br>DPQPLKEQPALNDSRYCLSSRLRVSATF<br>WQNPRNHFRCQVQFYGLSENDEWTQDR<br>AKPVTQIVSAEAWGRADCGFTSESYQQG<br>VLSATILYEILLGKATLYAVLVSALVLM<br>AMVKRKDSR (SEQ ID NO: 138) |
| 21 | QKEVEQNSGPLSVPEGAIASLNCTYS<br>DRGSQSFFWYRQYSGKSPELIMFIYS<br>NGDKEDGRFTAQLNKASQYVSLLIR<br>DSQPSDSATYLCAVMRAGGFKTIFGA<br>GTRLFVKANIQNPDPAVYQLRDSKSS<br>DKSVCLFTDFDSQTNVSQSKDSDVYI<br>TDKCVLDMRSMDFKSNSAVAWSNK<br>SDFACANAFNNSIIPEDTFFPSPESSCD<br>VKLVEKSFETDTNLNFQNLSVIGFRIL<br>LLKVAGFNLLMTLRLWSS (SEQ ID<br>NO: 139) | DSGVTQTPKHLITATGQRVTLRCSPRSGN<br>LSVYWYQQSLDQGLQFLIQYYNGEERA<br>KGNILERFSAQQFPDLHSELNLSSLELGD<br>SALYFCASSVVDGEQYFGPGTRLTVTED<br>LKNVFPPEVAVFEPSEAEISHTQKATLVC<br>LATGFYPDHVELSWWVNGKEVHSGVCT<br>DPQPLKEQPALNDSRYCLSSRLRVSATF<br>WQNPRNHFRCQVQFYGLSENDEWTQDR<br>AKPVTQIVSAEAWGRADCGFTSESYQQG<br>VLSATILYEILLGKATLYAVLVSALVLM<br>AMVKRKDSR (SEQ ID NO: 140) |
| 22 | QKEVEQNSGPLSVPEGAIASLNCTYS<br>DRGSQSFFWYRQYSGKSPELIMFIYS<br>NGDKEDGRFTAQLNKASQYVSLLIR<br>DSQPSDSATYLCAVMRAGGFKTIFGA<br>GTRLFVKANIQNPDPAVYQLRDSKSS<br>DKSVCLFTDFDSQTNVSQSKDSDVYI<br>TDKCVLDMRSMDFKSNSAVAWSNK<br>SDFACANAFNNSIIPEDTFFPSPESSCD<br>VKLVEKSFETDTNLNFQNLSVIGFRIL<br>LLKVAGFNLLMTLRLWSS (SEQ ID<br>NO: 139) | DSGVTQTPKHLITATGQRVTLRCSPRAG<br>DLSVYWYQQSLDQGLQFLIQYYNGEER<br>AKGNILERFSAQQFPDLHSELNLSSLELG<br>DSALYFCASSVVDGEQYFGPGTRLTVTE<br>DLKNVFPPEVAVFEPSEAEISHTQKATLV<br>CLATGFYPDHVELSWWVNGKEVHSGVC<br>TDPQPLKEQPALNDSRYCLSSRLRVSATF<br>WQNPRNHFRCQVQFYGLSENDEWTQDR<br>AKPVTQIVSAEAWGRADCGFTSESYQQG<br>VLSATILYEILLGKATLYAVLVSALVLM<br>AMVKRKDSR (SEQ ID NO: 141) |
| 23 | QKEVEQNSGPLSVPEGAIASLNCTYS<br>DRGSQSFFWYRQYSGKSPELIMFIYS<br>NGDKEDGRFTAQLNKASQYVSLLIR<br>DSQPSDSATYLCAVMRAGGFKTIFGA<br>GTRLFVKANIQNPDPAVYQLRDSKSS<br>DKSVCLFTDFDSQTNVSQSKDSDVYI<br>TDKCVLDMRSMDFKSNSAVAWSNK<br>SDFACANAFNNSIIPEDTFFPSPESSCD<br>VKLVEKSFETDTNLNFQNLSVIGFRIL<br>LLKVAGFNLLMTLRLWSS (SEQ ID<br>NO: 139) | DSGVTQTPKHLITATGQRVTLRCSPRSGD<br>LIVYWYQQSLDQGLQFLIQYYNGEERAK<br>GNILERFSAQQFPDLHSELNLSSLELGDS<br>ALYFCASSVVDGEQYFGPGTRLTVTEDL<br>KNVFPPEVAVFEPSEAEISHTQKATLVCL<br>ATGFYPDHVELSWWVNGKEVHSGVCTD<br>PQPLKEQPALNDSRYCLSSRLRVSATFW<br>QNPRNHFRCQVQFYGLSENDEWTQDRA<br>KPVTQIVSAEAWGRADCGFTSESYQQGV<br>LSATILYEILLGKATLYAVLVSALVLMA<br>MVKRKDSR (SEQ ID NO: 142) |
| 24 | QKEVEQNSGPLSVPEGAIASLNCTYS<br>DRGSQSFFWYRQYSGKSPELIMFIYS<br>NGDKEDGRFTAQLNKASQYVSLLIR<br>DSQPSDSATYLCAVMRAGGFKTIFGA<br>GTRLFVKANIQNPDPAVYQLRDSKSS<br>DKSVCLFTDFDSQTNVSQSKDSDVYI<br>TDKCVLDMRSMDFKSNSAVAWSNK<br>SDFACANAFNNSIIPEDTFFPSPESSCD<br>VKLVEKSFETDTNLNFQNLSVIGFRIL<br>LLKVAGFNLLMTLRLWSS (SEQ ID<br>NO: 139) | DSGVTQTPKHLITATGQRVTLRCSPRSG<br>WLSVYWYQQSLDQGLQFLIQYYNGEER<br>AKGNILERFSAQQFPDLHSELNLSSLELG<br>DSALYFCASSVVDGEQYFGPGTRLTVTE<br>DLKNVFPPEVAVFEPSEAEISHTQKATLV<br>CLATGFYPDHVELSWWVNGKEVHSGVC<br>TDPQPLKEQPALNDSRYCLSSRLRVSATF<br>WQNPRNHFRCQVQFYGLSENDEWTQDR<br>AKPVTQIVSAEAWGRADCGFTSESYQQG<br>VLSATILYEILLGKATLYAVLVSALVLM<br>AMVKRKDSR (SEQ ID NO: 143) |
| 25 | QKEVEQNSGPLSVPEGAIASLNCTYS<br>DRGSQSFFWYRQYSGKSPELIMFIYS<br>NGDKEDGRFTAQLNKASQYVSLLIR<br>DSQPSDSATYLCAVMRAGGFKTIFGA<br>GTRLFVKANIQNPDPAVYQLRDSKSS<br>DKSVCLFTDFDSQTNVSQSKDSDVYI<br>TDKCVLDMRSMDFKSNSAVAWSNK<br>SDFACANAFNNSIIPEDTFFPSPESSCD<br>VKLVEKSFETDTNLNFQNLSVIGFRIL<br>LLKVAGFNLLMTLRLWSS (SEQ ID<br>NO: 139) | DSGVTQTPKHLITATGQRVTLRCSPRSGD<br>LSVYWYQQSLDQGLQFLIQYYNGEERA<br>KGNILERFSAQQFPDLHSELNLSSLELGD<br>SALYFCASSVVDGEQTFGPGTRLTVTED<br>LKNVFPPEVAVFEPSEAEISHTQKATLVC<br>LATGFYPDHVELSWWVNGKEVHSGVCT<br>DPQPLKEQPALNDSRYCLSSRLRVSATF<br>WQNPRNHFRCQVQFYGLSENDEWTQDR<br>AKPVTQIVSAEAWGRADCGFTSESYQQG<br>VLSATILYEILLGKATLYAVLVSALVLM<br>AMVKRKDSR (SEQ ID NO: 144) |
| 26 | QKEVEQNSGPLSVPEGAIASLNCTYS<br>DRGSQSFFWYRQYSGKSPELIMFIYS<br>NGDKEDGRFTAQLNKASQYVSLLIR<br>DSQPSDSATYLCAVMRAGGFKTIFGA<br>GTRLFVKANIQNPDPAVYQLRDSKSS<br>DKSVCLFTDFDSQTNVSQSKDSDVYI<br>TDKCVLDMRSMDFKSNSAVAWSNK<br>SDFACANAFNNSIIPEDTFFPSPESSCD<br>VKLVEKSFETDTNLNFQNLSVIGFRIL<br>LLKVAGFNLLMTLRLWSS (SEQ ID<br>NO: 139) | DSGVTQTPKHLITATGQRVTLRCSPRSGD<br>LSVYWYQQSLDQGLQFLIQYYNGEERA<br>KGNILERFSAQQFPDLHSELNLSSLELGD<br>SALYFCASLVVDGEQYFGPGTRLTVTED<br>LKNVFPPEVAVFEPSEAEISHTQKATLVC<br>LATGFYPDHVELSWWVNGKEVHSGVCT<br>DPQPLKEQPALNDSRYCLSSRLRVSATF<br>WQNPRNHFRCQVQFYGLSENDEWTQDR<br>AKPVTQIVSAEAWGRADCGFTSESYQQG<br>VLSATILYEILLGKATLYAVLVSALVLM<br>AMVKRKDSR (SEQ ID NO: 145) |

TABLE A-continued

| TCR ID | Alpha Chain | Beta Chain |
|--------|-------------|------------|
| 27 | QKEVEQNSGPLSVPEGAIASLNCTYS DRGSQSFFWYRQYSGKSPELIMFIYS NGDKEDGRFTAQLNKASQYVSLLIR DSQPSDSATYLCAVMRAGGFKTIFGA GTRLFVKANIQNPDPAVYQLRDSKSS DKSVCLFTDFDSQTNVSQSKDSDVYI TDKCVLDMRSMDFKSNSAVAWSNK SDFACANAFNNSIIPEDTFFPSPESSCD VKLVEKSFETDTNLNFQNLSVIGFRIL LLKVAGFNLLMTLRLWSS (SEQ ID NO: 139) | DSGVTQTPKHLITATGQRVTLRCSPRSGD LSVYWYQQSLDQGLQFLIQYYNGEERA KGNILERFSAQQFPDLHSELNLSSLELGD SALYFCASSVQDGEQYFGPGTRLTVTED LKNVFPPEVAVFEPSEAEISHTQKATLVC LATGFYPDHVELSWWVNGKEVHSGVCT DPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 146) |
| 28 | QKEVEQNSGPLSVPEGAIASLNCTYS DRGSQSFFWYRQYSGKSPELIMFIYS NGDKEDGRFTAQLNKASQYVSLLIR DSQPSDSATYLCAVMRAGGFKTIFGA GTRLFVKANIQNPDPAVYQLRDSKSS DKSVCLFTDFDSQTNVSQSKDSDVYI TDKCVLDMRSMDFKSNSAVAWSNK SDFACANAFNNSIIPEDTFFPSPESSCD VKLVEKSFETDTNLNFQNLSVIGFRIL LLKVAGFNLLMTLRLWSS (SEQ ID NO: 139) | DSGVTQTPKHLITATGQRVTLRCSPRSGD LSVYWYQQSLDQGLQFLIQYYNGEERA KGNILERFSAQQFPDLHSELNLSSLELGD SALYFCASSVVDGEQFFGPGTRLTVTED LKNVFPPEVAVFEPSEAEISHTQKATLVC LATGFYPDHVELSWWVNGKEVHSGVCT DPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 147) |
| 29 | QKEVEQNSGPLSVPEGAIASLNCTYS DRGSQSFFWYRQYSGKSPELIMFIYS NGDKEDGRFTAQLNKASQYVSLLIR DSQPSDSATYLCAVMRAGGFKTIFGA GTRLFVKANIQNPDPAVYQLRDSKSS DKSVCLFTDFDSQTNVSQSKDSDVYI TDKCVLDMRSMDFKSNSAVAWSNK SDFACANAFNNSIIPEDTFFPSPESSCD VKLVEKSFETDTNLNFQNLSVIGFRIL LLKVAGFNLLMTLRLWSS (SEQ ID NO: 139) | DSGVTQTPKHLITATGQRVTLRCSPRSGD LSVYWYQQSLDQGLQFLIQYYNGEERA KGNILERFSAQQFPDLHSELNLSSLELGD SALYFCASSVVDIEQYFGPGTRLTVTEDL KNVFPPEVAVFEPSEAEISHTQKATLVCL ATGFYPDHVELSWWVNGKEVHSGVCTD PQPLKEQPALNDSRYCLSSRLRVSATFW QNPRNHFRCQVQFYGLSENDEWTQDRA KPVTQIVSAEAWGRADCGFTSESYQQGV LSATILYEILLGKATLYAVLVSALVLMA MVKRKDSR (SEQ ID NO: 148) |
| 30 | QKEVEQNSGPLSVPEGAIASLNCTYS DRGSQSFFWYRQYSGKSPELIMFIYS NGDKEDGRFTAQLNKASQYVSLLIR DSQPSDSATYLCAVMRAGGFKTIFGA GTRLFVKANIQNPDPAVYQLRDSKSS DKSVCLFTDFDSQTNVSQSKDSDVYI TDKCVLDMRSMDFKSNSAVAWSNK SDFACANAFNNSIIPEDTFFPSPESSCD VKLVEKSFETDTNLNFQNLSVIGFRIL LLKVAGFNLLMTLRLWSS (SEQ ID NO: 139) | DSGVTQTPKHLITATGQRVTLRCSPRSGN LSVYWYQQSLDQGLQFLIQYYNGEERA KGNILERFSAQQFPDLHSELNLSSLELGD SALYFCASSVVDGEQTFGPGTRLTVTED LKNVFPPEVAVFEPSEAEISHTQKATLVC LATGFYPDHVELSWWVNGKEVHSGVCT DPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 149) |
| 31 | QKEVEQNSGPLSVPEGAIASLNCTYS DRGSQSFFWYRQYSGKSPELIMFIYS NGDKEDGRFTAQLNKASQYVSLLIR DSQPSDSATYLCAVMRAGGFKTIFGA GTRLFVKANIQNPDPAVYQLRDSKSS DKSVCLFTDFDSQTNVSQSKDSDVYI TDKCVLDMRSMDFKSNSAVAWSNK SDFACANAFNNSIIPEDTFFPSPESSCD VKLVEKSFETDTNLNFQNLSVIGFRIL LLKVAGFNLLMTLRLWSS (SEQ ID NO: 139) | DSGVTQTPKHLITATGQRVTLRCSPRSGD LSVYWYQQSLDQGLQFLIQYYNGEER KGNILERFSAQQFPDLHSELNLSSLELGD SALYFCASLVVDGEQTFGPGTRLTVTED LKNVFPPEVAVFEPSEAEISHTQKATLVC LATGFYPDHVELSWWVNGKEVHSGVCT DPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 150) |
| 32 | QKEVEQNSGPLSVPEGAIASLNCTYS DRGSQSFFWYRQYSGKSPELIMFIYS NGDKEDGRFTAQLNKASQYVSLLIR DSQPSDSATYLCAVMRAGGFKTIFGA GTRLFVKANIQNPDPAVYQLRDSKSS DKSVCLFTDFDSQTNVSQSKDSDVYI TDKCVLDMRSMDFKSNSAVAWSNK SDFACANAFNNSIIPEDTFFPSPESSCD VKLVEKSFETDTNLNFQNLSVIGFRIL LLKVAGFNLLMTLRLWSS (SEQ ID NO: 139) | DSGVTQTPKHLITATGQRVTLRCSPRSGL LSVYWYQQSLDQGLQFLIQYYNGEER KGNILERFSAQQFPDLHSELNLSSLELGD SALYFCASSVVDGEQYFGPGTRLTVTED LKNVFPPEVAVFEPSEAEISHTQKATLVC LATGFYPDHVELSWWVNGKEVHSGVCT DPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 151) |
| 33 | QKEVEQNSGPLSVPEGAIASLNCTYS DRGSQSFFWYRQYSGKSPELIMFIYS NGDKEDGRFTAQLNKASQYVSLLIR DSQPSDSATYLCAVMRAGGFKTIFGA GTRLFVKANIQNPDPAVYQLRDSKSS | DSGVTQTPKHLITATGQRVTLRCSPRSGS LSVYWYQQSLDQGLQFLIQYYNGEERA KGNILERFSAQQFPDLHSELNLSSLELGD SALYFCASSVVDGEQYFGPGTRLTVTED LKNVFPPEVAVFEPSEAEISHTQKATLVC |

TABLE A-continued

| TCR ID | Alpha Chain | Beta Chain |
|---|---|---|
| | DKSVCLFTDFDSQTNVSQSKDSDVYI<br>TDKCVLDMRSMDFKSNSAVAWSNK<br>SDFACANAFNNSIIPEDTFFPSPESSCD<br>VKLVEKSFETDTNLNFQNLSVIGFRIL<br>LLKVAGFNLLMTLRLWSS (SEQ ID<br>NO: 139) | LATGFYPDHVELSWWVNGKEVHSGVCT<br>DPQPLKEQPALNDSRYCLSSRLRVSATF<br>WQNPRNHFRCVQFYGLSENDEWTQDR<br>AKPVTQIVSAEAWGRADCGFTSESYQQG<br>VLSATILYEILLGKATLYAVLVSALVLM<br>AMVKRKDSR (SEQ ID NO: 152) |
| 34 | QKEVEQNSGPLSVPEGAIASLNCTYS<br>DRGSQSFFWYRQYSGKSPELIMFIYS<br>NGDKEDGRFTAQLNKASQYVSLLIR<br>DSQPSDSATYLCAVMRAGGFKTIFGA<br>GTRLFVKANIQNPDPAVYQLRDSKSS<br>DKSVCLFTDFDSQTNVSQSKDSDVYI<br>TDKCVLDMRSMDFKSNSAVAWSNK<br>SDFACANAFNNSIIPEDTFFPSPESSCD<br>VKLVEKSFETDTNLNFQNLSVIGFRIL<br>LLKVAGFNLLMTLRLWSS (SEQ ID<br>NO: 139) | DSGVTQTPKHLITATGQRVTLRCSPRTG<br>DLSVYWYQQSLDQGLQFLIQYYNGEER<br>AKGNILERFSAQQFPDLHSELNLSSLELG<br>DSALYFCASSVVDGEQYFGPGTRLTVTE<br>DLKNVFPPEVAVFEPSEAEISHTQKATLV<br>CLATGFYPDHVELSWWVNGKEVHSGVC<br>TDPQPLKEQPALNDSRYCLSSRLRVSATF<br>WQNPRNHFRCQVQFYGLSENDEWTQDR<br>AKPVTQIVSAEAWGRADCGFTSESYQQG<br>VLSATILYEILLGKATLYAVLVSALVLM<br>AMVKRKDSR (SEQ ID NO: 153) |
| 35 | QKEVEQNSGPLSVPEGAIASLNCTYS<br>DRGSQSFFWYRQYSGKSPELIMFIYS<br>NGDKEDGRFTAQLNKASQYVSLLIR<br>DSQPSDSATYLCAVMRAGGFKTIFGA<br>GTRLFVKANIQNPDPAVYQLRDSKSS<br>DKSVCLFTDFDSQTNVSQSKDSDVYI<br>TDKCVLDMRSMDFKSNSAVAWSNK<br>SDFACANAFNNSIIPEDTFFPSPESSCD<br>VKLVEKSFETDTNLNFQNLSVIGFRIL<br>LLKVAGFNLLMTLRLWSS (SEQ ID<br>NO: 139) | DSGVTQTPKHLITATGQRVTLRCSPRSGD<br>LSVYWYQQSLDQGLQFLIQYYNGEERA<br>KGNILERFSAQQFPDLHSELNLSSLELGD<br>SALYFCASSVVDDEQYFGPGTRLTVTED<br>LKNVFPPEVAVFEPSEAEISHTQKATLVC<br>LATGFYPDHVELSWWVNGKEVHSGVCT<br>DPQPLKEQPALNDSRYCLSSRLRVSATF<br>WQNPRNHFRCQVQFYGLSENDEWTQDR<br>AKPVTQIVSAEAWGRADCGFTSESYQQG<br>VLSATILYEILLGKATLYAVLVSALVLM<br>AMVKRKDSR (SEQ ID NO: 154) |
| 36 | QKEVEQNSGPLSVPEGAIASLNCTYS<br>DRGSQSFFWYRQYSGKSPELIMFIYS<br>NGDKEDGRFTAQLNKASQYVSLLIR<br>DSQPSDSATYLCAVMRAGGFKTIFGA<br>GTRLFVKANIQNPDPAVYQLRDSKSS<br>DKSVCLFTDFDSQTNVSQSKDSDVYI<br>TDKCVLDMRSMDFKSNSAVAWSNK<br>SDFACANAFNNSIIPEDTFFPSPESSCD<br>VKLVEKSFETDTNLNFQNLSVIGFRIL<br>LLKVAGFNLLMTLRLWSS (SEQ ID<br>NO: 139) | DSGVTQTPKHLITATGQRVTLRCSPRSGD<br>LSVYWYQQSLDQGLQFLIQYYNGEERA<br>KGNILERFSAQQFPDLHSELNLSSLELGD<br>SALYFCASSVVDYEQYFGPGTRLTVTED<br>LKNVFPPEVAVFEPSEAEISHTQKATLVC<br>LATGFYPDHVELSWWVNGKEVHSGVCT<br>DPQPLKEQPALNDSRYCLSSRLRVSATF<br>WQNPRNHFRCQVQFYGLSENDEWTQDR<br>AKPVTQIVSAEAWGRADCGFTSESYQQG<br>VLSATILYEILLGKATLYAVLVSALVLM<br>AMVKRKDSR (SEQ ID NO: 155) |
| 38 | QKEVEQNSGPLSVPEGAIASLNCTYS<br>DRGSQSFFWYRQYSGKSPELIMFIYS<br>NGDKEDGRFTAQLNKASQYVSLLIR<br>DSQPSDSATYLCAVMRAGGFKTIFGA<br>GTRLFVKANIQNPDPAVYQLRDSKSS<br>DKSVCLFTDFDSQTNVSQSKDSDVYI<br>TDKCVLDMRSMDFKSNSAVAWSNK<br>SDFACANAFNNSIIPEDTFFPSPESSCD<br>VKLVEKSFETDTNLNFQNLSVIGFRIL<br>LLKVAGFNLLMTLRLWSS (SEQ ID<br>NO: 139) | DSGVTQTPKHLITATGQRVTLRCSPRSGD<br>LSVYWYQQSLDQGLQFLIQYYNGEERA<br>KGNILERFSAQQFPDLHSELNLSSLELGD<br>SALYFCASSVVDGEDYFGPGTRLTVTED<br>LKNVFPPEVAVFEPSEAEISHTQKATLVC<br>LATGFYPDHVELSWWVNGKEVHSGVCT<br>DPQPLKEQPALNDSRYCLSSRLRVSATF<br>WQNPRNHFRCQVQFYGLSENDEWTQDR<br>AKPVTQIVSAEAWGRADCGFTSESYQQG<br>VLSATILYEILLGKATLYAVLVSALVLM<br>AMVKRKDSR (SEQ ID NO: 156) |
| 39 | QKEVEQNSGPLSVPEGAIASLNCTYS<br>DRGSQSFFWYRQYSGKSPELIMFIYS<br>NGDKEDGRFTAQLNKASQYVSLLIR<br>DSQPSDSATYLCAVMRAGGFKTIFGA<br>GTRLFVKANIQNPDPAVYQLRDSKSS<br>DKSVCLFTDFDSQTNVSQSKDSDVYI<br>TDKCVLDMRSMDFKSNSAVAWSNK<br>SDFACANAFNNSIIPEDTFFPSPESSCD<br>VKLVEKSFETDTNLNFQNLSVIGFRIL<br>LLKVAGFNLLMTLRLWSS (SEQ ID<br>NO: 139) | DSGVTQTPKHLITATGQRVTLRCSPRSGN<br>LSVYWYQQSLDQGLQFLIQYYNGEERA<br>KGNILERFSAQQFPDLHSELNLSSLELGD<br>SALYFCASSVVDDEQYFGPGTRLTVTED<br>LKNVFPPEVAVFEPSEAEISHTQKATLVC<br>LATGFYPDHVELSWWVNGKEVHSGVCT<br>DPQPLKEQPALNDSRYCLSSRLRVSATF<br>WQNPRNHFRCQVQFYGLSENDEWTQDR<br>AKPVTQIVSAEAWGRADCGFTSESYQQG<br>VLSATILYEILLGKATLYAVLVSALVLM<br>AMVKRKDSR (SEQ ID NO: 157) |
| 47 | QKEVEQNSGPLSVPEGAIASLNCTYS<br>DRGSQSFFWYRQYSGKSPELIMFIYS<br>NGDKEDGRFTAQLNKASQYVSLLIR<br>DSQPSDSATYLCAVMRAGGFKTIFGA<br>GTRLFVKANIQNPDPAVYQLRDSKSS<br>DKSVCLFTDFDSQTNVSQSKDSDVYI<br>TDKCVLDMRSMDFKSNSAVAWSNK | DSGVTQTPKHLITATGQRVTLRCSPRSGD<br>LSVYWYQQSLDQGLQFLIQYYNGEERA<br>KGNILERFSAQQFPDLHSELNLSSLELGD<br>SALYFCASAVVDGEQYFGPGTRLTVTED<br>LKNVFPPEVAVFEPSEAEISHTQKATLVC<br>LATGFYPDHVELSWWVNGKEVHSGVCT<br>DPQPLKEQPALNDSRYCLSSRLRVSATF |

TABLE A-continued

| TCR ID | Alpha Chain | Beta Chain |
|---|---|---|
| | SDFACANAFNNSIIPEDTFFPSPESSCD VKLVEKSFETDTNLNFQNLSVIGFRIL LLKVAGFNLLMTLRLWSS (SEQ ID NO: 139) | WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 158) |
| 48 | QKEVEQNSGPLSVPEGAIASLNCTYS DRGSQSFFWYRQYSGKSPELIMFIYS NGDKEDGRFTAQLNKASQYVSLLIR DSQPSDSATYLCAVMRAGGFKTIFGA GTRLFVKANIQNPDPAVYQLRDSKSS DKSVCLFTDFDSQTNVSQSKDSDVYI TDKCVLDMRSMDFKSNSAVAWSNK SDFACANAFNNSIIPEDTFFPSPESSCD VKLVEKSFETDTNLNFQNLSVIGFRIL LLKVAGFNLLMTLRLWSS (SEQ ID NO: 139) | DSGVTQTPKHLITATGQRVTLRCSPRSGD LSVYWYQQSLDQGLQFLIQYYNGEERA KGNILERFSAQQFPDLHSELNLSSLELGD SALYFCASSNVDGEQYFGPGTRLTVTED LKNVFPPEVAVFEPSEAEISHTQKATLVC LATGFYPDHVELSWWVNGKEVHSGVCT DPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 159) |
| 49 | QKEVEQNSGPLSVPEGAIASLNCTYS DRGSQSFFWYRQYSGKSPELIMFIYS NGDKEDGRFTAQLNKASQYVSLLIR DSQPSDSATYLCAVMRAGGFKTIFGA GTRLFVKANIQNPDPAVYQLRDSKSS DKSVCLFTDFDSQTNVSQSKDSDVYI TDKCVLDMRSMDFKSNSAVAWSNK SDFACANAFNNSIIPEDTFFPSPESSCD VKLVEKSFETDTNLNFQNLSVIGFRIL LLKVAGFNLLMTLRLWSS (SEQ ID NO: 139) | DSGVTQTPKHLITATGQRVTLRCSPRMG DLSVYWYQQSLDQGLQFLIQYYNGEER AKGNILERFSAQQFPDLHSELNLSSLELG DSALYFCASSVVDGEQYFGPGTRLTVTE DLKNVFPPEVAVFEPSEAEISHTQKATLV CLATGFYPDHVELSWWVNGKEVHSGVC TDPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 160) |
| 50 | QKEVEQNSGPLSVPEGAIASLNCTYS DRGSQSFFWYRQYSGKSPELIMFIYS NGDKEDGRFTAQLNKASQYVSLLIR DSQPSDSATYLCAVMRAGGFKTIFGA GTRLFVKANIQNPDPAVYQLRDSKSS DKSVCLFTDFDSQTNVSQSKDSDVYI TDKCVLDMRSMDFKSNSAVAWSNK SDFACANAFNNSIIPEDTFFPSPESSCD VKLVEKSFETDTNLNFQNLSVIGFRIL LLKVAGFNLLMTLRLWSS (SEQ ID NO: 139) | DSGVTQTPKHLITATGQRVTLRCSPRSGD LSVYWYQQSLDQGLQFLIQYYNGEERA KGNILERFSAQQFPDLHSELNLSSLELGD SALYFCAWSVVDGEQYFGPGTRLTVTED LKNVFPPEVAVFEPSEAEISHTQKATLVC LATGFYPDHVELSWWVNGKEVHSGVCT DPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 161) |
| 51 | QKEVEQNSGPLSVPEGAIASLNCTYS DRGSQSFFWYRQYSGKSPELIMFIYS NGDKEDGRFTAQLNKASQYVSLLIR DSQPSDSATYLCANMRAGGFKTIFGA GTRLFVKANIQNPDPAVYQLRDSKSS DKSVCLFTDFDSQTNVSQSKDSDVYI TDKCVLDMRSMDFKSNSAVAWSNK SDFACANAFNNSIIPEDTFFPSPESSCD VKLVEKSFETDTNLNFQNLSVIGFRIL LLKVAGFNLLMTLRLWSS (SEQ ID NO: 162) | DSGVTQTPKHLITATGQRVTLRCSPRSGD LSVYWYQQSLDQGLQFLIQYYNGEERA KGNILERFSAQQFPDLHSELNLSSLELGD SALYFCASSVVDGEQYFGPGTRLTVTED LKNVFPPEVAVFEPSEAEISHTQKATLVC LATGFYPDHVELSWWVNGKEVHSGVCT DPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 163) |
| 52 | QKEVEQNSGPLSVPEGAIASLNCTYS DRGSQSFFWYRQYSGKSPELIMFIYS NGDKEDGRFTAQLNKASQYVSLLIR DSQPSDSATYLCAVMRAQGFKTIFGA GTRLFVKANIQNPDPAVYQLRDSKSS DKSVCLFTDFDSQTNVSQSKDSDVYI TDKCVLDMRSMDFKSNSAVAWSNK SDFACANAFNNSIIPEDTFFPSPESSCD VKLVEKSFETDTNLNFQNLSVIGFRIL LLKVAGFNLLMTLRLWSS (SEQ ID NO: 164) | DSGVTQTPKHLITATGQRVTLRCSPRSGD LSVYWYQQSLDQGLQFLIQYYNGEERA KGNILERFSAQQFPDLHSELNLSSLELGD SALYFCASSVVDGEQYFGPGTRLTVTED LKNVFPPEVAVFEPSEAEISHTQKATLVC LATGFYPDHVELSWWVNGKEVHSGVCT DPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 165) |
| 53 | QKEVEQNSGPLSVPEGAIASLNCTYS DRGSQSFFWYRQYSGKSPELIMFIYS NGDKEDGRFTAQLNKASQYVSLLIR DSQPSDSATYLCAVMRAAGFKTIFGA GTRLFVKANIQNPDPAVYQLRDSKSS DKSVCLFTDFDSQTNVSQSKDSDVYI TDKCVLDMRSMDFKSNSAVAWSNK SDFACANAFNNSIIPEDTFFPSPESSCD VKLVEKSFETDTNLNFQNLSVIGFRIL LLKVAGFNLLMTLRLWSS (SEQ ID NO: 166) | DSGVTQTPKHLITATGQRVTLRCSPRSGD LSVYWYQQSLDQGLQFLIQYYNGEERA KGNILERFSAQQFPDLHSELNLSSLELGD SALYFCASSVVDGEQYFGPGTRLTVTED LKNVFPPEVAVFEPSEAEISHTQKATLVC LATGFYPDHVELSWWVNGKEVHSGVCT DPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 167) |

TABLE A-continued

| TCR ID | Alpha Chain | Beta Chain |
|--------|-------------|------------|
| 54 | QKEVEQNSGPLSVPEGAIASLNCTYS DRGSQSFFWYRQYSGKSPELIMFIYS NGDKEDGRFTAQLNKASQYVSLLIR DSQPSDSATYLCAVMFAGGFKTIFGA GTRLFVKANIQNPDPAVYQLRDSKSS DKSVCLFTDFDSQTNVSQSKDSDVYI TDKCVLDMRSMDFKSNSAVAWSNK SDFACANAFNNSIIPEDTFFPSPESSCD VKLVEKSFETDTNLNFQNLSVIGFRIL LLKVAGFNLLMTLRLWSS (SEQ ID NO: 168) | DSGVTQTPKHLITATGQRVTLRCSPRSGD LSVYWYQQSLDQGLQFLIQYYNGEERA KGNILERFSAQQFPDLHSELNLSSLELGD SALYFCASSVVDGEQYFGPGTRLTVTED LKNVFPPEVAVFEPSEAEISHTQKATLVC LATGFYPDHVELSWWVNGKEVHSGVCT DPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 169) |
| 55 | QKEVEQNSGPLSVPEGAIASLNCTYS DRGSQSFFWYRQYSGKSPELIMFIYS NGDKEDGRFTAQLNKASQYVSLLIR DSQPSDSATYLCAVMRAGGFKTAFG AGTRLFVKANIQNPDPAVYQLRDSKS SDKSVCLFTDFDSQTNVSQSKDSDVY ITDKCVLDMRSMDFKSNSAVAWSNK SDFACANAFNNSIIPEDTFFPSPESSCD VKLVEKSFETDTNLNFQNLSVIGFRIL LLKVAGFNLLMTLRLWSS (SEQ ID NO: 170) | DSGVTQTPKHLITATGQRVTLRCSPRSGD LSVYWYQQSLDQGLQFLIQYYNGEERA KGNILERFSAQQFPDLHSELNLSSLELGD SALYFCASSVVDGEQYFGPGTRLTVTED LKNVFPPEVAVFEPSEAEISHTQKATLVC LATGFYPDHVELSWWVNGKEVHSGVCT DPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 171) |
| 56 | QKEVEQNSGPLSVPEGAIASLNCTYS DRGSQSFFWYRQYSGKSPELIMFIYS NGDKEDGRFTAQLNKASQYVSLLIR DSQPSDSATYLCAVMRAVGFKTIFGA GTRLFVKANIQNPDPAVYQLRDSKSS DKSVCLFTDFDSQTNVSQSKDSDVYI TDKCVLDMRSMDFKSNSAVAWSNK SDFACANAFNNSIIPEDTFFPSPESSCD VKLVEKSFETDTNLNFQNLSVIGFRIL LLKVAGFNLLMTLRLWSS (SEQ ID NO: 172) | DSGVTQTPKHLITATGQRVTLRCSPRSGD LSVYWYQQSLDQGLQFLIQYYNGEERA KGNILERFSAQQFPDLHSELNLSSLELGD SALYFCASSVVDGEQYFGPGTRLTVTED LKNVFPPEVAVFEPSEAEISHTQKATLVC LATGFYPDHVELSWWVNGKEVHSGVCT DPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 173) |
| 57 | QKEVEQNSGPLSVPEGAIASLNCTYS DRGSQSFFWYRQYSGKSPELIMFIYS NGDKEDGRFTAQLNKASQYVSLLIR DSQPSDSATYLCAVMRAYGFKTIFGA GTRLFVKANIQNPDPAVYQLRDSKSS DKSVCLFTDFDSQTNVSQSKDSDVYI TDKCVLDMRSMDFKSNSAVAWSNK SDFACANAFNNSIIPEDTFFPSPESSCD VKLVEKSFETDTNLNFQNLSVIGFRIL LLKVAGFNLLMTLRLWSS (SEQ ID NO: 174) | DSGVTQTPKHLITATGQRVTLRCSPRSGD LSVYWYQQSLDQGLQFLIQYYNGEERA KGNILERFSAQQFPDLHSELNLSSLELGD SALYFCASSVVDGEQYFGPGTRLTVTED LKNVFPPEVAVFEPSEAEISHTQKATLVC LATGFYPDHVELSWWVNGKEVHSGVCT DPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 175) |
| 58 | QKEVEQNSGPLSVPEGAIASLNCTYS DRGSQSFFWYRQYSGKSPELIMFIYS NGDKEDGRFTAQLNKASQYVSLLIR DSQPSDSATYLCAVMRAFGFKTIFGA GTRLFVKANIQNPDPAVYQLRDSKSS DKSVCLFTDFDSQTNVSQSKDSDVYI TDKCVLDMRSMDFKSNSAVAWSNK SDFACANAFNNSIIPEDTFFPSPESSCD VKLVEKSFETDTNLNFQNLSVIGFRIL LLKVAGFNLLMTLRLWSS (SEQ ID NO: 117) | DSGVTQTPKHLITATGQRVTLRCSPRSGD LSVYWYQQSLDQGLQFLIQYYNGEERA KGNILERFSAQQFPDLHSELNLSSLELGD SALYFCASSVVDGEQYFGPGTRLTVTED LKNVFPPEVAVFEPSEAEISHTQKATLVC LATGFYPDHVELSWWVNGKEVHSGVCT DPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 176) |
| 59 | QKEVEQNSGPLSVPEGAIASLNCTYS DRGSQSFFWYRQYSGKSPELIMFIYS NGDKEDGRFTAQLNKASQYVSLLIR DSQPSDSATYLCAVMRASGFKTIFGA GTRLFVKANIQNPDPAVYQLRDSKSS DKSVCLFTDFDSQTNVSQSKDSDVYI TDKCVLDMRSMDFKSNSAVAWSNK SDFACANAFNNSIIPEDTFFPSPESSCD VKLVEKSFETDTNLNFQNLSVIGFRIL LLKVAGFNLLMTLRLWSS (SEQ ID NO: 177) | DSGVTQTPKHLITATGQRVTLRCSPRSGD LSVYWYQQSLDQGLQFLIQYYNGEERA KGNILERFSAQQFPDLHSELNLSSLELGD SALYFCASSVVDGEQYFGPGTRLTVTED LKNVFPPEVAVFEPSEAEISHTQKATLVC LATGFYPDHVELSWWVNGKEVHSGVCT DPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 178) |
| 60 | QKEVEQNSGPLSVPEGAIASLNCTYS DRGSQSFFWYRQYSGKSPELIMFIYS NGDKEDGRFTAQLNKASQYVSLLIR DSQPSDSATYLCAVMRALGFKTIFGA GTRLFVKANIQNPDPAVYQLRDSKSS DKSVCLFTDFDSQTNVSQSKDSDVYI | DSGVTQTPKHLITATGQRVTLRCSPRSGD LSVYWYQQSLDQGLQFLIQYYNGEERA KGNILERFSAQQFPDLHSELNLSSLELGD SALYFCASSVVDGEQYFGPGTRLTVTED LKNVFPPEVAVFEPSEAEISHTQKATLVC LATGFYPDHVELSWWVNGKEVHSGVCT |

TABLE A-continued

| TCR ID | Alpha Chain | Beta Chain |
|---|---|---|
| | TDKCVLDMRSMDFKSNSAVAWSNK<br>SDFACANAFNNSIIPEDTFFPSPESSCD<br>VKLVEKSFETDTNLNFQNLSVIGFRIL<br>LLKVAGFNLLMTLRLWSS (SEQ ID<br>NO: 179) | DPQPLKEQPALNDSRYCLSSRLRVSATF<br>WQNPRNHFRCQVQFYGLSENDEWTQDR<br>AKPVTQIVSAEAWGRADCGFTSESYQQG<br>VLSATILYEILLGKATLYAVLVSALVLM<br>AMVKRKDSR (SEQ ID NO: 180) |
| 61 | QKEVEQNSGPLSVPEGAIASLNCTYS<br>DRGSQSFFWYRQYSGKSPELIMFIYS<br>NGDKEDGRFTAQLNKASQYVSLLIR<br>DSQPSDSATYLCAVMRAGGFKTFFG<br>AGTRLFVKANIQNPDPAVYQLRDSKS<br>SDKSVCLFTDFDSQTNVSQSKDSDVY<br>ITDKCVLDMRSMDFKSNSAVAWSNK<br>SDFACANAFNNSIIPEDTFFPSPESSCD<br>VKLVEKSFETDTNLNFQNLSVIGFRIL<br>LLKVAGFNLLMTLRLWSS (SEQ ID<br>NO: 181) | DSGVTQTPKHLITATGQRVTLRCSPRSGD<br>LSVYWYQQSLDQGLQFLIQYYNGEERA<br>KGNILERFSAQQFPDLHSELNLSSLELGD<br>SALYFCASSVVDGEQYFGPGTRLTVTED<br>LKNVFPPEVAVFEPSEAEISHTQKATLVC<br>LATGFYPDHVELSWWVNGKEVHSGVCT<br>DPQPLKEQPALNDSRYCLSSRLRVSATF<br>WQNPRNHFRCQVQFYGLSENDEWTQDR<br>AKPVTQIVSAEAWGRADCGFTSESYQQG<br>VLSATILYEILLGKATLYAVLVSALVLM<br>AMVKRKDSR (SEQ ID NO: 182) |
| 62 | QKEVEQNSGPLSVPEGAIASLNCTYS<br>DRGSQSFFWYRQYSGKSPELIMFIYS<br>NGDKEDGRFTAQLNKASQYVSLLIR<br>DSQPSDSATYLCAVMRAMGFKTIFG<br>AGTRLFVKANIQNPDPAVYQLRDSKS<br>SDKSVCLFTDFDSQTNVSQSKDSDVY<br>ITDKCVLDMRSMDFKSNSAVAWSNK<br>SDFACANAFNNSIIPEDTFFPSPESSCD<br>VKLVEKSFETDTNLNFQNLSVIGFRIL<br>LLKVAGFNLLMTLRLWSS (SEQ ID<br>NO: 183) | DSGVTQTPKHLITATGQRVTLRCSPRSGD<br>LSVYWYQQSLDQGLQFLIQYYNGEERA<br>KGNILERFSAQQFPDLHSELNLSSLELGD<br>SALYFCASSVVDGEQYFGPGTRLTVTED<br>LKNVFPPEVAVFEPSEAEISHTQKATLVC<br>LATGFYPDHVELSWWVNGKEVHSGVCT<br>DPQPLKEQPALNDSRYCLSSRLRVSATF<br>WQNPRNHFRCQVQFYGLSENDEWTQDR<br>AKPVTQIVSAEAWGRADCGFTSESYQQG<br>VLSATILYEILLGKATLYAVLVSALVLM<br>AMVKRKDSR (SEQ ID NO: 184) |
| 63 | QKEVEQNSGPLSVPEGAIASLNCTYS<br>QRGSQSFFWYRQYSGKSPELIMFIYS<br>NGDKEDGRFTAQLNKASQYVSLLIR<br>DSQPSDSATYLCAVMRAGGFKTIFGA<br>GTRLFVKANIQNPDPAVYQLRDSKSS<br>DKSVCLFTDFDSQTNVSQSKDSDVYI<br>TDKCVLDMRSMDFKSNSAVAWSNK<br>SDFACANAFNNSIIPEDTFFPSPESSCD<br>VKLVEKSFETDTNLNFQNLSVIGFRIL<br>LLKVAGFNLLMTLRLWSS (SEQ ID<br>NO: 185) | DSGVTQTPKHLITATGQRVTLRCSPRSGD<br>LSVYWYQQSLDQGLQFLIQYYNGEERA<br>KGNILERFSAQQFPDLHSELNLSSLELGD<br>SALYFCASSVVDGEQYFGPGTRLTVTED<br>LKNVFPPEVAVFEPSEAEISHTQKATLVC<br>LATGFYPDHVELSWWVNGKEVHSGVCT<br>DPQPLKEQPALNDSRYCLSSRLRVSATF<br>WQNPRNHFRCQVQFYGLSENDEWTQDR<br>AKPVTQIVSAEAWGRADCGFTSESYQQG<br>VLSATILYEILLGKATLYAVLVSALVLM<br>AMVKRKDSR (SEQ ID NO: 186) |
| 64 | QKEVEQNSGPLSVPEGAIASLNCTYS<br>DRGNQSFFWYRQYSGKSPELIMFIYS<br>NGDKEDGRFTAQLNKASQYVSLLIR<br>DSQPSDSATYLCAVMRAGGFKTIFGA<br>GTRLFVKANIQNPDPAVYQLRDSKSS<br>DKSVCLFTDFDSQTNVSQSKDSDVYI<br>TDKCVLDMRSMDFKSNSAVAWSNK<br>SDFACANAFNNSIIPEDTFFPSPESSCD<br>VKLVEKSFETDTNLNFQNLSVIGFRIL<br>LLKVAGFNLLMTLRLWSS (SEQ ID<br>NO: 187) | DSGVTQTPKHLITATGQRVTLRCSPRSGD<br>LSVYWYQQSLDQGLQFLIQYYNGEERA<br>KGNILERFSAQQFPDLHSELNLSSLELGD<br>SALYFCASSVVDGEQYFGPGTRLTVTED<br>LKNVFPPEVAVFEPSEAEISHTQKATLVC<br>LATGFYPDHVELSWWVNGKEVHSGVCT<br>DPQPLKEQPALNDSRYCLSSRLRVSATF<br>WQNPRNHFRCQVQFYGLSENDEWTQDR<br>AKPVTQIVSAEAWGRADCGFTSESYQQG<br>VLSATILYEILLGKATLYAVLVSALVLM<br>AMVKRKDSR (SEQ ID NO: 188) |
| 65 | QKEVEQNSGPLSVPEGAIASLNCTYS<br>DRGSQSFFWYRQYSGKSPELIMFIYS<br>NGDKEDGRFTAQLNKASQYVSLLIR<br>DSQPSDSATYLCAVMRAGGFKTIFGA<br>GTRLFVKANIQNPDPAVYQLRDSKSS<br>DKSVCLFTDFDSQTNVSQSKDSDVYI<br>TDKCVLDMRSMDFKSNSAVAWSNK<br>SDFACANAFNNSIIPEDTFFPSPESSCD<br>VKLVEKSFETDTNLNFQNLSVIGFRIL<br>LLKVAGFNLLMTLRLWSS (SEQ ID<br>NO: 139) | DSGVTQTPKHLITATGQRVTLRCSPRGG<br>DLSVYWYQQSLDQGLQFLIQYYNGEER<br>AKGNILERFSAQQFPDLHSELNLSSLELG<br>DSALYFCASSVVDGEQYFGPGTRLTVTE<br>DLKNVFPPEVAVFEPSEAEISHTQKATLV<br>CLATGFYPDHVELSWWVNGKEVHSGVC<br>TDPQPLKEQPALNDSRYCLSSRLRVSATF<br>WQNPRNHFRCQVQFYGLSENDEWTQDR<br>AKPVTQIVSAEAWGRADCGFTSESYQQG<br>VLSATILYEILLGKATLYAVLVSALVLM<br>AMVKRKDSR (SEQ ID NO: 189) |
| 66 | QKEVEQNSGPLSVPEGAIASLNCTYS<br>DRGSQSFFWYRQYSGKSPELIMFIYS<br>NGDKEDGRFTAQLNKASQYVSLLIR<br>DSQPSDSATYLCAVMRAGGFKTIFGA<br>GTRLFVKANIQNPDPAVYQLRDSKSS<br>DKSVCLFTDFDSQTNVSQSKDSDVYI<br>TDKCVLDMRSMDFKSNSAVAWSNK<br>SDFACANAFNNSIIPEDTFFPSPESSCD<br>VKLVEKSFETDTNLNFQNLSVIGFRIL<br>LLKVAGFNLLMTLRLWSS (SEQ ID<br>NO: 139) | DSGVTQTPKHLITATGQRVTLRCSPRSGD<br>LSVYWYQQSLDQGLQFLIQYYNGEERA<br>KGNILERFSAQQFPDLHSELNLSSLELGD<br>SALYFCASSVVDGEMYFGPGTRLTVTED<br>LKNVFPPEVAVFEPSEAEISHTQKATLVC<br>LATGFYPDHVELSWWVNGKEVHSGVCT<br>DPQPLKEQPALNDSRYCLSSRLRVSATF<br>WQNPRNHFRCQVQFYGLSENDEWTQDR<br>AKPVTQIVSAEAWGRADCGFTSESYQQG<br>VLSATILYEILLGKATLYAVLVSALVLM<br>AMVKRKDSR (SEQ ID NO: 190) |

TABLE A-continued

| TCR ID | Alpha Chain | Beta Chain |
| --- | --- | --- |
| 67 | QKEVEQNSGPLSVPEGAIASLNCTYS DRGSQSFFWYRQYSGKSPELIMFIYS NGDKEDGRFTAQLNKASQYVSLLIR DSQPSDSATYLCAVMRAGGFKTIFGA GTRLFVKANIQNPDPAVYQLRDSKSS DKSVCLFTDFDSQTNVSQSKDSDVYI TDKCVLDMRSMDFKSNSAVAWSNK SDFACANAFNNSIIPEDTFFPSPESSCD VKLVEKSFETDTNLNFQNLSVIGFRIL LLKVAGFNLLMTLRLWSS (SEQ ID NO: 139) | DSGVTQTPKHLITATGQRVTLRCSPRSGD LSVYWYQQSLDQGLQFLIQYYNGEER KGNILERFSAQQFPDLHSELNLSSLELGD SALYFCASSVVDGEGYFGPGTRLTVTED LKNVFPPEVAVFEPSEAEISHTQKATLVC LATGFYPDHVELSWWVNGKEVHSGVCT DPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 191) |
| 68 | QKEVEQNSGPLSVPEGAIASLNCTYS DRGSQSFFWYRQYSGKSPELIMFIYS NGDKEDGRFTAQLNKASQYVSLLIR DSQPSDSATYLCAVMRAGGFKTIFGA GTRLFVKANIQNPDPAVYQLRDSKSS DKSVCLFTDFDSQTNVSQSKDSDVYI TDKCVLDMRSMDFKSNSAVAWSNK SDFACANAFNNSIIPEDTFFPSPESSCD VKLVEKSFETDTNLNFQNLSVIGFRIL LLKVAGFNLLMTLRLWSS (SEQ ID NO: 139) | DSGVTQTPKHLITATGQRVTLRCSPRSGD LSVYWYQQSLDQGLQFLIQYYNGEERA KGNILERFSAQQFPDLHSELNLSSLELGD SALYFCASSVVDGENYFGPGTRLTVTED LKNVFPPEVAVFEPSEAEISHTQKATLVC LATGFYPDHVELSWWVNGKEVHSGVCT DPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 192) |
| 69 | QKEVEQNSGPLSVPEGAIASLNCTYS DRGSQSFFWYRQYSGKSPELIMFIYS NGDKEDGRFTAQLNKASQYVSLLIR DSQPSDSATYLCAVMRAGGFKTIFGA GTRLFVKANIQNPDPAVYQLRDSKSS DKSVCLFTDFDSQTNVSQSKDSDVYI TDKCVLDMRSMDFKSNSAVAWSNK SDFACANAFNNSIIPEDTFFPSPESSCD VKLVEKSFETDTNLNFQNLSVIGFRIL LLKVAGFNLLMTLRLWSS (SEQ ID NO: 139) | DSGVTQTPKHLITATGQRVTLRCSPRSGD LSVYWYQQSLDQGLQFLIQYYNGEERA KGNILERFSAQQFPDLHSELNLSSLELGD SALYFCASSVVDGEEYFGPGTRLTVTED LKNVFPPEVAVFEPSEAFISHTQKATLVC LATGFYPDHVELSWWVNGKEVHSGVCT DPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 193) |
| 70 | QKEVEQNSGPLSVPEGAIASLNCTYS DRGSQSFFWYRQYSGKSPELIMFIYS NGDKEDGRFTAQLNKASQYVSLLIR DSQPSDSATYLCAVMRAGGFKTIFGA GTRLFVKANIQNPDPAVYQLRDSKSS DKSVCLFTDFDSQTNVSQSKDSDVYI TDKCVLDMRSMDFKSNSAVAWSNK SDFACANAFNNSIIPEDTFFPSPESSCD VKLVEKSFETDTNLNFQNLSVIGFRIL LLKVAGFNLLMTLRLWSS (SEQ ID NO: 139) | DSGVTQTPKHLITATGQRVTLRCSPRSGD LSVYWYQQSLDQGLQFLIQYYNGEERA KGNILERFSAQQFPDLHSELNLSSLELGD SALYFCASSVVDGNQYFGPGTRLTVTED LKNVFPPEVAVFEPSEAEISHTQKATLVC LATGFYPDHVELSWWVNGKEVHSGVCT DPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 194) |
| 71 | QKEVEQNSGPLSVPEGAIASLNCTYS DRGSQGFFWYRQYSGKSPELIMFIYS NGDKEDGRFTAQLNKASQYVSLLIR DSQPSDSATYLCAVMRAGGFKTIFGA GTRLFVKANIQNPDPAVYQLRDSKSS DKSVCLFTDFDSQTNVSQSKDSDVYI TDKCVLDMRSMDFKSNSAVAWSNK SDFACANAFNNSIIPEDTFFPSPESSCD VKLVEKSFETDTNLNFQNLSVIGFRIL LLKVAGFNLLMTLRLWSS (SEQ ID NO: 195) | DSGVTQTPKHLITATGQRVTLRCSPRSGD LSVYWYQQSLDQGLQFLIQYYNGEERA KGNILERFSAQQFPDLHSELNLSSLELGD SALYFCASSVVDGEQYFGPGTRLTVTED LKNVFPPEVAVFEPSEAEISHTQKATLVC LATGFYPDHVELSWWVNGKEVHSGVCT DPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 196) |
| 72 | QKEVEQNSGPLSVPEGAIASLNCTYS WRGSQSFFWYRQYSGKSPELIMFIYS NGDKEDGRFTAQLNKASQYVSLLIR DSQPSDSATYLCAVMRAGGFKTIFGA GTRLFVKANIQNPDPAVYQLRDSKSS DKSVCLFTDFDSQTNVSQSKDSDVYI TDKCVLDMRSMDFKSNSAVAWSNK SDFACANAFNNSIPEDTFFPSPESSCD VKLVEKSFETDTNLNFQNLSVIGFRIL LLKVAGFNLLMTLRLWSS (SEQ ID NO: 197) | QKEVEQNSGPLSVPEGAIASLNCTYSWR GSQSFFWYRQYSGKSPELIMFIYSNGDKE DGRFTAQLNKASQYVSLLIRDSQPSDSAT YLCAVMRAGGFKTIFGAGTRLFVKANIQ NPDPAVYQLRDSKSSDKSVCLFTDFDSQ TNVSQSKDSDVYITDKCVLDMRSMDFKS NSAVAWSNKSDFACANAFNNSIIPEDTFF PSPESSCDVKLVEKSFETDTNLNFQNLSV IGFRILLLKVAGFNLLMTLRLWSS (SEQ ID NO: 198) |
| 73 | QKEVEQNSGPLSVPEGAIASLNCTYS DRGSQSFFWYRQYSGKSPELIMFIYS NGDKEDGRFTAQLNKASQYVSLLIR DSQPSDSATYLCAVMRAGGFKTQFG AGTRLFVKANIQNPDPAVYQLRDSKS SDKSVCLFTDFDSQTNVSQSKDSDVY | DSGVTQTPKHLITATGQRVTLRCSPRSGD LSVYWYQQSLDQGLQFLIQYYNGEERA KGNILERFSAQQFPDLHSELNLSSLELGD SALYFCASSVVDGEQYFGPGTRLTVTED LKNVFPPEVAVFEPSEAEISHTQKATLVC LATGFYPDHVELSWWVNGKEVHSGVCT |

TABLE A-continued

| TCR ID | Alpha Chain | Beta Chain |
|---|---|---|
| | ITDKCVLDMRSMDFKSNSAVAWSNK SDFACANAFNNSIIPEDTFFPSPESSCD VKLVEKSFETDTNLNFQNLSVIGFRIL LLKVAGFNLLMTLRLWSS (SEQ ID NO: 199) | DPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 200) |
| 74 | QKEVEQNSGPLSVPEGAIASLNCTYS DRGAQSFFWYRQYSGKSPELIMFIYS NGDKEDGRFTAQLNKASQYVSLLIR DSQPSDSATYLCAVMRAGGFKTIFGA GTRLFVKANIQNPDPAVYQLRDSKSS DKSVCLFTDFDSQTNVSQSKDSDVYI TDKCVLDMRSMDFKSNSAVAWSNK SDFACANAFNNSIIPEDTFFPSPESSCD VKLVEKSFETDTNLNFQNLSVIGFRIL LLKVAGFNLLMTLRLWSS (SEQ ID NO: 201) | DSGVTQTPKHLITATGQRVTLRCSPRSGD LSVYWYQQSLDQGLQFLIQYYNGEER KGNILERFSAQQFPDLHSELNLSSLELGD SALYFCASSVVDGEQYFGPGTRLTVTED LKNVFPPEVAVFEPSEAEISHTQKATLVC LATGFYPDHVELSWWVNGKEVHSGVCT DPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 202) |
| 75 | QKEVEQNSGPLSVPEGAIASLNCTYS DRGSQSFFWYRQYSGKSPELIMFIYS NGDKEDGRFTAQLNKASQYVSLLIR DSQPSDSATYLCAVMRAGGFKTIFGA GTRLFVKANIQNPDPAVYQLRDSKSS DKSVCLFTDFDSQTNVSQSKDSDVYI TDKCVLDMRSMDFKSNSAVAWSNK SDFACANAFNNSIIPEDTFFPSPESSCD VKLVEKSFETDTNLNFQNLSVIGFRIL LLKVAGFNLLMTLRLWSS (SEQ ID NO: 139) | DSGVTQTPKHLITATGQRVTLRCSPRSGD LSVYWYQQSLDQGLQFLIQYYNGEERA KGNILERFSAQQFPDLHSELNLSSLELGD SALYFCASSVVDGEQVFGPGTRLTVTED LKNVFPPEVAVFEPSEAEISHTQKATLVC LATGFYPDHVELSWWVNGKEVHSGVCT DPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 203) |
| 76 | QKEVEQNSGPLSVPEGAIASLNCTYS DRGSQSFFWYRQYSGKSPELIMFIYS NGDKEDGRFTAQLNKASQYVSLLIR DSQPSDSATYLCASMRAGGFKTIFGA GTRLFVKANIQNPDPAVYQLRDSKSS DKSVCLFTDFDSQTNVSQSKDSDVYI TDKCVLDMRSMDFKSNSAVAWSNK SDFACANAFNNSIIPEDTFFPSPESSCD VKLVEKSFETDTNLNFQNLSVIGFRIL LLKVAGFNLLMTLRLWSS (SEQ ID NO: 204) | DSGVTQTPKHLITATGQRVTLRCSPRSGD LSVYWYQQSLDQGLQFLIQYYNGEERA KGNILERFSAQQFPDLHSELNLSSLELGD SALYFCASSVVDGEQYFGPGTRLTVTED LKNVFPPEVAVFEPSEAEISHTQKATLVC LATGFYPDHVELSWWVNGKEVHSGVCT DPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 205) |
| 77 | QKEVEQNSGPLSVPEGAIASLNCTYS DWGSQSFFWYRQYSGKSPELIMFIYS NGDKEDGRFTAQLNKASQYVSLLIR DSQPSDSATYLCAVMRAGGFKTIFGA GTRLFVKANIQNPDPAVYQLRDSKSS DKSVCLFTDFDSQTNVSQSKDSDVYI TDKCVLDMRSMDFKSNSAVAWSNK SDFACANAFNNSIIPEDTFFPSPESSCD VKLVEKSFETDTNLNFQNLSVIGFRIL LLKVAGFNLLMTLRLWSS (SEQ ID NO: 206) | DSGVTQTPKHLITATGQRVTLRCSPRSGD LSVYWYQQSLDQGLQFLIQYYNGEERA KGNILERFSAQQFPDLHSELNLSSLELGD SALYFCASSVVDGEQYFGPGTRLTVTED LKNVFPPEVAVFEPSEAEISHTQKATLVC LATGFYPDHVELSWWVNGKEVHSGVCT DPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 207) |
| 78 | QKEVEQNSGPLSVPEGAIASLNCTYS DRGSQSFFWYRQYSGKSPELIMFIYS NGDKEDGRFTAQLNKASQYVSLLIR DSQPSDSATYLCAVMRAGGFKTIFGA GTRLFVKANIQNPDPAVYQLRDSKSS DKSVCLFTDFDSQTNVSQSKDSDVYI TDKCVLDMRSMDFKSNSAVAWSNK SDFACANAFNNSIIPEDTFFPSPESSCD VKLVEKSFETDTNLNFQNLSVIGFRIL LLKVAGFNLLMTLRLWSS (SEQ ID NO: 139) | DSGVTQTPKHLITATGQRVTLRCSPRWG DLSVYWYQQSLDQGLQFLIQYYNGEER AKGNILERFSAQQFPDLHSELNLSSLELG DSALYFCASSVVDGEQYFGPGTRLTVTE DLKNVFPPEVAVFEPSEAEISHTQKATLV CLATGFYPDHVELSWWVNGKEVHSGVC TDPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 208) |
| 79 | QKEVEQNSGPLSVPEGAIASLNCTYS DGGSQSFFWYRQYSGKSPELIMFIYS NGDKEDGRFTAQLNKASQYVSLLIR DSQPSDSATYLCAVMRAGGFKTIFGA GTRLFVKANIQNPDPAVYQLRDSKSS DKSVCLFTDFDSQTNVSQSKDSDVYI TDKCVLDMRSMDFKSNSAVAWSNK SDFACANAFNNSIIPEDTFFPSPESSCD VKLVEKSFETDTNLNFQNLSVIGFRIL LLKVAGFNLLMTLRLWSS (SEQ ID NO: 209) | DSGVTQTPKHLITATGQRVTLRCSPRSGD LSVYWYQQSLDQGLQFLIQYYNGEERA KGNILERFSAQQFPDLHSELNLSSLELGD SALYFCASSVVDGEQYFGPGTRLTVTED LKNVFPPEVAVFEPSEAEISHTQKATLVC LATGFYPDHVELSWWVNGKEVHSGVCT DPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 210) |

TABLE A-continued

| TCR ID | Alpha Chain | Beta Chain |
|---|---|---|
| 80 | QKEVEQNSGPLSVPEGAIASLNCTYS DRPSQSFFWYRQYSGKSPELIMFIYSN GDKEDGRFTAQLNKASQYVSLLIRDS QPSDSATYLCAVMRAGGFKTIFGAG TRLFVKANIQNPDPAVYQLRDSKSSD KSVCLFTDFDSQTNVSQSKDSDVYIT DKCVLDMRSMDFKSNSAVAWSNKS DFACANAFNNSIIPEDTFFPSPESSCD VKLVEKSFETDTNLNFQNLSVIGFRIL LLKVAGFNLLMTLRLWSS (SEQ ID NO: 211) | DSGVTQTPKHLITATGQRVTLRCSPRSGD LSVYWYQQSLDQGLQFLIQYYNGEERA KGNILERFSAQQFPDLHSELNLSSLELGD SALYFCASSVVDGEQYFGPGTRLTVTED LKNVFPPEVAVFEPSEAEISHTQKATLVC LATGFYPDHVELSWWVNGKEVHSGVCT DPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 212) |
| 81 | QKEVEQNSGPLSVPEGAIASLNCTYS DRGSQSFFWYRQYSGKSPELIMFIYS NGDKEDGRFTAQLNKASQYVSLLIR DSQPSDSATYLCAVMRAGGFKTIFGA GTRLFVKANIQNPDPAVYQLRDSKSS DKSVCLFTDFDSQTNVSQSKDSDVYI TDKCVLDMRSMDFKSNSAVAWSNK SDFACANAFNNSIIPEDTFFPSPESSCD VKLVEKSFETDTNLNFQNLSVIGFRIL LLKVAGFNLLMTLRLWSS (SEQ ID NO: 139) | DSGVTQTPKHLITATGQRVTLRCSPRIGD LSVYWYQQSLDQGLQFLIQYYNGEERA KGNILERFSAQQFPDLHSELNLSSLELGD SALYFCASSVVDGEQYFGPGTRLTVTED LKNVFPPEVAVFEPSEAEISHTQKATLVC LATGFYPDHVELSWWVNGKEVHSGVCT DPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 213) |
| 82 | QKEVEQNSGPLSVPEGAIASLNCTYS HRGSQSFFWYRQYSGKSPELIMFIYS NGDKEDGRFTAQLNKASQYVSLLIR DSQPSDSATYLCAVMRAGGFKTIFGA GTRLFVKANIQNPDPAVYQLRDSKSS DKSVCLFTDFDSQTNVSQSKDSDVYI TDKCVLDMRSMDFKSNSAVAWSNK SDFACANAFNNSIIPEDTFFPSPESSCD VKLVEKSFETDTNLNFQNLSVIGFRIL LLKVAGFNLLMTLRLWSS (SEQ ID NO: 214) | DSGVTQTPKHLITATGQRVTLRCSPRSGD LSVYWYQQSLDQGLQFLIQYYNGEERA KGNILERFSAQQFPDLHSELNLSSLELGD SALYFCASSVVDGEQYFGPGTRLTVTED LKNVFPPEVAVFEPSEAEISHTQKATLVC LATGFYPDHVELSWWVNGKEVHSGVCT DPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 215) |
| 83 | QKEVEQNSGPLSVPEGAIASLNCTYS DRSSQSFFWYRQYSGKSPELIMFIYSN GDKEDGRFTAQLNKASQYVSLLIRDS QPSDSATYLCAVMRAGGFKTIFGAG TRLFVKANIQNPDPAVYQLRDSKSSD KSVCLFTDFDSQTNVSQSKDSDVYIT DKCVLDMRSMDFKSNSAVAWSNKS DFACANAFNNSIIPEDTFFPSPESSCD VKLVEKSFETDTNLNFQNLSVIGFRIL LLKVAGFNLLMTLRLWSS (SEQ ID NO: 216) | DSGVTQTPKHLITATGQRVTLRCSPRSGD LSVYWYQQSLDQGLQFLIQYYNGEERA KGNILERFSAQQFPDLHSELNLSSLELGD SALYFCASSVVDGEQYFGPGTRLTVTED LKNVFPPEVAVFEPSEAEISHTQKATLVC LATGFYPDHVELSWWVNGKEVHSGVCT DPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 217) |
| 84 | QKEVEQNSGPLSVPEGAIASLNCTYS DRGSQSFFWYRQYSGKSPELIMFIYS NGDKEDGRFTAQLNKASQYVSLLIR DSQPSDSATYLCLVMRAGGFKTIFGA GTRLFVKANIQNPDPAVYQLRDSKSS DKSVCLFTDFDSQTNVSQSKDSDVYI TDKCVLDMRSMDFKSNSAVAWSNK SDFACANAFNNSIIPEDTFFPSPESSCD VKLVEKSFETDTNLNFQNLSVIGFRIL LLKVAGFNLLMTLRLWSS (SEQ ID NO: 218) | DSGVTQTPKHLITATGQRVTLRCSPRSGD LSVYWYQQSLDQGLQFLIQYYNGEERA KGNILERFSAQQFPDLHSELNLSSLELGD SALYFCASSVVDGEQYFGPGTRLTVTED LKNVFPPEVAVFEPSEAEISHTQKATLVC LATGFYPDHVELSWWVNGKEVHSGVCT DPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 219) |
| 85 | QKEVEQNSGPLSVPEGAIASLNCTYS DRGSQSFFWYRQYSGKSPELIMFIYS NGDKEDGRFTAQLNKASQYVSLLIR DSQPSDSATYLCAVMRAGGFKTIFGA GTRLFVKANIQNPDPAVYQLRDSKSS DKSVCLFTDFDSQTNVSQSKDSDVYI TDKCVLDMRSMDFKSNSAVAWSNK SDFACANAFNNSIIPEDTFFPSPESSCD VKLVEKSFETDTNLNFQNLSVIGFRIL LLKVAGFNLLMTLRLWSS (SEQ ID NO: 139) | DSGVTQTPKHLITATGQRVTLRCSPRQG DLSVYWYQQSLDQGLQFLIQYYNGEER AKGNILERFSAQQFPDLHSELNLSSLELG DSALYFCASSVVDGEQYFGPGTRLTVTE DLKNVFPPEVAVFEPSEAEISHTQKATLV CLATGFYPDHVELSWWVNGKEVHSGVC TDPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 220) |
| 86 | QKEVEQNSGPLSVPEGAIASLNCTYS DRGFQSFFWYRQYSGKSPELIMFIYS NGDKEDGRFTAQLNKASQYVSLLIR DSQPSDSATYLCAVMRAGGFKTIFGA GTRLFVKANIQNPDPAVYQLRDSKSS DKSVCLFTDFDSQTNVSQSKDSDVYI | DSGVTQTPKHLITATGQRVTLRCSPRSGD LSVYWYQQSLDQGLQFLIQYYNGEER KGNILERFSAQQFPDLHSELNLSSLELGD SALYFCASSVVDGEQYFGPGTRLTVTED LKNVFPPEVAVFEPSEAEISHTQKATLVC LATGFYPDHVELSWWVNGKEVHSGVCT |

TABLE A-continued

| TCR ID | Alpha Chain | Beta Chain |
|---|---|---|
| | TDKCVLDMRSMDFKSNSAVAWSNK<br>SDFACANAFNNSIIPEDTFFPSPESSCD<br>VKLVEKSFETDTNLNFQNLSVIGFRIL<br>LLKVAGFNLLMTLRLWSS (SEQ ID<br>NO: 221) | DPQPLKEQPALNDSRYCLSSRLRVSATF<br>WQNPRNHFRCQVQFYGLSENDEWTQDR<br>AKPVTQIVSAEAWGRADCGFTSESYQQG<br>VLSATILYEILLGKATLYAVLVSALVLM<br>AMVKRKDSR (SEQ ID NO: 222) |
| 87 | QKEVEQNSGPLSVPEGAIASLNCTYS<br>DRFSQSFFWYRQYSGKSPELIMFIYSN<br>GDKEDGRFTAQLNKASQYVSLLIRDS<br>QPSDSATYLCAVVRAGGFKTIFGAGT<br>RLFVKANIQNPDPAVYQLRDSKSSDK<br>SVCLFTDFDSQTNVSQSKDSDVYITD<br>KCVLDMRSMDFKSNSAVAWSNKSD<br>FACANAFNNSIIPEDTFFPSPESSCDV<br>KLVEKSFETDTNLNFQNLSVIGFRILL<br>LKVAGFNLLMTLRLWSS (SEQ ID<br>NO: 223) | DSGVTQTPKHLITATGQRVTLRCSPRSGD<br>LSVYWYQQSLDQGLQFLIQYYNGEERA<br>KGNILERFSAQQFPDLHSELNLSSLELGD<br>SALYFCASSVVDGEQYFGPGTRLTVTED<br>LKNVFPPEVAVFEPSEAEISHTQKATLVC<br>LATGFYPDHVELSWWVNGKEVHSGVCT<br>DPQPLKEQPALNDSRYCLSSRLRVSATF<br>WQNPRNHFRCQVQFYGLSENDEWTQDR<br>AKPVTQIVSAEAWGRADCGFTSESYQQG<br>VLSATILYEILLGKATLYAVLVSALVLM<br>AMVKRKDSR (SEQ ID NO: 224) |
| 88 | QKEVEQNSGPLSVPEGAIASLNCTYS<br>DRFSQSFFWYRQYSGKSPELIMFIYSN<br>GDKEDGRFTAQLNKASQYVSLLIRDS<br>QPSDSATYLCAVLRAGGFKTIFGAGT<br>RLFVKANIQNPDPAVYQLRDSKSSDK<br>SVCLFTDFDSQTNVSQSKDSDVYITD<br>KCVLDMRSMDFKSNSAVAWSNKSD<br>FACANAFNNSIIPEDTFFPSPESSCDV<br>KLVEKSFETDTNLNFQNLSVIGFRILL<br>LKVAGFNLLMTLRLWSS (SEQ ID<br>NO: 225) | DSGVTQTPKHLITATGQRVTLRCSPRSGD<br>LSVYWYQQSLDQGLQFLIQYYNGEERA<br>KGNILERFSAQQFPDLHSELNLSSLELGD<br>SALYFCASSVVDGEQYFGPGTRLTVTED<br>LKNVFPPEVAVFEPSEAEISHTQKATLVC<br>LATGFYPDHVELSWWVNGKEVHSGVCT<br>DPQPLKEQPALNDSRYCLSSRLRVSATF<br>WQNPRNHFRCQVQFYGLSENDEWTQDR<br>AKPVTQIVSAEAWGRADCGFTSESYQQG<br>VLSATILYEILLGKATLYAVLVSALVLM<br>AMVKRKDSR (SEQ ID NO: 226) |
| 89 | QKEVEQNSGPLSVPEGAIASLNCTYS<br>DRFSQSFFWYRQYSGKSPELIMFIYSN<br>GDKEDGRFTAQLNKASQYVSLLIRDS<br>QPSDSATYLCATMRAGGFKTIFGAGT<br>RLFVKANIQNPDPAVYQLRDSKSSDK<br>SVCLFTDFDSQTNVSQSKDSDVYITD<br>KCVLDMRSMDFKSNSAVAWSNKSD<br>FACANAFNNSIIPEDTFFPSPESSCDV<br>KLVEKSFETDTNLNFQNLSVIGFRILL<br>LKVAGFNLLMTLRLWSS (SEQ ID<br>NO: 227) | DSGVTQTPKHLITATGQRVTLRCSPRSGD<br>LSVYWYQQSLDQGLQFLIQYYNGEERA<br>KGNILERFSAQQFPDLHSELNLSSLELGD<br>SALYFCASSVVDGEQYFGPGTRLTVTED<br>LKNVFPPEVAVFEPSEAEISHTQKATLVC<br>LATGFYPDHVELSWWVNGKEVHSGVCT<br>DPQPLKEQPALNDSRYCLSSRLRVSATF<br>WQNPRNHFRCQVQFYGLSENDEWTQDR<br>AKPVTQIVSAEAWGRADCGFTSESYQQG<br>VLSATILYEILLGKATLYAVLVSALVLM<br>AMVKRKDSR (SEQ ID NO: 228) |
| 90 | QKEVEQNSGPLSVPEGAIASLNCTYS<br>DRGSQSFFWYRQYSGKSPELIMFIYS<br>NGDKEDGRFTAQLNKASQYVSLLIR<br>DSQPSDSATYLCAVVRAGGFKTIFGA<br>GTRLFVKANIQNPDPAVYQLRDSKSS<br>DKSVCLFTDFDSQTNVSQSKDSDVYI<br>TDKCVLDMRSMDFKSNSAVAWSNK<br>SDFACANAFNNSIIPEDTFFPSPESSCD<br>VKLVEKSFETDTNLNFQNLSVIGFRIL<br>LLKVAGFNLLMTLRLWSS (SEQ ID<br>NO: 105) | DSGVTQTPKHLITATGQRVTLRCSPRSGD<br>LSVYWYQQSLDQGLQFLIQYYNGEERA<br>KGNILERFSAQQFPDLHSELNLSSLELGD<br>SALYFCASSVVDGEQFFGPGTRLTVTED<br>LKNVFPPEVAVFEPSEAEISHTQKATLVC<br>LATGFYPDHVELSWWVNGKEVHSGVCT<br>DPQPLKEQPALNDSRYCLSSRLRVSATF<br>WQNPRNHFRCQVQFYGLSENDEWTQDR<br>AKPVTQIVSAEAWGRADCGFTSESYQQG<br>VLSATILYEILLGKATLYAVLVSALVLM<br>AMVKRKDSR (SEQ ID NO: 229) |
| 91 | QKEVEQNSGPLSVPEGAIASLNCTYS<br>DRGSQSFFWYRQYSGKSPELIMFIYS<br>NGDKEDGRFTAQLNKASQYVSLLIR<br>DSQPSDSATYLCAVLRAGGFKTIFGA<br>GTRLFVKANIQNPDPAVYQLRDSKSS<br>DKSVCLFTDFDSQTNVSQSKDSDVYI<br>TDKCVLDMRSMDFKSNSAVAWSNK<br>SDFACANAFNNSIIPEDTFFPSPESSCD<br>VKLVEKSFETDTNLNFQNLSVIGFRIL<br>LLKVAGFNLLMTLRLWSS (SEQ ID<br>NO: 107) | DSGVTQTPKHLITATGQRVTLRCSPRSGD<br>LSVYWYQQSLDQGLQFLIQYYNGEERA<br>KGNILERFSAQQFPDLHSELNLSSLELGD<br>SALYFCASSVVDGEQFFGPGTRLTVTED<br>LKNVFPPEVAVFEPSEAEISHTQKATLVC<br>LATGFYPDHVELSWWVNGKEVHSGVCT<br>DPQPLKEQPALNDSRYCLSSRLRVSATF<br>WQNPRNHFRCQVQFYGLSENDEWTQDR<br>AKPVTQIVSAEAWGRADCGFTSESYQQG<br>VLSATILYEILLGKATLYAVLVSALVLM<br>AMVKRKDSR (SEQ ID NO: 230) |
| 92 | QKEVEQNSGPLSVPEGAIASLNCTYS<br>DRGSQSFFWYRQYSGKSPELIMFIYS<br>NGDKEDGRFTAQLNKASQYVSLLIR<br>DSQPSDSATYLCATMRAGGFKTIFGA<br>GTRLFVKANIQNPDPAVYQLRDSKSS<br>DKSVCLFTDFDSQTNVSQSKDSDVYI<br>TDKCVLDMRSMDFKSNSAVAWSNK<br>SDFACANAFNNSIIPEDTFFPSPESSCD<br>VKLVEKSFETDTNLNFQNLSVIGFRIL<br>LLKVAGENLLMTLRLWSS (SEQ ID<br>NO: 121) | DSGVTQTPKHLITATGQRVTLRCSPRSGD<br>LSVYWYQQSLDQGLQFLIQYYNGEERA<br>KGNILERFSAQQFPDLHSELNLSSLELGD<br>SALYFCASSVVDGEQFFGPGTRLTVTED<br>LKNVFPPEVAVFEPSEAEISHTQKATLVC<br>LATGFYPDHVELSWWVNGKEVHSGVCT<br>DPQPLKEQPALNDSRYCLSSRLRVSAT<br>WQNPRNHFRCQVQFYGLSENDEWTQDR<br>AKPVTQIVSAEAWGRADCGFTSESYQQG<br>VLSATILYEILLGKATLYAVLVSALVLM<br>AMVKRKDSR (SEQ ID NO: 231) |

TABLE A-continued

| TCR ID | Alpha Chain | Beta Chain |
|---|---|---|
| 93 | QKEVEQNSGPLSVPEGAIASLNCTYS DRGSQSFFWYRQYSGKSPELIMFIYS NGDKEDGRFTAQLNKASQYVSLLIR DSQPSDSATYLCAVVRAGGFKTIFGA GTRLFVKANIQNPDPAVYQLRDSKSS DKSVCLFTDFDSQTNVSQSKDSDVYI TDKCVLDMRSMFKSNSAVAWSNK SDFACANAFNNSIIPEDTFFPSPESSCD VKLVEKSFETDTNLNFQNLSVIGFRIL LLKVAGFNLLMTLRLWSS (SEQ ID NO: 105) | DSGVTQTPKHLITATGQRVTLRCSPRTG DLSVYWYQQSLDQGLQFLIQYYNGEER AKGNILERFSAQQFPDLHSELNLSSLELG DSALYFCASSVVDGEQYFGPGTRLTVTE DLKNVFPPEVAVFEPSEAEISHTQKATLV CLATGFYPDHVELSWWVNGKEVHSGVC TDPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 232) |
| 94 | QKEVEQNSGPLSVPEGAIASLNCTYS DRGSQSFFWYRQYSGKSPELIMFIYS NGDKEDGRFTAQLNKASQYVSLLIR DSQPSDSATYLCAVLRAGGFKTIFGA GTRLFVKANIQNPDPAVYQLRDSKSS DKSVCLFTDFDSQTNVSQSKDSDVYI TDKCVLDMRSMDFKSNSAVAWSNK SDFACANAFNNSIIPEDTFFPSPESSCD VKLVEKSFETDTNLNFQNLSVIGFRIL LLKVAGFNLLMTLRLWSS (SEQ ID NO: 107) | DSGVTQTPKHLITATGQRVTLRCSPRTG DLSVYWYQQSLDQGLQFLIQYYNGEER AKGNILERFSAQQFPDLHSELNLSSLELG DSALYFCASSVVDGEQYFGPGTRLTVTE DLKNVFPPEVAVFEPSEAEISHTQKATLV CLATGFYPDHVELSWWVNGKEVHSGVC TDPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 233) |
| 95 | QKEVEQNSGPLSVPEGAIASLNCTYS DRGSQSFFWYRQYSGKSPELIMFIYS NGDKEDGRFTAQLNKASQYVSLLIR DSQPSDSATYLCATMRAGGFKTIFGA GTRLFVKANIQNPDPAVYQLRDSKSS DKSVCLFTDFDSQTNVSQSKDSDVYI TDKCVLDMRSMDFKSNSAVAWSNK SDFACANAFNNSIIPEDTFFPSPESSCD VKLVEKSFETDTNLNFQNLSVIGFRIL LLKVAGFNLLMTLRLWSS (SEQ ID NO: 121) | DSGVTQTPKHLITATGQRVTLRCSPRTG DLSVYWYQQSLDQGLQFLIQYYNGEER AKGNILERFSAQQFPDLHSELNLSSLELG DSALYFCASSVVDGEQYFGPGTRLTVTE DLKNVFPPEVAVFEPSEAEISHTQKATLV CLATGFYPDHVELSWWVNGKEVHSGVC TDPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 234) |
| 96 | QKEVEQNSGPLSVPEGAIASLNCTYS DRFSQSFFWYRQYSGKSPELIMFIYSN GDKEDGRFTAQLNKASQYVSLLIRDS QPSDSATYLCAVMRAGGFKTIFGAG TRLFVKANIQNPDPAVYQLRDSKSSD KSVCLFTDFDSQTNVSQSKDSDVYIT DKCVLDMRSMDFKSNSAVAWSNKS DFACANAFNNSIIPEDTFFPSPESSCD VKLVEKSFETDTNLNFQNLSVIGFRIL LLKVAGFNLLMTLRLWSS (SEQ ID NO: 89) | DSGVTQTPKHLITATGQRVTLRCSPRSGD LSVYWYQQSLDQGLQFLIQYYNGEERA KGNILERFSAQQFPDLHSELNLSSLELGD SALYFCASSVVDGEQFFGPGTRLTVTED LKNVFPPEVAVFEPSEAEISHTQKATLVC LATGFYPDHVELSWWVNGKEVHSGVCT DPQPLKEQPALNDSRYCLSSRLRVSATF AKPVTQIVSAEAWGRADCGFTSESYQQG WQNPRNHFRCQVQFYGLSENDEWTQDR VLSATILYEILLGKATLYAVLVSALVLM AMVKRKDSR (SEQ ID NO: 235) |
| 97 | QKEVEQNSGPLSVPEGAIASLNCTYS DRFSQSFFWYRQYSGKSPELIMFIYSN GDKEDGRFTAQLNKASQYVSLLIRDS QPSDSATYLCAVMRAGGFKTIFGAG TRLFVKANIQNPDPAVYQLRDSKSSD KSVCLFTDFDSQTNVSQSKDSDVYIT DKCVLDMRSMDFKSNSAVAWSNKS DFACANAFNNSIIPEDTFFPSPESSCD VKLVEKSFETDTNLNFQNLSVIGFRIL LLKVAGFNLLMTLRLWSS (SEQ ID NO: 89) | DSGVTQTPKHLITATGQRVTLRCSPRTG DLSVYWYQQSLDQGLQFLIQYYNGEER AKGNILERFSAQQFPDLHSELNLSSLELG DSALYFCASSVVDGEQYFGPGTRLTVTE DLKNVFPPEVAVFEPSEAEISHTQKATLV CLATGFYPDHVELSWWVNGKEVHSGVC TDPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 236) |
| 98 | QKEVEQNSGPLSVPEGAIASLNCTYS DRGSQSFFWYRQYSGKSPELIMFIYS NGDKEDGRFTAQLNKASQYVSLLIR DSQPSDSATYLCAVMRAGGFKTIFGA GTRLFVKANIQNPDPAVYQLRDSKSS DKSVCLFTDFDSQTNVSQSKDSDVYI TDKCVLDMRSMDFKSNSAVAWSNK SDFACANAFNNSIIPEDTFFPSPESSCD VKLVEKSFETDTNLNFQNLSVIGFRIL LLKVAGFNLLMTLRLWSS (SEQ ID NO: 139) | DSGVTQTPKHLITATGQRVTLRCSPRTG DLSVYWYQQSLDQGLQFLIQYYNGEER AKGNILERFSAQQFPDLHSELNLSSLELG DSALYFCASSVVDGEQFFGPGTRLTVTE DLKNVFPPEVAVFEPSEAEISHTQKATLV CLATGFYPDHVELSWWVNGKEVHSGVC TDPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 237) |
| 99 | QKEVEQNSGPLSVPEGAIASLNCTYS DRFSQSFFWYRQYSGKSPELIMFIYSN GDKEDGRFTAQLNKASQYVSLLIRDS QPSDSATYLCAVVRAGGFKTIFGAGT RLFVKANIQNPDPAVYQLRDSKSSDK SVCLFTDFDSQTNVSQSKDSDVYITD | DSGVTQTPKHLITATGQRVTLRCSPRTG DLSVYWYQQSLDQGLQFLIQYYNGEER AKGNILERFSAQQFPDLHSELNLSSLELG DSALYFCASSVVDGEQYFGPGTRLTVTE DLKNVFPPEVAVFEPSEAEISHTQKATLV CLATGFYPDHVELSWWVNGKEVHSGV |

| TCR ID | Alpha Chain | Beta Chain |
| --- | --- | --- |
| | KCVLDMRSMDFKSNSAVAWSNKSD FACANAFNNSIIPEDTFFPSPESSCDV KLVEKSFETDTNLNFQNLSVIGFRILL LKVAGFNLLMTLRLWSS (SEQ ID NO: 223) | TDPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 238) |
| 100 | QKEVEQNSGPLSVPEGAIASLNCTYS DRFSQSFFWYRQYSGKSPELIMFIYSN GDKEDGRFTAQLNKASQYVSLLIRDS QPSDSATYLCAVLRAGGFKTIFGAGT RLFVKANIQNPDPAVYQLRDSKSSDK SVCLFTDFDSQTNVSQSKDSDVYITD KCVLDMRSMDFKSNSAVAWSNKSD FACANAFNNSIIPEDTFFPSPESSCDV KLVEKSFETDTNLNFQNLSVIGFRILL LKVAGFNLLMTLRLWSS (SEQ ID NO: 225) | DSGVTQTPKHLITATGQRVTLRCSPRTG DLSVYWYQQSLDQGLQFLIQYYNGEER AKGNILERFSAQQFPDLHSELNLSSLELG DSALYFCASSVVDGEQYFGPGTRLTVTE DLKNVFPPEVAVFEPSEAEISHTQKATLV CLATGFYPDHVELSWWVNGKEVHSGV TDPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 239) |
| 101 | QKEVEQNSGPLSVPEGAIASLNCTYS DRFSQSFFWYRQYSGKSPELIMFIYSN GDKEDGRFTAQLNKASQYVSLLIRDS QPSDSATYLCATMRAGGFKTIFGAGT RLFVKANIQNPDPAVYQLRDSKSSDK SVCLFTDFDSQTNVSQSKDSDVYITD KCVLDMRSMDFKSNSAVAWSNKSD FACANAFNNSIIPEDTFFPSPESSCDV KLVEKSFETDTNLNFQNLSVIGFRILL LKVAGFNLLMTLRLWSS (SEQ ID NO: 227) | DSGVTQTPKHLITATGQRVTLRCSPRTG DLSVYWYQQSLDQGLQFLIQYYNGEER AKGNILERFSAQQFPDLHSELNLSSLELG DSALYFCASSVVDGEQYFGPGTRLTVTE DLKNVFPPEVAVFEPSEAEISHTQKATLV CLATGFYPDHVELSWWVNGKEVHSGVC TDPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 240) |
| 102 | QKEVEQNSGPLSVPEGAIASLNCTYS DRFSQSFFWYRQYSGKSPELIMFIYSN GDKEDGRFTAQLNKASQYVSLLIRDS QPSDSATYLCAVVRAGGFKTIFGAGT RLFVKANIQNPDPAVYQLRDSKSSDK SVCLFTDFDSQTNVSQSKDSDVYITD KCVLDMRSMDFKSNSAVAWSNKSD FACANAFNNSIIPEDTFFPSPESSCDV KLVEKSFETDTNLNFQNLSVIGFRILL LKVAGFNLLMTLRLWSS (SEQ ID NO: 223) | DSGVTQTPKHLITATGQRVTLRCSPRSGD LSVYWYQQSLDQGLQFLIQYYNGEERA KGNILERFSAQQFPDLHSELNLSSLELGD SALYFCASSVVDGEQFFGPGTRLTVTED LKNVFPPEVAVFEPSEAEISHTQKATLVC LATGFYPDHVELSWWVNGKEVHSGVCT DPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 241) |
| 103 | QKEVEQNSGPLSVPEGAIASLNCTYS DRFSQSFFWYRQYSGKSPELIMFIYSN GDKEDGRFTAQLNKASQYVSLLIRDS QPSDSATYLCAVLRAGGFKTIFGAGT RLFVKANIQNPDPAVYQLRDSKSSDK SVCLFTDFDSQTNVSQSKDSDVYITD KCVLDMRSMDFKSNSAVAWSNKSD FACANAFNNSIIPEDTFFPSPESSCDV KLVEKSFETDTNLNFQNLSVIGFRILL LKVAGFNLLMTLRLWSS (SEQ ID NO: 225) | DSGVTQTPKHLITATGQRVTLRCSPRSGD LSVYWYQQSLDQGLQFLIQYYNGEERA KGNILERFSAQQFPDLHSELNLSSLELGD SALYFCASSVVDGEQFFGPGTRLTVTED LKNVFPPEVAVFEPSEAEISHTQKATLVC LATGFYPDHVELSWWVNGKEVHSGVCT DPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 242) |
| 104 | QKEVEQNSGPLSVPEGAIASLNCTYS DRFSQSFFWYRQYSGKSPELIMFIYSN GDKEDGRFTAQLNKASQYVSLLIRDS QPSDSATYLCATMRAGGFKTIFGAGT RLFVKANIQNPDPAVYQLRDSKSSDK SVCLFTDFDSQTNVSQSKDSDVYITD KCVLDMRSMDFKSNSAVAWSNKSD FACANAFNNSIIPEDTFFPSPESSCDV KLVEKSFETDTNLNFQNLSVIGFRILL LKVAGFNLLMTLRLWSS (SEQ ID NO: 227) | DSGVTQTPKHLITATGQRVTLRCSPRSGD LSVYWYQQSLDQGLQFLIQYYNGEERA KGNILERFSAQQFPDLHSELNLSSLELGD SALYFCASSVVDGEQFFGPGTRLTVTED LKNVFPPEVAVFEPSEAEISHTQKATLVC LATGFYPDHVELSWWVNGKEVHSGVCT DPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 243) |
| 105 | QKEVEQNSGPLSVPEGAIASLNCTYS DRGSQSFFWYRQYSGKSPELIMFIYS NGDKEDGRFTAQLNKASQYVSLLIR DSQPSDSATYLCAVVRAGGFKTIFGA GTRLFVKANIQNPDPAVYQLRDSKSS DKSVCLFTDFDSQTNVSQSKDSDVYI TDKCVLDMRSMDFKSNSAVAWSNK SDFACANAFNNSIIPEDTFFPSPESSCD VKLVEKSFETDTNLNFQNLSVIGFRIL LLKVAGFNLLMTLRLWSS (SEQ ID NO: 105) | DSGVTQTPKHLITATGQRVTLRCSPRTG DLSVYWYQQSLDQGLQFLIQYYNGEER AKGNILERFSAQQFPDLHSELNLSSLELG DSALYFCASSVVDGEQFFGPGTRLTVTE DLKNVFPPEVAVFEPSEAEISHTQKATLV CLATGFYPDHVELSWWVNGKEVHSGVC TDPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 244) |

TABLE A-continued

| TCR ID | Alpha Chain | Beta Chain |
|---|---|---|
| 106 | QKEVEQNSGPLSVPEGAIASLNCTYS DRGSQSFFWYRQYSGKSPELIMFIYS NGDKEDGRFTAQLNKASQYVSLLIR DSQPSDSATYLCAVLRAGGFKTIFGA GTRLFVKANIQNPDPAVYQLRDSKSS DKSVCLFTDFDSQTNVSQSKDSDVYI TDKCVLDMRSMDFKSNSAVAWSNK SDFACANAFNNSIIPEDTFFPSPESSCD VKLVEKSFETDTNLNFQNLSVIGFRIL LLKVAGFNLLMTLRLWSS (SEQ ID NO: 107) | DSGVTQTPKHLITATGQRVTLRCSPRTG DLSVYWYQQSLDQGLQFLIQYYNGEER AKGNILERFSAQQFPDLHSELNLSSLELG DSALYFCASSVVDGEQFFGPGTRLTVTE DLKNVFPPEVAVFEPSEAEISHTQKATLV CLATGFYPDHVELSWWVNGKEVHSGVC TDPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 245) |
| 107 | QKEVEQNSGPLSVPEGAIASLNCTYS DRGSQSFFWYRQYSGKSPELIMFIYS NGDKEDGRFTAQLNKASQYVSLLIR DSQPSDSATYLCATMRAGGFKTIFGA GTRLFVKANIQNPDPAVYQLRDSKSS DKSVCLFTDFDSQTNVSQSKDSDVYI TDKCVLDMRSMDFKSNSAVAWSNK SDFACANAFNNSIIPEDTFFPSPESSCD VKLVEKSFETDTNLNFQNLSVIGFRIL LLKVAGFNLLMTLRLWSS (SEQ ID NO: 121) | DSGVTQTPKHLITATGQRVTLRCSPRTG DLSVYWYQQSLDQGLQFLIQYYNGEER AKGNILERFSAQQFPDLHSELNLSSLELG DSALYFCASSVVDGEQFFGPGTRLTVTE DLKNVFPPEVAVFEPSEAEISHTQKATLV CLATGFYPDHVELSWWVNGKEVHSGVC TDPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 246) |
| 108 | QKEVEQNSGPLSVPEGAIASLNCTYS DRFSQSFFWYRQYSGKSPELIMFIYSN GDKEDGRFTAQLNKASQYVSLLIRDS QPSDSATYLCAVVRAGGFKTIFGAGT RLFVKANIQNPDPAVYQLRDSKSSDK SVCLFTDFDSQTNVSQSKDSDVYITD KCVLDMRSMDFKSNSAVAWSNKSD FACANAFNNSIIPEDTFFPSPESSCDV KLVEKSFETDTNLNFQNLSVIGFRILL LKVAGFNLLMTLRLWSS (SEQ ID NO: 223) | DSGVTQTPKHLITATGQRVTLRCSPRTG DLSVYWYQQSLDQGLQFLIQYYNGEER AKGNILERFSAQQFPDLHSELNLSSLELG DSALYFCASSVVDGEQFFGPGTRLTVTE DLKNVFPPEVAVFEPSEAEISHTQKATLV CLATGFYPDHVELSWWVNGKEVHSGVC TDPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 247) |
| 109 | QKEVEQNSGPLSVPEGAIASLNCTYS DRFSQSFFWYRQYSGKSPELIMFIYSN GDKEDGRFTAQLNKASQYVSLLIRDS QPSDSATYLCATMRAGGFKTIFGAGT RLFVKANIQNPDPAVYQLRDSKSSDK SVCLFTDFDSQTNVSQSKDSDVYITD KCVLDMRSMDFKSNSAVAWSNKSD FACANAFNNSIIPEDTFFPSPESSCDV KLVEKSFETDTNLNFQNLSVIGFRILL LKVAGFNLLMTLRLWSS (SEQ ID NO: 227) | DSGVTQTPKHLITATGQRVTLRCSPRTG DLSVYWYQQSLDQGLQFLIQYYNGEER AKGNILERFSAQQFPDLHSELNLSSLELG DSALYFCASSVVDGEQFFGPGTRLTVTE DLKNVFPPEVAVFEPSEAEISHTQKATLV CLATGFYPDHVELSWWVNGKEVHSGVC TDPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 248) |
| 110 | QKEVEQNSGPLSVPEGAIASLNCTYS DRFSQSFFWYRQYSGKSPELIMFIYSN GDKEDGRFTAQLNKASQYVSLLIRDS QPSDSATYLCAVLRAGGFKTIFGAGT RLFVKANIQNPDPAVYQLRDSKSSDK SVCLFTDFDSQTNVSQSKDSDVYITD KCVLDMRSMDFKSNSAVAWSNKSD FACANAFNNSIIPEDTFFPSPESSCDV KLVEKSFETDTNLNFQNLSVIGFRILL LKVAGFNLLMTLRLWSS (SEQ ID NO: 225) | DSGVTQTPKHLITATGQRVTLRCSPRTG DLSVYWYQQSLDQGLQFLIQYYNGEER AKGNILERFSAQQFPDLHSELNLSSLELG DSALYFCASSVVDGEQFFGPGTRLTVTE DLKNVFPPEVAVFEPSEAEISHTQKATLV CLATGFYPDHVELSWWVNGKEVHSGVC TDPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 249) |
| 111 | QKEVEQNSGPLSVPEGAIASLNCTYS DRGSQSFFWYRQYSGKSPELIMFIYS NGDKEDGRFTAQLNKASQYVSLLIR DSQPSDSATYLCATVRAGGFKTIFGA GTRLFVKANIQNPDPAVYQLRDSKSS DKSVCLFTDFDSQTNVSQSKDSDVYI TDKCVLDMRSMDFKSNSAVAWSNK SDFACANAFNNSIIPEDTFFPSPESSCD VKLVEKSFETDTNLNFQNLSVIGFRIL LLKVAGFNLLMTLRLWSS (SEQ ID NO: 250) | DSGVTQTPKHLITATGQRVTLRCSPRSGD LSVYWYQQSLDQGLQFLIQYYNGEER KGNILERFSAQQFPDLHSELNLSSLELGD SALYFCASSVVDGEQYFGPGTRLTVTED LKNVFPPEVAVFEPSEAEISHTQKATLVC LATGFYPDHVELSWWVNGKEVHSGVCT DPQPLKEQPALNDSRYCLSSRLRVSATF WQNPRNHFRCQVQFYGLSENDEWTQDR AKPVTQIVSAEAWGRADCGFTSESYQQG VLSATILYEILLGKATLYAVLVSALVLM AMVKRKDSR (SEQ ID NO: 251) |
| 112 | QKEVEQNSGPLSVPEGAIASLNCTYS DRGSQSFFWYRQYSGKSPELIMFIYS NGDKEDGRFTAQLNKASQYVSLLIR DSQPSDSATYLCATLRAGGFKTIFGA GTRLFVKANIQNPDPAVYQLRDSKSS DKSVCLFTDFDSQTNVSQSKDSDVYI | DSGVTQTPKHLITATGQRVTLRCSPRSGD LSVYWYQQSLDQGLQFLIQYYNGEER KGNILERFSAQQFPDLHSELNLSSLELGD SALYFCASSVVDGEQYFGPGTRLTVTED LKNVFPPEVAVFEPSEAEISHTQKATLVC LATGFYPDHVELSWWVNGKEVHSGVCT |

TABLE A-continued

| TCR ID | Alpha Chain | Beta Chain |
|--------|-------------|------------|
|  | TDKCVLDMRSMDFKSNSAVAWSNK<br>SDFACANAFNNSIIPEDTFFPSPESSCD<br>VKLVEKSFETDTNLNFQNLSVIGFRIL<br>LLKVAGFNLLMTLRLWSS (SEQ ID<br>NO: 252) | DPQPLKEQPALNDSRYCLSSRLRVSATF<br>WQNPRNHFRCQVQFYGLSENDEWTQDR<br>AKPVTQIVSAEAWGRADCGFTSESYQQG<br>VLSATILYEILLGKATLYAVLVSALVLM<br>AMVKRKDSR (SEQ ID NO: 253) |
| 113 | QKEVEQNSGPLSVPEGAIASLNCTYS<br>DRFSQSFFWYRQYSGKSPELIMFIYSN<br>GDKEDGRFTAQLNKASQYVSLLIRDS<br>QPSDSATYLCATVRAGGFKTIFGAGT<br>RLFVKANIQNPDPAVYQLRDSKSSDK<br>SVCLFTDFDSQTNVSQSKDSDVYITD<br>KCVLDMRSMDFKSNSAVAWSNKSD<br>FACANAFNNSIIPEDTFFPSPESSCDV<br>KLVEKSFETDTNLNFQNLSVIGFRILL<br>LKVAGFNLLMTLRLWSS (SEQ ID<br>NO: 254) | DSGVTQTPKHLITATGQRVTLRCSPRSGD<br>LSVYWYQQSLDQGLQFLIQYYNGEERA<br>KGNILERFSAQQFPDLHSELNLSSLELGD<br>SALYFCASSVVDGEQYFGPGTRLTVTED<br>LKNVFPPEVAVFEPSEAEISHTQKATLVC<br>LATGFYPDHVELSWWVNGKEVHSGVCT<br>DPQPLKEQPALNDSRYCLSSRLRVSATF<br>WQNPRNHFRCQVQFYGLSENDEWTQDR<br>AKPVTQIVSAEAWGRADCGFTSESYQQG<br>VLSATILYEILLGKATLYAVLVSALVLM<br>AMVKRKDSR (SEQ ID NO: 255) |
| 114 | QKEVEQNSGPLSVPEGAIASLNCTYS<br>DRFSQSFFWYRQYSGKSPELIMFIYSN<br>GDKEDGRFTAQLNKASQYVSLLIRDS<br>QPSDSATYLCATLRAGGFKTIFGAGT<br>RLFVKANIQNPDPAVYQLRDSKSSDK<br>SVCLFTDFDSQTNVSQSKDSDVYITD<br>KCVLDMRSMDFKSNSAVAWSNKSD<br>FACANAFNNSIIPEDTFFPSPESSCDV<br>KLVEKSFETDTNLNFQNLSVIGFRILL<br>LKVAGFNLLMTLRLWSS (SEQ ID<br>NO: 256) | DSGVTQTPKHLITATGQRVTLRCSPRSGD<br>LSVYWYQQSLDQGLQFLIQYYNGEERA<br>KGNILERFSAQQFPDLHSELNLSSLELGD<br>SALYFCASSVVDGEQYFGPGTRLTVTED<br>LKNVFPPEVAVFEPSEAEISHTQKATLVC<br>LATGFYPDHVELSWWVNGKEVHSGVCT<br>DPQPLKEQPALNDSRYCLSSRLRVSATF<br>WQNPRNHFRCQVQFYGLSENDEWTQDR<br>AKPVTQIVSAEAWGRADCGFTSESYQQG<br>VLSATILYEILLGKATLYAVLVSALVLM<br>AMVKRKDSR (SEQ ID NO: 257) |

BRIEF DESCRIPTION OF THE DRAWINGS

FIG. 8 shows the number of NY-ESO-1-activated TCRs obtained from each of 23 patient samples.

FIG. 34 shows the top activating off-target peptides identified by 3T-TRACE which bear little sequence similarity to the intended NY-ESO-1 epitope.

DETAILED DESCRIPTION

Figure 1:
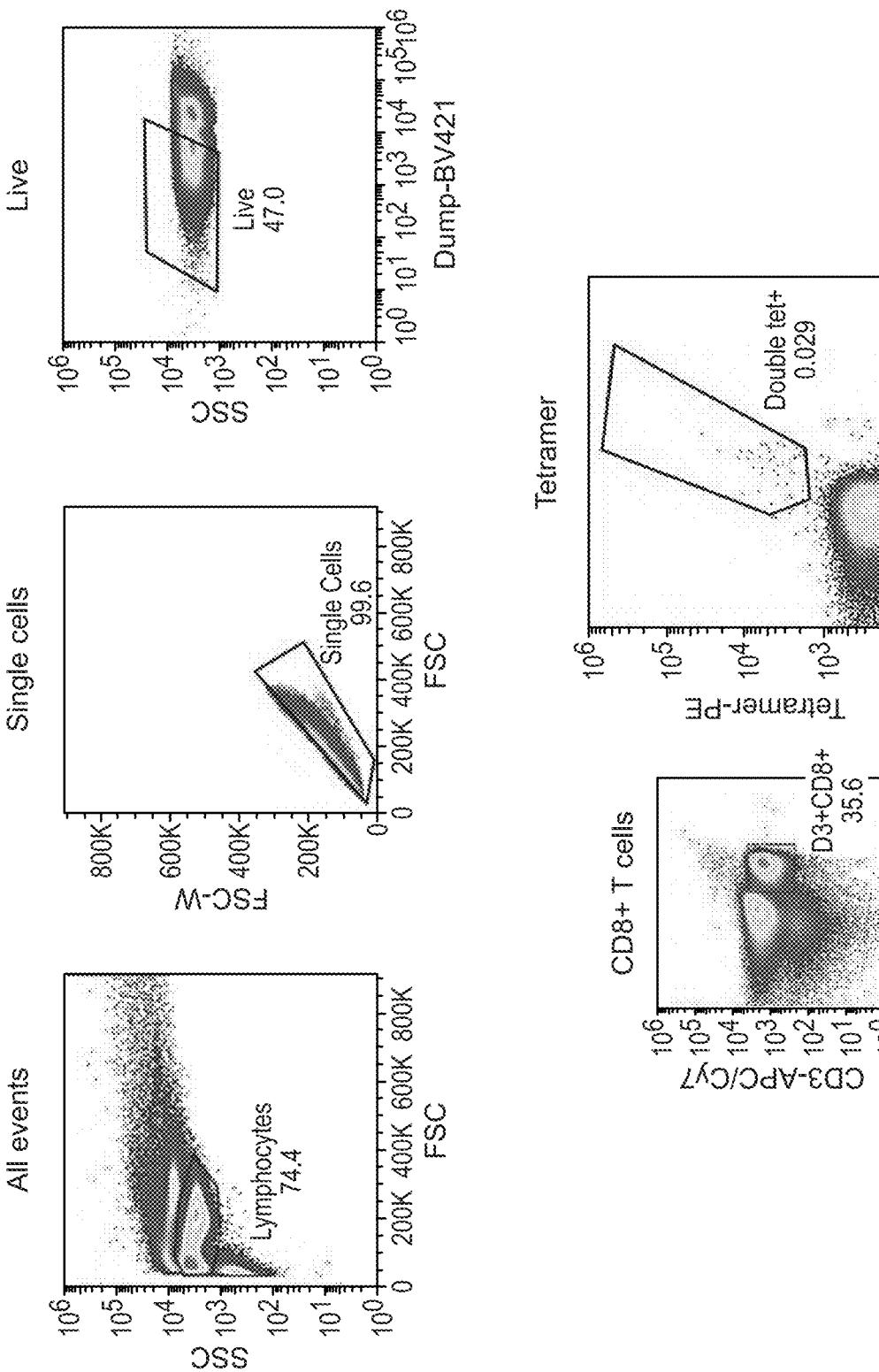
FIG. 1 shows the flow cytometry gating scheme used for single-cell tetramer sorting of cells from patient peripheral blood samples.

Provided are methods for isolating T-cells with T cell receptors (TCRs) optimized for reactivity to specific peptides and decreased cross-reactivity to non-target peptides. Advantageously, TCRs of the invention can be optimized to target cancer antigens and peptides while having reducing reactivity to healthy cells. Methods of the invention utilize a novel combination of culturing conditions that increase T-cell activation and allow for validation of TCR activity. Culturing conditions of the invention further reduce culturing times generally needed to achieve expanded reactive T-cells. Because of the robust nature of the activation and validation conditions of the present invention, variants of identified TCRs can also be optimized and validated for their response to peptides, including cancer peptides.

Definitions

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

The term "major histocompatibility complex" (MHC) proteins (also called human leukocyte antigens, HLA, or the H2 locus in the mouse) are protein molecules expressed on the surface of cells that confer a unique antigenic identity to these cells. MHC/HLA antigens are target molecules that are recognized by T-cells and natural killer (NK) cells as being derived from the same source of hematopoietic reconstituting stem cells as the immune effector cells ("self") or as being derived from another source of hematopoietic reconstituting cells ("non-self"). Two main classes of HLA antigens are recognized: HLA class I and HLA class II. MHC proteins as used herein includes MHC proteins from any mammalian or avian species, e.g. primate sp., particularly humans; rodents, including mice, rats and hamsters; rabbits; equines, bovines, canines, felines, etc. Of particular interest are the human HLA proteins, and the murine H-2 proteins. Included in the HLA proteins are the class II subunits HLA-DPα, HLA-DPβ, HLA-DQα, HLA-DQβ, HLA-DRα and HLA-DRβ, and the class I proteins HLA-A, HLA-B, HLA-C, and B2-microglobulin. Included in the murine H-2 subunits are the class I H-2K, H-2D, H-2L, and the class II I-Aα, I-Aβ, I-Eα and I-Eβ, and β2-microglobulin.

As used herein, the term "class II HLA/MHC" binding domains comprise the α1 and α2 domains for the α chain, and the β1 and β2 domains for the β chain. Not more than about 10, usually not more than about 5, preferably none of the amino acids of the transmembrane domain will be included. The deletion will be such that it does not interfere with the ability of the α2 or β2 domain to bind target peptides (i.e., peptide ligands). Class II HLA/MHC binding domains also refers to the binding domains of a major histocompatibility complex protein that are soluble domains of Class II α and β chain. Class II HLA/MHC binding domains include domains that have been subjected to mutagenesis and selected for amino acid changes that enhance the solubility of the single chain polypeptide, without altering the peptide binding contacts.

As used herein, the term "class I HLA/MHC" binding domains includes the α1, α2 and α3 domain of a Class I allele, including without limitation HLA-A, HLA-B, HLA-C, H-2K, H-2D, H-2L, which are combined with β2-microglobulin. Not more than about 10, usually not more than about 5, preferably none of the amino acids of the transmembrane domain will be included. The deletion will be such that it does not interfere with the ability of the domains to bind target peptides (i.e., peptide ligands).

The "MHC binding domains", as used herein, refers to a soluble form of the normally membrane-bound protein. The soluble form is derived from the native form by deletion of the transmembrane domain. The MHC binding domain protein is truncated, removing both the cytoplasmic and transmembrane domains and includes soluble domains of Class II alpha and beta chain. "MHC binding domains" also refers to binding domains that have been subjected to mutagenesis and selected for amino acid changes that enhance the solubility of the single chain polypeptide, without altering the peptide binding contacts.

"MHC context" as used herein refers to an interaction being in the presence of an MHC with non-covalent interactions with the MHC and an antigen. The function of MHC molecules is to bind peptide fragments derived from pathogens and display them on the cell surface for recognition by the appropriate T cells. Thus, TCR recognition can be influenced by the MHC protein that is presenting the antigen. The term MHC context refers to the recognition by a TCR of a given peptide, when it is presented by a specific MHC protein.

"T cell receptor" (TCR), refers to an antigen/MHC binding heterodimeric protein product of a vertebrate (e.g., mammalian, TCR gene complex, including the human TCR α, β, γ, and δ chains). For example, the complete sequence of the human β TCR locus has been sequenced, as published by Rowen 1996; the human TCR locus has been sequenced and resequenced, for example, see Mackelprang 2006; see a general analysis of the T-cell receptor variable gene segment families in Arden 1995; each of which is herein specifically incorporated by reference for the sequence information provided and referenced in the publication.

The terms "recipient," "individual," "subject," "host," and "patient" are used interchangeably herein and refer to any mammalian subject for whom diagnosis, treatment, or therapy is desired, particularly humans. "Mammal" for purposes of treatment refers to any animal classified as a mammal, including humans, domestic and farm animals, and zoo, sports, or pet animals, such as dogs, horses, cats, cows, sheep, goats, pigs, etc. Preferably, the mammal is human.

The terms "peptide," "polypeptide," and "protein" are used interchangeably to refer to a polymer of amino acid residues, and are not limited to a minimum length, though a number of amino acid residues may be specified (e.g., 9mer is nine amino acid residues). Polypeptides may include amino acid residues including natural and/or non-natural amino acid residues. Polypeptides may also include fusion proteins. The terms also include post-expression modifications of the polypeptide, for example, glycosylation, sialylation, acetylation, phosphorylation, and the like. In some embodiments, the polypeptides may contain modifications with respect to a native or natural sequence, as long as the protein maintains the desired activity. These modifications may be deliberate, such as through site-directed mutagenesis, or may be accidental, such as through mutations of hosts which produce the proteins or errors due to PCR amplification.

The term "Epitope" as used herein comprises the terms "structural epitope" and "functional epitope". The "Structural Epitope" are those amino acids of the antigen, e.g. peptide-MHC complex, that are covered by the antigen binding protein when bound to the antigen. Typically, all amino acids of the antigen are considered covered that are within 5 A of any atom of an amino acid of the antigen binding protein. The structural epitope of an antigen may be determined by art known methods including X-ray crystallography or NMR analysis. The structural epitope of an antibody typically comprises 20 to 30 amino acids. The structural epitope of a TCR typically comprises 20 to 30 amino acids. The "Functional Epitope" is a subset of those amino acids forming the structural epitope and comprises the amino acids of the antigen that are critical for formation of the interface with the antigen binding protein of the invention, either by directly forming non-covalent interactions such as H-bonds, salt bridges, aromatic stacking or hydrophobic interactions or by indirectly stabilizing the binding conformation of the antigen and is, for instance, determined by mutational scanning. The term "epitope" includes any molecule, structure, amino acid sequence, or protein determinant that is recognized and specifically bound by a cognate binding molecule, such as a chimeric antigen receptor, or other binding molecule, domain, or protein.

A "conservative substitution" refers to amino acid substitutions that do not significantly affect or alter binding characteristics of a particular protein. Generally, conservative substitutions are ones in which a substituted amino acid residue is replaced with an amino acid residue having a similar side chain. Conservative substitutions include a substitution found in one of the following groups: Group 1: Alanine (Ala or A), Glycine (Gly or G), Serine (Ser or S), Threonine (Thr or T); Group 2: Aspartic acid (Asp or D), Glutamic acid (Glu or Z); Group 3: Asparagine (Asn or N), Glutamine (Gln or Q); Group 4: Arginine (Arg or R), Lysine (Lys or K), Histidine (His or H); Group 5: Isoleucine (Ile or I), Leucine (Leu or L), Methionine (Met or M), Valine (Val or V); and Group 6: Phenylalanine (Phe or F), Tyrosine (Tyr or Y), Tryptophan (Trp or W). Additionally, or alternatively, amino acids can be grouped into conservative substitution groups by similar function, chemical structure, or composition (e.g., acidic, basic, aliphatic, aromatic, or sulfur-containing). For example, an aliphatic grouping may include, for purposes of substitution, Gly, Ala, Val, Leu, and Ile. Other conservative substitutions groups include sulfur-containing: Met and Cysteine (Cys or C); acidic: Asp, Glu, Asn, and Gln; small aliphatic, nonpolar, or slightly polar residues: Ala, Ser, Thr, Pro, and Gly; polar, negatively charged residues and their amides: Asp, Asn, Glu, and Gln; polar, positively charged residues: His, Arg, and Lys; large aliphatic, nonpolar residues: Met, Leu, Ile, Val, and Cys; and large aromatic residues: Phe, Tyr, and Trp. Additional information can be found in Creighton (1984) Proteins, W.H. Freeman and Company. Variant proteins, peptides, polypeptides, and amino acid sequences of the present disclosure can, in certain embodiments, comprise one or more conservative substitutions relative to a reference amino acid sequence.

"Nucleic acid molecule" or "polynucleotide" refers to a polymeric compound including covalently linked nucleotides comprising natural subunits (e.g., purine or pyrimidine bases). Purine bases include adenine and guanine, and pyrimidine bases include uracil, thymine, and cytosine. Nucleic acid molecules include polyribonucleic acid (RNA) and polydeoxyribonucleic acid (DNA), which includes cDNA, genomic DNA, and synthetic DNA, either of which may be single or double-stranded. A nucleic acid molecule encoding an amino acid sequence includes all nucleotide sequences that encode the same amino acid sequence.

A "functional variant" refers to a polypeptide or polynucleotide that is structurally similar or substantially structurally similar to a parent or reference compound of this disclosure, but differs, in some contexts slightly, in composition (e.g., one base, atom, or functional group is different, added, or removed; or one or more amino acids are substituted, mutated, inserted, or deleted), such that the polypeptide or encoded polypeptide is capable of performing at least one function of the encoded parent polypeptide with at least 50% efficiency of activity of the parent polypeptide.

As used herein, a "functional portion" or "functional fragment" refers to a polypeptide or polynucleotide that comprises only a domain, motif, portion, or fragment of a parent or reference compound, and the polypeptide or encoded polypeptide retains at least 50% activity associated with the domain, portion, or fragment of the parent or reference compound.

In certain embodiments, a functional variant or functional portion or functional fragment each refers to a "signaling portion" of an effector molecule, effector domain, costimulatory molecule, or costimulatory domain. In other aspects, a functional variant or functional portion or functional fragment each refers to a linking function or a leader peptide function as disclosed herein. In certain aspects, a functional variant/portion/fragment refers to a linking function or a leader peptide function as described herein. In specific aspects, variant linkers and leader peptides are at least 60% as efficient, at least 70% as efficient, at least 80% as efficient, at least 90% as efficient, at least 95% as efficient, or at least 99% as efficient as the reference/parent polypeptides disclosed herein.

The term "expression," as used herein, refers to the process by which a polypeptide is produced based on the encoding sequence of a nucleic acid molecule, such as a gene. The process may include transcription, post-transcriptional control, post-transcriptional modification, translation, post-translational control, post-translational modification, or any combination thereof. An expressed nucleic acid molecule is typically operably linked to an expression control sequence (e.g., a promoter).

The term "operably linked" refers to the association of two or more nucleic acid molecules on a single nucleic acid fragment so that the function of one is affected by the other.

Editing a cell means altering the gene expression of the cell. Any known method for editing the gene expression of a cell may be used in combination with methods of the invention. For example, editing may comprise transfection with a vector, electroporation, recombination (e.g., homologous recombination), transformation, transduction, or gene editing (e.g., introducing a CRISPR-Cas9 system, a TALEN system, or a ZNF system into cells).

An exemplary editing system comprises a nuclease and a guide RNA. For example, a CRISPR system comprises a CRISPR nuclease (e.g., CRISPR (clustered regularly interspaced short palindromic repeats)-associated (Cas) endonuclease or a variant thereof, such as Cas9) and a guide RNA. The CRISPR nuclease associates with a guide RNA that directs nucleic acid cleavage by the associated endonuclease by hybridizing to a recognition site in a polynucleotide. The guide RNA comprises a direct repeat and a guide sequence, which is complementary to the target recognition site. In certain embodiments, the CRISPR system further comprises a tracrRNA (trans-activating CRISPR RNA) or sgRNA (synthetic guide RNA) that is complementary (fully or partially) to the direct repeat sequence present on the guide RNA. A "TALEN" nuclease is an endonuclease comprising a DNA-binding domain comprising a plurality of TAL domain repeats fused to a nuclease domain or an active portion thereof from an endonuclease or exonuclease, including but not limited to a restriction endonuclease, homing endonuclease, and yeast HO endonuclease. A "zinc finger nuclease" or "ZFN" is a chimeric protein comprising a zinc finger DNA-binding domain fused to a nuclease domain from an endonuclease or exonuclease, including but not limited to a restriction endonuclease, homing endonuclease, and yeast HO endonuclease.

As used herein, "expression vector" refers to a DNA construct containing a nucleic acid molecule that is operably linked to a suitable control sequence capable of effecting the expression of the nucleic acid molecule in a suitable host. Such control sequences include a promoter to effect transcription, an optional operator sequence to control such transcription, a sequence encoding suitable mRNA ribosome binding sites, and sequences which control termination of transcription and translation. The vector may be a plasmid, a phage particle, a virus, or simply a potential genomic insert. Once transformed into a suitable host, the vector may replicate and function independently of the host genome, or may, in some instances, integrate into the genome itself. For example, the vector may be a lentivirus or an adenovirus. Here, "plasmid," "expression plasmid," "virus," and "vector" are often used interchangeably.

The terms "modify," "modifying," or "modification" in the context of making alterations to nucleic compositions of a cell, and the term "introduced" in the context of inserting a nucleic acid molecule into a cell, include reference to the alteration or incorporation of a nucleic acid molecule in a eukaryotic cell wherein the nucleic acid molecule may be incorporated into the genome of a cell and converted into an autonomous replicon. "Modification" or "introduction" of nucleic compositions in a cell may be accomplished by a variety of methods known in the art, including, but not limited to, transfection, transformation, transduction, or gene editing. As used herein, the term "engineered," "recombinant," "modified," or "non-natural" refers to an organism, microorganism, cell, nucleic acid molecule, or vector that includes at least one genetic alteration or has been modified by introduction of an exogenous nucleic acid molecule, wherein such alterations or modifications are introduced by genetic engineering. Genetic alterations include, for example, modifications and/or introductions of expressible nucleic acid molecules encoding polypeptide, such as additions, deletions, substitutions, mutations, or other functional changes of a cell's genetic material.

The term "construct" refers to any polynucleotide that contains a recombinant nucleic acid molecule. A construct may be present in a vector (e.g., a bacterial vector, a viral vector) or may be integrated into a genome. A "vector" is a nucleic acid molecule that is capable of transporting another nucleic acid molecule. Vectors may be, for example, plasmids, cosmids, viruses, an RNA vector or a linear or circular DNA or RNA molecule that may include chromosomal, non-chromosomal, semi-synthetic, or synthetic nucleic acid molecules. Exemplary vectors are those capable of autonomous replication (episomal vector), capable of delivering a polynucleotide to a cell genome (e.g., viral vector), or capable of expressing nucleic acid molecules to which they are linked (expression vectors).

As used herein, the term "host" refers to a cell or microorganism targeted for genetic modification with a heterologous nucleic acid molecule to produce a polypeptide of interest. In certain embodiments, a host cell may optionally already possess or be modified to include other genetic modifications that confer desired properties related, or unrelated to, biosynthesis of the heterologous protein.

As used herein, "enriched" or "depleted" with respect to amounts of cell types in a mixture refers to an increase in the number of the "enriched" type, a decrease in the number of the "depleted" cells, or both, in a mixture of cells resulting from one or more enriching or depleting processes or steps. In certain embodiments, amounts of a certain cell type in a mixture will be enriched and amounts of a different cell type will be depleted, such as enriching for CD4+ cells while depleting CD8+ cells, or enriching for CD8+ cells while depleting CD4+ cells, or combinations thereof.

"Antigen" as used herein refers to an immunogenic molecule that provokes an immune response. This immune response may involve antibody production, activation of specific immunologically-competent cells, or both. An antigen may be, for example, a peptide, glycopeptide, polypeptide, glycopolypeptide, polynucleotide, polysaccharide, lipid, or the like. It is readily apparent that an antigen can be synthesized, produced recombinantly, or derived from a biological sample. Exemplary biological samples that can contain one or more antigens include tissue samples, tumor samples, cells, biological fluids, or combinations thereof. Antigens can be produced by cells that have been modified or genetically engineered to express an antigen.

"Exogenous" with respect to a nucleic acid or polynucleotide indicates that the nucleic acid is part of a recombinant nucleic acid construct or is not in its natural environment. For example, an exogenous nucleic acid can be a sequence from one species introduced into another species (i.e., a heterologous nucleic acid). Typically, such an exogenous nucleic acid is introduced into the other species via a recombinant nucleic acid construct. An exogenous nucleic acid also can be a sequence that is native to an organism and that has been reintroduced into cells of that organism. An exogenous nucleic acid that includes a native sequence can often be distinguished from the naturally occurring sequence by the presence of non-natural sequences linked to the exogenous nucleic acid, for example, non-native regulatory sequences flanking a native sequence in a recombinant nucleic acid construct. In addition, stably transformed exogenous nucleic acids typically are integrated at positions other than the position where the native sequence is found. The exogenous elements may be added to a construct, for example, using genetic recombination. Genetic recombination is the breaking and rejoining of DNA strands to form new molecules of DNA encoding a novel set of genetic information.

Any cell assay systems may be used in combination with the assays of the invention. For example, cells may be first separated into reaction chamber, for example using a droplet separation system. Cells for example a microplate comprising 6, 12, 24, 48, 96, 384 or 1536. Cells may be separated, and each cell subjected to separate culture conditions. For example, in validation, cross-reactivity, and optimization assays, each separated cell may be cultured with a different peptide to analyze peptide responses.

Sequencing platforms that can be used in the present disclosure include but are not limited to: pyrosequencing, sequencing-by-synthesis, single-molecule sequencing, second-generation sequencing, nanopore sequencing, sequencing by ligation, or sequencing by hybridization. Preferred sequencing platforms are those commercially available from Illumina (RNA-Seq) and Helicos (Digital Gene Expression or "DGE"). "Next generation" sequencing methods include, but are not limited to those commercialized by: 1) 454/Roche Lifesciences including but not limited to the methods and apparatus described in Margulies et al., Nature (2005) 437:376-380 (2005); and U.S. Pat. Nos. 7,244,559; 7,335, 762; 7,211,390; 7,244,567; 7,264,929; 7,323,305; 2) Helicos BioSciences Corporation (Cambridge, MA) as described in U.S. application Ser. No. 11/167,046, and U.S. Pat. Nos. 7,501,245; 7,491,498; 7,276,720; and in U.S. Patent Application Publication Nos. US20090061439; US20080087826; US20060286566; US20060024711; US20060024678; US20080213770; and US20080103058; 3) Applied Biosystems (e.g. SOLID sequencing); 4) Dover Systems (e.g., Polonator G.007 sequencing); 5) Illumina as described U.S. Pat. Nos. 5,750,341; 6,306,597; and 5,969,119; and 6) Pacific Biosciences as described in U.S. Pat. Nos. 7,462,452; 7,476,504; 7,405,281; 7,170,050; 7,462,468; 7,476,503; 7,315,019; 7,302,146; 7,313,308; and US Application Publication Nos. US20090029385; US20090068655; US20090024331; and US20080206764. All references are herein incorporated by reference.

Antigen binding region (ABR). As used herein, the term ABR refers to a combination of variable heavy (VH and variable light (VL) polypeptides to associate to form a variable region domain. An ABR is the minimum antibody fragment that contains a complete antigen-recognition and binding site. This region consists of heavy- and one light-chain variable domain in tight, noncovalent association, as a single polypeptide or as a dimer. It is in this configuration that the three CDRs of each variable domain interact to define an antigen-binding site on the surface of the domain. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a b-sheet configuration, connected by three CDRs, which form loops connecting, and in some cases forming part of, the b-sheet structure. The CDRs in each chain are held together in close proximity by the FR regions and, with the CDRs from the other chain, contribute to the formation of the antigen-20) binding site of antibodies (see Kabat et al., Sequences of Proteins of Immunological Interest, Fifth Edition, National Institute of Health, Bethesda, Md. (1991)). The constant domains are not involved directly in binding an antibody to an antigen, but exhibit various effector functions, such as participation of the antibody in antibody dependent cellular toxicity.

A "T cell" or "T lymphocyte" is an immune system cell that matures in the thymus and produces TCRs, including <®T cells and @TMT cells. T cells can be naïve (not exposed to antigen; increased expression of CD62L, CCR7, CD28, CD3, CD127, and CD45RA, and decreased expression of CD45RO as compared to TCM), memory T cells (TM) (antigen-experienced and long-lived), and effector cells (antigen-experienced, cytotoxic). TM can be further divided into subsets of central memory T cells (TCM, increased expression of CD62L, CCR7, CD28, CD127, CD45RO, and CD95, and decreased expression of CD54RA as compared to naïve T cells) and effector memory T cells (TEM, decreased expression of CD62L, CCR7, CD28, CD45RA, and increased expression of CD127 as compared to naïve T cells or TCM).

T2 T cells are a subpopulation of T cells that generally express low amounts of HLA-A2 on the cell surface and are thought to only present exogenous peptides. Binding of exogenous peptides to HLA-A2 stabilizes the HLA-A2-peptide complexes.

CD8-positive T cells are a subpopulation of MHC class I-restricted T cells and are mediators of adaptive immunity. They include cytotoxic T cells, which are important for killing cancerous or virally infected cells, and CD8-positive suppressor T cells, which restrain certain types of immune response.

"NY-ESO-1" or New York esophageal squamous cell carcinoma 1 is a protein belonging to the family of Cancer Testis Antigens (CTA) that are expressed in a variety of malignant tumors. CTAs have been found to induce a spontaneous immune responses, with NY-ESO-1 being one of the most immunogenic among the family members.

"CD69" is one of the earliest cell surface antigens expressed by T cells following activation. Once expressed, CD69 acts as a costimulatory molecule for T cell activation and proliferation. In addition to mature T cells, CD69 is inducibly expressed by immature thymocytes, B cells, natural killer (NK) cells, monocytes, neutrophils and eosinophils, and is constitutively expressed by mature thymocytes and platelets.

TCR Variants

Advantageously, methods and compositions of the invention allow for the identification, expansion, optimization, and validation of variants of TCRs, having one or more amino acid substitutions in the alpha and/or beta chains of the TCR. Preferably, variants have substitutions within the CDR1 or CDR3 of the alpha and/or beta chain of the TCR.

In aspects of the invention, the TCR or a nucleic acid encoding a TCR may be at least about 85%, 87.5%, 90%, 95%, 97%, 98%, or 99% homologous to the identified active TCR or nucleic acid encoding the TCR. Also envisioned within the present disclosure are randomized polypeptide antigen truncations of TCRs that have 1, 2, 3, 4, 5, 6, 7, 8, 9, 10, 15, 20, or 25 amino acids truncated from the N-terminus or truncated from the C-terminus. For instance, the sequence FR1-a, FR2-a, FR3-a and FR4-a and FR1-b, FR2-b, FR3-b and FR4-b may differ from the reference sequences.

Modifications and changes may be made in the amino acid sequence of the antigen binding protein of the present invention, and in the DNA sequences encoding them, and still result in a functional antigen binding protein or polypeptide with desirable characteristics.

An antigen binding protein of TCR variants of the present invention preferably retain the antigen binding/recognizing ability of the parent molecule, in particular its specificity and/or selectivity as defined above, wherein the parent molecule may be either the parental TCR or, comprising the variable domains of said parental TCR. For instance, the sequence of the first variable domain may differ from the reference sequences as defined in i), ii) and iii), as appropriate, by at least one amino acid substitution(s), in particular by at least one conservative amino acid substitution(s) and/or substitution(s) with canonical residues. In particular, the sequences of the first and the second variable domain may differ from the reference sequences as defined in i), ii) and iii) by conservative amino acid substitution(s), only.

TCR variants are discussed in PCT International Publication No. WO 2021/144020, the entirety of which is incorporated by reference herein.

Libraries of variants and/or nucleic acid encoding variants are also envisioned by the present invention. The library may comprise antigen binding regions with specific or randomized positions or variation in one or more CDR regions. Conventional methods of assembling the coding sequences can be used. In order to generate the diversity of peptide ligands, randomization, error prone PCR, mutagenic primers, and the like as known in the art, are used to create a set of polynucleotides. In various embodiments the library is provided as a purified polynucleotide composition encoding polypeptides.

TOR Mutations

TCRs of the invention may include optimized CDRs, for example with mutations such as knobs-into-holes (KiH) mutations and effector null mutations.

In KiH mutations, a "knob" is created by replacing an amino acid, for example T366, with a bulky residue, such as W, on one heavy chain, and a corresponding "hole" on the partner light chain. For example, a hole may be created using the triple mutations of T366S, L368A and Y407V on the partner HC. Knob-into-holes mutations that may be used with the present invention are described in U.S. Pat. Nos. 7,183,076; 7,951,917; 8,642,745; 8,765,412; and 9,409,989, the contents of each of which are herein incorporated by reference in their entirety.

In effector null mutations, point mutations may be inserted in the lower hinge and/or N-terminal end of the heavy chain, for example a CH2 domain. Polypeptides with effector null mutations are limited in their ability to bind and stimulate effector functions, such as immune system recruitment. Effector null mutations may provide the advantage of limiting toxicity caused by upregulation of an endogenous immune response. Effector null mutations that may be used with the present invention are described invention are described in U.S. Pat. Nos. 8,969,526; 10,093,714; and 11,046,776, the contents of each of which are herein incorporated by reference in their entirety.

Cellular Therapy Products

The engineered T-cells of the present invention may be administered as a cellular therapy product. The cellular therapy product may be a population of cells including a genetically-engineered T-cell.

The population of cells can be homogeneous or heterogeneous. A cellular therapy product can further include one or more cell media components, for example buffers, antibiotics, salts, vitamins, growth factors, amino acids and/or therapeutic compounds to maintain the population of cells and/or treat a disease. For example, a cellular therapy product can include a genetically-engineered T-cell and an antibiotic. Cellular therapy products can further include additional therapeutic agents. Additional therapeutic agents and pharmaceutical reagents and/or excipients suitable for therapeutic application can also be included in contemplated cellular therapy products. Additional reagents may also be included in cellular therapy products.

Cells can be taken from an individual (autologous source) to be treated, genetically-modified, and introduced (e.g., by injection) back into the individual to. In one embodiment, such a cellular therapy product can be derived from an apheresis product taken from the individual. In another embodiment, a cellular therapy product intended for an individual can be derived from an apheresis product taken from another individual (heterologous source) or from another cell source.

The source of T-cells may be a concentrated solution generated by fractionating peripheral blood obtained from the patient. Fractionating peripheral blood comprises preparing a suspension of peripheral blood mononuclear cells (PBMCs) and inducing the PBMCs to differentiate into macrophages. Preparing a suspension of PBMCs from peripheral blood can be performed by any method commonly known in the art. PBMCs may be prepared by gradient centrifugation. In gradient centrifugation, whole blood is then gently overlayed onto a tube and centrifuged. After centrifugation, there remains a pellet of red blood cells, a white layer comprising PBMCs, and a plasma layer. The white layer comprising PBMCs can then be removed from the tube.

The culture medium to be used may be a basic culture medium containing components (inorganic salts, carbohydrates, hormones, essential amino acids, non-essential amino acids, and vitamins) and the like required for the cell's viable growth. Examples of the culture medium include Dulbecco's Modified Eagle's Medium (DMEM), Minimum Essential Medium (MEM), Basal Medium Eagle (BME), Dulbecco's Modified Eagle's Medium: Nutrient Mixture F-12 (DMEM/F-12), Glasgow Minimum Essential Medium (Glasgow MEM), the culture sold under the trade name GIBCO RPMI 1640 culture medium and manufactured by Life Technologies, HL-1 known composition, serum-free culture medium, and the like. In the culturing process, the culture medium may be suitably replaced with a new one according to the growth rate of the cells.

In addition, a compound inducing the differentiation of or trait of the T-cell may be added to the culture medium to be used. By adding the compound, the rate of differentiation or trait change can be further accelerated, and differentiation or trait can be controlled in a certain direction. Examples of compounds that trait-induce the macrophage into the M1- type macrophage include Thl cytokines such as interferon (IFN)-y, tumor necrosis factor (TNF)-a, lipopolysaccharide (LPS) and the like, and two or more of these compounds may be used in combination. In addition, examples of compounds that trait-induce the macrophage into the M2-type macrophage include Th2 cytokines such as interleukin (IL)-4 and IL-13, and two or more of these compounds may be used in combination. In addition, the compounds trait-inducing into the Ml macrophage and the compounds trait-inducing into the M2 macrophage may be used in combination.

Administration of genetically-engineered T-cells can be through any means generally accepted for the administration of cells to an individual, for example intravenously. In some embodiments, genetically-engineered macrophages can be introduced into an individual in need thereof by portal vein injection, intracardiac injection, or intravenous (IV) injection.

The cells may be provided frozen. Consequently, the cells may contain a cryoprotectant. Any cryoprotectant known in the art may be used. For example and without limitation, the cryoprotectant may be DMSO, dextran having an average molecular weight of 40 kDa, serum, e.g., bovine serum, albumin, e.g., human serum albumin, or cell culture medium. The cryoprotectant may be present at a defined concentration. For example, the cellular product may contain about 1% DMSO, about 2% DMSO, about 5% DMSO, about 7.5% DMSO, about 10% DMSO, about 12.5% DMSO, about 15% DMSO, or about 20% DMSO. The cellular product may contain about 1% dextran, about 2% dextran, about 5% dextran, about 7.5% dextran, about 10% dextran, about 12.5% dextran, about 15% dextran, or about 20% dextran. Cryoprotection is discussed in each of Strober et al., U.S. Pat. No. 9,504,717 and Strober et al., U.S. Pat. No. 9,561,253, the contents of each of which are incorporated by reference herein in their entirety.

The cellular composition can be supplied in the form of a pharmaceutical composition, comprising an isotonic excipient prepared under sufficiently sterile conditions for human administration. Choice of the cellular excipient and any accompanying elements of the composition is adapted in accordance with the route and device used for administration. For general principles in medicinal formulation, see Cell Therapy: Stem Cell Transplantation, Gene Therapy, and Cellular Immunotherapy, by G. Morstyn & W. Sheridan. eds., Cambridge University Press, 1996, and Hematopoietic Stem Cell Therapy, E. D. Ball, J. Lister & P. Law, Churchill Livingstone, 2000, the entirety of the contents of each of which are incorporated by reference herein.

An engineered T-cell of the invention may be incorporated into carrier systems containing one or more of the therapeutic compositions described herein. In certain embodiments, the carrier system can be a nanoparticle that includes disulfide-crosslinked polyethyleneimine (CLPEI) and a lipid. The lipid may be a bile acid, such as cholic acid, deoxycholic acid, and lithocholic acid. Other exemplary carrier systems are described for example in Wittrup and Lieberman (2015) "Knocking down disease: a progress report on siRNA therapeutics", Nat Rev Genet, 16 (9): 543-552, the contents of which are incorporated by reference herein in their entirety.

The effective amount of the engineered T-cell can readily be determined by the skilled person, having regard to typical factors each as the age, weight, sex and clinical history of the patient. In general, a suitable daily amount of the composition of the invention will be that amount of the T-cell which is the lowest amount effective to produce a therapeutic effect. Such an effective amount will generally depend upon the factors described above.

If desired, the effective daily amount of the engineered T-cells may be administered as two, three, four, five, six or more sub-doses administered separately at appropriate intervals throughout the day, optionally, in unit dosage forms.

A therapeutically effective amount of the engineered T-cells of the present invention may vary according to factors such as the disease state, age, sex, and weight of the subject, and the ability of the engineered T-cells to elicit a desired response in the subject. A therapeutically effective amount is also one in which any toxic or detrimental effects of the composition are outweighed by the therapeutically beneficial effects.

It is especially advantageous to formulate parenteral compositions in dosage unit form for ease of administration and uniformity of concentrations. Actual levels of the engineered T-cells in the compositions of this invention may be varied so as to obtain an amount of the engineered T-cells which are effective to achieve the desired therapeutic response for a particular subject, composition, and mode of administration, without being toxic to the patient.

EXAMPLES

Tetramer Sorting

Endogenous TCRs specific to NY-ESO-1/HLA-A2 were identified from patient samples. 47 patient PBMC samples were screened with 23 HLA-A2+ samples identified. Following dual color NY-ESO-1/HLA-A2 tetramer staining, 483 single cells were sorted from the 23 patients. Single cells were sequenced using the kit sold under the trade name TAKARA SMARTer scVDJ. From these sequenced cells, 210 unique TCR alpha/beta pairings were identified.

FIG. 1 shows the flow cytometry gating scheme used for single-cell tetramer sorting of cells from patient peripheral blood samples.

TCR Expansion

In order to identify strongly active TCRs, TCRs were expanded and sorted over a period of 25 to 45 days period in the presence of dendritic cells (DC) cultured with target NY-ESO-1 peptides.

Figure 2:
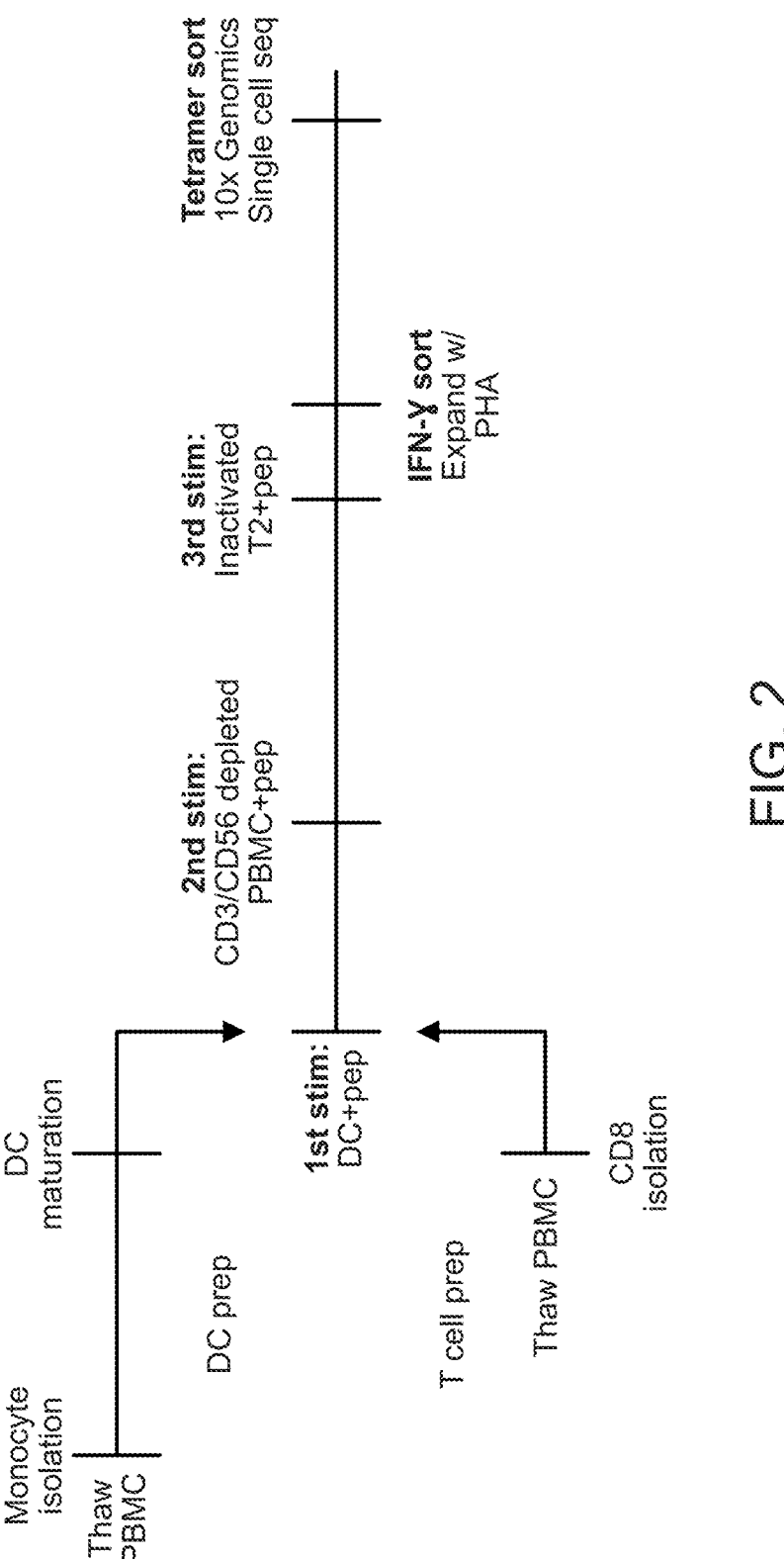
FIG. 2 depicts an exemplary TCR Expansion work-flow according to the invention.

FIG. 2 depicts an exemplary TCR Expansion work flow according to the invention.

Monocytes were isolated from a first portion of PBMCs, and these monocytes were differentiated into DCs and then matured. CD8+ T-cells were also isolated from a second portion of PBMCs. The matured DCs were cultured together with the NY-ESO-1 peptide. In a first stimulation round for the T-cells, the NY-ESO-1 peptide-pulsed DCs were co-cultured with the isolated CD8+ T-cells.

After between 5 and 15 days, in a second stimulation round, a third portion of PBMCs is depleted for natural killer cells and T cells, preferably by depleting CD3+ and CD56+ cells, and this depleted PBMC sample is incubated with the target peptide and then added to the culture containing expanding T cells. Following another 5 to 15 days, in a third stimulation round, T2 cells are inactivated by mitomycin C and incubated with target peptide, and then added to the culture containing expanding T cells.

Within a five day period, the culture is then sorted for IFN-γ secreting cells and expanded with phytohemagglutinin (PHA).

After a final 5 to 15 day period, the cells are stained using NY-ESO-1/HLA-A2 tetramers, sorted based on tetramer staining intensity, and sequenced. Remarkably, highly active T-cells are identified within this expedited time frame. T cells can be sorted by any known method, for example 10× Genomics single cells sequencing, including droplet sequencing and FACS sorting. TCRs can be sequenced by any known sequencing method, for example next generation sequencing (NGS), including for example using protocols developed by Illumina, for example using the product sold under the trade name HISEQ.

PBMCs were obtained from patients with grade III/IV melanoma or lung cancer, previously treated with checkpoint inhibitors. Patients were not pre-screened for immunity to NY-ESO-1. PBMCs had low started T cell numbers, for example, for DLScpiLUN29, the CD8 population was 900k; for DLScpiLUN30, the CD8 population was 300k; and for DLScpiMEL25, the CD8 population was 500k.

Figure 3:
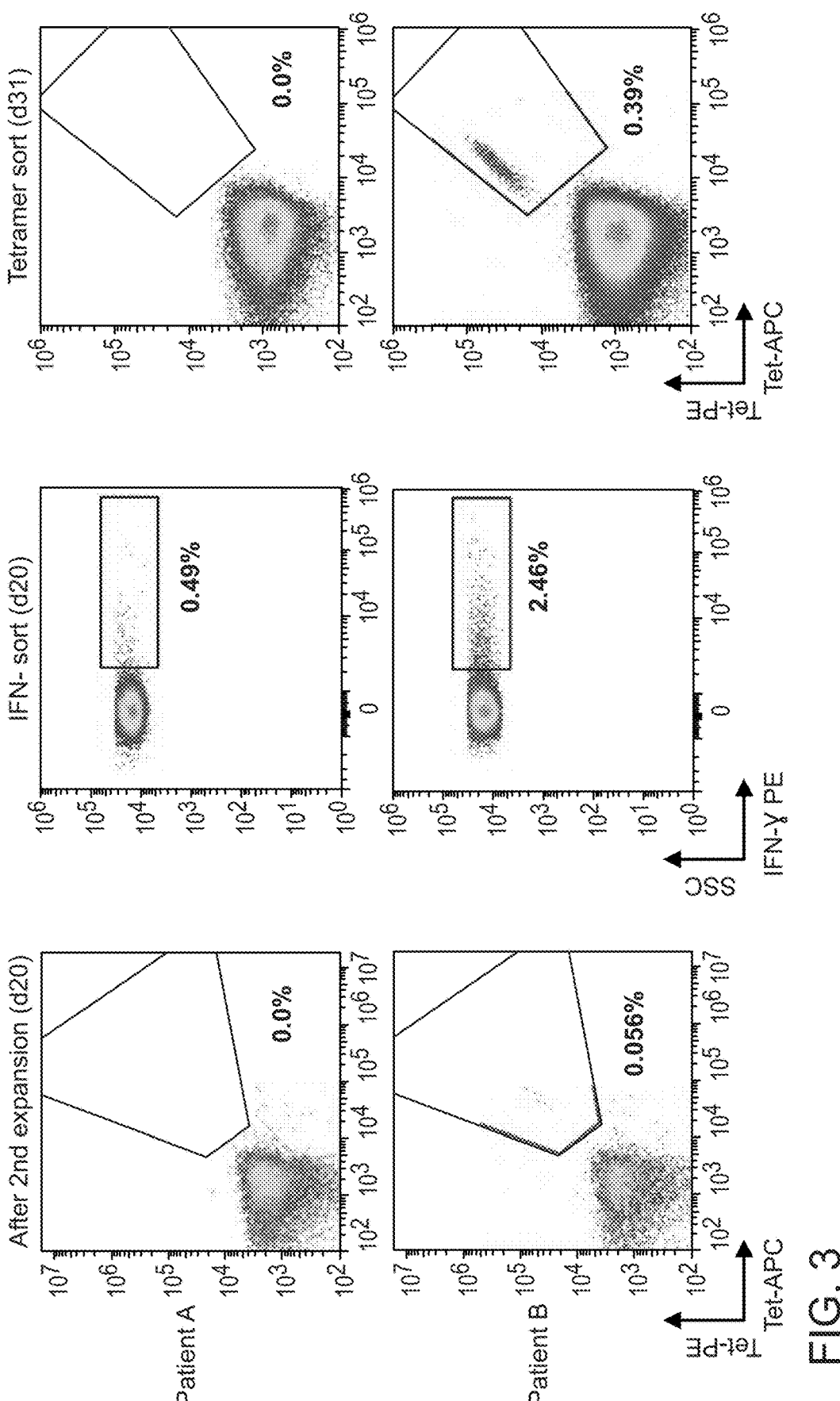
FIG. 3 shows flow cytometry results tracking the progress of TCR Expansion for two patients.

FIG. 3 shows flow cytometry results tracking the progress of TCR Expansion for two patients.

Blood from Patient A did not produce any NY-ESO-1 reactive T cells at the end of the expansion procedure, whereas blood from Patient B did produce NY-ESO-1 reactive T cells. Notably, identified from Patient B was the NY7 TCR discussed below.

TCR Validation

TCRs identified by the Tetramer Sorting or TCR Expansion methods described above were validated for activation by NY-ESO-1. Previous approaches to validation utilized lentivirus vectors which proved to be slow and cumbersome for gene delivery and validation.

Jurkat cells were electroporated with plasmid DNA encoding, in order:

—a TCRβ—a 2A peptide—a TCRα—IRES—LNGFR—

Transfected cells were cocultured with T2 cells and NY-ESO-1 peptide. After 20-24 hours of culturing, expression of the activation marker CD69 was assessed.

Figure 4:
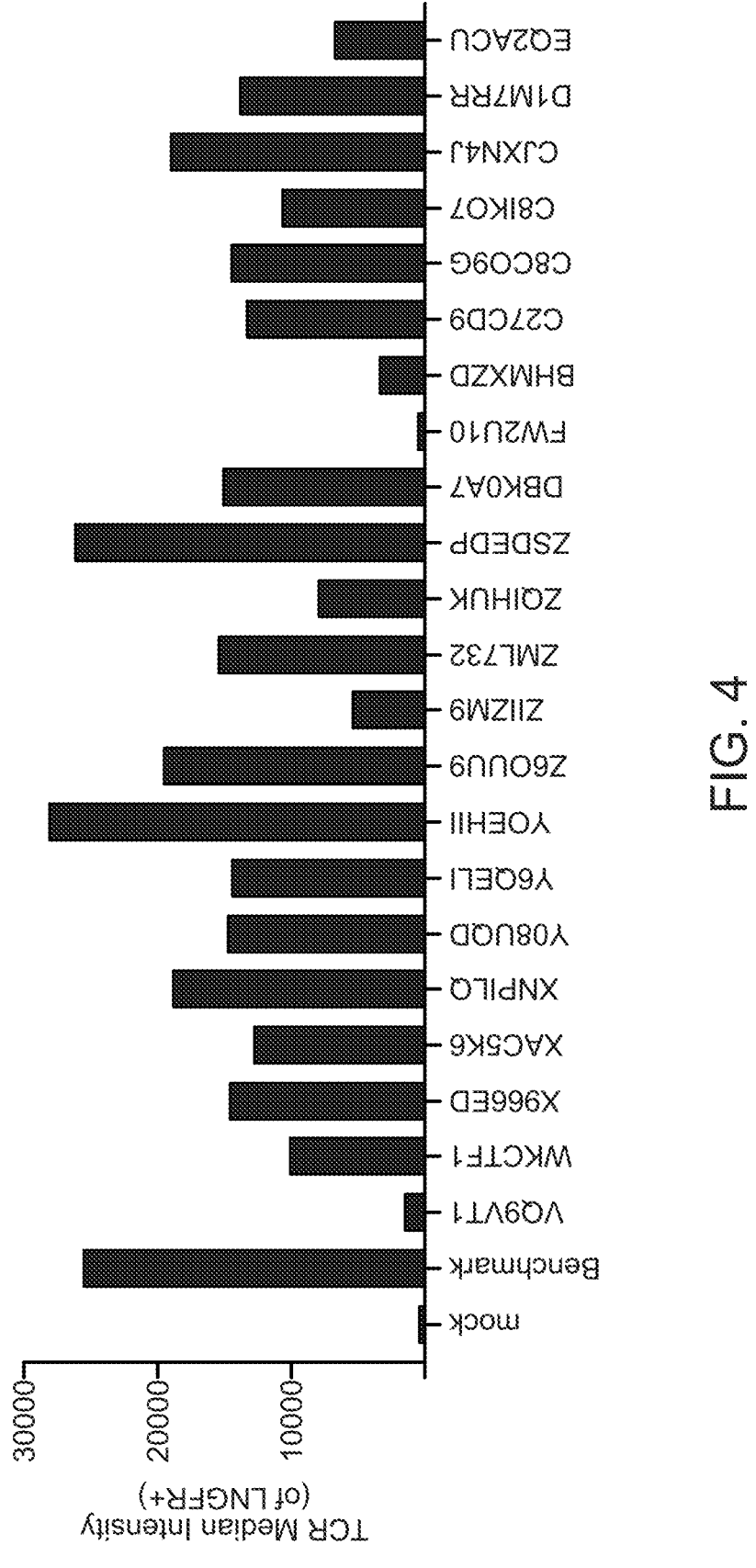
FIG. 4 shows TCR cell surface expression from Jurkat cells transiently transfected with TCR plasmid DNA.

FIG. 4 shows TCR cell surface expression from Jurkat cells transiently transfected with TCR plasmid DNA Co-expression of the cell surface marker LNGFR allowed for quick validation of transfection by the plasmid as well as quantification of TCR cell surface expression on transfected cells, which can be influenced by alpha and beta chain pairing and the quality of the transfected DNA. This resulted in a greatly decreased gene delivery time in comparison with lentiviral vector delivery, allowing for both high sensitivity and TCR validation speed, even in view of more moderated cell viability. For these experiments, the Jurkat cells lacked expression of endogenous TCR alpha and beta chains, allowing for specific detection of the ectopically expressed TCR.

Figure 5:
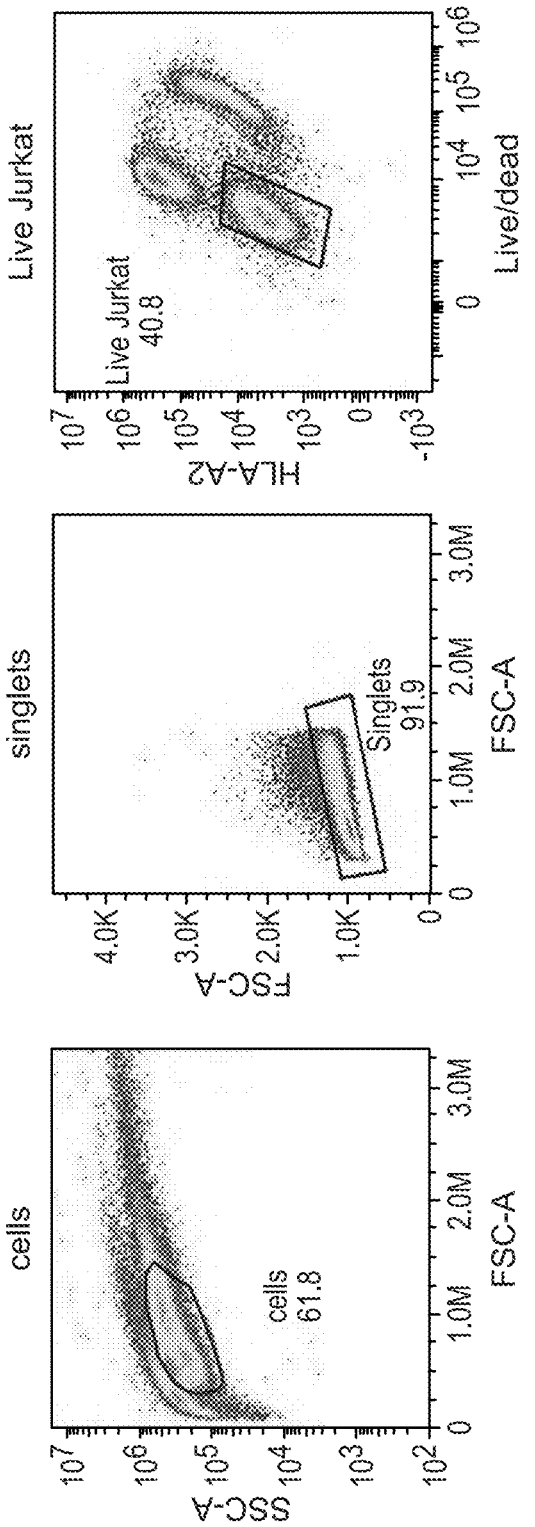
FIG. 5 shows the flow cytometry gating scheme used to measure CD69 expression on Jurkat cells transfected with TCR plasmid DNA
Figure 5:
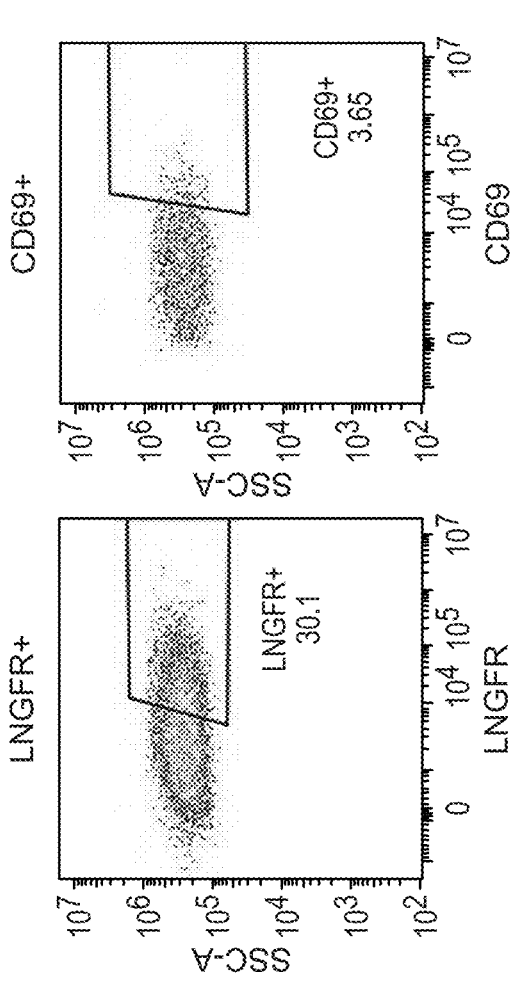

FIG. 5 shows the flow cytometry gating scheme used to measure CD69 expression on Jurkat cells transfected with TCR plasmid DNA.

Gating on live cells and LNGFR+ cells ensures that the sensitivity of CD69 detection is not adversely impacted by total cell viability or transfection efficiency.

Of the 210 TCRs identified by NY-ESO-1/HLA-A2 tetramer staining, only 27 were found to be activated by NY-ESO-1 peptide in the Jurkat CD69 activation assay. This speaks to the importance of functional validation of TCRs identified by peptide-HLA tetramer staining.

Figure 6:
FIG. 6 shows results from an exemplary NY-ESO-1 reactivity screen.

FIG. 6 shows results from an exemplary NY-ESO-1 reactivity screen for TCRs.

Figure 7:
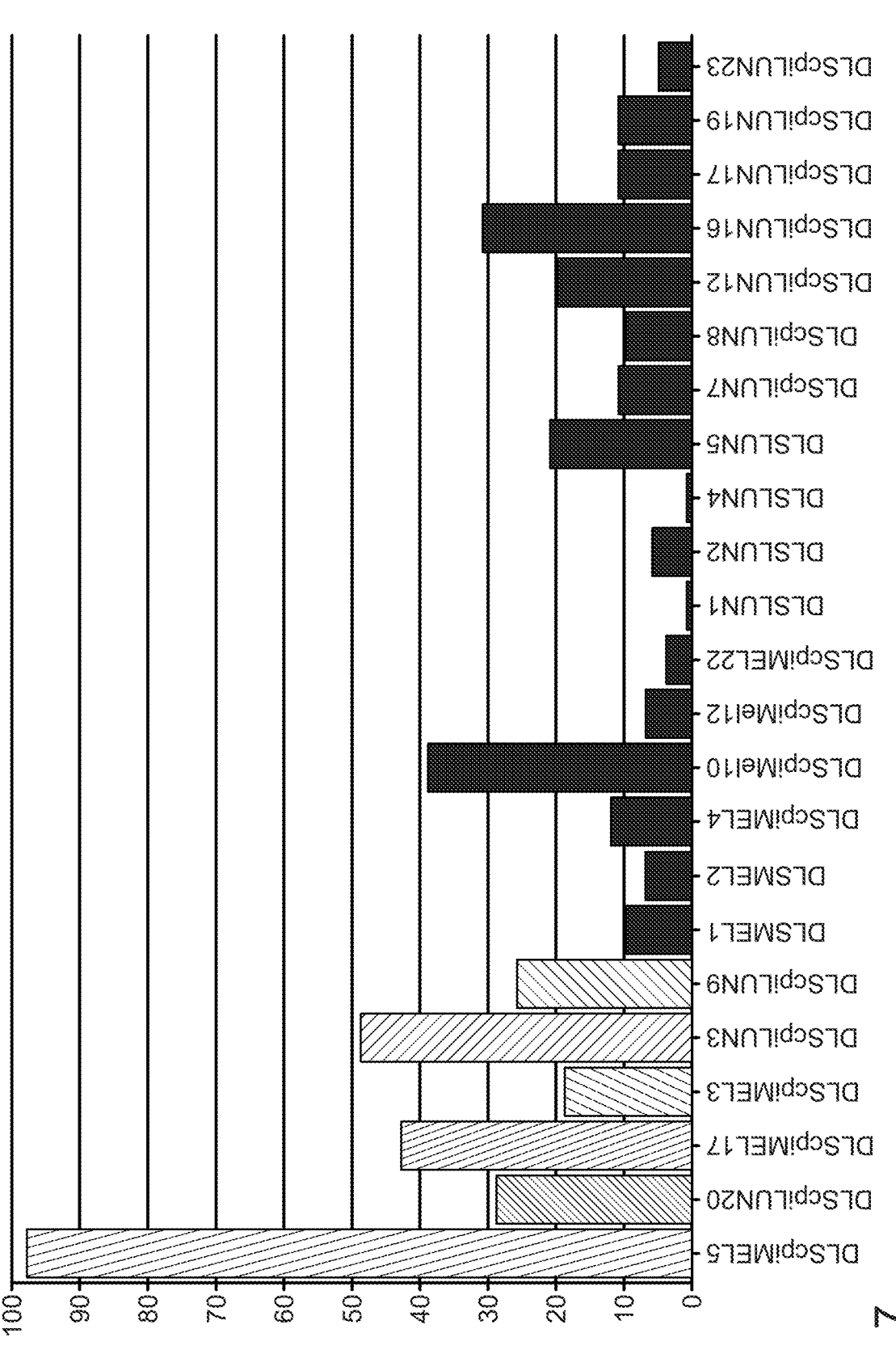
FIG. 7 shows the number of NY-ESO-1/HLA-A2 tetramer-binding T cells sorted from each of 23 patient samples.

FIG. 7 shows the number of NY-ESO-1/HLA-A2 tetramer-binding T cells sorted from each of 23 patient samples.

Figure 8:
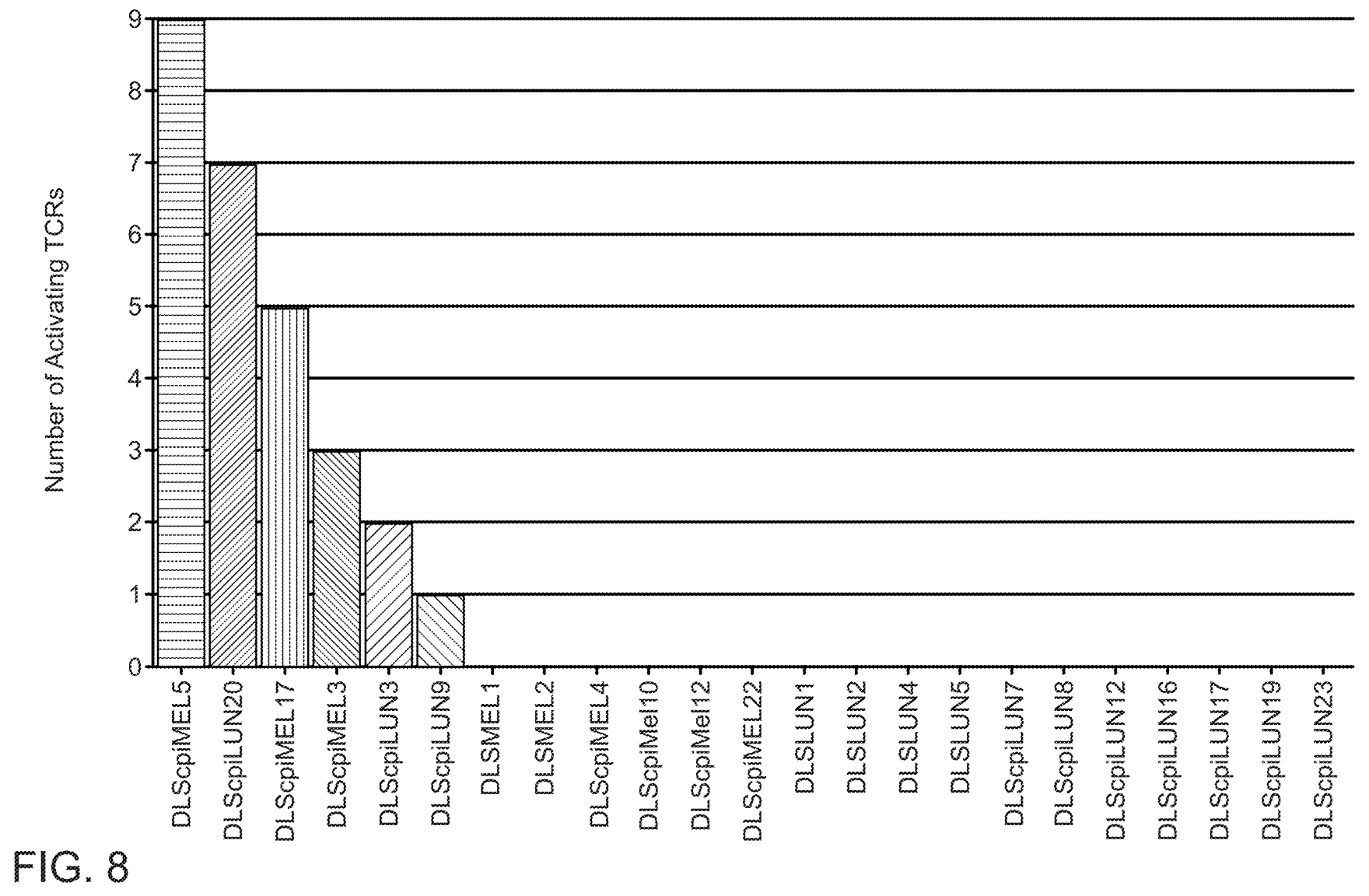

FIG. 8 shows the number of NY-ESO-1-activated TCRs obtained from each of 23 patient samples.

Of the 23 patients from which NY-ESO-1/HLA-A2 tetramer-binding cells were obtained, only 6 patients (26%) yielded TCRs that were activated by NY-ESO-1. This speaks to the importance of the TCR Validation assay to identify functional TCRs.

To measure peptide-dose response, mRNA electroporation was used, with mRNA encoding:

—a TCRβ—a 2A peptide—a TCRα— mRNA electroporation provided the advantages of higher TCR expression and improved cell viability. This enabled more quantitative measurements of TCR potency. Advantageously, mRNA was introduced into cells more efficiently than DNA, which eliminated the need for the LNGFR marker to gate on transfected cells. Further, because the Jurkat cells used express no endogenous TCR alpha or beta chains, transfection efficiency could be monitored by expression of TCR or CD3. Jurkat cells along with the TCR mRNAs were electroporated and rested and then cocultured with T2 cells and NY-ESO-1 peptide. After 20-24 hours of culturing, CD69 activation was assessed.

Figure 9:
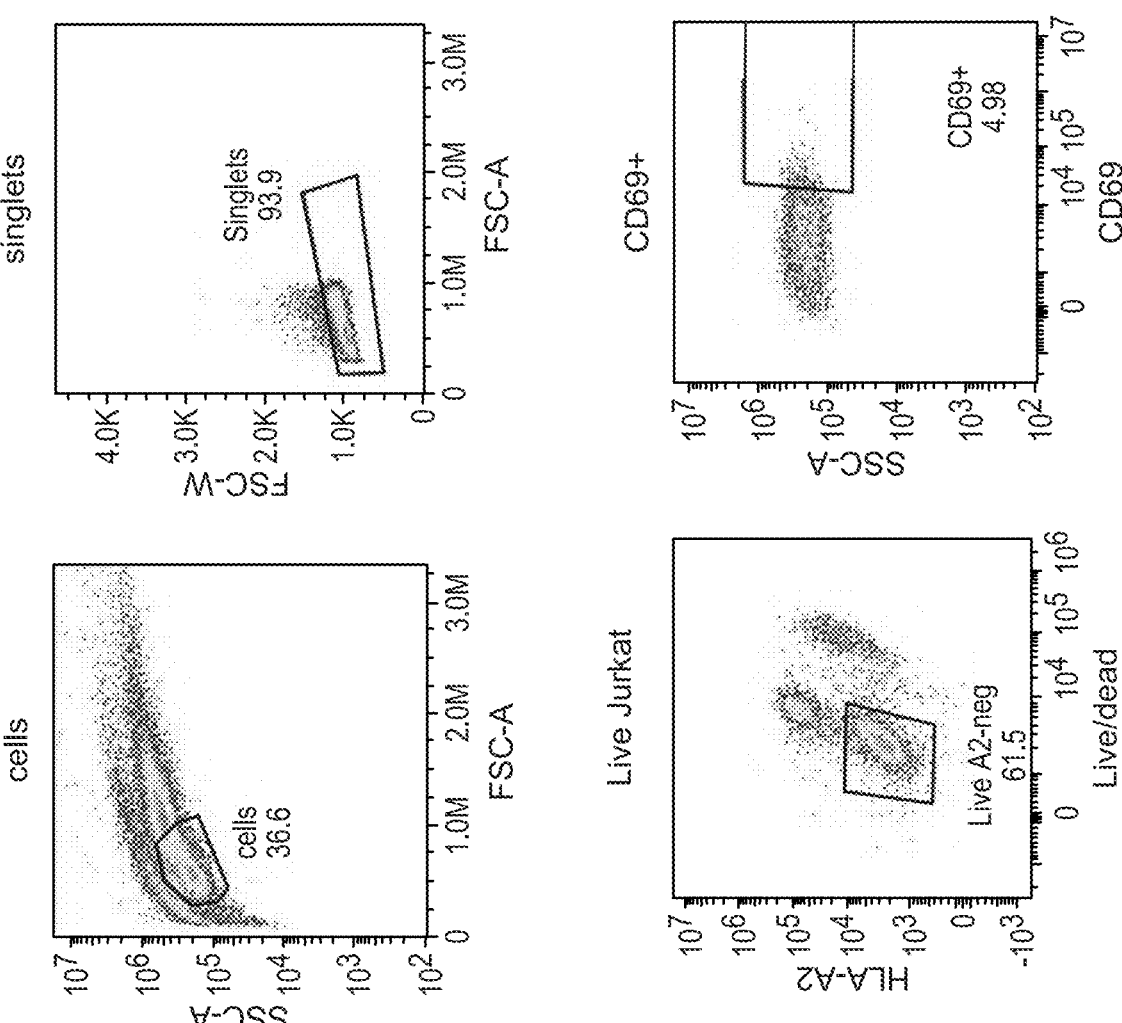
FIG. 9 shows the flow cytometry gating scheme used to measure CD69 expression on Jurkat cells transfected with TCR mRNA

FIG. 9 shows the flow cytometry gating scheme used to measure CD69 expression on Jurkat cells transfected with TCR mRNA.

Figure 10:
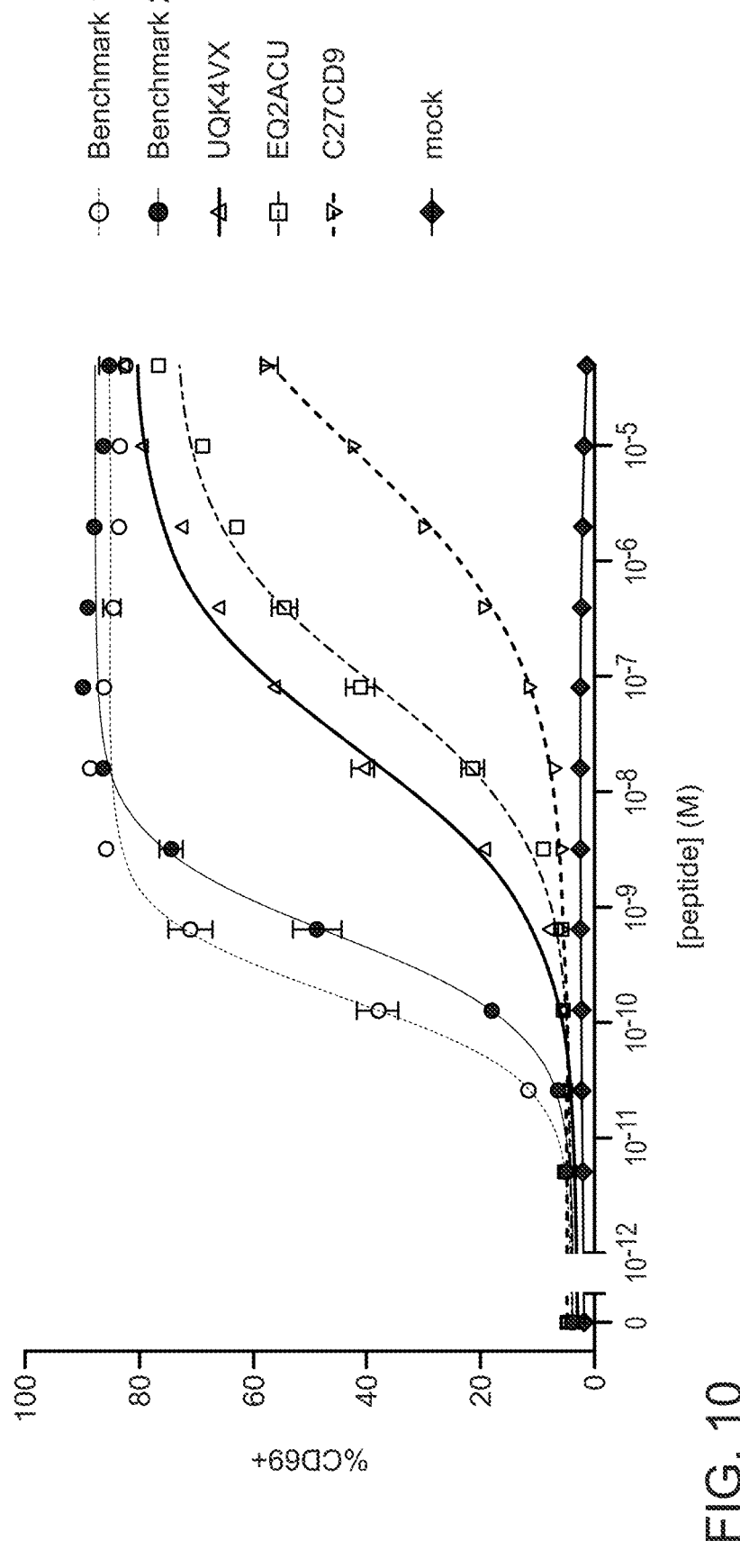
FIG. 10 shows a peptide dose response by CD69 activation for top TCRs expressed by mRNA transfection in Jurkat cells

FIG. 10 shows a peptide dose response by CD69 activation for top TCRs expressed by mRNA transfection in Jurkat cells.

Figure 11:
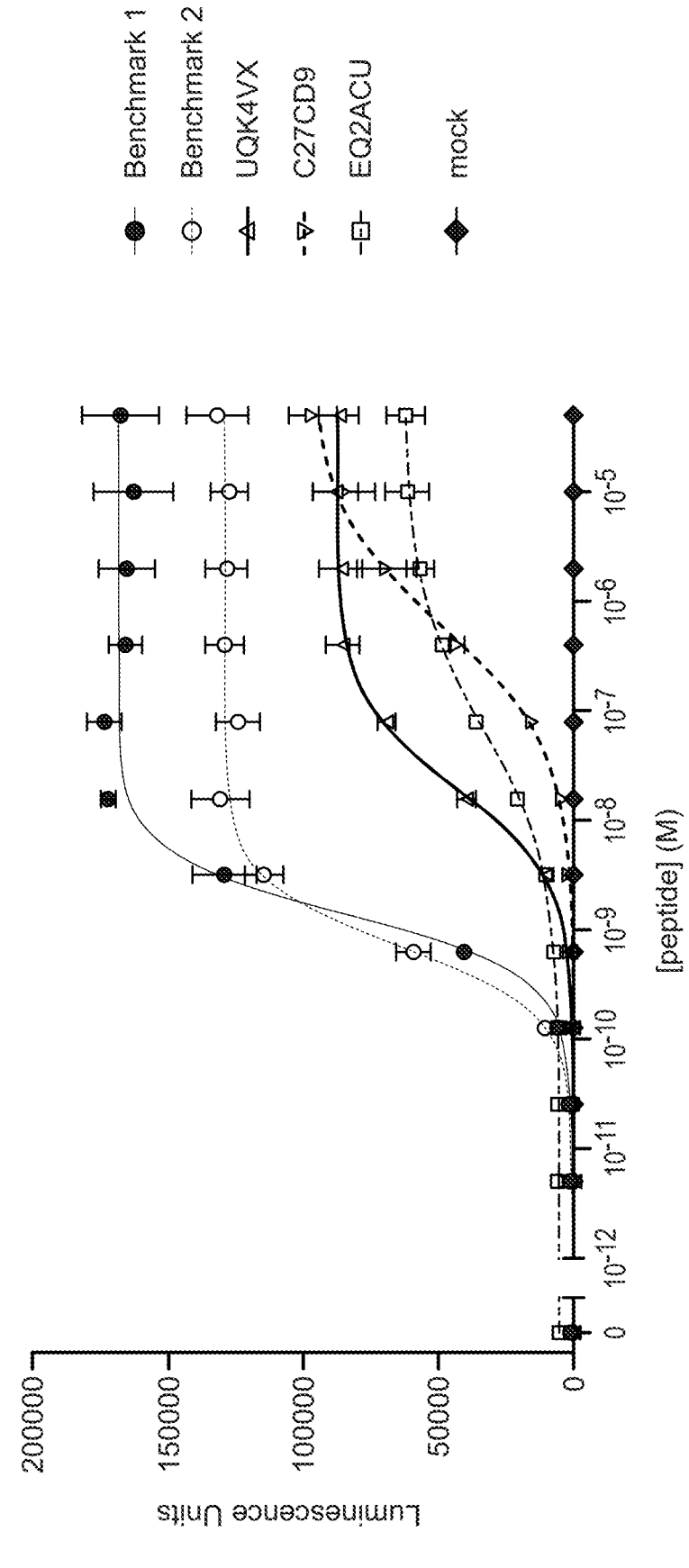
FIG. 11 shows a peptide dose response by NFAT-Luciferase activation for top TCRs expressed by mRNA transfection in Jurkat cells

FIG. 11 shows a peptide dose response by NFAT-Luciferase activation for top TCRs expressed by mRNA transfection in Jurkat cells.

Figure 12:
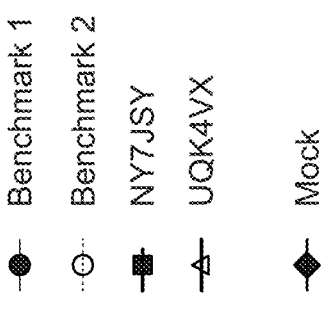
FIG. 12 shows a peptide dose response by NFAT-Luciferase activation for top TCRs expressed by mRNA transfection in Jurkat cells
Figure 12:
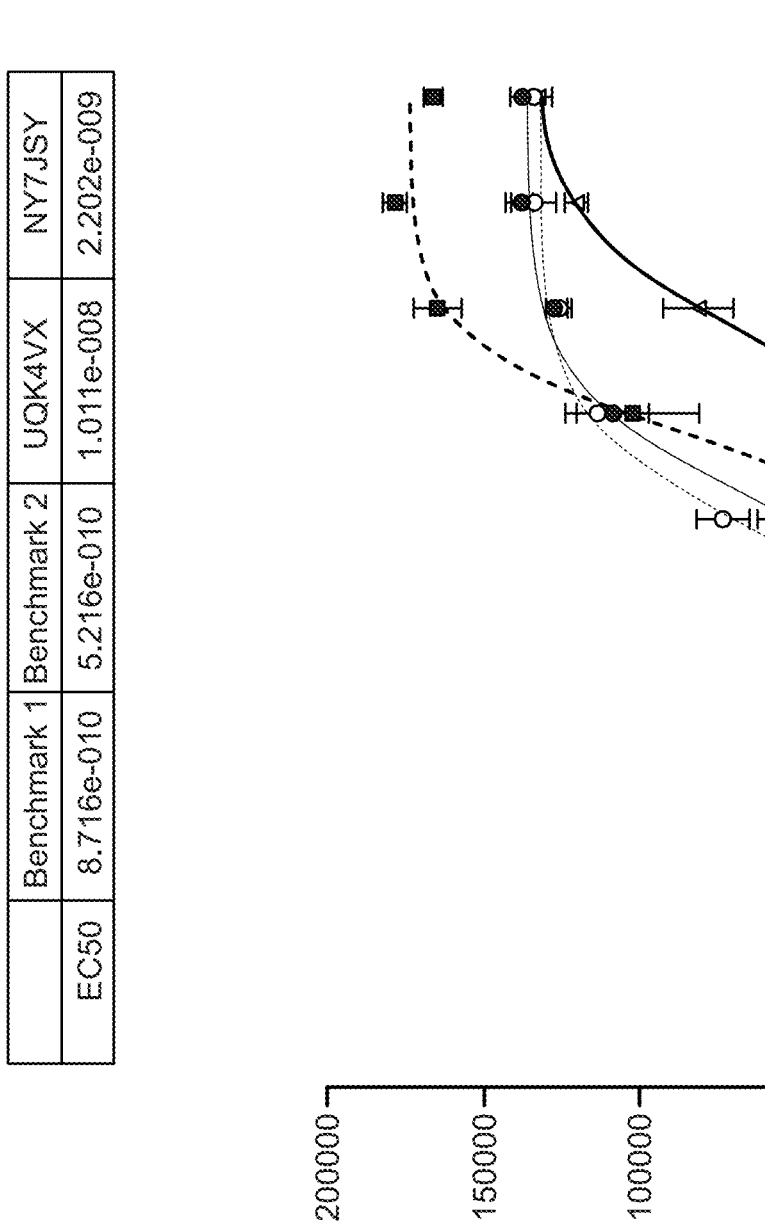

FIG. 12 shows a peptide dose response by NFAT-Luciferase activation for top TCRs expressed by mRNA transfection in Jurkat cells.

TCR Cross-Reactivity

In order to investigate cross-reactivity, top TCRs were screened for activity against a panel of peptides. This peptide panel included both peptide mimotopes (non-native peptide sequences which bind a TCR of interest), as well as off-target human peptides predicted to bind to each TCR.

Jurkat cells were electroporated with mRNA encoding each of six NY-ESO-1 TCRs identified by the tetramer sorting and TCR expansion methods described above (TCRs: NY7JSY, UQK4VX, EQ2ACU, C27CD9, OLXJA9, RW462M) or two benchmark TCRs as controls. Following mRNA electroporation and recovery, Jurkat cells were cocultured with T2 cells and off-target human peptides or peptide mimotopes to assess cross-reactivity. Activation was measured by luminescence from an NFAT-Luciferase reporter.

Figure 13:
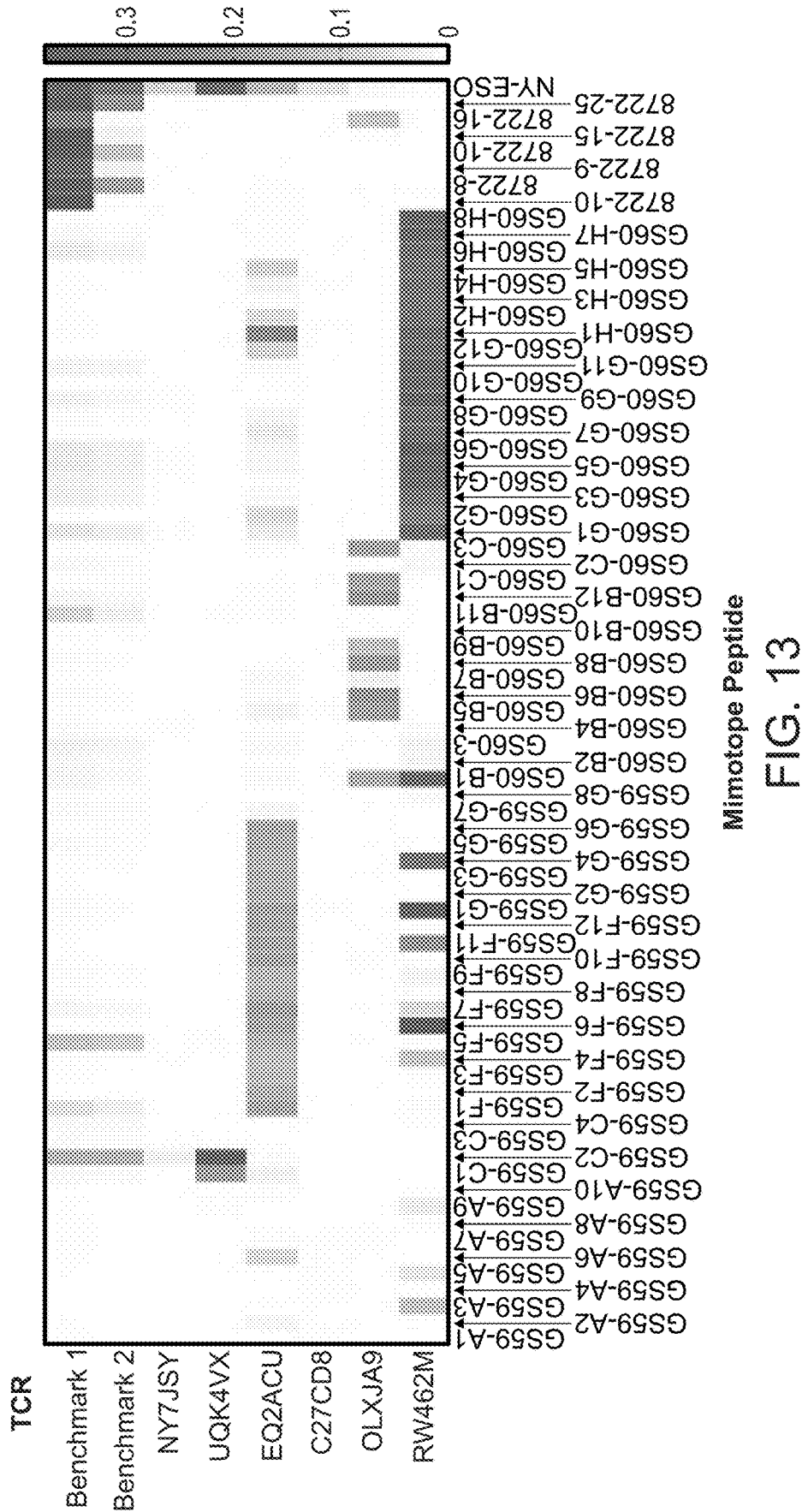
FIG. 13 shows results of a cross-reactivity screen against mimotope peptides

FIG. 13 shows results of a cross-reactivity screen against mimotope peptides.

Figure 14:
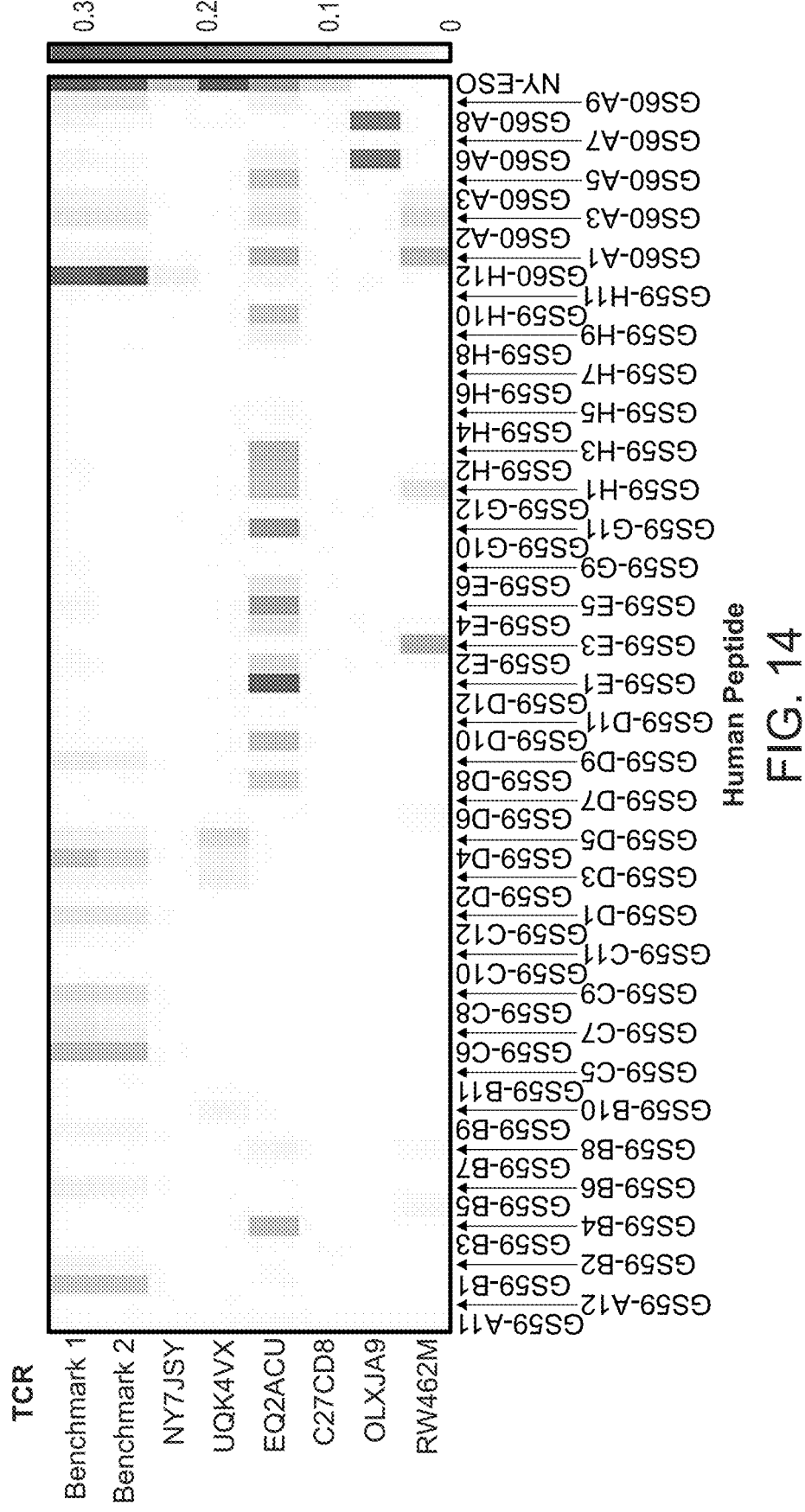
FIG. 14 shows results of a cross-reactivity screen against off-target human peptides
Figure 14:
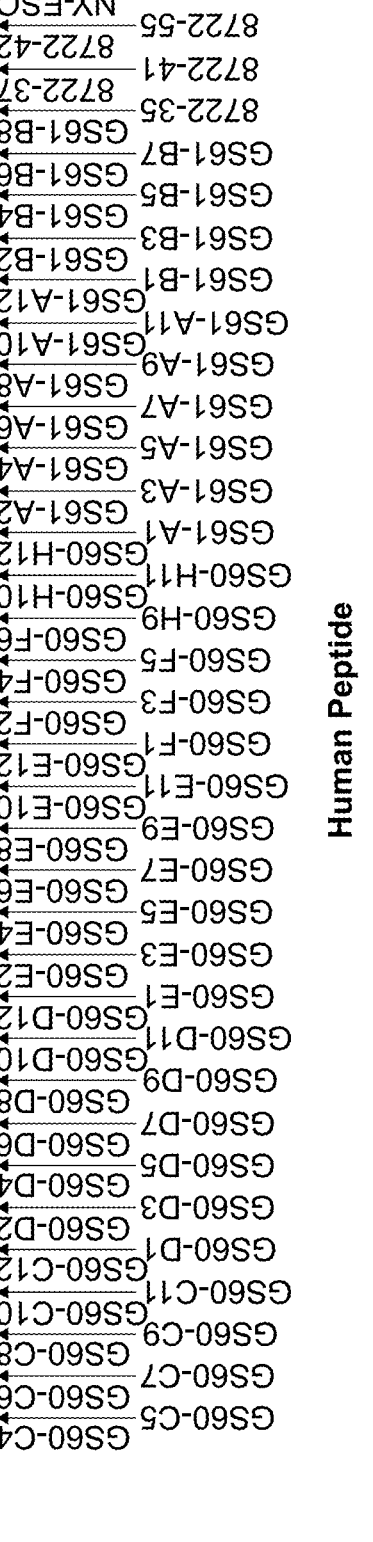

FIG. 14 shows results of a cross-reactivity screen against off-target human peptides.

Several off-target human peptides stimulated the Benchmark TCRs at low levels, and one peptide, GS59-H12 stimulated both TCRs to high levels.

TCR EQ2ACU exhibited some cross-reactivity to human off-target peptides, with one peptide, GS59-E1, activating it to a greater extent than the intended target NY-ESO-1.

TCRs UQK4VX, NY7JSY, and C27CD8 exhibited low levels of off-target reactivity.

TCR RW462M was broadly cross-reactive to many of the human off-target peptides tested, and displayed low reactivity to the intended target NY-ESO-1.

This demonstrates that TCRs isolated based on reactivity to a common target can display disparate patterns of cross-reactivity, speaking to the importance of a cross-reactivity assessment.

Figure 15:
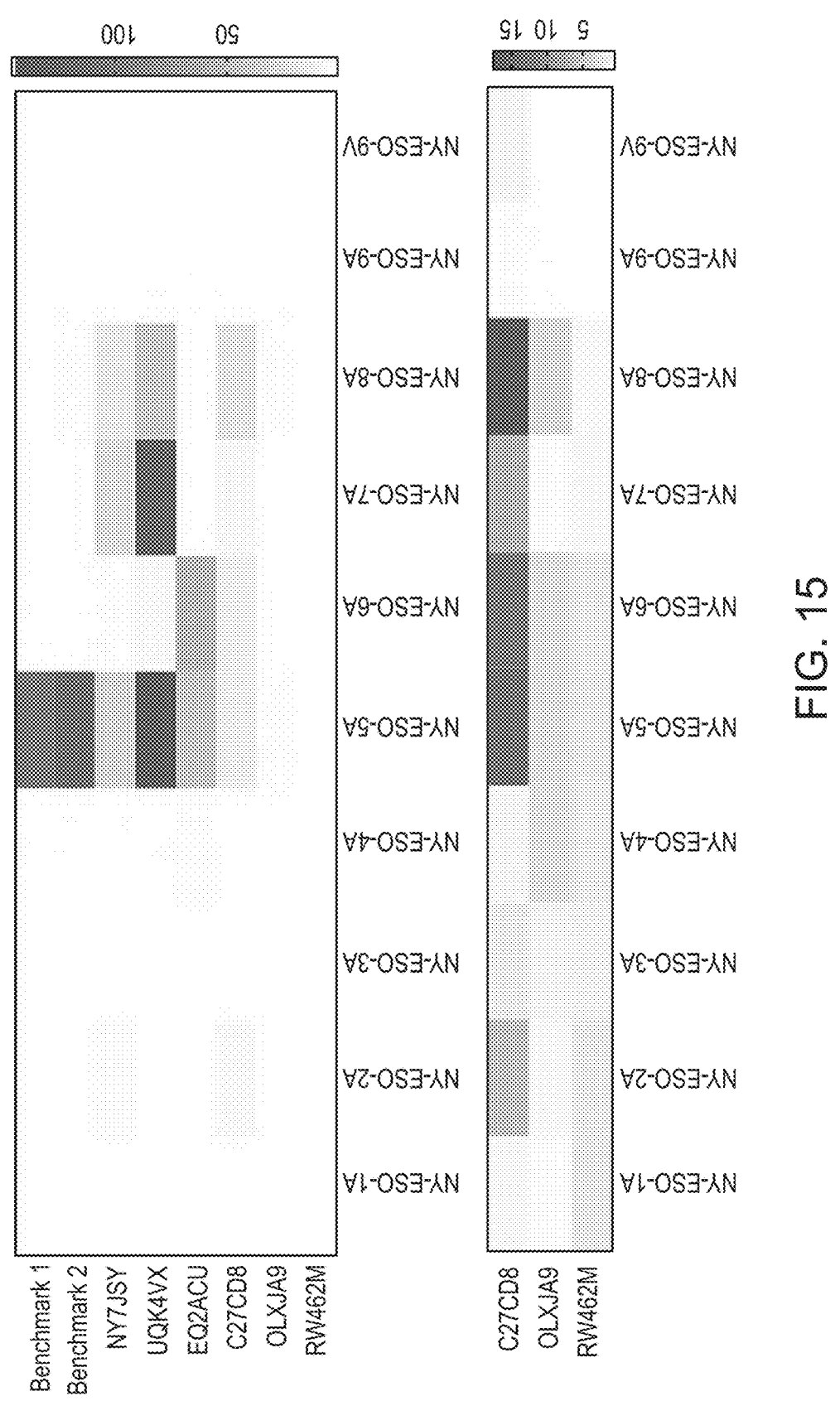
FIG. 15 shows results of an alanine scan of the NY-ESO-1 peptide with top NY-ESO-1 TCRs.

FIG. 15 shows results of an alanine scan of the NY-ESO-1 peptide with top NY-ESO-1 TCRs.

Alanine scans were further conducted to assess position dependence for recognition of the NY-ESO-1 peptide by top identified TCRs. Peptide position 5 was important for recognition by most of the TCRs tested. Beyond this critical residue, TCRs exhibited varying degrees of dependence on other peptide positions. For example, the two Benchmark TCRs depend solely on position 5 for peptide recognition, whereas EQ2ACU depends on positions 5 and 6, and UQK4VX and NY7JSY depend on positions 5, 7, and 8. The number of critical positions was generally inversely correlated with the amount of off-target activation, with the more specific TCRs depending on a larger number of peptide residues for recognition.

TCR Optimization I

With an understanding of critical positions of identified TCRs, variants were expressed and validated to optimize TCR activation and cross-reactivity.

Figure 16:
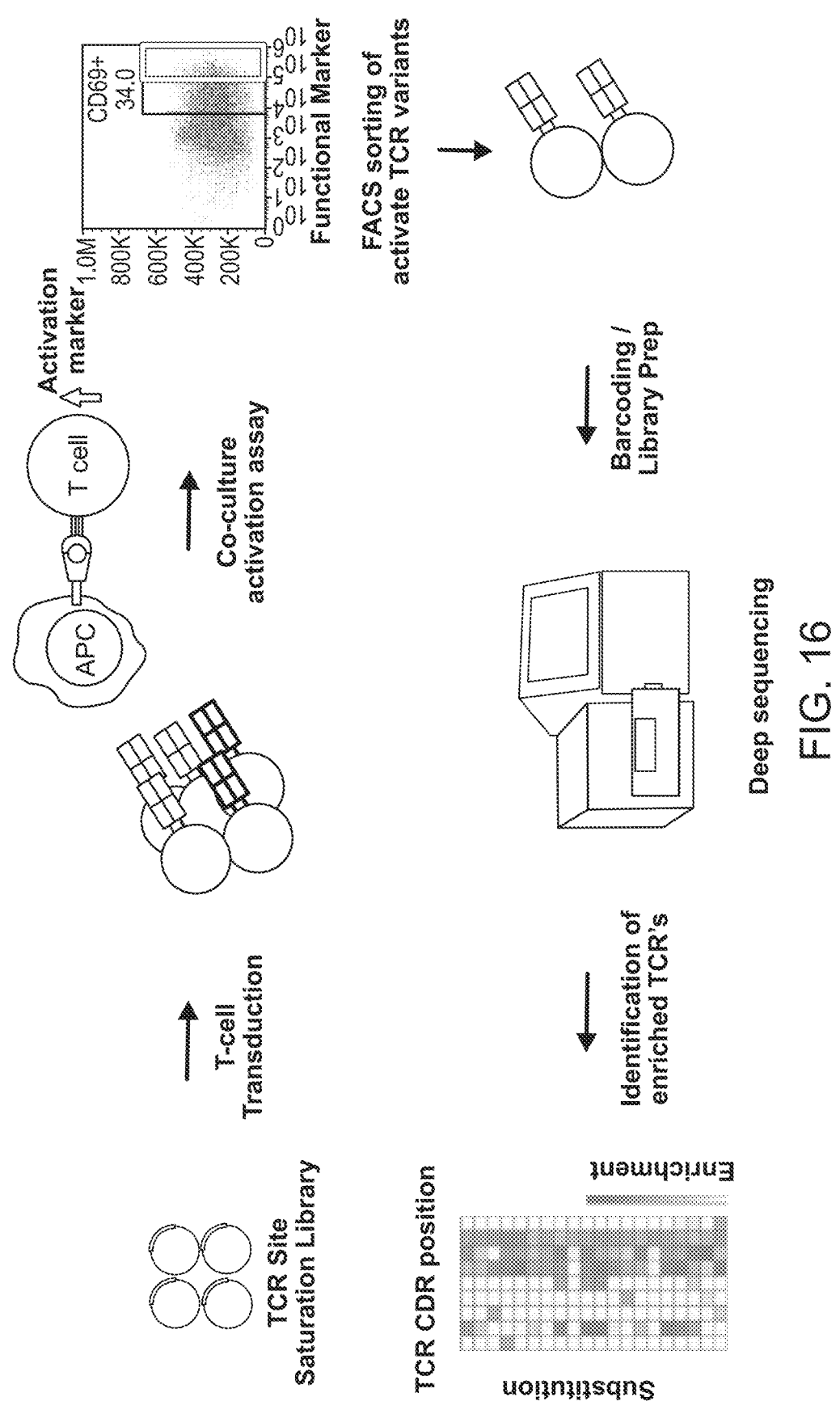
FIG. 16 depicts workflow for TCR optimization according to the invention.

FIG. 16 depicts a workflow for TCR optimization according to the invention.

A library of plasmids or mRNAs encoding TCR variants of an identified parent TCR was created. Each variant includes one or more amino substitution from the parent TCR, most preferably in the CDR1 or CDR3 of the alpha and/or beta chain.

T-cells were transduced with the library of identified TCR variants and co-cultured according to the expression assays of the invention. For example, as described above, DCs are prepared and cultured with a target peptide for the TCR variants, and the T-cells with the TCR variants are then co-cultured with the enriched DCs.

The cultured T-cells expressing the TCR variants are sorted, for example by FACS.

The sorted T-cells expressing the TCR variants are then barcoded and prepared for sequencing. Following sequencing of each T-cell, identification of the TCR variants expressed along with their specification substitutions are identified. The identified variants can then be validated for activation by the target peptide and cross-reactivity assays against non-target peptides.

TCR Variants—NY7JSY (Also Referred to as NY7)

Exemplary analysis of variants of NY7 were conducted, although the analysis is applied to all identified TCRs.

NY7 variants at 31 positions in the alpha and beta CDR1 and CDR3 sequences with 19 possible amino acids (all other than cysteine) were created, resulting in 589 variants.

The base NY7 sequence prior to substitution was as follows, with unsubstituted amino acids underlined.

Alpha Chain:

| CDR1 | CDR2 | CDR3 |
|---|---|---|
| DRGSQS (SEQ ID NO: 1) | IYSNGD (SEQ ID NO: 2) | AVMRAGGFKTI (SEQ ID NO: 258) |

Beta Chain:

| CDR1 | CDR2 | CDR3 |
|---|---|---|
| SGDLS (SEQ ID NO: 4) | YYNGEE (SEQ ID NO: 5) | ASSVVDGEQY (SEQ ID NO: 259) |

NY7 variants were divided into two samples, with one sample undergoing a first round of selection by NY-ESO-1 and the second sample undergoing a first round of selection by MART-1 as a negative control. The first sample (NY-ESO-1 selection round 1) was then further divided for a second round of selection by NY-ESO-1 or MART-1.

Figure 17:
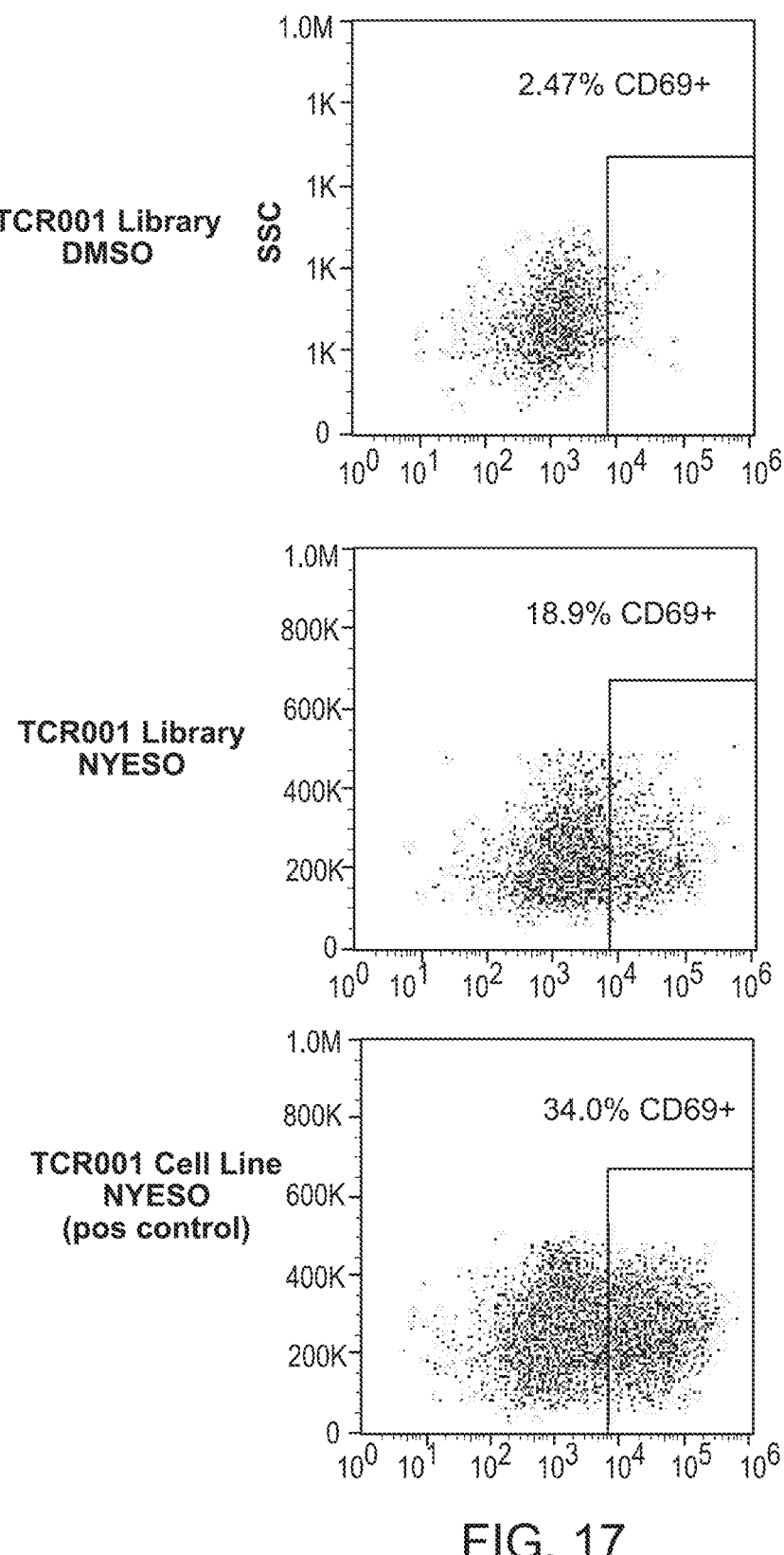
FIG. 17 shows results for NY7 TCR variant library and control parental cell line CD69 activation for DMSO and NY-ESO-1.

FIG. 17 shows results for NY7 TCR variant CD69 activation for DMSO and NY-ESO-1, for both variant library and cell line NY7. The NY7 library had diminished activity, indicating that some of the variant diversity impaired NY7 function.

Figure 18:
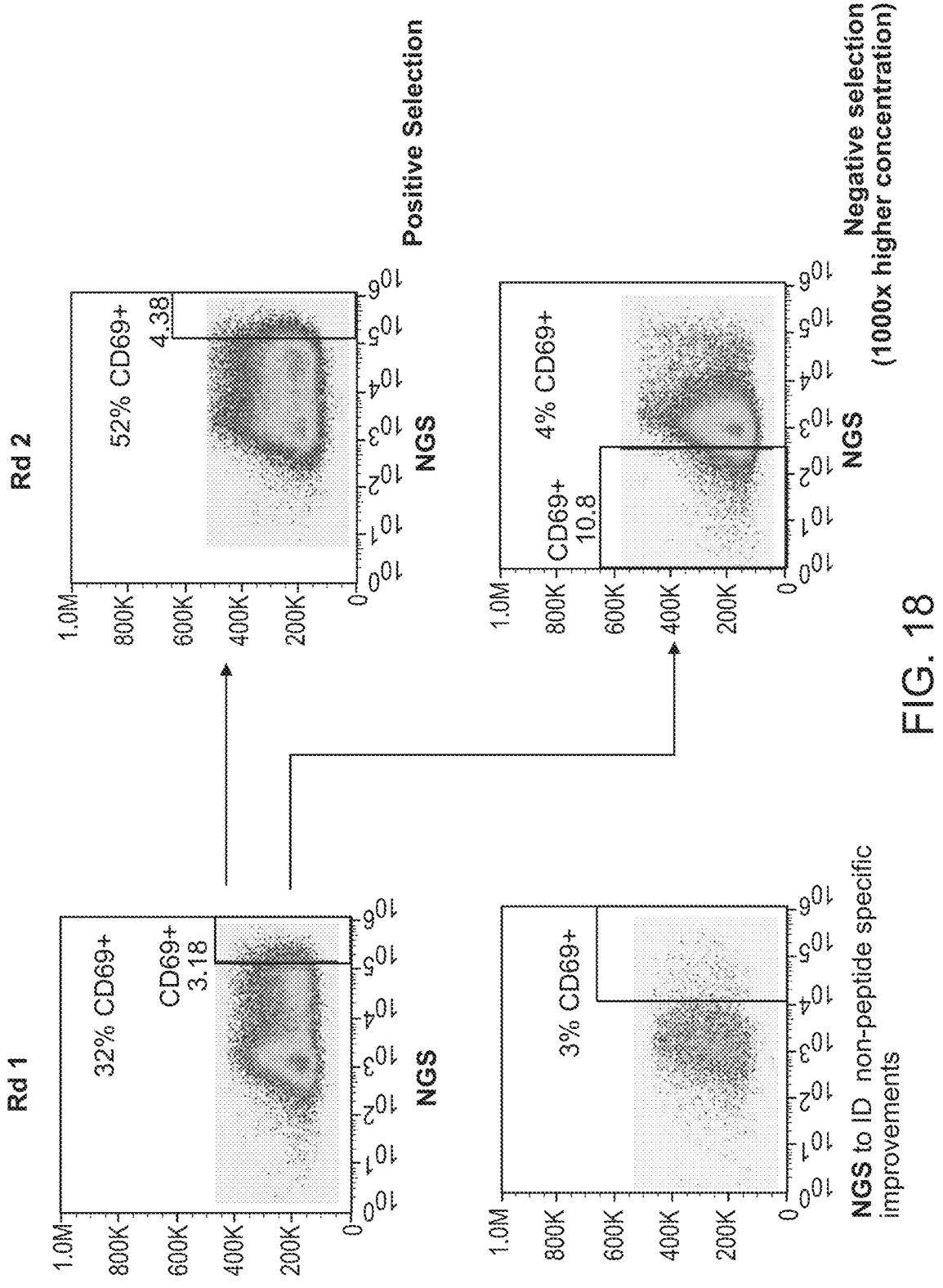
FIG. 18 shows results for negative (MART-1) and positive selection of TCR library.

FIG. 18 shows results for negative and positive selection of TCRs.

The second round of enrichment and tetramer staining moderately improved over the two rounds.

Figure 19:
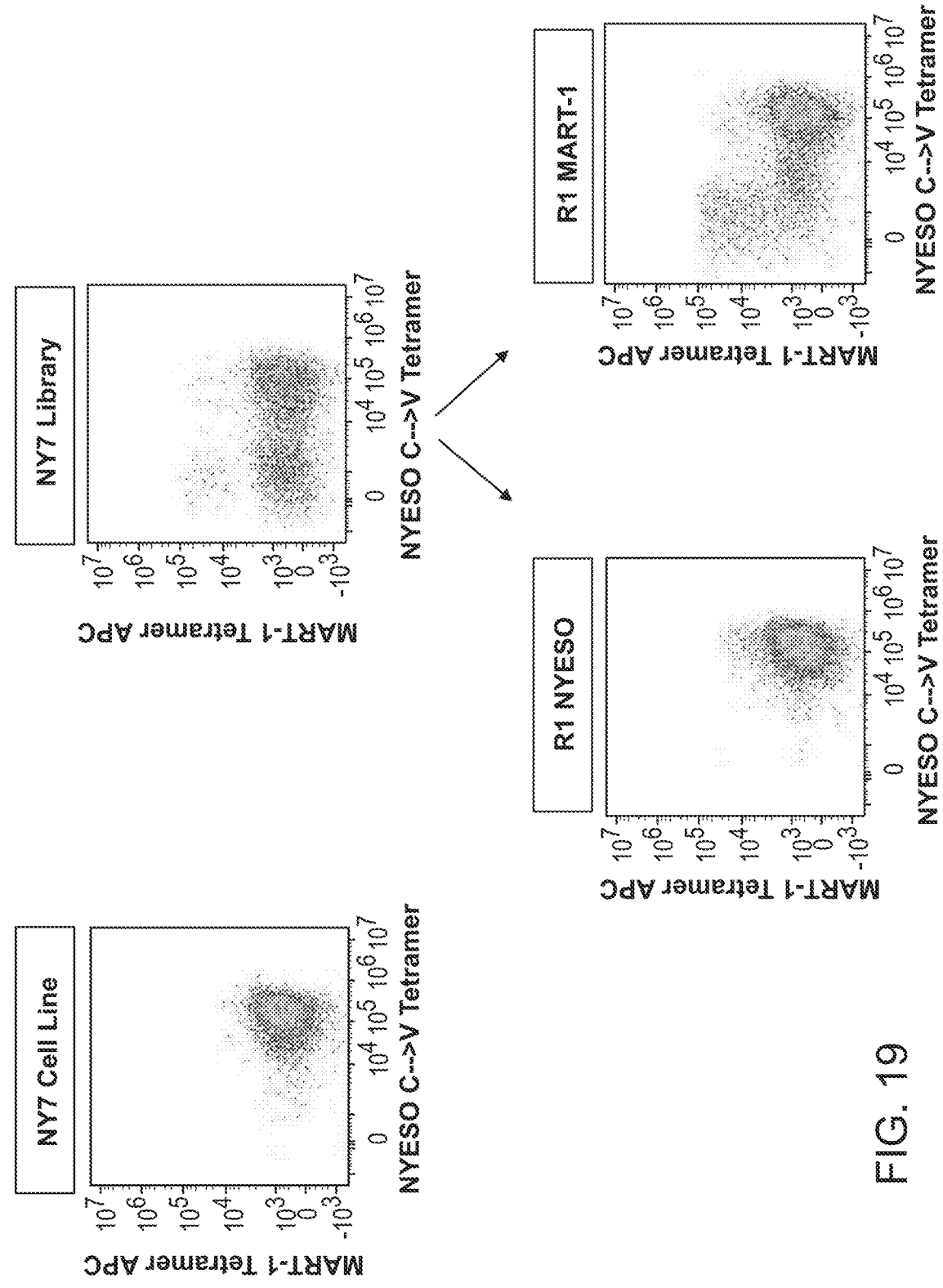
FIG. 19 shows results of NY-ESO-1 and MART-1 co-tetramer staining.

FIG. 19 shows results of NY-ESO-1 and MART-1 co-tetramer staining.

Enrichment by NY-ESO-1 led to a selection pool that was all reactive to NY-ESO-1 binding.

Figure 20:
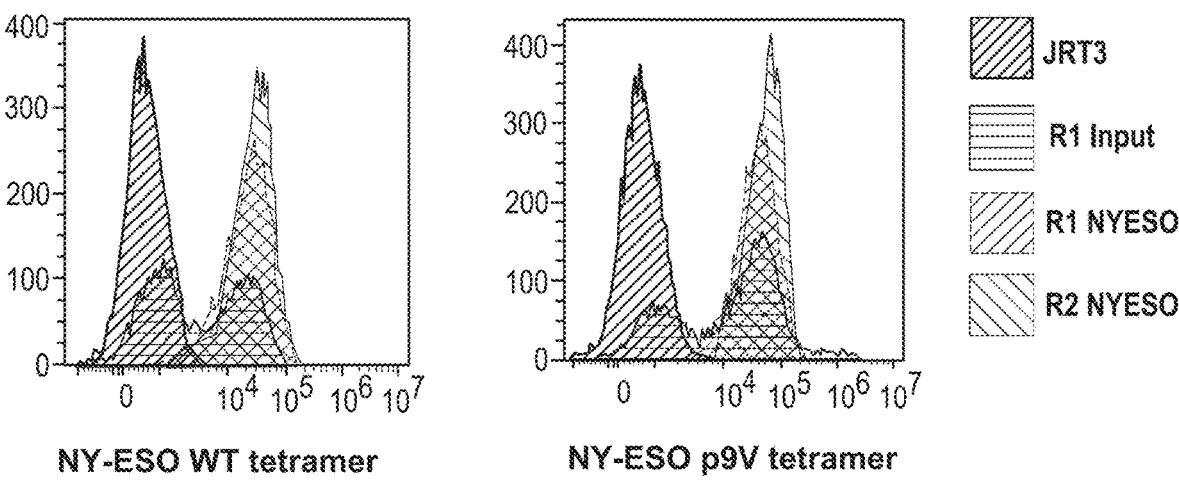
FIG. 20 shows NY-ESO-1 tetramer binding results following two rounds of enrichment.

FIG. 20 shows NY-ESO-1 tetramer binding results following two rounds of enrichment.

Figure 21:
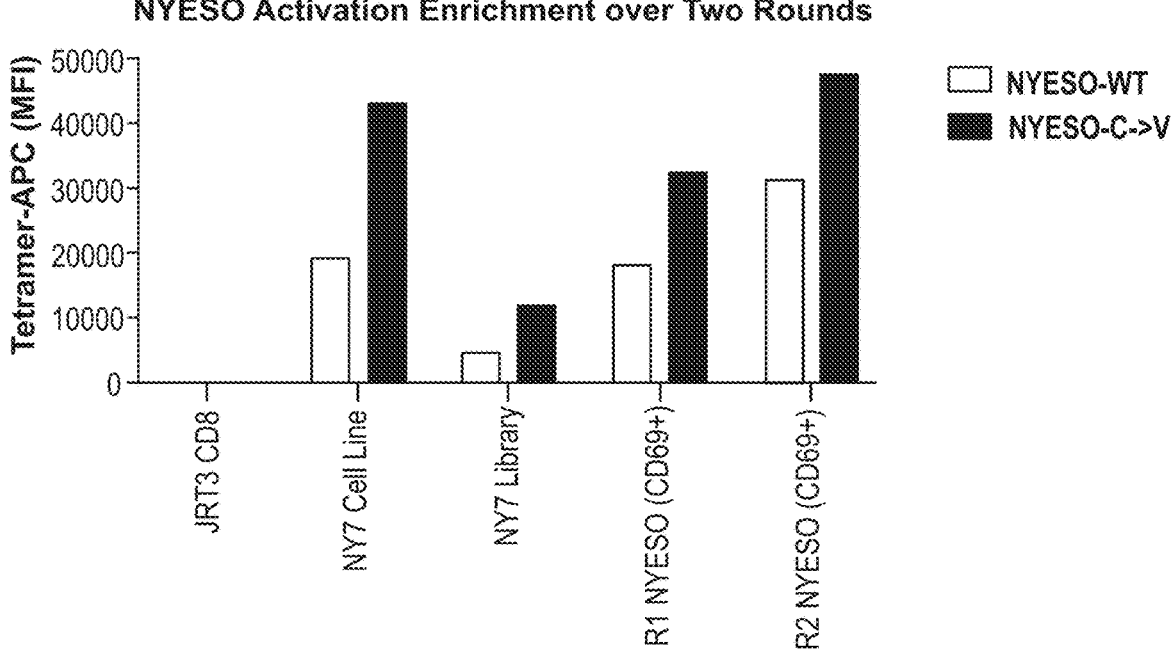
FIG. 21 shows NY-ESO-1 tetramer binding results after following two rounds of activation based enrichment.

FIG. 21 shows NY-ESO-1 tetramer binding results after following two rounds of activation based enrichment.

Figure 22:
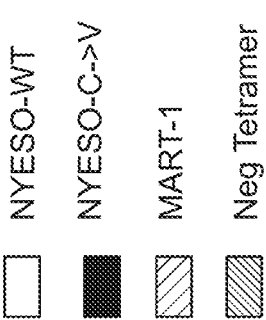
FIG. 22 shows a summary of the binding reactivity of the selection pools from two selection rounds to various tetramers.

FIG. 22 shows a summary of the binding reactivity of the selection pools from two selection rounds to various tetramers.

NY7 variant TCRs isolated by the work flow above were then functionally tested for potency and specificity. TCRs were expressed in Jurkat cells using a lentivirus vector, and TCR-expressing Jurkat cells were co-cultured with T2 cells and a varying dose of the NY-ESO-1 peptide. Activation was measured by luminescence using an NFAT-Luciferase reporter.

Figure 23:
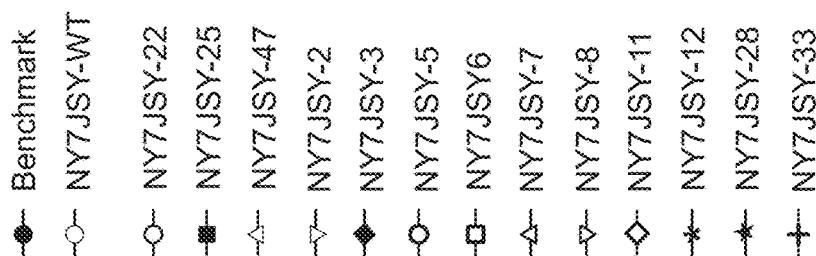
FIG. 23 shows results of peptide dose response activation by NY7 variants.

FIG. 23 shows results of peptide dose response activation by NY7 variants.

Figure 24:
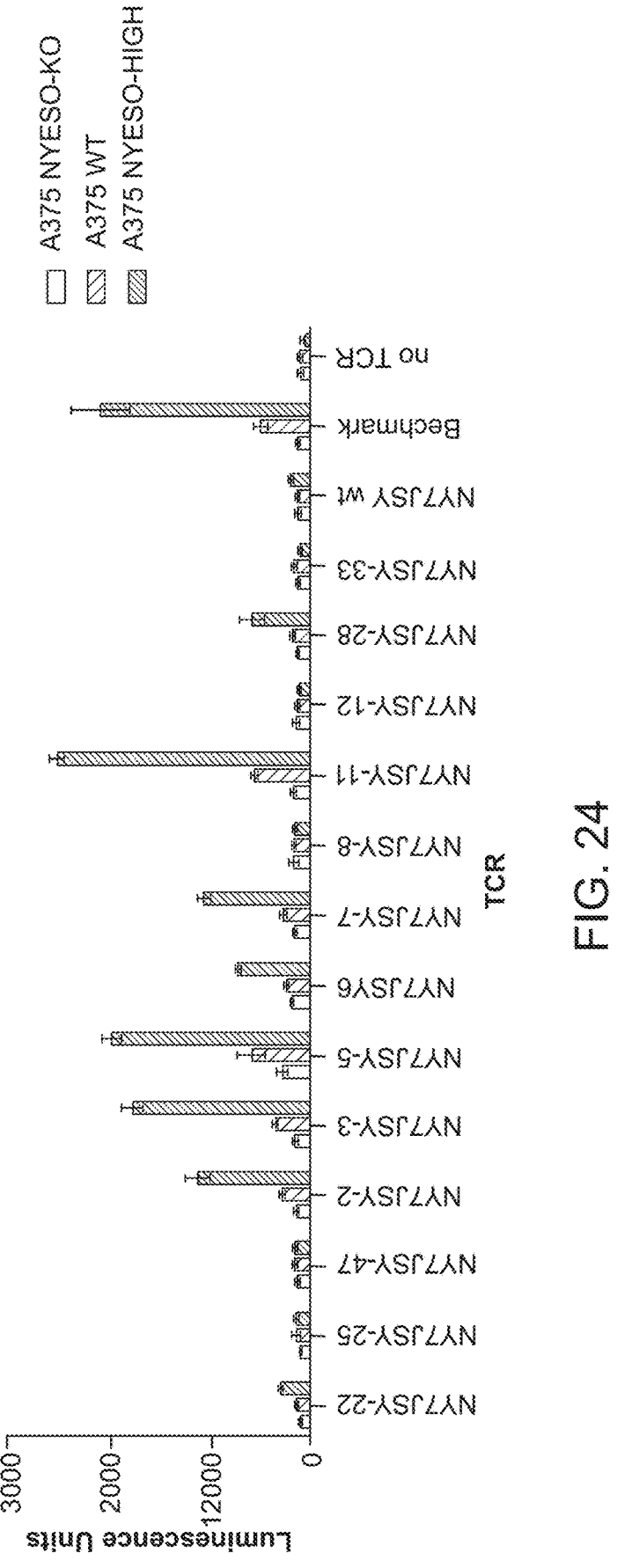
FIG. 24 shows NFAT-Luciferase activation results with Jurkat cells expressing NY7 variant TCRs cultured with melanoma cells expressing varying levels of NY-ESO-1.

FIG. 24 shows NFAT-Luciferase activation results with Jurkat cells expressing NY7 variant TCRs cultured with melanoma cells expressing varying levels of NY-ESO-1.

Wild type A-375 melanoma cells express low, endogenous levels of NY-ESO-1, A-375 NYESO-KO cells express no NY-ESO-1, and A-375 NYESO-HIGH cells over-express NY-ESO-1. Notably, whereas the wild type NY7 TCR was not activated by any of the A-375 lines, 7 of the NY7 variants tested here gained the ability to respond to the over-expressing and/or wild type A-375 lines. This demonstrates that the TCR Optimization work flow was successful in generating TCR variants with enhanced potency.

To investigate TCR variant potency and specificity in a more physiological context, TCR variants were expressed in primary human T cells. Primary T cells from healthy donors were activated and edited to express NY7 variant TCRs using CRISPR/Cas9.

The edited T cells were cultured alone and with T2 cells pulsed with NY-ESO-1 peptide, DMSO, or Mart-1 peptide. T cell activation was detected by CD137 expression using flow cytometry.

Figure 25:
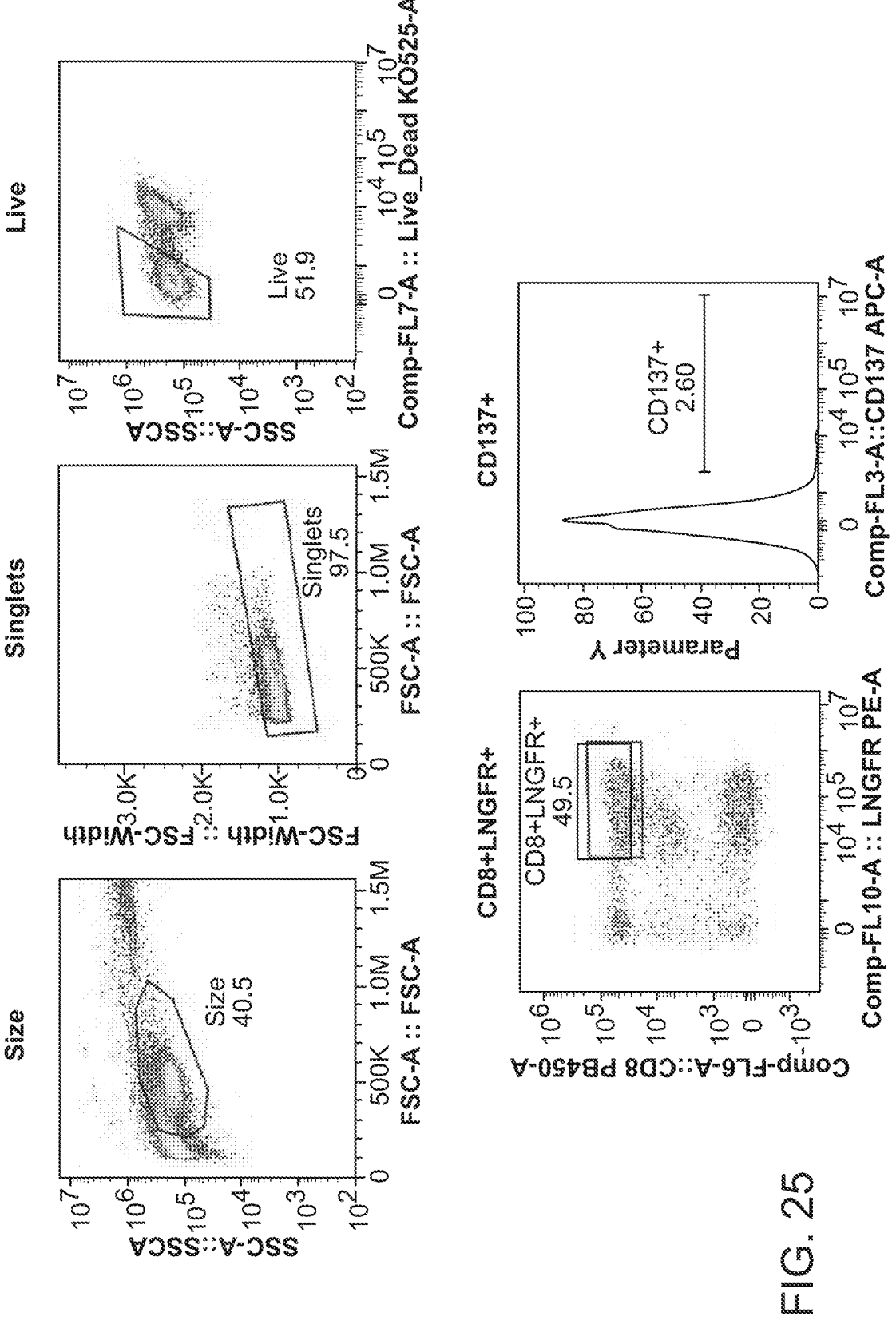
FIG. 25 shows the flow cytometry gating scheme used to measure CD137 expression on primary T cells expressing NY7 variant TCRs
Figure 26:
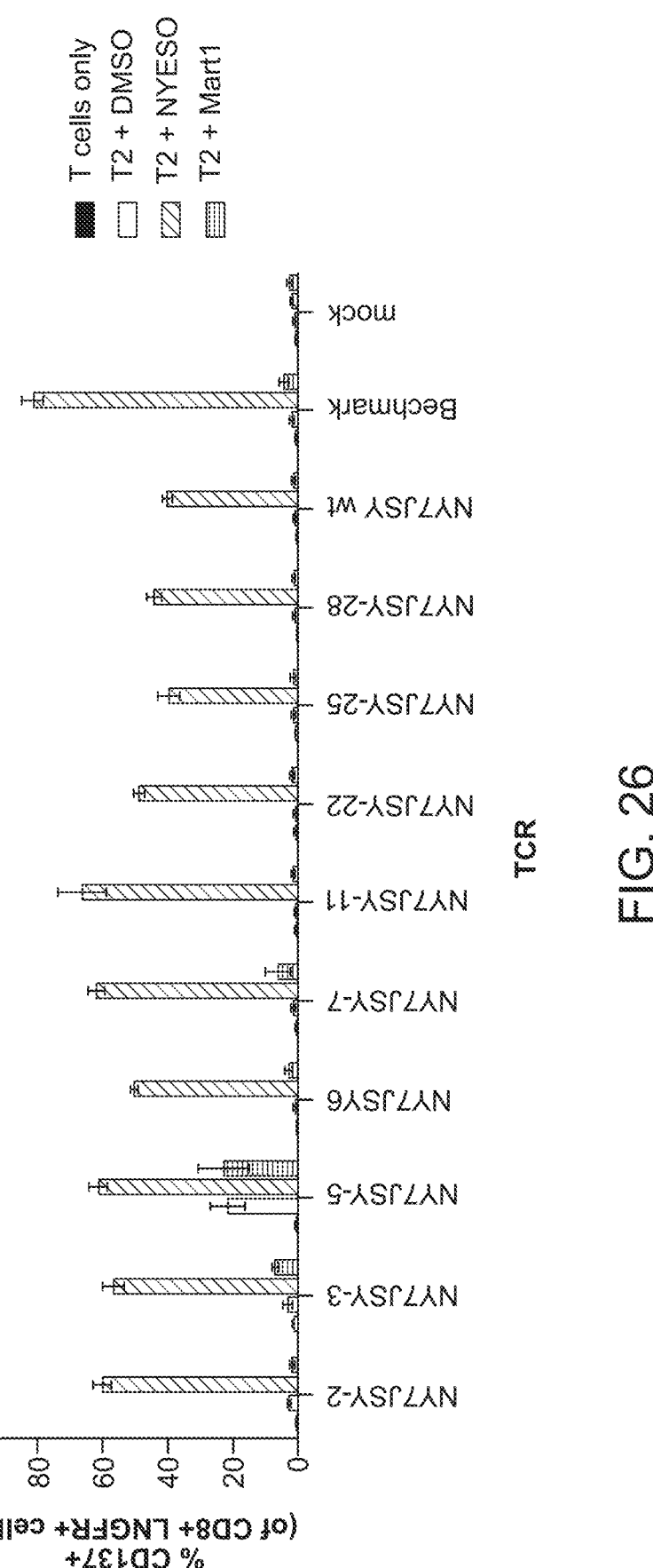
FIG. 26 shows CD137 activation results with primary T cells expressing NY7 variant TCRs cultured with T2 cells pulsed with peptide

FIG. 25 shows the flow cytometry gating scheme used to measure CD137 expression on primary T cells expressing NY7 variant TCRs FIG. 26 shows CD137 activation results with primary T cells expressing NY7 variant TCRs cultured with T2 cells pulsed with peptide.

As expected, all TCR variants were activated by NY-ESO-1 peptide. Unexpectedly, variant 5 was also activated by T2 cells without added peptide (DMSO only) or with the irrelevant Mart-1 peptide, indicating cross-reactivity. This demonstrates that single point mutations in a TCR can have unintended consequences, and underscores the importance for functional testing of cross-reactivity.

The edited T cells were also cultured with melanoma cells expressing varying levels of NY-ESO-1. Activation was measured by CD137 staining, detected by flow cytometry, and target cell killing was measured using Incucyte live cell microscopy assays.

Figure 27:
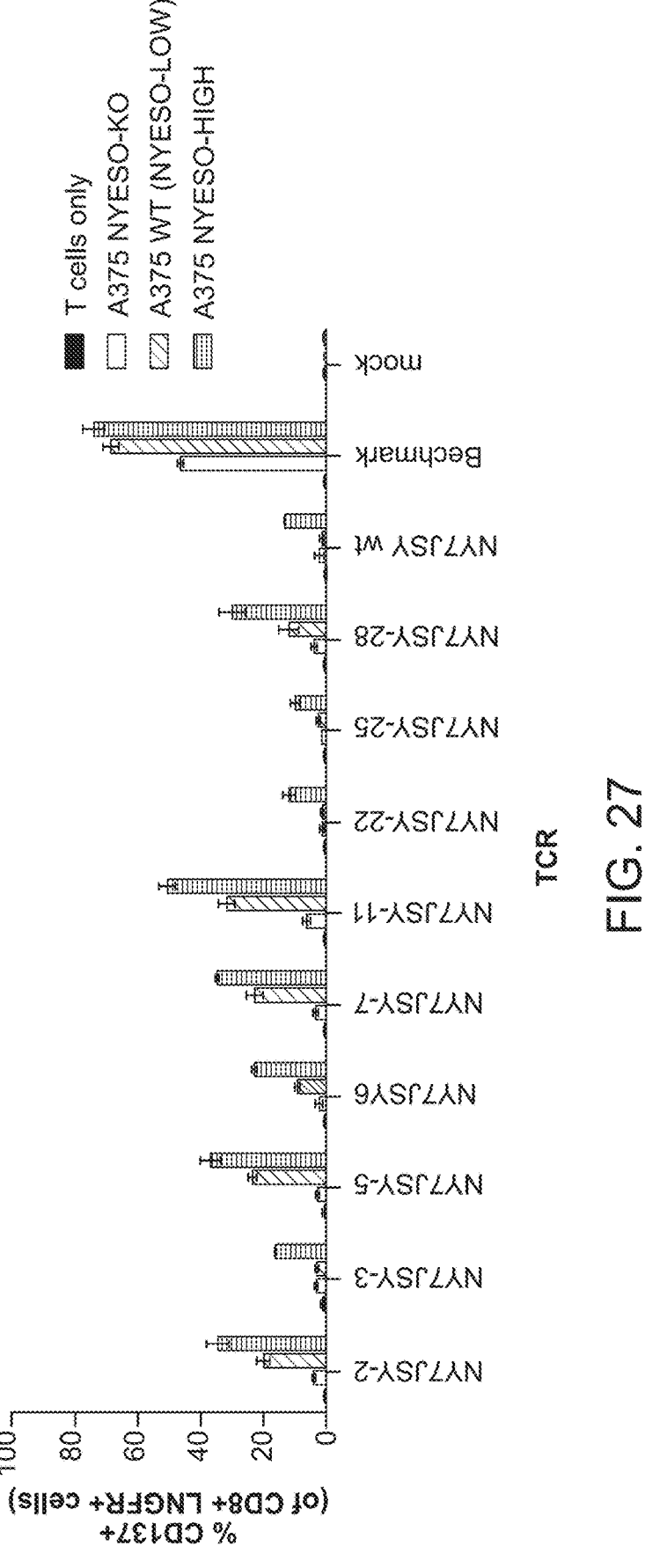
FIG. 27 shows CD137 activation results with primary T cells expressing NY7 variant TCRs cultured with melanoma cells expressing varying levels of NY-ESO-1

FIG. 27 shows CD137 activation results with primary T cells expressing NY7 variant TCRs cultured with melanoma cells expressing varying levels of NY-ESO-1

Whereas the wild type NY7JSY TCR was not potent enough to react toward the wild type A-375 melanoma cells, the engineered variants indicated with arrows gained reactivity toward this line, demonstrating an increase in potency. Of the NY7 variants, 6/9 engineered variants gained reactivity against wild type A-375 melanoma cells.

Figure 28:
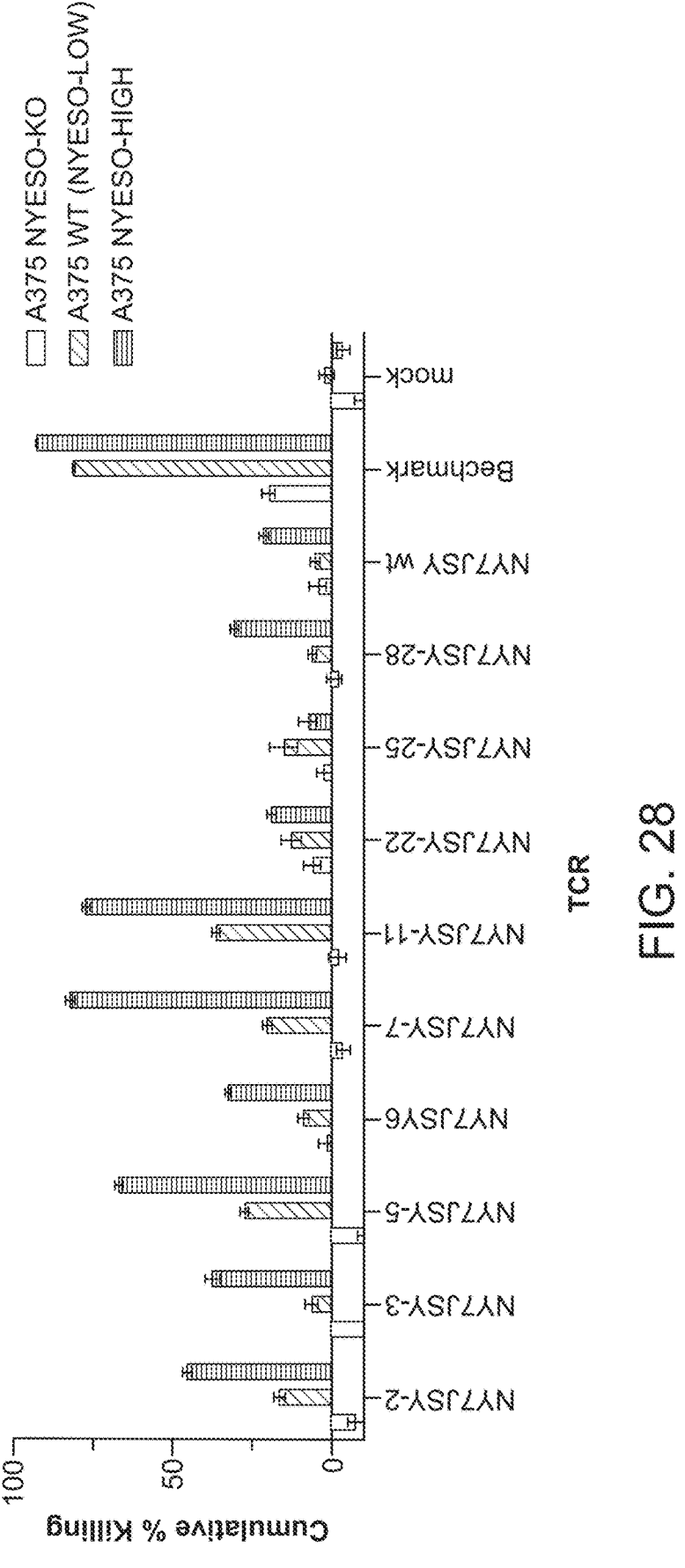
FIG. 28 shows killing of melanoma cells by primary T cells expressing NY7 variant TCRs

FIG. 28 shows killing of melanoma cells by primary T cells expressing NY7 variant TCRs.

Of the NY7 variants tested, 7/9 show enhanced killing of NY-ESO-1 overexpressing cells, and 4/9 variants show enhanced killing of wild type A-375 cells.

Discussion

Methods for isolating T-cells with TCRs optimized for reactivity to NY-ESO-1 allowed for both the identification of highly active NY-ESO-1 TCRs and the analysis of cross-reactivity of the TCRs.

TCRs with low cross-reactivity were then further optimized with amino acid substitutions to generate optimized TCRs with enhanced activity against NY-ESO-1. Because of the robust and efficient nature of the expansion and activation assays, an exemplary NY-ESO-1 TCR, NY7, was identified.

It is understood that methods of the invention can be utilized to identify optimized TCRs with low reactivity against further antigens and epitopes.

3T-Trace and TCR Analysis

Peptide-HLA (pHLA)-targeting therapeutics, such as T cell receptor-engineered T cells (TCR-T), have had clinical success in treating solid tumors. However, challenges related to safety exist; major concerns remain surrounding the cross-reactivity of T cell receptors (TCRs) as well as the ability of therapeutics to discriminate between on-target and off-target pHLAs while maintaining high potency. Therefore, approaches that survey the diversity of the T cell repertoire to discover optimal TCRs, as well as platforms to comprehensively identify potential off-target liabilities, are critical to de-risking and accelerating the development of this promising class of pHLA-targeting therapeutics.

The TCR repertoire was queried to enrich and identify multiple active, sequence-distinct endogenous TCRs. 3T-TRACE, a high-diversity pHLA library, was used to screen for cross-reactivity. Functional selections were exploited to simultaneously optimize for TCR potency and specificity.

This approach was used to identify TCRs of optimal specificity and potency targeting a peptide derived from the cancer-testis antigen NY-ESO-1 (SLLMWITQC) (SEQ ID NO: 260) displayed by HLA-A2. 4 sequence-distinct TCRs were profiled using 3T-TRACE and their potential off-target cross-reactivities identified. Many of the identified off-targets exhibited little to no sequence homology to the NY-ESO-1 epitope, highlighting the importance of diverse combinatorial libraries in identifying unexpected cross-reactivities.

Leveraging the off-target liabilities identified by 3T-TRACE, a functional library and selection scheme was designed that enabled the identification of TCRs with increased potency and specificity. Optimized TCRs exhibited enhanced killing activity and improved safety against an NY-ESO-1-expressing melanoma cell line compared to benchmark TCRs, indicating that this approach has potential to improve clinical safety and efficacy.

This multi-faceted and comprehensive approach was used to rapidly identified highly potent and specific TCRs against NY-ESO-1. Identifying cross-reactivities using 3T-TRACE proved to be critical in selecting TCRs suitable for engineering and functional selections. This approach can be extended to any pHLA target to create safe and effective TCR-Ts for clinical development.

Figure 29:
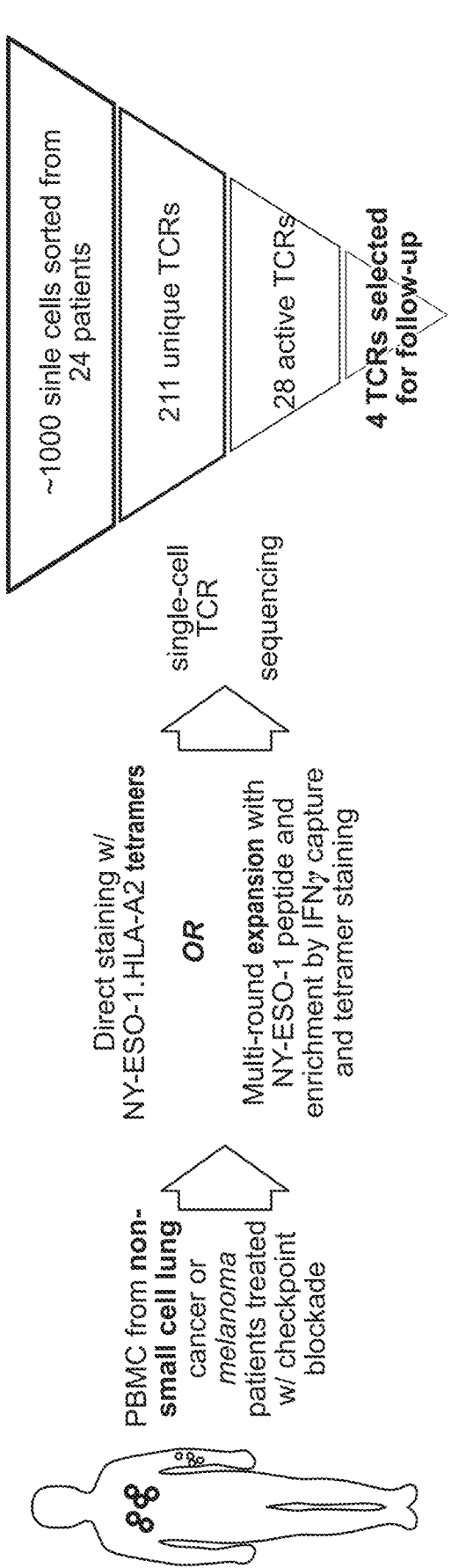
FIG. 29 depicts a flow chart of two parallel approaches to TCR identification.

FIG. 29 depicts a flow chart of two parallel approaches to TCR identification. NY-ESO-1 reactive T cells were isolated from Non-Small Cell Lung Cancer (NSCLC) or melanoma patients. Using one of two methods: direct tetramer sorting from PBMC, or an expansion protocol consisting of three rounds of in vitro expansion with NY-ESO-1 peptide and alternating enrichment by IFNγ gamma capture and tetramer sorting. TCRs were identified from isolated cells by single-cell RNAseq.

Figure 30:
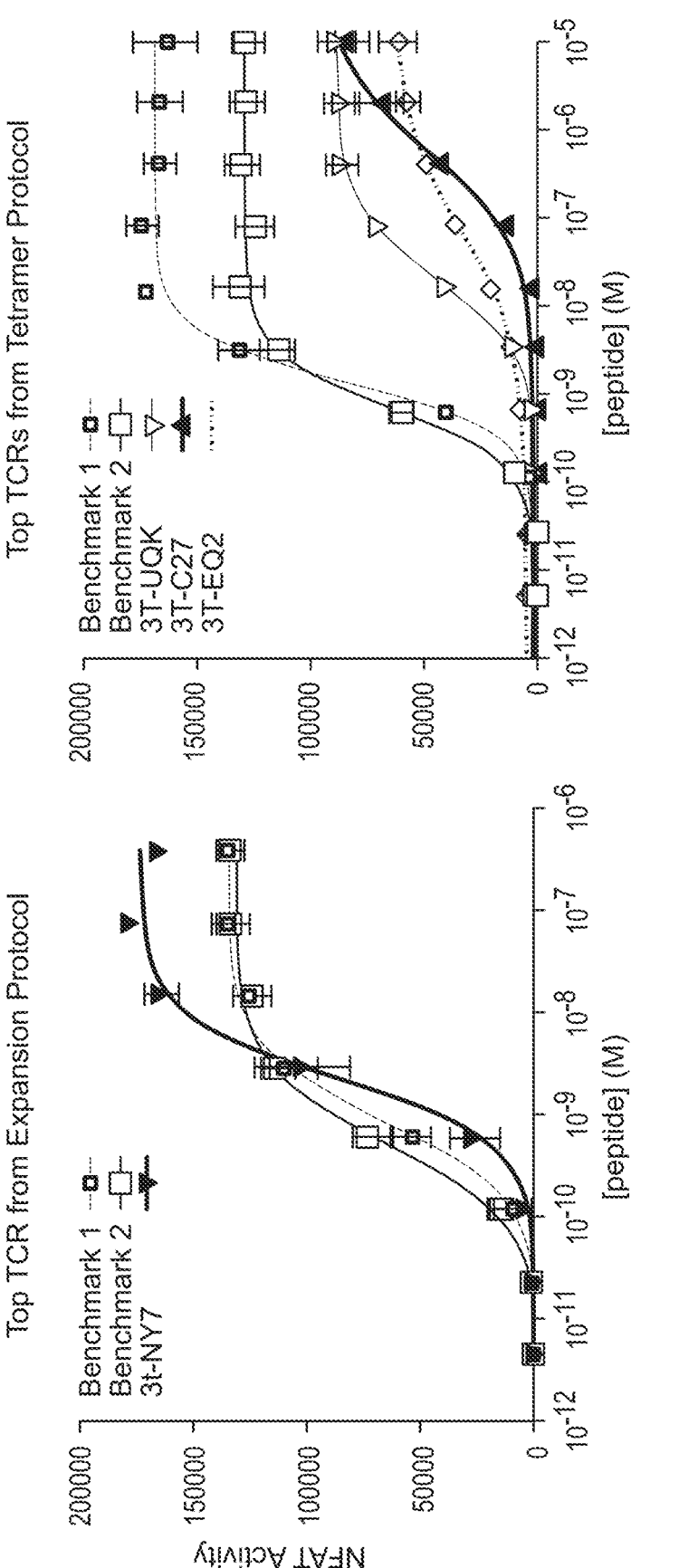
FIG. 30 shows an assessment of potency of patient TCRs.

FIG. 30 shows an assessment of potency of patient TCRs. Patient-derived TCRs and benchmark comparators were lentivirally transduced into NFAT-Luciferase reporter Jurkat cells and their activity was measured by co-culture with T2 cells and varying concentrations of NY-ESO-1 peptide.

In 3T-TRACE, a TCR of interest is used as bait to query a pool of yeast displaying a library of peptides presented by HLA-A2. Sequential rounds of selection enrich for peptides bound by the TCR, and these peptide sequences are read out by next-generation sequencing. This produces a comprehensive binding profile, which is used to computationally predict target peptides from the human proteome. This approach can be used for de novo target identification or for identification of off-target liabilities.

Figure 31:
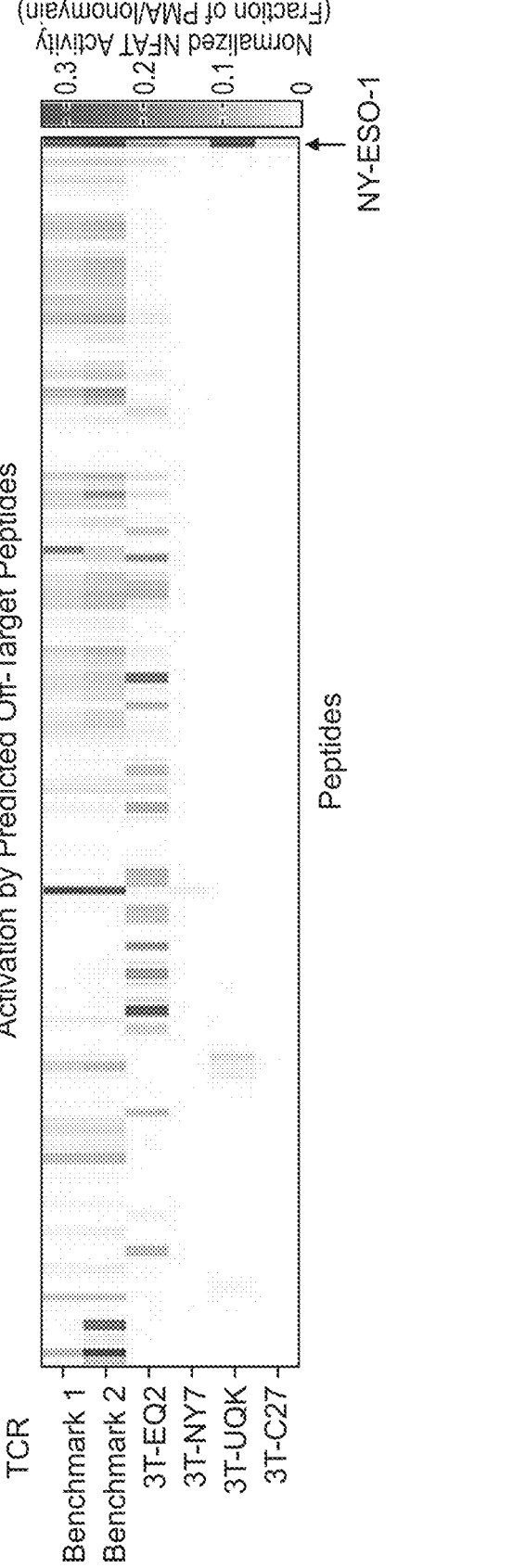
FIG. 31 shows activation by predicted off-target peptides by NY-ESO-1 using an NFAT-Luciferase reporter.

FIG. 31 shows activation by predicted off-target peptides by NY-ESO-1 using an NFAT-Luciferase reporter.

Figures 32, 33:
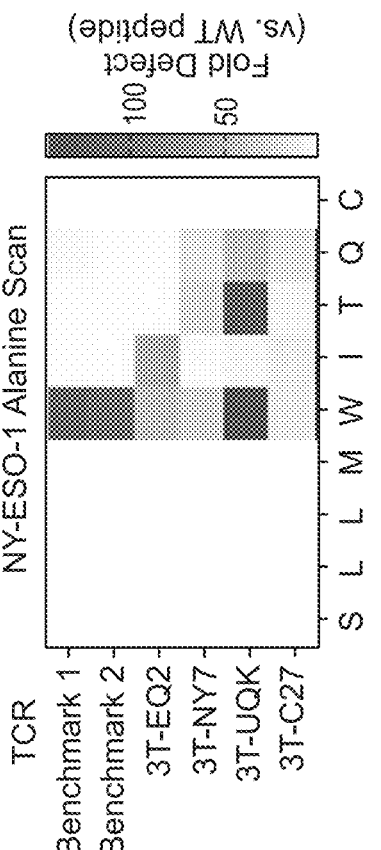
FIG. 32 shows activation by predicted off-target peptides by NY-ESO-1 Alanine scan mutants
FIG. 33 shows a comparison of TCR cross-reactivity calculated from NY-ESO alanine scan mutants and peptide binding footprints.

FIG. 32 shows activation by predicted off-target peptides by NY-ESO-1 Alanine scan mutants Jurkat cells were electroporated with mRNA encoding patient-derived TCRs or Benchmark TCRs and cultured with T2 cells plus a panel of predicted off-target peptides identified by 3T-TRACE.

FIG. 33 shows a comparison of TCR cross-reactivity calculated from NY-ESO alanine scan mutants and peptide binding footprints.

FIG. 34 shows the top activating off-target peptides identified and detected by 3T-TRACE which bear little sequence similarity to the intended NY-ESO-1 epitope and are derived from proteins expressed in healthy tissues (Human Protein Atlas).

Figure 35:
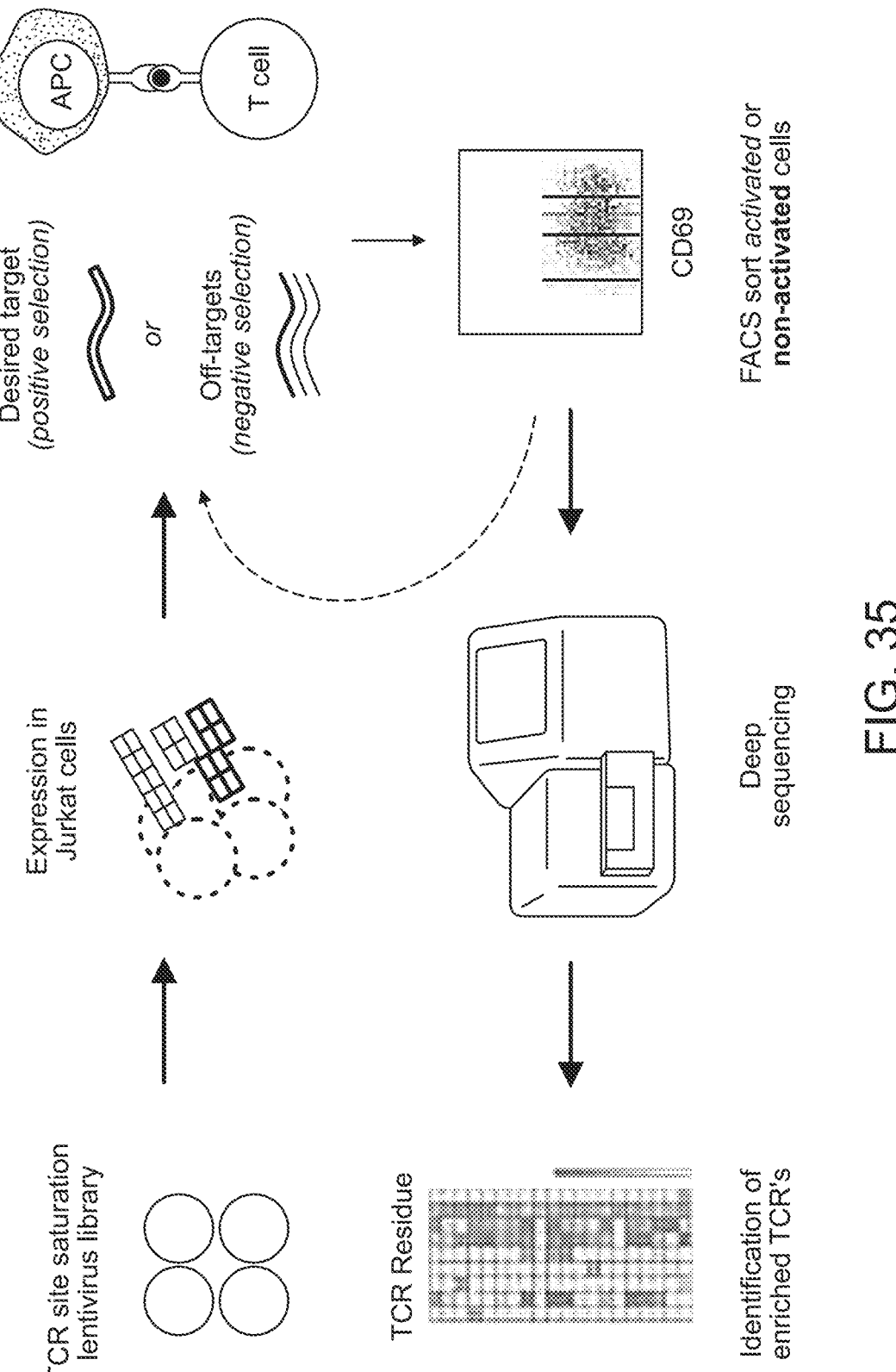
FIG. 35 shows a flow chart of a functional selection approach to optimize TCR potency and specificity.

FIG. 35 shows a flow chart of a functional selection approach to optimize TCR potency and specificity. A site-saturation mutagenesis library of select TCR residues is lentivirally transduced into Jurkat cells. The Jurkat library is cultured with T2 cells pulsed with either the on-target peptide or with one or several off-target peptides. Cells are stained for the activation marker CD69 and the highest (positive selection) or lowest (negative selection) expressing cells are sorted by FACS. If desired, the culture and sorting steps are repeated for multiple sequential rounds of selection. The resulting cell pool is sequenced and relative enrichment of individual amino acid substitutions were determined to identify TCR variants of interest.

Figure 36:
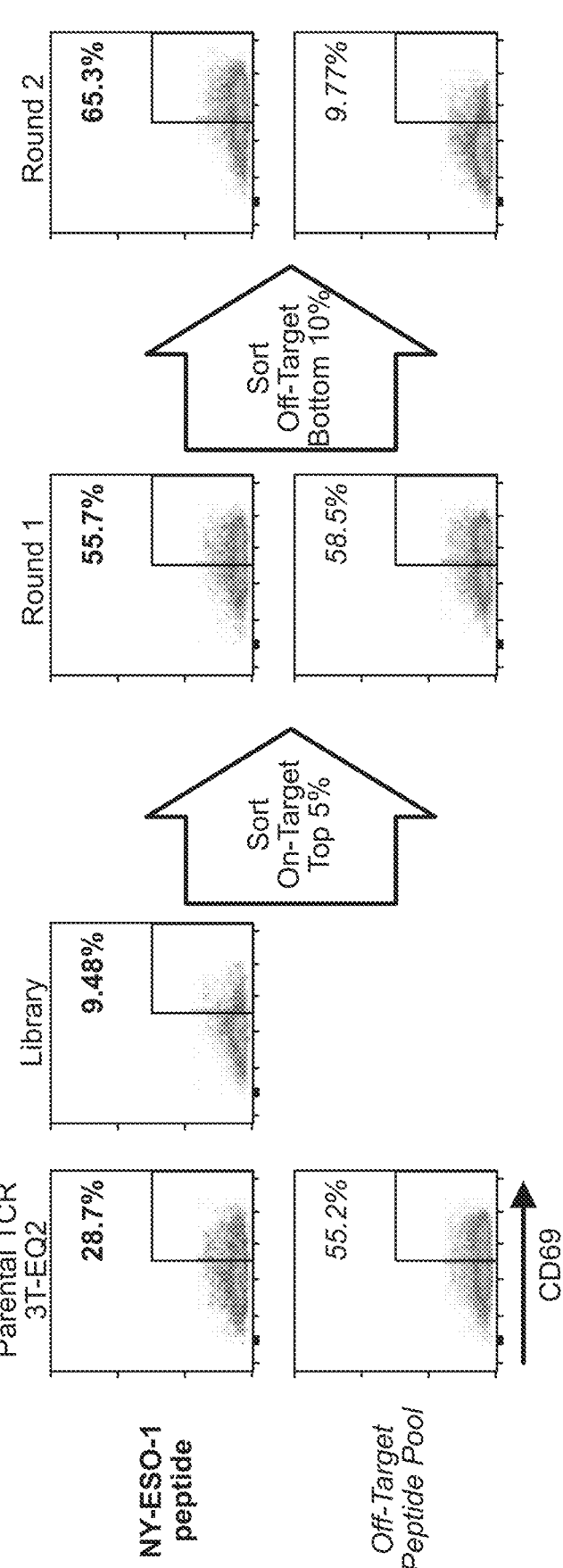
FIG. 36 shows two-round functional selection of TCR 3T-EQ2 to enhance on-target and reduce off-target activity.

FIG. 36 shows two-round functional selection of TCR 3T-EQ2 to enhance on-target and reduce off-target activity. Jurkat cells transduced with TCR 3T-EQ2 or a mutagenesis library derived from 3T-EQ2 were incubated with T2 cells and NY-ESO-1 peptide or a pool of off-target peptides. After 24 hours, activation was measured by CD69 staining. After two rounds of selection, on-target activity (NY-ESO-1) was enhanced and reactivity to off-targets was diminished.

Figure 37:
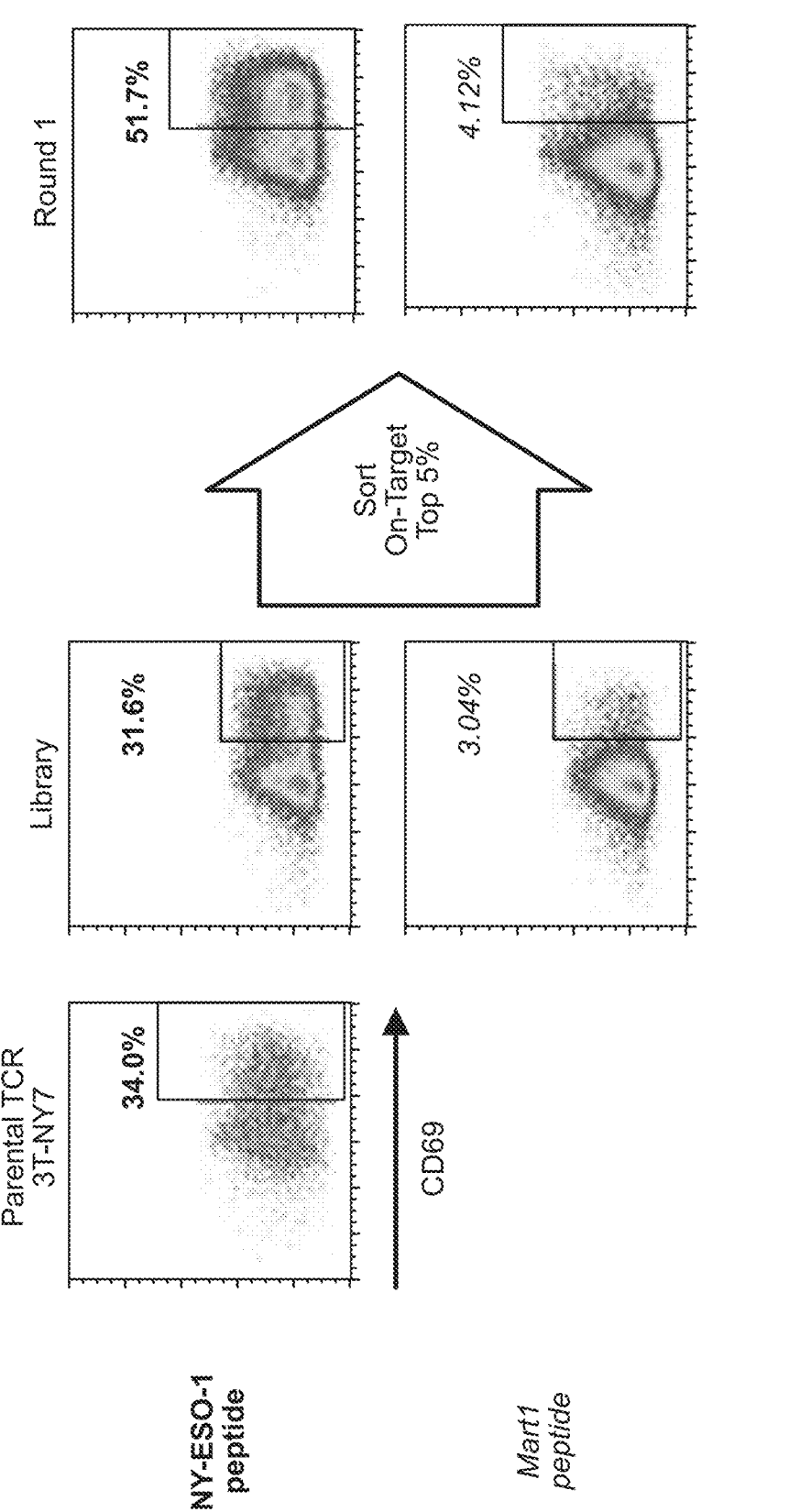
FIG. 37 shows one-round functional selection of TCR-3T-NY7 to enhance on-target activity.
Figure 38:
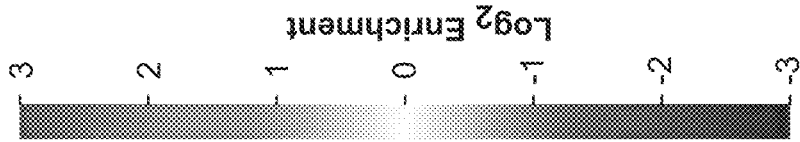
FIG. 38 shows the result of TCR sequencing of the 3T-NY7 library.
Figure 38:
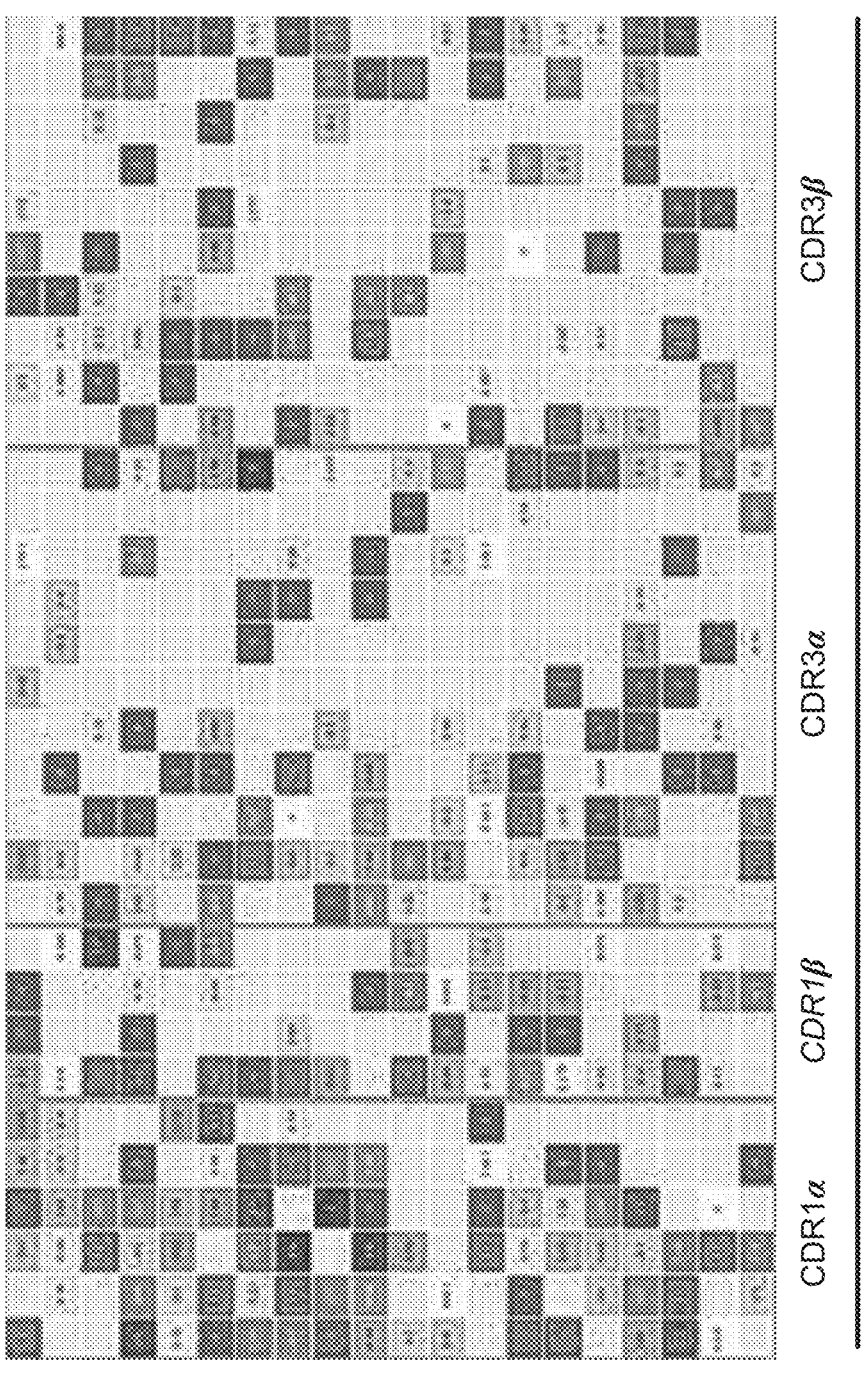

FIG. 37 shows one-round functional selection of TCR-3T-NY7 to enhance on-target activity. Jurkat cells transduced with TCR 3T-NY7 or the corresponding library were incubated with T2 cells and peptide, and activation was measured by CD69 staining. Because no potent off-targets of 3T-NY7 were identified by 3T-TRACE, an HLA-A2 restricted peptide from MART1 was used as a proxy off-target. After one round of selection, on-target activity was enhanced while maintaining low off-target activity FIG. 38 shows the result of TCR sequencing of the 3T-NY7 library. TCR sequencing was performed on the initial 3T-NY7 library and on the enriched pool after one round of selection. Fold enrichment of each amino acid substitution is shown, with empty light gray squares indicating substitutions that were not present in the library or not detected.

Figure 39:
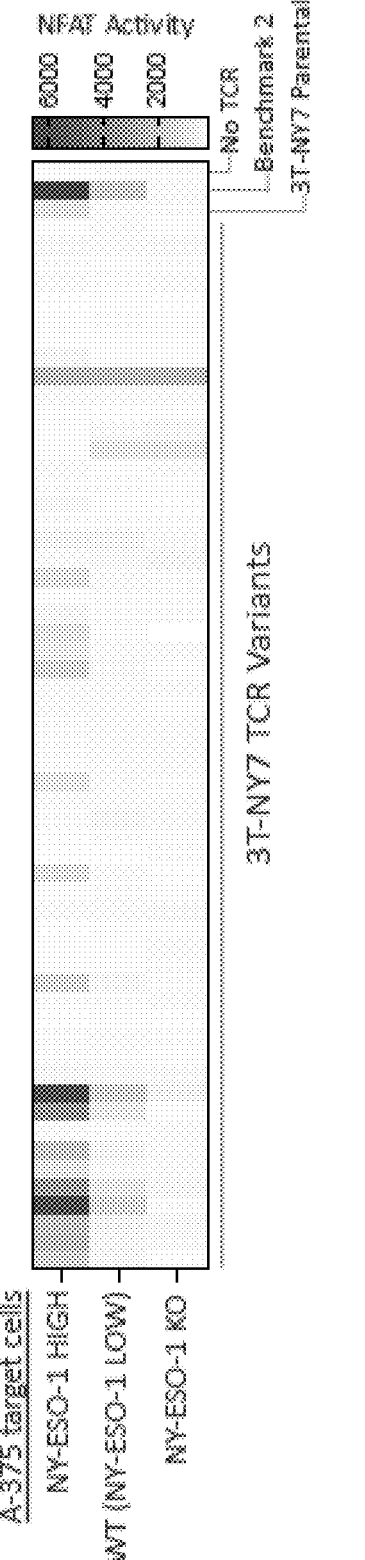
FIG. 39 shows an activity screen against NY-ESO-1 expressing cancer cells of 3T-NY7 variants.

FIG. 39 shows an activity screen against NY-ESO-1 expressing cancer cells of 3T-NY7 variants. Jurkat cells were transduced with a series of 3T-NY7 TCR variants identified in by one-round functional selection and sequencing, and then cultured with A-375 melanoma cells (expressing endogenous low levels of NY-ESO-1), A-375 NY-ESO-1 knock-out cells, or A-375 cells overexpressing high levels of NY-ESO-1. Activity was measured using an NFAT-Luciferase reporter. Most active 3T-NY8 variants were identified.

Figure 40:
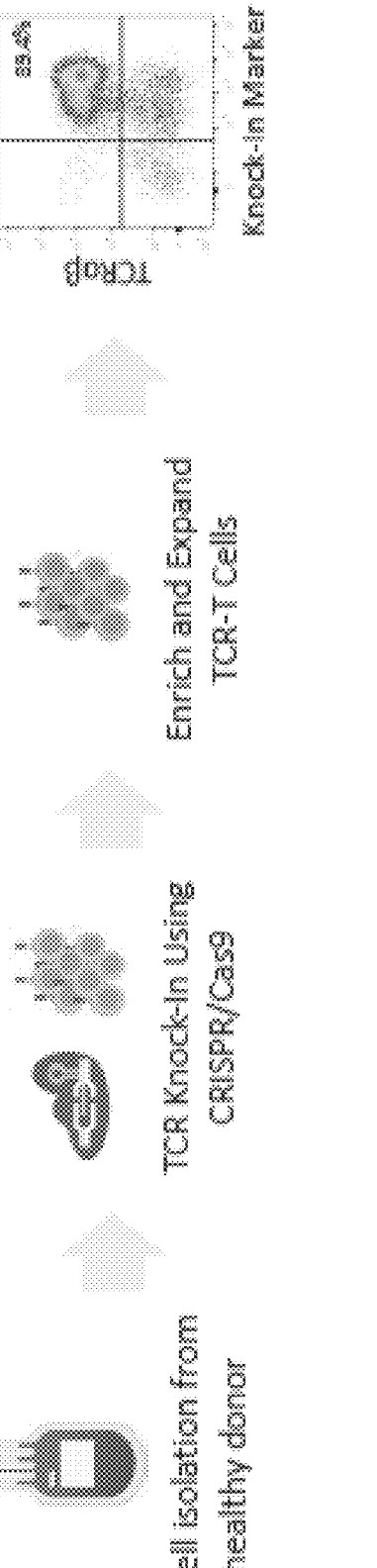
FIG. 40 shows a flowchart of the preparation of TCR-T cells.

FIG. 40 shows a flowchart of the preparation of TCR-T cells. T cells were isolated from a healthy donor and activated, and TCRs of interest were expressed by CRISPR/

Cas9-mediated genomic knock-in. Cells were expanded and enriched for TCR-T cells, and purity assessed by flow cytometry staining for TCRαβ and a cell surface marker of transgene expression.

Figure 41:
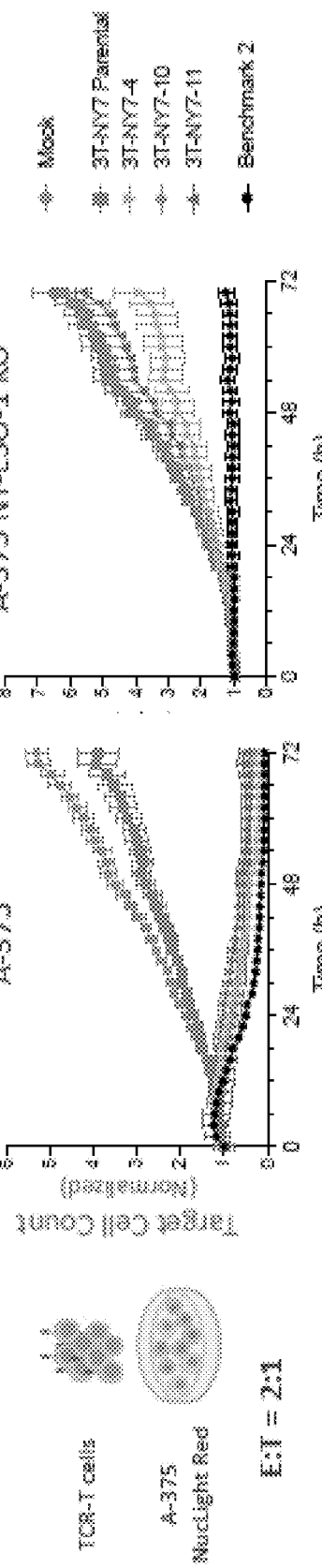
FIG. 41 shows the potency and enhanced specificity of optimized 3T-NY7 variants in killing A-375 melanoma cells.

FIG. 41 shows the potency and enhanced specificity of optimized 3T-NY7 variants in killing A-375 melanoma cells. TCR-T cells were cultured with target cells (A-375 or A-375 NY-ESO-1 knock-out) cell lines expressing a nucleus-localized red fluorescent protein (RFP), as sold under the trade name INCUCYTE NUCLIGHT RED. Target cell killing was monitored using an INCUCYTE automated fluorescence microscope, plotted as target cell count normalized to t=0.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

SEQUENCE LISTING

```
Sequence total quantity: 260
SEQ ID NO: 1              moltype = AA   length = 6
FEATURE                   Location/Qualifiers
REGION                    1..6
                          note = Synthetic
source                    1..6
                          mol_type = protein
                          organism = synthetic construct
SEQUENCE: 1
DRGSQS                                                                 6

SEQ ID NO: 2              moltype = AA   length = 6
FEATURE                   Location/Qualifiers
REGION                    1..6
                          note = Synthetic
source                    1..6
                          mol_type = protein
                          organism = synthetic construct
SEQUENCE: 2
IYSNGD                                                                 6

SEQ ID NO: 3              moltype = AA   length = 12
FEATURE                   Location/Qualifiers
REGION                    1..12
                          note = Synthetic
source                    1..12
                          mol_type = protein
                          organism = synthetic construct
SEQUENCE: 3
CAVMRAGGFK TI                                                         12

SEQ ID NO: 4              moltype = AA   length = 5
FEATURE                   Location/Qualifiers
REGION                    1..5
                          note = Synthetic
source                    1..5
```

```
                         mol_type = protein
                         organism = synthetic construct
SEQUENCE: 4
SGDLS                                                               5

SEQ ID NO: 5            moltype = AA   length = 6
FEATURE                 Location/Qualifiers
REGION                  1..6
                         note = Synthetic
source                  1..6
                         mol_type = protein
                         organism = synthetic construct
SEQUENCE: 5
YYNGEE                                                              6

SEQ ID NO: 6            moltype = AA   length = 11
FEATURE                 Location/Qualifiers
REGION                  1..11
                         note = Synthetic
source                  1..11
                         mol_type = protein
                         organism = synthetic construct
SEQUENCE: 6
CASSVVDGEQ Y                                                        11

SEQ ID NO: 7            moltype = AA   length = 6
FEATURE                 Location/Qualifiers
REGION                  1..6
                         note = Synthetic
source                  1..6
                         mol_type = protein
                         organism = synthetic construct
SEQUENCE: 7
DRGVQS                                                              6

SEQ ID NO: 8            moltype = AA   length = 6
FEATURE                 Location/Qualifiers
REGION                  1..6
                         note = Synthetic
source                  1..6
                         mol_type = protein
                         organism = synthetic construct
SEQUENCE: 8
DRFSQS                                                              6

SEQ ID NO: 9            moltype = AA   length = 6
FEATURE                 Location/Qualifiers
REGION                  1..6
                         note = Synthetic
source                  1..6
                         mol_type = protein
                         organism = synthetic construct
SEQUENCE: 9
DRGIQS                                                              6

SEQ ID NO: 10           moltype = AA   length = 6
FEATURE                 Location/Qualifiers
REGION                  1..6
                         note = Synthetic
source                  1..6
                         mol_type = protein
                         organism = synthetic construct
SEQUENCE: 10
DRGSQA                                                              6

SEQ ID NO: 11           moltype = AA   length = 6
FEATURE                 Location/Qualifiers
REGION                  1..6
                         note = Synthetic
source                  1..6
                         mol_type = protein
                         organism = synthetic construct
SEQUENCE: 11
DRWSQS                                                              6

SEQ ID NO: 12           moltype = AA   length = 6
FEATURE                 Location/Qualifiers
REGION                  1..6
                         note = Synthetic
```

```
source                   1..6
                         mol_type = protein
                         organism = synthetic construct
SEQUENCE: 12
FRGSQS                                                                        6

SEQ ID NO: 13            moltype = AA  length = 6
FEATURE                  Location/Qualifiers
REGION                   1..6
                         note = Synthetic
source                   1..6
                         mol_type = protein
                         organism = synthetic construct
SEQUENCE: 13
RRGSQS                                                                        6

SEQ ID NO: 14            moltype = AA  length = 6
FEATURE                  Location/Qualifiers
REGION                   1..6
                         note = Synthetic
source                   1..6
                         mol_type = protein
                         organism = synthetic construct
SEQUENCE: 14
DRYSQS                                                                        6

SEQ ID NO: 15            moltype = AA  length = 6
FEATURE                  Location/Qualifiers
REGION                   1..6
                         note = Synthetic
source                   1..6
                         mol_type = protein
                         organism = synthetic construct
SEQUENCE: 15
DRGSGS                                                                        6

SEQ ID NO: 16            moltype = AA  length = 6
FEATURE                  Location/Qualifiers
REGION                   1..6
                         note = Synthetic
source                   1..6
                         mol_type = protein
                         organism = synthetic construct
SEQUENCE: 16
DRGLQS                                                                        6

SEQ ID NO: 17            moltype = AA  length = 6
FEATURE                  Location/Qualifiers
REGION                   1..6
                         note = Synthetic
source                   1..6
                         mol_type = protein
                         organism = synthetic construct
SEQUENCE: 17
QRGSQS                                                                        6

SEQ ID NO: 18            moltype = AA  length = 6
FEATURE                  Location/Qualifiers
REGION                   1..6
                         note = Synthetic
source                   1..6
                         mol_type = protein
                         organism = synthetic construct
SEQUENCE: 18
DRGNQS                                                                        6

SEQ ID NO: 19            moltype = AA  length = 6
FEATURE                  Location/Qualifiers
REGION                   1..6
                         note = Synthetic
source                   1..6
                         mol_type = protein
                         organism = synthetic construct
SEQUENCE: 19
DRGSQG                                                                        6

SEQ ID NO: 20            moltype = AA  length = 6
FEATURE                  Location/Qualifiers
REGION                   1..6
```

```
                          note = Synthetic
source                    1..6
                          mol_type = protein
                          organism = synthetic construct
SEQUENCE: 20
WRGSQS                                                                      6

SEQ ID NO: 21            moltype = AA   length = 6
FEATURE                  Location/Qualifiers
REGION                   1..6
                          note = Synthetic
source                    1..6
                          mol_type = protein
                          organism = synthetic construct
SEQUENCE: 21
DRGAQS                                                                      6

SEQ ID NO: 22            moltype = AA   length = 6
FEATURE                  Location/Qualifiers
REGION                   1..6
                          note = Synthetic
source                    1..6
                          mol_type = protein
                          organism = synthetic construct
SEQUENCE: 22
DWGSQS                                                                      6

SEQ ID NO: 23            moltype = AA   length = 6
FEATURE                  Location/Qualifiers
REGION                   1..6
                          note = Synthetic
source                    1..6
                          mol_type = protein
                          organism = synthetic construct
SEQUENCE: 23
DGGSQS                                                                      6

SEQ ID NO: 24            moltype = AA   length = 6
FEATURE                  Location/Qualifiers
REGION                   1..6
                          note = Synthetic
source                    1..6
                          mol_type = protein
                          organism = synthetic construct
SEQUENCE: 24
DRPSQS                                                                      6

SEQ ID NO: 25            moltype = AA   length = 6
FEATURE                  Location/Qualifiers
REGION                   1..6
                          note = Synthetic
source                    1..6
                          mol_type = protein
                          organism = synthetic construct
SEQUENCE: 25
HRGSQS                                                                      6

SEQ ID NO: 26            moltype = AA   length = 6
FEATURE                  Location/Qualifiers
REGION                   1..6
                          note = Synthetic
source                    1..6
                          mol_type = protein
                          organism = synthetic construct
SEQUENCE: 26
DRSSQS                                                                      6

SEQ ID NO: 27            moltype = AA   length = 6
FEATURE                  Location/Qualifiers
REGION                   1..6
                          note = Synthetic
source                    1..6
                          mol_type = protein
                          organism = synthetic construct
SEQUENCE: 27
DRGFQS                                                                      6

SEQ ID NO: 28            moltype = AA   length = 12
FEATURE                  Location/Qualifiers
```

```
REGION                    1..12
                          note = Synthetic
source                    1..12
                          mol_type = protein
                          organism = synthetic construct
SEQUENCE: 28
CAVMRAMGFK TI                                                         12

SEQ ID NO: 29             moltype = AA   length = 12
FEATURE                   Location/Qualifiers
REGION                    1..12
                          note = Synthetic
source                    1..12
                          mol_type = protein
                          organism = synthetic construct
SEQUENCE: 29
CAVVRAGGFK TI                                                         12

SEQ ID NO: 30             moltype = AA   length = 12
FEATURE                   Location/Qualifiers
REGION                    1..12
                          note = Synthetic
source                    1..12
                          mol_type = protein
                          organism = synthetic construct
SEQUENCE: 30
CAVLRAGGFK TI                                                         12

SEQ ID NO: 31             moltype = AA   length = 12
FEATURE                   Location/Qualifiers
REGION                    1..12
                          note = Synthetic
source                    1..12
                          mol_type = protein
                          organism = synthetic construct
SEQUENCE: 31
CAYMRAGGFK TI                                                         12

SEQ ID NO: 32             moltype = AA   length = 12
FEATURE                   Location/Qualifiers
REGION                    1..12
                          note = Synthetic
source                    1..12
                          mol_type = protein
                          organism = synthetic construct
SEQUENCE: 32
CAVMRAGYFK TI                                                         12

SEQ ID NO: 33             moltype = AA   length = 12
FEATURE                   Location/Qualifiers
REGION                    1..12
                          note = Synthetic
source                    1..12
                          mol_type = protein
                          organism = synthetic construct
SEQUENCE: 33
CAVMRAGGFK EI                                                         12

SEQ ID NO: 34             moltype = AA   length = 12
FEATURE                   Location/Qualifiers
REGION                    1..12
                          note = Synthetic
source                    1..12
                          mol_type = protein
                          organism = synthetic construct
SEQUENCE: 34
CAVMRAFGFK TI                                                         12

SEQ ID NO: 35             moltype = AA   length = 12
FEATURE                   Location/Qualifiers
REGION                    1..12
                          note = Synthetic
source                    1..12
                          mol_type = protein
                          organism = synthetic construct
SEQUENCE: 35
CATMRAGGFK TI                                                         12

SEQ ID NO: 36             moltype = AA   length = 12
```

-continued

```
FEATURE                  Location/Qualifiers
REGION                   1..12
                         note = Synthetic
source                   1..12
                         mol_type = protein
                         organism = synthetic construct
SEQUENCE: 36
CAVWRAGGFK TI                                                        12

SEQ ID NO: 37            moltype = AA  length = 12
FEATURE                  Location/Qualifiers
REGION                   1..12
                         note = Synthetic
source                   1..12
                         mol_type = protein
                         organism = synthetic construct
SEQUENCE: 37
CAYMRAGGFK EI                                                        12

SEQ ID NO: 38            moltype = AA  length = 12
FEATURE                  Location/Qualifiers
REGION                   1..12
                         note = Synthetic
source                   1..12
                         mol_type = protein
                         organism = synthetic construct
SEQUENCE: 38
CAVMRAGGFK TS                                                        12

SEQ ID NO: 39            moltype = AA  length = 12
FEATURE                  Location/Qualifiers
REGION                   1..12
                         note = Synthetic
source                   1..12
                         mol_type = protein
                         organism = synthetic construct
SEQUENCE: 39
CAAMRAGGFK TI                                                        12

SEQ ID NO: 40            moltype = AA  length = 12
FEATURE                  Location/Qualifiers
REGION                   1..12
                         note = Synthetic
source                   1..12
                         mol_type = protein
                         organism = synthetic construct
SEQUENCE: 40
CAVQRAGGFK TI                                                        12

SEQ ID NO: 41            moltype = AA  length = 12
FEATURE                  Location/Qualifiers
REGION                   1..12
                         note = Synthetic
source                   1..12
                         mol_type = protein
                         organism = synthetic construct
SEQUENCE: 41
CAVMRIGGFK TI                                                        12

SEQ ID NO: 42            moltype = AA  length = 12
FEATURE                  Location/Qualifiers
REGION                   1..12
                         note = Synthetic
source                   1..12
                         mol_type = protein
                         organism = synthetic construct
SEQUENCE: 42
CAVMRMGGFK TI                                                        12

SEQ ID NO: 43            moltype = AA  length = 12
FEATURE                  Location/Qualifiers
REGION                   1..12
                         note = Synthetic
source                   1..12
                         mol_type = protein
                         organism = synthetic construct
SEQUENCE: 43
CAVMRATGFK TI                                                        12
```

-continued

```
SEQ ID NO: 44         moltype = AA   length = 12
FEATURE               Location/Qualifiers
REGION                1..12
                      note = Synthetic
source                1..12
                      mol_type = protein
                      organism = synthetic construct
SEQUENCE: 44
CAVMRAHGFK TI                                                   12

SEQ ID NO: 45         moltype = AA   length = 12
FEATURE               Location/Qualifiers
REGION                1..12
                      note = Synthetic
source                1..12
                      mol_type = protein
                      organism = synthetic construct
SEQUENCE: 45
CANMRAGGFK TI                                                   12

SEQ ID NO: 46         moltype = AA   length = 12
FEATURE               Location/Qualifiers
REGION                1..12
                      note = Synthetic
source                1..12
                      mol_type = protein
                      organism = synthetic construct
SEQUENCE: 46
CAVMRAQGFK TI                                                   12

SEQ ID NO: 47         moltype = AA   length = 12
FEATURE               Location/Qualifiers
REGION                1..12
                      note = Synthetic
source                1..12
                      mol_type = protein
                      organism = synthetic construct
SEQUENCE: 47
CAVMRAAGFK TI                                                   12

SEQ ID NO: 48         moltype = AA   length = 12
FEATURE               Location/Qualifiers
REGION                1..12
                      note = Synthetic
source                1..12
                      mol_type = protein
                      organism = synthetic construct
SEQUENCE: 48
CAVMFAGGFK TI                                                   12

SEQ ID NO: 49         moltype = AA   length = 12
FEATURE               Location/Qualifiers
REGION                1..12
                      note = Synthetic
source                1..12
                      mol_type = protein
                      organism = synthetic construct
SEQUENCE: 49
CAVMRAGGFK TA                                                   12

SEQ ID NO: 50         moltype = AA   length = 12
FEATURE               Location/Qualifiers
REGION                1..12
                      note = Synthetic
source                1..12
                      mol_type = protein
                      organism = synthetic construct
SEQUENCE: 50
CAVMRAVGFK TI                                                   12

SEQ ID NO: 51         moltype = AA   length = 12
FEATURE               Location/Qualifiers
REGION                1..12
                      note = Synthetic
source                1..12
                      mol_type = protein
                      organism = synthetic construct
SEQUENCE: 51
CAVMRAYGFK TI                                                   12
```

-continued

```
SEQ ID NO: 52        moltype = AA   length = 12
FEATURE              Location/Qualifiers
REGION               1..12
                     note = Synthetic
source               1..12
                     mol_type = protein
                     organism = synthetic construct

SEQUENCE: 52
CAVMRASGFK TI                                                    12

SEQ ID NO: 53        moltype = AA   length = 12
FEATURE              Location/Qualifiers
REGION               1..12
                     note = Synthetic
source               1..12
                     mol_type = protein
                     organism = synthetic construct

SEQUENCE: 53
CAVMRALGFK TI                                                    12

SEQ ID NO: 54        moltype = AA   length = 12
FEATURE              Location/Qualifiers
REGION               1..12
                     note = Synthetic
source               1..12
                     mol_type = protein
                     organism = synthetic construct

SEQUENCE: 54
CAVMRAGGFK TF                                                    12

SEQ ID NO: 55        moltype = AA   length = 12
FEATURE              Location/Qualifiers
REGION               1..12
                     note = Synthetic
source               1..12
                     mol_type = protein
                     organism = synthetic construct

SEQUENCE: 55
CAVMRAGGFK TQ                                                    12

SEQ ID NO: 56        moltype = AA   length = 12
FEATURE              Location/Qualifiers
REGION               1..12
                     note = Synthetic
source               1..12
                     mol_type = protein
                     organism = synthetic construct

SEQUENCE: 56
CASMRAGGFK TI                                                    12

SEQ ID NO: 57        moltype = AA   length = 12
FEATURE              Location/Qualifiers
REGION               1..12
                     note = Synthetic
source               1..12
                     mol_type = protein
                     organism = synthetic construct

SEQUENCE: 57
CLVMRAGGFK TI                                                    12

SEQ ID NO: 58        moltype = AA   length = 5
FEATURE              Location/Qualifiers
REGION               1..5
                     note = Synthetic
source               1..5
                     mol_type = protein
                     organism = synthetic construct

SEQUENCE: 58
SGNLS                                                            5

SEQ ID NO: 59        moltype = AA   length = 5
FEATURE              Location/Qualifiers
REGION               1..5
                     note = Synthetic
source               1..5
                     mol_type = protein
                     organism = synthetic construct

SEQUENCE: 59
```

-continued

```
AGDLS                                                                        5

SEQ ID NO: 60          moltype = AA  length = 5
FEATURE                Location/Qualifiers
REGION                 1..5
                       note = Synthetic
source                 1..5
                       mol_type = protein
                       organism = synthetic construct
SEQUENCE: 60
SGDLI                                                                        5

SEQ ID NO: 61          moltype = AA  length = 5
FEATURE                Location/Qualifiers
REGION                 1..5
                       note = Synthetic
source                 1..5
                       mol_type = protein
                       organism = synthetic construct
SEQUENCE: 61
SGWLS                                                                        5

SEQ ID NO: 62          moltype = AA  length = 5
FEATURE                Location/Qualifiers
REGION                 1..5
                       note = Synthetic
source                 1..5
                       mol_type = protein
                       organism = synthetic construct
SEQUENCE: 62
SGLLS                                                                        5

SEQ ID NO: 63          moltype = AA  length = 5
FEATURE                Location/Qualifiers
REGION                 1..5
                       note = Synthetic
source                 1..5
                       mol_type = protein
                       organism = synthetic construct
SEQUENCE: 63
SGSLS                                                                        5

SEQ ID NO: 64          moltype = AA  length = 5
FEATURE                Location/Qualifiers
REGION                 1..5
                       note = Synthetic
source                 1..5
                       mol_type = protein
                       organism = synthetic construct
SEQUENCE: 64
TGDLS                                                                        5

SEQ ID NO: 65          moltype = AA  length = 5
FEATURE                Location/Qualifiers
REGION                 1..5
                       note = Synthetic
source                 1..5
                       mol_type = protein
                       organism = synthetic construct
SEQUENCE: 65
MGDLS                                                                        5

SEQ ID NO: 66          moltype = AA  length = 5
FEATURE                Location/Qualifiers
REGION                 1..5
                       note = Synthetic
source                 1..5
                       mol_type = protein
                       organism = synthetic construct
SEQUENCE: 66
GGDLS                                                                        5

SEQ ID NO: 67          moltype = AA  length = 5
FEATURE                Location/Qualifiers
REGION                 1..5
                       note = Synthetic
source                 1..5
                       mol_type = protein
                       organism = synthetic construct
```

-continued

```
SEQUENCE: 67
WGDLS                                                              5

SEQ ID NO: 68          moltype = AA  length = 5
FEATURE                Location/Qualifiers
REGION                 1..5
                       note = Synthetic
source                 1..5
                       mol_type = protein
                       organism = synthetic construct
SEQUENCE: 68
IGDLS                                                              5

SEQ ID NO: 69          moltype = AA  length = 5
FEATURE                Location/Qualifiers
REGION                 1..5
                       note = Synthetic
source                 1..5
                       mol_type = protein
                       organism = synthetic construct
SEQUENCE: 69
QGDLS                                                              5

SEQ ID NO: 70          moltype = AA  length = 11
FEATURE                Location/Qualifiers
REGION                 1..11
                       note = Synthetic
source                 1..11
                       mol_type = protein
                       organism = synthetic construct
SEQUENCE: 70
CASSVVDGEQ T                                                       11

SEQ ID NO: 71          moltype = AA  length = 11
FEATURE                Location/Qualifiers
REGION                 1..11
                       note = Synthetic
source                 1..11
                       mol_type = protein
                       organism = synthetic construct
SEQUENCE: 71
CASLVVDGEQ Y                                                       11

SEQ ID NO: 72          moltype = AA  length = 11
FEATURE                Location/Qualifiers
REGION                 1..11
                       note = Synthetic
source                 1..11
                       mol_type = protein
                       organism = synthetic construct
SEQUENCE: 72
CASSVQDGEQ Y                                                       11

SEQ ID NO: 73          moltype = AA  length = 11
FEATURE                Location/Qualifiers
REGION                 1..11
                       note = Synthetic
source                 1..11
                       mol_type = protein
                       organism = synthetic construct
SEQUENCE: 73
CASSVVDGEQ F                                                       11

SEQ ID NO: 74          moltype = AA  length = 11
FEATURE                Location/Qualifiers
REGION                 1..11
                       note = Synthetic
source                 1..11
                       mol_type = protein
                       organism = synthetic construct
SEQUENCE: 74
CASSVVDIEQ Y                                                       11

SEQ ID NO: 75          moltype = AA  length = 11
FEATURE                Location/Qualifiers
REGION                 1..11
                       note = Synthetic
source                 1..11
                       mol_type = protein
```

-continued

```
                                         organism = synthetic construct
SEQUENCE: 75
CASSVVDDEQ Y                                                              11

SEQ ID NO: 76              moltype = AA  length = 11
FEATURE                   Location/Qualifiers
REGION                    1..11
                          note = Synthetic
source                    1..11
                          mol_type = protein
                          organism = synthetic construct
SEQUENCE: 76
CASSVVDYEQ Y                                                              11

SEQ ID NO: 77              moltype = AA  length = 11
FEATURE                   Location/Qualifiers
REGION                    1..11
                          note = Synthetic
source                    1..11
                          mol_type = protein
                          organism = synthetic construct
SEQUENCE: 77
CASSVVDGED Y                                                              11

SEQ ID NO: 78              moltype = AA  length = 11
FEATURE                   Location/Qualifiers
REGION                    1..11
                          note = Synthetic
source                    1..11
                          mol_type = protein
                          organism = synthetic construct
SEQUENCE: 78
CASAVVDGEQ Y                                                              11

SEQ ID NO: 79              moltype = AA  length = 11
FEATURE                   Location/Qualifiers
REGION                    1..11
                          note = Synthetic
source                    1..11
                          mol_type = protein
                          organism = synthetic construct
SEQUENCE: 79
CASSNVDGEQ Y                                                              11

SEQ ID NO: 80              moltype = AA  length = 11
FEATURE                   Location/Qualifiers
REGION                    1..11
                          note = Synthetic
source                    1..11
                          mol_type = protein
                          organism = synthetic construct
SEQUENCE: 80
CAWSVVDGEQ Y                                                              11

SEQ ID NO: 81              moltype = AA  length = 11
FEATURE                   Location/Qualifiers
REGION                    1..11
                          note = Synthetic
source                    1..11
                          mol_type = protein
                          organism = synthetic construct
SEQUENCE: 81
CASLVVDGEQ T                                                              11

SEQ ID NO: 82              moltype = AA  length = 11
FEATURE                   Location/Qualifiers
REGION                    1..11
                          note = Synthetic
source                    1..11
                          mol_type = protein
                          organism = synthetic construct
SEQUENCE: 82
CASSVVDGEM Y                                                              11

SEQ ID NO: 83              moltype = AA  length = 11
FEATURE                   Location/Qualifiers
REGION                    1..11
                          note = Synthetic
source                    1..11
```

-continued

```
                              mol_type = protein
                              organism = synthetic construct
SEQUENCE: 83
CASSVVDGEG Y                                                             11

SEQ ID NO: 84          moltype = AA  length = 11
FEATURE                Location/Qualifiers
REGION                 1..11
                       note = Synthetic
source                 1..11
                       mol_type = protein
                       organism = synthetic construct
SEQUENCE: 84
CASSVVDGEE Y                                                             11

SEQ ID NO: 85          moltype = AA  length = 11
FEATURE                Location/Qualifiers
REGION                 1..11
                       note = Synthetic
source                 1..11
                       mol_type = protein
                       organism = synthetic construct
SEQUENCE: 85
CASSVVDGEN Y                                                             11

SEQ ID NO: 86          moltype = AA  length = 11
FEATURE                Location/Qualifiers
REGION                 1..11
                       note = Synthetic
source                 1..11
                       mol_type = protein
                       organism = synthetic construct
SEQUENCE: 86
CASSVVDGEQ V                                                             11

SEQ ID NO: 87          moltype = AA  length = 252
FEATURE                Location/Qualifiers
REGION                 1..252
                       note = Synthetic
source                 1..252
                       mol_type = protein
                       organism = synthetic construct
SEQUENCE: 87
QKEVEQNSGP LSVPEGAIAS LNCTYSDRGV QSFFWYRQYS GKSPELIMFI YSNGDKEDGR   60
FTAQLNKASQ YVSLLIRDSQ PSDSATYLCA VMRAGGFKTI FGAGTRLFVK ANIQNPDPAV   120
YQLRDSKSSD KSVCLFTDFD SQTNVSQSKD SDVYITDKCV LDMRSMDFKS NSAVAWSNKS   180
DFACANAFNN SIIPEDTFFP SPESSCDVKL VEKSFETDTN LNFQNLSVIG FRILLLKVAG   240
FNLLMTLRLW SS                                                        252

SEQ ID NO: 88          moltype = AA  length = 289
FEATURE                Location/Qualifiers
REGION                 1..289
                       note = Synthetic
source                 1..289
                       mol_type = protein
                       organism = synthetic construct
SEQUENCE: 88
DSGVTQTPKH LITATGQRVT LRCSPRSGDL SVYWYQQSLD QGLQFLIQYY NGEERAKGNI   60
LERFSAQQFP DLHSELNLSS LELGDSALYF CASSVVDGEQ YFGPGTRLTV TEDLKNVFPP   120
EVAVFEPSEA EISHTQKATL VCLATGFYPD HVELSWWVNG KEVHSGVCTD PQPLKEQPAL   180
NDSRYCLSSR LRVSATFWQN PRNHFRCQVQ FYGLSENDEW TQDRAKPVTQ IVSAEAWGRA   240
DCGFTSESYQ QGVLSATILY EILLGKATLY AVLVSALVLM AMVKRKDSR              289

SEQ ID NO: 89          moltype = AA  length = 252
FEATURE                Location/Qualifiers
REGION                 1..252
                       note = Synthetic
source                 1..252
                       mol_type = protein
                       organism = synthetic construct
SEQUENCE: 89
QKEVEQNSGP LSVPEGAIAS LNCTYSDRFS QSFFWYRQYS GKSPELIMFI YSNGDKEDGR   60
FTAQLNKASQ YVSLLIRDSQ PSDSATYLCA VMRAGGFKTI FGAGTRLFVK ANIQNPDPAV   120
YQLRDSKSSD KSVCLFTDFD SQTNVSQSKD SDVYITDKCV LDMRSMDFKS NSAVAWSNKS   180
DFACANAFNN SIIPEDTFFP SPESSCDVKL VEKSFETDTN LNFQNLSVIG FRILLLKVAG   240
FNLLMTLRLW SS                                                        252

SEQ ID NO: 90          moltype = AA  length = 289
FEATURE                Location/Qualifiers
```

```
REGION                  1..289
                        note = Synthetic
source                  1..289
                        mol_type = protein
                        organism = synthetic construct
SEQUENCE: 90
DSGVTQTPKH LITATGQRVT LRCSPRSGDL SVYWYQQSLD QGLQFLIQYY NGEERAKGNI   60
LERFSAQQFP DLHSELNLSS LELGDSALYF CASSVVDGEQ YFGPGTRLTV TEDLKNVFPP  120
EVAVFEPSEA EISHTQKATL VCLATGFYPD HVELSWWVNG KEVHSGVCTD PQPLKEQPAL  180
NDSRYCLSSR LRVSATFWQN PRNHFRCQVQ FYGLSENDEW TQDRAKPVTQ IVSAEAWGRA  240
DCGFTSESYQ QGVLSATILY EILLGKATLY AVLVSALVLM AMVKRKDSR              289

SEQ ID NO: 91          moltype = AA  length = 252
FEATURE                Location/Qualifiers
REGION                 1..252
                       note = Synthetic
source                 1..252
                       mol_type = protein
                       organism = synthetic construct
SEQUENCE: 91
QKEVEQNSGP LSVPEGAIAS LNCTYSDRGI QSFFWYRQYS GKSPELIMFI YSNGDKEDGR   60
FTAQLNKASQ YVSLLIRDSQ PSDSATYLCA VMRAGGFKTI FGAGTRLFVK ANIQNPDPAV  120
YQLRDSKSSD KSVCLFTDFD SQTNVSQSKD SDVYITDKCV LDMRSMDFKS NSAVAWSNKS  180
DFACANAFNN SIIPEDTFFP SPESSCDVKL VEKSFETDTN LNFQNLSVIG FRILLLKVAG  240
FNLLMTLRLW SS                                                      252

SEQ ID NO: 92          moltype = AA  length = 289
FEATURE                Location/Qualifiers
REGION                 1..289
                       note = Synthetic
source                 1..289
                       mol_type = protein
                       organism = synthetic construct
SEQUENCE: 92
DSGVTQTPKH LITATGQRVT LRCSPRSGDL SVYWYQQSLD QGLQFLIQYY NGEERAKGNI   60
LERFSAQQFP DLHSELNLSS LELGDSALYF CASSVVDGEQ YFGPGTRLTV TEDLKNVFPP  120
EVAVFEPSEA EISHTQKATL VCLATGFYPD HVELSWWVNG KEVHSGVCTD PQPLKEQPAL  180
NDSRYCLSSR LRVSATFWQN PRNHFRCQVQ FYGLSENDEW TQDRAKPVTQ IVSAEAWGRA  240
DCGFTSESYQ QGVLSATILY EILLGKATLY AVLVSALVLM AMVKRKDSR              289

SEQ ID NO: 93          moltype = AA  length = 252
FEATURE                Location/Qualifiers
REGION                 1..252
                       note = Synthetic
source                 1..252
                       mol_type = protein
                       organism = synthetic construct
SEQUENCE: 93
QKEVEQNSGP LSVPEGAIAS LNCTYSDRGS QAFFWYRQYS GKSPELIMFI YSNGDKEDGR   60
FTAQLNKASQ YVSLLIRDSQ PSDSATYLCA VMRAGGFKTI FGAGTRLFVK ANIQNPDPAV  120
YQLRDSKSSD KSVCLFTDFD SQTNVSQSKD SDVYITDKCV LDMRSMDFKS NSAVAWSNKS  180
DFACANAFNN SIIPEDTFFP SPESSCDVKL VEKSFETDTN LNFQNLSVIG FRILLLKVAG  240
FNLLMTLRLW SS                                                      252

SEQ ID NO: 94          moltype = AA  length = 289
FEATURE                Location/Qualifiers
REGION                 1..289
                       note = Synthetic
source                 1..289
                       mol_type = protein
                       organism = synthetic construct
SEQUENCE: 94
DSGVTQTPKH LITATGQRVT LRCSPRSGDL SVYWYQQSLD QGLQFLIQYY NGEERAKGNI   60
LERFSAQQFP DLHSELNLSS LELGDSALYF CASSVVDGEQ YFGPGTRLTV TEDLKNVFPP  120
EVAVFEPSEA EISHTQKATL VCLATGFYPD HVELSWWVNG KEVHSGVCTD PQPLKEQPAL  180
NDSRYCLSSR LRVSATFWQN PRNHFRCQVQ FYGLSENDEW TQDRAKPVTQ IVSAEAWGRA  240
DCGFTSESYQ QGVLSATILY EILLGKATLY AVLVSALVLM AMVKRKDSR              289

SEQ ID NO: 95          moltype = AA  length = 252
FEATURE                Location/Qualifiers
REGION                 1..252
                       note = Synthetic
source                 1..252
                       mol_type = protein
                       organism = synthetic construct
SEQUENCE: 95
QKEVEQNSGP LSVPEGAIAS LNCTYSDRWS QSFFWYRQYS GKSPELIMFI YSNGDKEDGR   60
FTAQLNKASQ YVSLLIRDSQ PSDSATYLCA VMRAGGFKTI FGAGTRLFVK ANIQNPDPAV  120
YQLRDSKSSD KSVCLFTDFD SQTNVSQSKD SDVYITDKCV LDMRSMDFKS NSAVAWSNKS  180
```

-continued

```
DFACANAFNN SIIPEDTFFP SPESSCDVKL VEKSFETDTN LNFQNLSVIG FRILLLKVAG   240
FNLLMTLRLW SS                                                       252

SEQ ID NO: 96              moltype = AA   length = 289
FEATURE                    Location/Qualifiers
REGION                     1..289
                           note = Synthetic
source                     1..289
                           mol_type = protein
                           organism = synthetic construct
SEQUENCE: 96
DSGVTQTPKH LITATGQRVT LRCSPRSGDL SVYWYQQSLD QGLQFLIQYY NGEERAKGNI   60
LERFSAQQFP DLHSELNLSS LELGDSALYF CASSVVDGEQ YFGPGTRLTV TEDLKNVFPP   120
EVAVFEPSEA EISHTQKATL VCLATGFYPD HVELSWWVNG KEVHSGVCTD PQPLKEQPAL   180
NDSRYCLSSR LRVSATFWQN PRNHFRCQVQ FYGLSENDEW TQDRAKPVTQ IVSAEAWGRA   240
DCGFTSESYQ QGVLSATILY EILLGKATLY AVLVSALVLM AMVKRKDSR              289

SEQ ID NO: 97              moltype = AA   length = 252
FEATURE                    Location/Qualifiers
REGION                     1..252
                           note = Synthetic
source                     1..252
                           mol_type = protein
                           organism = synthetic construct
SEQUENCE: 97
QKEVEQNSGP LSVPEGAIAS LNCTYSFRGS QSFFWYRQYS GKSPELIMFI YSNGDKEDGR   60
FTAQLNKASQ YVSLLIRDSQ PSDSATYLCA VMRAGGFKTI FGAGTRLFVK ANIQNPDPAV   120
YQLRDSKSSD KSVCLFTDFD SQTNVSQSKD SDVYITDKCV LDMRSMDFKS NSAVAWSNKS   180
DFACANAFNN SIIPEDTFFP SPESSCDVKL VEKSFETDTN LNFQNLSVIG FRILLLKVAG   240
FNLLMTLRLW SS                                                       252

SEQ ID NO: 98              moltype = AA   length = 289
FEATURE                    Location/Qualifiers
REGION                     1..289
                           note = Synthetic
source                     1..289
                           mol_type = protein
                           organism = synthetic construct
SEQUENCE: 98
DSGVTQTPKH LITATGQRVT LRCSPRSGDL SVYWYQQSLD QGLQFLIQYY NGEERAKGNI   60
LERFSAQQFP DLHSELNLSS LELGDSALYF CASSVVDGEQ YFGPGTRLTV TEDLKNVFPP   120
EVAVFEPSEA EISHTQKATL VCLATGFYPD HVELSWWVNG KEVHSGVCTD PQPLKEQPAL   180
NDSRYCLSSR LRVSATFWQN PRNHFRCQVQ FYGLSENDEW TQDRAKPVTQ IVSAEAWGRA   240
DCGFTSESYQ QGVLSATILY EILLGKATLY AVLVSALVLM AMVKRKDSR              289

SEQ ID NO: 99              moltype = AA   length = 252
FEATURE                    Location/Qualifiers
REGION                     1..252
                           note = Synthetic
source                     1..252
                           mol_type = protein
                           organism = synthetic construct
SEQUENCE: 99
QKEVEQNSGP LSVPEGAIAS LNCTYSDRYS QSFFWYRQYS GKSPELIMFI YSNGDKEDGR   60
FTAQLNKASQ YVSLLIRDSQ PSDSATYLCA VMRAGGFKTI FGAGTRLFVK ANIQNPDPAV   120
YQLRDSKSSD KSVCLFTDFD SQTNVSQSKD SDVYITDKCV LDMRSMDFKS NSAVAWSNKS   180
DFACANAFNN SIIPEDTFFP SPESSCDVKL VEKSFETDTN LNFQNLSVIG FRILLLKVAG   240
FNLLMTLRLW SS                                                       252

SEQ ID NO: 100             moltype = AA   length = 289
FEATURE                    Location/Qualifiers
REGION                     1..289
                           note = Synthetic
source                     1..289
                           mol_type = protein
                           organism = synthetic construct
SEQUENCE: 100
DSGVTQTPKH LITATGQRVT LRCSPRSGDL SVYWYQQSLD QGLQFLIQYY NGEERAKGNI   60
LERFSAQQFP DLHSELNLSS LELGDSALYF CASSVVDGEQ YFGPGTRLTV TEDLKNVFPP   120
EVAVFEPSEA EISHTQKATL VCLATGFYPD HVELSWWVNG KEVHSGVCTD PQPLKEQPAL   180
NDSRYCLSSR LRVSATFWQN PRNHFRCQVQ FYGLSENDEW TQDRAKPVTQ IVSAEAWGRA   240
DCGFTSESYQ QGVLSATILY EILLGKATLY AVLVSALVLM AMVKRKDSR              289

SEQ ID NO: 101             moltype = AA   length = 252
FEATURE                    Location/Qualifiers
REGION                     1..252
                           note = Synthetic
source                     1..252
                           mol_type = protein
```

```
                          organism = synthetic construct
SEQUENCE: 101
QKEVEQNSGP LSVPEGAIAS LNCTYSDRGS GSFFWYRQYS GKSPELIMFI YSNGDKEDGR   60
FTAQLNKASQ YVSLLIRDSQ PSDSATYLCA VMRAGGFKTI FGAGTRLFVK ANIQNPDPAV  120
YQLRDSKSSD KSVCLFTDFD SQTNVSQSKD SDVYITDKCV LDMRSMDFKS NSAVAWSNKS  180
DFACANAFNN SIIPEDTFFP SPESSCDVKL VEKSFETDTN LNFQNLSVIG FRILLLKVAG  240
FNLLMTLRLW SS                                                      252

SEQ ID NO: 102            moltype = AA   length = 289
FEATURE                   Location/Qualifiers
REGION                    1..289
                          note = Synthetic
source                    1..289
                          mol_type = protein
                          organism = synthetic construct
SEQUENCE: 102
DSGVTQTPKH LITATGQRVT LRCSPRSGDL SVYWYQQSLD QGLQFLIQYY NGEERAKGNI   60
LERFSAQQFP DLHSELNLSS LELGDSALYF CASSVVDGEQ YFGPGTRLTV TEDLKNVFPP  120
EVAVFEPSEA EISHTQKATL VCLATGFYPD HVELSWWVNG KEVHSGVCTD PQPLKEQPAL  180
NDSRYCLSSR LRVSATFWQN PRNHFRCQVQ FYGLSENDEW TQDRAKPVTQ IVSAEAWGRA  240
DCGFTSESYQ QGVLSATILY EILLGKATLY AVLVSALVLM AMVKRKDSR              289

SEQ ID NO: 103            moltype = AA   length = 252
FEATURE                   Location/Qualifiers
REGION                    1..252
                          note = Synthetic
source                    1..252
                          mol_type = protein
                          organism = synthetic construct
SEQUENCE: 103
QKEVEQNSGP LSVPEGAIAS LNCTYSDRGS QSFFWYRQYS GKSPELIMFI YSNGDKEDGR   60
FTAQLNKASQ YVSLLIRDSQ PSDSATYLCA VMRAHGFKTI FGAGTRLFVK ANIQNPDPAV  120
YQLRDSKSSD KSVCLFTDFD SQTNVSQSKD SDVYITDKCV LDMRSMDFKS NSAVAWSNKS  180
DFACANAFNN SIIPEDTFFP SPESSCDVKL VEKSFETDTN LNFQNLSVIG FRILLLKVAG  240
FNLLMTLRLW SS                                                      252

SEQ ID NO: 104            moltype = AA   length = 289
FEATURE                   Location/Qualifiers
REGION                    1..289
                          note = Synthetic
source                    1..289
                          mol_type = protein
                          organism = synthetic construct
SEQUENCE: 104
DSGVTQTPKH LITATGQRVT LRCSPRSGDL SVYWYQQSLD QGLQFLIQYY NGEERAKGNI   60
LERFSAQQFP DLHSELNLSS LELGDSALYF CASSVVDGEQ YFGPGTRLTV TEDLKNVFPP  120
EVAVFEPSEA EISHTQKATL VCLATGFYPD HVELSWWVNG KEVHSGVCTD PQPLKEQPAL  180
NDSRYCLSSR LRVSATFWQN PRNHFRCQVQ FYGLSENDEW TQDRAKPVTQ IVSAEAWGRA  240
DCGFTSESYQ QGVLSATILY EILLGKATLY AVLVSALVLM AMVKRKDSR              289

SEQ ID NO: 105            moltype = AA   length = 252
FEATURE                   Location/Qualifiers
REGION                    1..252
                          note = Synthetic
source                    1..252
                          mol_type = protein
                          organism = synthetic construct
SEQUENCE: 105
QKEVEQNSGP LSVPEGAIAS LNCTYSDRGS QSFFWYRQYS GKSPELIMFI YSNGDKEDGR   60
FTAQLNKASQ YVSLLIRDSQ PSDSATYLCA VVRAGGFKTI FGAGTRLFVK ANIQNPDPAV  120
YQLRDSKSSD KSVCLFTDFD SQTNVSQSKD SDVYITDKCV LDMRSMDFKS NSAVAWSNKS  180
DFACANAFNN SIIPEDTFFP SPESSCDVKL VEKSFETDTN LNFQNLSVIG FRILLLKVAG  240
FNLLMTLRLW SS                                                      252

SEQ ID NO: 106            moltype = AA   length = 289
FEATURE                   Location/Qualifiers
REGION                    1..289
                          note = Synthetic
source                    1..289
                          mol_type = protein
                          organism = synthetic construct
SEQUENCE: 106
DSGVTQTPKH LITATGQRVT LRCSPRSGDL SVYWYQQSLD QGLQFLIQYY NGEERAKGNI   60
LERFSAQQFP DLHSELNLSS LELGDSALYF CASSVVDGEQ YFGPGTRLTV TEDLKNVFPP  120
EVAVFEPSEA EISHTQKATL VCLATGFYPD HVELSWWVNG KEVHSGVCTD PQPLKEQPAL  180
NDSRYCLSSR LRVSATFWQN PRNHFRCQVQ FYGLSENDEW TQDRAKPVTQ IVSAEAWGRA  240
DCGFTSESYQ QGVLSATILY EILLGKATLY AVLVSALVLM AMVKRKDSR              289

SEQ ID NO: 107            moltype = AA   length = 252
```

```
FEATURE               Location/Qualifiers
REGION                1..252
                      note = Synthetic
source                1..252
                      mol_type = protein
                      organism = synthetic construct
SEQUENCE: 107
QKEVEQNSGP LSVPEGAIAS LNCTYSDRGS QSFFWYRQYS GKSPELIMFI YSNGDKEDGR   60
FTAQLNKASQ YVSLLIRDSQ PSDSATYLCA VLRAGGFKTI FGAGTRLFVK ANIQNPDPAV  120
YQLRDSKSSD KSVCLFTDFD SQTNVSQSKD SDVYITDKCV LDMRSMDFKS NSAVAWSNKS  180
DFACANAFNN SIIPEDTFFP SPESSCDVKL VEKSFETDTN LNFQNLSVIG FRILLLKVAG  240
FNLLMTLRLW SS                                                      252

SEQ ID NO: 108         moltype = AA   length = 289
FEATURE               Location/Qualifiers
REGION                1..289
                      note = Synthetic
source                1..289
                      mol_type = protein
                      organism = synthetic construct
SEQUENCE: 108
DSGVTQTPKH LITATGQRVT LRCSPRSGDL SVYWYQQSLD QGLQFLIQYY NGEERAKGNI   60
LERFSAQQFP DLHSELNLSS LELGDSALYF CASSVVDGEQ YFGPGTRLTV TEDLKNVFPP  120
EVAVFEPSEA EISHTQKATL VCLATGFYPD HVELSWWVNG KEVHSGVCTD PQPLKEQPAL  180
NDSRYCLSSR LRVSATFWQN PRNHFRCQVQ FYGLSENDEW TQDRAKPVTQ IVSAEAWGRA  240
DCGFTSESYQ QGVLSATILY EILLGKATLY AVLVSALVLM AMVKRKDSR              289

SEQ ID NO: 109         moltype = AA   length = 252
FEATURE               Location/Qualifiers
REGION                1..252
                      note = Synthetic
source                1..252
                      mol_type = protein
                      organism = synthetic construct
SEQUENCE: 109
QKEVEQNSGP LSVPEGAIAS LNCTYSDRGS QSFFWYRQYS GKSPELIMFI YSNGDKEDGR   60
FTAQLNKASQ YVSLLIRDSQ PSDSATYLCA YMRAGGFKTI FGAGTRLFVK ANIQNPDPAV  120
YQLRDSKSSD KSVCLFTDFD SQTNVSQSKD SDVYITDKCV LDMRSMDFKS NSAVAWSNKS  180
DFACANAFNN SIIPEDTFFP SPESSCDVKL VEKSFETDTN LNFQNLSVIG FRILLLKVAG  240
FNLLMTLRLW SS                                                      252

SEQ ID NO: 110         moltype = AA   length = 289
FEATURE               Location/Qualifiers
REGION                1..289
                      note = Synthetic
source                1..289
                      mol_type = protein
                      organism = synthetic construct
SEQUENCE: 110
DSGVTQTPKH LITATGQRVT LRCSPRSGDL SVYWYQQSLD QGLQFLIQYY NGEERAKGNI   60
LERFSAQQFP DLHSELNLSS LELGDSALYF CASSVVDGEQ YFGPGTRLTV TEDLKNVFPP  120
EVAVFEPSEA EISHTQKATL VCLATGFYPD HVELSWWVNG KEVHSGVCTD PQPLKEQPAL  180
NDSRYCLSSR LRVSATFWQN PRNHFRCQVQ FYGLSENDEW TQDRAKPVTQ IVSAEAWGRA  240
DCGFTSESYQ QGVLSATILY EILLGKATLY AVLVSALVLM AMVKRKDSR              289

SEQ ID NO: 111         moltype = AA   length = 252
FEATURE               Location/Qualifiers
REGION                1..252
                      note = Synthetic
source                1..252
                      mol_type = protein
                      organism = synthetic construct
SEQUENCE: 111
QKEVEQNSGP LSVPEGAIAS LNCTYSDRGS QSFFWYRQYS GKSPELIMFI YSNGDKEDGR   60
FTAQLNKASQ YVSLLIRDSQ PSDSATYLCA VMRAGYFKTI FGAGTRLFVK ANIQNPDPAV  120
YQLRDSKSSD KSVCLFTDFD SQTNVSQSKD SDVYITDKCV LDMRSMDFKS NSAVAWSNKS  180
DFACANAFNN SIIPEDTFFP SPESSCDVKL VEKSFETDTN LNFQNLSVIG FRILLLKVAG  240
FNLLMTLRLW SS                                                      252

SEQ ID NO: 112         moltype = AA   length = 289
FEATURE               Location/Qualifiers
REGION                1..289
                      note = Synthetic
source                1..289
                      mol_type = protein
                      organism = synthetic construct
SEQUENCE: 112
DSGVTQTPKH LITATGQRVT LRCSPRSGDL SVYWYQQSLD QGLQFLIQYY NGEERAKGNI   60
LERFSAQQFP DLHSELNLSS LELGDSALYF CASSVVDGEQ YFGPGTRLTV TEDLKNVFPP  120
```

```
EVAVFEPSEA EISHTQKATL VCLATGFYPD HVELSWWVNG KEVHSGVCTD PQPLKEQPAL  180
NDSRYCLSSR LRVSATFWQN PRNHFRCQVQ FYGLSENDEW TQDRAKPVTQ IVSAEAWGRA  240
DCGFTSESYQ QGVLSATILY EILLGKATLY AVLVSALVLM AMVKRKDSR              289

SEQ ID NO: 113            moltype = AA  length = 252
FEATURE                   Location/Qualifiers
REGION                    1..252
                          note = Synthetic
source                    1..252
                          mol_type = protein
                          organism = synthetic construct
SEQUENCE: 113
QKEVEQNSGP LSVPEGAIAS LNCTYSDRGS QSFFWYRQYS GKSPELIMFI YSNGDKEDGR  60
FTAQLNKASQ YVSLLIRDSQ PSDSATYLCA VMRAGGFKEI FGAGTRLFVK ANIQNPDPAV  120
YQLRDSKSSD KSVCLFTDFD SQTNVSQSKD SDVYITDKCV LDMRSMDFKS NSAVAWSNKS  180
DFACANAFNN SIIPEDTFFP SPESSCDVKL VEKSFETDTN LNFQNLSVIG FRILLLKVAG  240
FNLLMTLRLW SS                                                     252

SEQ ID NO: 114            moltype = AA  length = 289
FEATURE                   Location/Qualifiers
REGION                    1..289
                          note = Synthetic
source                    1..289
                          mol_type = protein
                          organism = synthetic construct
SEQUENCE: 114
DSGVTQTPKH LITATGQRVT LRCSPRSGDL SVYWYQQSLD QGLQFLIQYY NGEERAKGNI  60
LERFSAQQFP DLHSELNLSS LELGDSALYF CASSVVDGEQ YFGPGTRLTV TEDLKNVFPP  120
EVAVFEPSEA EISHTQKATL VCLATGFYPD HVELSWWVNG KEVHSGVCTD PQPLKEQPAL  180
NDSRYCLSSR LRVSATFWQN PRNHFRCQVQ FYGLSENDEW TQDRAKPVTQ IVSAEAWGRA  240
DCGFTSESYQ QGVLSATILY EILLGKATLY AVLVSALVLM AMVKRKDSR              289

SEQ ID NO: 115            moltype = AA  length = 252
FEATURE                   Location/Qualifiers
REGION                    1..252
                          note = Synthetic
source                    1..252
                          mol_type = protein
                          organism = synthetic construct
SEQUENCE: 115
QKEVEQNSGP LSVPEGAIAS LNCTYSDRGS QSFFWYRQYS GKSPELIMFI YSNGDKEDGR  60
FTAQLNKASQ YVSLLIRDSQ PSDSATYLCA VMRMGGFKTI FGAGTRLFVK ANIQNPDPAV  120
YQLRDSKSSD KSVCLFTDFD SQTNVSQSKD SDVYITDKCV LDMRSMDFKS NSAVAWSNKS  180
DFACANAFNN SIIPEDTFFP SPESSCDVKL VEKSFETDTN LNFQNLSVIG FRILLLKVAG  240
FNLLMTLRLW SS                                                     252

SEQ ID NO: 116            moltype = AA  length = 289
FEATURE                   Location/Qualifiers
REGION                    1..289
                          note = Synthetic
source                    1..289
                          mol_type = protein
                          organism = synthetic construct
SEQUENCE: 116
DSGVTQTPKH LITATGQRVT LRCSPRSGDL SVYWYQQSLD QGLQFLIQYY NGEERAKGNI  60
LERFSAQQFP DLHSELNLSS LELGDSALYF CASSVVDGEQ YFGPGTRLTV TEDLKNVFPP  120
EVAVFEPSEA EISHTQKATL VCLATGFYPD HVELSWWVNG KEVHSGVCTD PQPLKEQPAL  180
NDSRYCLSSR LRVSATFWQN PRNHFRCQVQ FYGLSENDEW TQDRAKPVTQ IVSAEAWGRA  240
DCGFTSESYQ QGVLSATILY EILLGKATLY AVLVSALVLM AMVKRKDSR              289

SEQ ID NO: 117            moltype = AA  length = 252
FEATURE                   Location/Qualifiers
REGION                    1..252
                          note = Synthetic
source                    1..252
                          mol_type = protein
                          organism = synthetic construct
SEQUENCE: 117
QKEVEQNSGP LSVPEGAIAS LNCTYSDRGS QSFFWYRQYS GKSPELIMFI YSNGDKEDGR  60
FTAQLNKASQ YVSLLIRDSQ PSDSATYLCA VMRAFGFKTI FGAGTRLFVK ANIQNPDPAV  120
YQLRDSKSSD KSVCLFTDFD SQTNVSQSKD SDVYITDKCV LDMRSMDFKS NSAVAWSNKS  180
DFACANAFNN SIIPEDTFFP SPESSCDVKL VEKSFETDTN LNFQNLSVIG FRILLLKVAG  240
FNLLMTLRLW SS                                                     252

SEQ ID NO: 118            moltype = AA  length = 289
FEATURE                   Location/Qualifiers
REGION                    1..289
                          note = Synthetic
source                    1..289
```

```
                              mol_type = protein
                              organism = synthetic construct
SEQUENCE: 118
DSGVTQTPKH LITATGQRVT LRCSPRSGDL SVYWYQQSLD QGLQFLIQYY NGEERAKGNI  60
LERFSAQQFP DLHSELNLSS LELGDSALYF CASSVVDGEQ YFGPGTRLTV TEDLKNVFPP  120
EVAVFEPSEA EISHTQKATL VCLATGFYPD HVELSWWVNG KEVHSGVCTD PQPLKEQPAL  180
NDSRYCLSSR LRVSATFWQN PRNHFRCQVQ FYGLSENDEW TQDRAKPVTQ IVSAEAWGRA  240
DCGFTSESYQ QGVLSATILY EILLGKATLY AVLVSALVLM AMVKRKDSR             289

SEQ ID NO: 119          moltype = AA  length = 252
FEATURE                 Location/Qualifiers
REGION                  1..252
                        note = Synthetic
source                  1..252
                        mol_type = protein
                        organism = synthetic construct
SEQUENCE: 119
QKEVEQNSGP LSVPEGAIAS LNCTYSDRGS QSFFWYRQYS GKSPELIMFI YSNGDKEDGR  60
FTAQLNKASQ YVSLLIRDSQ PSDSATYLCA VMRATGFKTI FGAGTRLFVK ANIQNPDPAV  120
YQLRDSKSSD KSVCLFTDFD SQTNVSQSKD SDVYITDKCV LDMRSMDFKS NSAVAWSNKS  180
DFACANAFNN SIIPEDTFFP SPESSCDVKL VEKSFETDTN LNFQNLSVIG FRILLLKVAG  240
FNLLMTLRLW SS                                                      252

SEQ ID NO: 120          moltype = AA  length = 289
FEATURE                 Location/Qualifiers
REGION                  1..289
                        note = Synthetic
source                  1..289
                        mol_type = protein
                        organism = synthetic construct
SEQUENCE: 120
DSGVTQTPKH LITATGQRVT LRCSPRSGDL SVYWYQQSLD QGLQFLIQYY NGEERAKGNI  60
LERFSAQQFP DLHSELNLSS LELGDSALYF CASSVVDGEQ YFGPGTRLTV TEDLKNVFPP  120
EVAVFEPSEA EISHTQKATL VCLATGFYPD HVELSWWVNG KEVHSGVCTD PQPLKEQPAL  180
NDSRYCLSSR LRVSATFWQN PRNHFRCQVQ FYGLSENDEW TQDRAKPVTQ IVSAEAWGRA  240
DCGFTSESYQ QGVLSATILY EILLGKATLY AVLVSALVLM AMVKRKDSR             289

SEQ ID NO: 121          moltype = AA  length = 252
FEATURE                 Location/Qualifiers
REGION                  1..252
                        note = Synthetic
source                  1..252
                        mol_type = protein
                        organism = synthetic construct
SEQUENCE: 121
QKEVEQNSGP LSVPEGAIAS LNCTYSDRGS QSFFWYRQYS GKSPELIMFI YSNGDKEDGR  60
FTAQLNKASQ YVSLLIRDSQ PSDSATYLCA TMRAGGFKTI FGAGTRLFVK ANIQNPDPAV  120
YQLRDSKSSD KSVCLFTDFD SQTNVSQSKD SDVYITDKCV LDMRSMDFKS NSAVAWSNKS  180
DFACANAFNN SIIPEDTFFP SPESSCDVKL VEKSFETDTN LNFQNLSVIG FRILLLKVAG  240
FNLLMTLRLW SS                                                      252

SEQ ID NO: 122          moltype = AA  length = 289
FEATURE                 Location/Qualifiers
REGION                  1..289
                        note = Synthetic
source                  1..289
                        mol_type = protein
                        organism = synthetic construct
SEQUENCE: 122
DSGVTQTPKH LITATGQRVT LRCSPRSGDL SVYWYQQSLD QGLQFLIQYY NGEERAKGNI  60
LERFSAQQFP DLHSELNLSS LELGDSALYF CASSVVDGEQ YFGPGTRLTV TEDLKNVFPP  120
EVAVFEPSEA EISHTQKATL VCLATGFYPD HVELSWWVNG KEVHSGVCTD PQPLKEQPAL  180
NDSRYCLSSR LRVSATFWQN PRNHFRCQVQ FYGLSENDEW TQDRAKPVTQ IVSAEAWGRA  240
DCGFTSESYQ QGVLSATILY EILLGKATLY AVLVSALVLM AMVKRKDSR             289

SEQ ID NO: 123          moltype = AA  length = 252
FEATURE                 Location/Qualifiers
REGION                  1..252
                        note = Synthetic
source                  1..252
                        mol_type = protein
                        organism = synthetic construct
SEQUENCE: 123
QKEVEQNSGP LSVPEGAIAS LNCTYSDRGS QSFFWYRQYS GKSPELIMFI YSNGDKEDGR  60
FTAQLNKASQ YVSLLIRDSQ PSDSATYLCA VWRAGGFKTI FGAGTRLFVK ANIQNPDPAV  120
YQLRDSKSSD KSVCLFTDFD SQTNVSQSKD SDVYITDKCV LDMRSMDFKS NSAVAWSNKS  180
DFACANAFNN SIIPEDTFFP SPESSCDVKL VEKSFETDTN LNFQNLSVIG FRILLLKVAG  240
FNLLMTLRLW SS                                                      252
```

```
SEQ ID NO: 124              moltype = AA   length = 289
FEATURE                    Location/Qualifiers
REGION                     1..289
                           note = Synthetic
source                     1..289
                           mol_type = protein
                           organism = synthetic construct
SEQUENCE: 124
DSGVTQTPKH LITATGQRVT LRCSPRSGDL SVYWYQQSLD QGLQFLIQYY NGEERAKGNI   60
LERFSAQQFP DLHSELNLSS LELGDSALYF CASSVVDGEQ YFGPGTRLTV TEDLKNVFPP  120
EVAVFEPSEA EISHTQKATL VCLATGFYPD HVELSWWVNG KEVHSGVCTD PQPLKEQPAL  180
NDSRYCLSSR LRVSATFWQN PRNHFRCQVQ FYGLSENDEW TQDRAKPVTQ IVSAEAWGRA  240
DCGFTSESYQ QGVLSATILY EILLGKATLY AVLVSALVLM AMVKRKDSR              289

SEQ ID NO: 125              moltype = AA   length = 252
FEATURE                    Location/Qualifiers
REGION                     1..252
                           note = Synthetic
source                     1..252
                           mol_type = protein
                           organism = synthetic construct
SEQUENCE: 125
QKEVEQNSGP LSVPEGAIAS LNCTYSDRGS QSFFWYRQYS GKSPELIMFI YSNGDKEDGR   60
FTAQLNKASQ YVSLLIRDSQ PSDSATYLCA YMRAGGFKEI FGAGTRLFVK ANIQNPDPAV  120
YQLRDSKSSD KSVCLFTDFD SQTNVSQSKD SDVYITDKCV LDMRSMDFKS NSAVAWSNKS  180
DFACANAFNN SIIPEDTFFP SPESSCDVKL VEKSFETDTN LNFQNLSVIG FRILLLKVAG  240
FNLLMTLRLW SS                                                      252

SEQ ID NO: 126              moltype = AA   length = 289
FEATURE                    Location/Qualifiers
REGION                     1..289
                           note = Synthetic
source                     1..289
                           mol_type = protein
                           organism = synthetic construct
SEQUENCE: 126
DSGVTQTPKH LITATGQRVT LRCSPRSGDL SVYWYQQSLD QGLQFLIQYY NGEERAKGNI   60
LERFSAQQFP DLHSELNLSS LELGDSALYF CASSVVDGEQ YFGPGTRLTV TEDLKNVFPP  120
EVAVFEPSEA EISHTQKATL VCLATGFYPD HVELSWWVNG KEVHSGVCTD PQPLKEQPAL  180
NDSRYCLSSR LRVSATFWQN PRNHFRCQVQ FYGLSENDEW TQDRAKPVTQ IVSAEAWGRA  240
DCGFTSESYQ QGVLSATILY EILLGKATLY AVLVSALVLM AMVKRKDSR              289

SEQ ID NO: 127              moltype = AA   length = 252
FEATURE                    Location/Qualifiers
REGION                     1..252
                           note = Synthetic
source                     1..252
                           mol_type = protein
                           organism = synthetic construct
SEQUENCE: 127
QKEVEQNSGP LSVPEGAIAS LNCTYSDRGS QSFFWYRQYS GKSPELIMFI YSNGDKEDGR   60
FTAQLNKASQ YVSLLIRDSQ PSDSATYLCA VMRAGGFKTS FGAGTRLFVK ANIQNPDPAV  120
YQLRDSKSSD KSVCLFTDFD SQTNVSQSKD SDVYITDKCV LDMRSMDFKS NSAVAWSNKS  180
DFACANAFNN SIIPEDTFFP SPESSCDVKL VEKSFETDTN LNFQNLSVIG FRILLLKVAG  240
FNLLMTLRLW SS                                                      252

SEQ ID NO: 128              moltype = AA   length = 289
FEATURE                    Location/Qualifiers
REGION                     1..289
                           note = Synthetic
source                     1..289
                           mol_type = protein
                           organism = synthetic construct
SEQUENCE: 128
DSGVTQTPKH LITATGQRVT LRCSPRSGDL SVYWYQQSLD QGLQFLIQYY NGEERAKGNI   60
LERFSAQQFP DLHSELNLSS LELGDSALYF CASSVVDGEQ YFGPGTRLTV TEDLKNVFPP  120
EVAVFEPSEA EISHTQKATL VCLATGFYPD HVELSWWVNG KEVHSGVCTD PQPLKEQPAL  180
NDSRYCLSSR LRVSATFWQN PRNHFRCQVQ FYGLSENDEW TQDRAKPVTQ IVSAEAWGRA  240
DCGFTSESYQ QGVLSATILY EILLGKATLY AVLVSALVLM AMVKRKDSR              289

SEQ ID NO: 129              moltype = AA   length = 252
FEATURE                    Location/Qualifiers
REGION                     1..252
                           note = Synthetic
source                     1..252
                           mol_type = protein
                           organism = synthetic construct
SEQUENCE: 129
QKEVEQNSGP LSVPEGAIAS LNCTYSDRGS QSFFWYRQYS GKSPELIMFI YSNGDKEDGR   60
```

```
FTAQLNKASQ YVSLLIRDSQ PSDSATYLCA AMRAGGFKTI FGAGTRLFVK ANIQNPDPAV   120
YQLRDSKSSD KSVCLFTDFD SQTNVSQSKD SDVYITDKCV LDMRSMDFKS NSAVAWSNKS   180
DPACANAFNN SIIPEDTFFP SPESSCDVKL VEKSFETDTN LNFQNLSVIG FRILLLKVAG   240
FNLLMTLRLW SS                                                       252

SEQ ID NO: 130              moltype = AA   length = 289
FEATURE                    Location/Qualifiers
REGION                     1..289
                           note = Synthetic
source                     1..289
                           mol_type = protein
                           organism = synthetic construct
SEQUENCE: 130
DSGVTQTPKH LITATGQRVT LRCSPRSGDL SVYWYQQSLD QGLQFLIQYY NGEERAKGNI   60
LERFSAQQFP DLHSELNLSS LELGDSALYF CASSVVDGEQ YFGPGTRLTV TEDLKNVFPP   120
EVAVFEPSEA EISHTQKATL VCLATGFYPD HVELSWWVNG KEVHSGVCTD PQPLKEQPAL   180
NDSRYCLSSR LRVSATFWQN PRNHFRCQVQ FYGLSENDEW TQDRAKPVTQ IVSAEAWGRA   240
DCGFTSESYQ QGVLSATILY EILLGKATLY AVLVSALVLM AMVKRKDSR              289

SEQ ID NO: 131              moltype = AA   length = 252
FEATURE                    Location/Qualifiers
REGION                     1..252
                           note = Synthetic
source                     1..252
                           mol_type = protein
                           organism = synthetic construct
SEQUENCE: 131
QKEVEQNSGP LSVPEGAIAS LNCTYSDRGS QSFFWYRQYS GKSPELIMFI YSNGDKEDGR   60
FTAQLNKASQ YVSLLIRDSQ PSDSATYLCA VQRAGGFKTI FGAGTRLFVK ANIQNPDPAV   120
YQLRDSKSSD KSVCLFTDFD SQTNVSQSKD SDVYITDKCV LDMRSMDFKS NSAVAWSNKS   180
DPACANAFNN SIIPEDTFFP SPESSCDVKL VEKSFETDTN LNFQNLSVIG FRILLLKVAG   240
FNLLMTLRLW SS                                                       252

SEQ ID NO: 132              moltype = AA   length = 289
FEATURE                    Location/Qualifiers
REGION                     1..289
                           note = Synthetic
source                     1..289
                           mol_type = protein
                           organism = synthetic construct
SEQUENCE: 132
DSGVTQTPKH LITATGQRVT LRCSPRSGDL SVYWYQQSLD QGLQFLIQYY NGEERAKGNI   60
LERFSAQQFP DLHSELNLSS LELGDSALYF CASSVVDGEQ YFGPGTRLTV TEDLKNVFPP   120
EVAVFEPSEA EISHTQKATL VCLATGFYPD HVELSWWVNG KEVHSGVCTD PQPLKEQPAL   180
NDSRYCLSSR LRVSATFWQN PRNHFRCQVQ FYGLSENDEW TQDRAKPVTQ IVSAEAWGRA   240
DCGFTSESYQ QGVLSATILY EILLGKATLY AVLVSALVLM AMVKRKDSR              289

SEQ ID NO: 133              moltype = AA   length = 252
FEATURE                    Location/Qualifiers
REGION                     1..252
                           note = Synthetic
source                     1..252
                           mol_type = protein
                           organism = synthetic construct
SEQUENCE: 133
QKEVEQNSGP LSVPEGAIAS LNCTYSRRGS QSFFWYRQYS GKSPELIMFI YSNGDKEDGR   60
FTAQLNKASQ YVSLLIRDSQ PSDSATYLCA VMRAGGFKTI FGAGTRLFVK ANIQNPDPAV   120
YQLRDSKSSD KSVCLFTDFD SQTNVSQSKD SDVYITDKCV LDMRSMDFKS NSAVAWSNKS   180
DPACANAFNN SIIPEDTFFP SPESSCDVKL VEKSFETDTN LNFQNLSVIG FRILLLKVAG   240
FNLLMTLRLW SS                                                       252

SEQ ID NO: 134              moltype = AA   length = 289
FEATURE                    Location/Qualifiers
REGION                     1..289
                           note = Synthetic
source                     1..289
                           mol_type = protein
                           organism = synthetic construct
SEQUENCE: 134
DSGVTQTPKH LITATGQRVT LRCSPRSGDL SVYWYQQSLD QGLQFLIQYY NGEERAKGNI   60
LERFSAQQFP DLHSELNLSS LELGDSALYF CASSVVDGEQ YFGPGTRLTV TEDLKNVFPP   120
EVAVFEPSEA EISHTQKATL VCLATGFYPD HVELSWWVNG KEVHSGVCTD PQPLKEQPAL   180
NDSRYCLSSR LRVSATFWQN PRNHFRCQVQ FYGLSENDEW TQDRAKPVTQ IVSAEAWGRA   240
DCGFTSESYQ QGVLSATILY EILLGKATLY AVLVSALVLM AMVKRKDSR              289

SEQ ID NO: 135              moltype = AA   length = 252
FEATURE                    Location/Qualifiers
REGION                     1..252
                           note = Synthetic
```

```
source                    1..252
                          mol_type = protein
                          organism = synthetic construct
SEQUENCE: 135
QKEVEQNSGP LSVPEGAIAS LNCTYSDRGL QSFFWYRQYS GKSPELIMFI YSNGDKEDGR    60
FTAQLNKASQ YVSLLIRDSQ PSDSATYLCA VMRAGGFKTI FGAGTRLFVK ANIQNPDPAV   120
YQLRDSKSSD KSVCLFTDFD SQTNVSQSKD SDVYITDKCV LDMRSMDFKS NSAVAWSNKS   180
DFACANAFNN SIIPEDTFFP SPESSCDVKL VEKSFETDTN LNFQNLSVIG FRILLLKVAG   240
FNLLMTLRLW SS                                                       252

SEQ ID NO: 136            moltype = AA   length = 289
FEATURE                   Location/Qualifiers
REGION                    1..289
                          note = Synthetic
source                    1..289
                          mol_type = protein
                          organism = synthetic construct
SEQUENCE: 136
DSGVTQTPKH LITATGQRVT LRCSPRSGDL SVYWYQQSLD QGLQFLIQYY NGEERAKGNI    60
LERFSAQQFP DLHSELNLSS LELGDSALYF CASSVVDGEQ YFGPGTRLTV TEDLKNVFPP   120
EVAVFEPSEA EISHTQKATL VCLATGFYPD HVELSWWVNG KEVHSGVCTD PQPLKEQPAL   180
NDSRYCLSSR LRVSATFWQN PRNHFRCQVQ FYGLSENDEW TQDRAKPVTQ IVSAEAWGRA   240
DCGFTSESYQ QGVLSATILY EILLGKATLY AVLVSALVLM AMVKRKDSR              289

SEQ ID NO: 137            moltype = AA   length = 252
FEATURE                   Location/Qualifiers
REGION                    1..252
                          note = Synthetic
source                    1..252
                          mol_type = protein
                          organism = synthetic construct
SEQUENCE: 137
QKEVEQNSGP LSVPEGAIAS LNCTYSDRGS QSFFWYRQYS GKSPELIMFI YSNGDKEDGR    60
FTAQLNKASQ YVSLLIRDSQ PSDSATYLCA VMRIGGFKTI FGAGTRLFVK ANIQNPDPAV   120
YQLRDSKSSD KSVCLFTDFD SQTNVSQSKD SDVYITDKCV LDMRSMDFKS NSAVAWSNKS   180
DFACANAFNN SIIPEDTFFP SPESSCDVKL VEKSFETDTN LNFQNLSVIG FRILLLKVAG   240
FNLLMTLRLW SS                                                       252

SEQ ID NO: 138            moltype = AA   length = 289
FEATURE                   Location/Qualifiers
REGION                    1..289
                          note = Synthetic
source                    1..289
                          mol_type = protein
                          organism = synthetic construct
SEQUENCE: 138
DSGVTQTPKH LITATGQRVT LRCSPRSGDL SVYWYQQSLD QGLQFLIQYY NGEERAKGNI    60
LERFSAQQFP DLHSELNLSS LELGDSALYF CASSVVDGEQ YFGPGTRLTV TEDLKNVFPP   120
EVAVFEPSEA EISHTQKATL VCLATGFYPD HVELSWWVNG KEVHSGVCTD PQPLKEQPAL   180
NDSRYCLSSR LRVSATFWQN PRNHFRCQVQ FYGLSENDEW TQDRAKPVTQ IVSAEAWGRA   240
DCGFTSESYQ QGVLSATILY EILLGKATLY AVLVSALVLM AMVKRKDSR              289

SEQ ID NO: 139            moltype = AA   length = 252
FEATURE                   Location/Qualifiers
REGION                    1..252
                          note = Synthetic
source                    1..252
                          mol_type = protein
                          organism = synthetic construct
SEQUENCE: 139
QKEVEQNSGP LSVPEGAIAS LNCTYSDRGS QSFFWYRQYS GKSPELIMFI YSNGDKEDGR    60
FTAQLNKASQ YVSLLIRDSQ PSDSATYLCA VMRAGGFKTI FGAGTRLFVK ANIQNPDPAV   120
YQLRDSKSSD KSVCLFTDFD SQTNVSQSKD SDVYITDKCV LDMRSMDFKS NSAVAWSNKS   180
DFACANAFNN SIIPEDTFFP SPESSCDVKL VEKSFETDTN LNFQNLSVIG FRILLLKVAG   240
FNLLMTLRLW SS                                                       252

SEQ ID NO: 140            moltype = AA   length = 289
FEATURE                   Location/Qualifiers
REGION                    1..289
                          note = Synthetic
source                    1..289
                          mol_type = protein
                          organism = synthetic construct
SEQUENCE: 140
DSGVTQTPKH LITATGQRVT LRCSPRSGNL SVYWYQQSLD QGLQFLIQYY NGEERAKGNI    60
LERFSAQQFP DLHSELNLSS LELGDSALYF CASSVVDGEQ YFGPGTRLTV TEDLKNVFPP   120
EVAVFEPSEA EISHTQKATL VCLATGFYPD HVELSWWVNG KEVHSGVCTD PQPLKEQPAL   180
NDSRYCLSSR LRVSATFWQN PRNHFRCQVQ FYGLSENDEW TQDRAKPVTQ IVSAEAWGRA   240
DCGFTSESYQ QGVLSATILY EILLGKATLY AVLVSALVLM AMVKRKDSR              289
```

-continued

```
SEQ ID NO: 141          moltype = AA  length = 289
FEATURE                 Location/Qualifiers
REGION                  1..289
                        note = Synthetic
source                  1..289
                        mol_type = protein
                        organism = synthetic construct
SEQUENCE: 141
DSGVTQTPKH LITATGQRVT LRCSPRAGDL SVYWYQQSLD QGLQFLIQYY NGEERAKGNI  60
LERFSAQQFP DLHSELNLSS LELGDSALYF CASSVVDGEQ YFGPGTRLTV TEDLKNVFPP  120
EVAVFEPSEA EISHTQKATL VCLATGFYPD HVELSWWVNG KEVHSGVCTD PQPLKEQPAL  180
NDSRYCLSSR LRVSATFWQN PRNHFRCQVQ FYGLSENDEW TQDRAKPVTQ IVSAEAWGRA  240
DCGFTSESYQ QGVLSATILY EILLGKATLY AVLVSALVLM AMVKRKDSR            289

SEQ ID NO: 142          moltype = AA  length = 289
FEATURE                 Location/Qualifiers
REGION                  1..289
                        note = Synthetic
source                  1..289
                        mol_type = protein
                        organism = synthetic construct
SEQUENCE: 142
DSGVTQTPKH LITATGQRVT LRCSPRSGDL IVYWYQQSLD QGLQFLIQYY NGEERAKGNI  60
LERFSAQQFP DLHSELNLSS LELGDSALYF CASSVVDGEQ YFGPGTRLTV TEDLKNVFPP  120
EVAVFEPSEA EISHTQKATL VCLATGFYPD HVELSWWVNG KEVHSGVCTD PQPLKEQPAL  180
NDSRYCLSSR LRVSATFWQN PRNHFRCQVQ FYGLSENDEW TQDRAKPVTQ IVSAEAWGRA  240
DCGFTSESYQ QGVLSATILY EILLGKATLY AVLVSALVLM AMVKRKDSR            289

SEQ ID NO: 143          moltype = AA  length = 289
FEATURE                 Location/Qualifiers
REGION                  1..289
                        note = Synthetic
source                  1..289
                        mol_type = protein
                        organism = synthetic construct
SEQUENCE: 143
DSGVTQTPKH LITATGQRVT LRCSPRSGWL SVYWYQQSLD QGLQFLIQYY NGEERAKGNI  60
LERFSAQQFP DLHSELNLSS LELGDSALYF CASSVVDGEQ YFGPGTRLTV TEDLKNVFPP  120
EVAVFEPSEA EISHTQKATL VCLATGFYPD HVELSWWVNG KEVHSGVCTD PQPLKEQPAL  180
NDSRYCLSSR LRVSATFWQN PRNHFRCQVQ FYGLSENDEW TQDRAKPVTQ IVSAEAWGRA  240
DCGFTSESYQ QGVLSATILY EILLGKATLY AVLVSALVLM AMVKRKDSR            289

SEQ ID NO: 144          moltype = AA  length = 289
FEATURE                 Location/Qualifiers
REGION                  1..289
                        note = Synthetic
source                  1..289
                        mol_type = protein
                        organism = synthetic construct
SEQUENCE: 144
DSGVTQTPKH LITATGQRVT LRCSPRSGDL SVYWYQQSLD QGLQFLIQYY NGEERAKGNI  60
LERFSAQQFP DLHSELNLSS LELGDSALYF CASSVVDGEQ TFGPGTRLTV TEDLKNVFPP  120
EVAVFEPSEA EISHTQKATL VCLATGFYPD HVELSWWVNG KEVHSGVCTD PQPLKEQPAL  180
NDSRYCLSSR LRVSATFWQN PRNHFRCQVQ FYGLSENDEW TQDRAKPVTQ IVSAEAWGRA  240
DCGFTSESYQ QGVLSATILY EILLGKATLY AVLVSALVLM AMVKRKDSR            289

SEQ ID NO: 145          moltype = AA  length = 289
FEATURE                 Location/Qualifiers
REGION                  1..289
                        note = Synthetic
source                  1..289
                        mol_type = protein
                        organism = synthetic construct
SEQUENCE: 145
DSGVTQTPKH LITATGQRVT LRCSPRSGDL SVYWYQQSLD QGLQFLIQYY NGEERAKGNI  60
LERFSAQQFP DLHSELNLSS LELGDSALYF CASLVVDGEQ YFGPGTRLTV TEDLKNVFPP  120
EVAVFEPSEA EISHTQKATL VCLATGFYPD HVELSWWVNG KEVHSGVCTD PQPLKEQPAL  180
NDSRYCLSSR LRVSATFWQN PRNHFRCQVQ FYGLSENDEW TQDRAKPVTQ IVSAEAWGRA  240
DCGFTSESYQ QGVLSATILY EILLGKATLY AVLVSALVLM AMVKRKDSR            289

SEQ ID NO: 146          moltype = AA  length = 289
FEATURE                 Location/Qualifiers
REGION                  1..289
                        note = Synthetic
source                  1..289
                        mol_type = protein
                        organism = synthetic construct
SEQUENCE: 146
```

-continued

```
DSGVTQTPKH LITATGQRVT LRCSPRSGDL SVYWYQQSLD QGLQFLIQYY NGEERAKGNI    60
LERFSAQQFP DLHSELNLSS LELGDSALYF CASSVQDGEQ YFGPGTRLTV TEDLKNVFPP   120
EVAVFEPSEA EISHTQKATL VCLATGFYPD HVELSWWVNG KEVHSGVCTD PQPLKEQPAL   180
NDSRYCLSSR LRVSATFWQN PRNHFRCQVQ FYGLSENDEW TQDRAKPVTQ IVSAEAWGRA   240
DCGFTSESYQ QGVLSATILY EILLGKATLY AVLVSALVLM AMVKRKDSR               289

SEQ ID NO: 147           moltype = AA   length = 289
FEATURE                  Location/Qualifiers
REGION                   1..289
                         note = Synthetic
source                   1..289
                         mol_type = protein
                         organism = synthetic construct
SEQUENCE: 147
DSGVTQTPKH LITATGQRVT LRCSPRSGDL SVYWYQQSLD QGLQFLIQYY NGEERAKGNI    60
LERFSAQQFP DLHSELNLSS LELGDSALYF CASSVVDGEQ FFGPGTRLTV TEDLKNVFPP   120
EVAVFEPSEA EISHTQKATL VCLATGFYPD HVELSWWVNG KEVHSGVCTD PQPLKEQPAL   180
NDSRYCLSSR LRVSATFWQN PRNHFRCQVQ FYGLSENDEW TQDRAKPVTQ IVSAEAWGRA   240
DCGFTSESYQ QGVLSATILY EILLGKATLY AVLVSALVLM AMVKRKDSR               289

SEQ ID NO: 148           moltype = AA   length = 289
FEATURE                  Location/Qualifiers
REGION                   1..289
                         note = Synthetic
source                   1..289
                         mol_type = protein
                         organism = synthetic construct
SEQUENCE: 148
DSGVTQTPKH LITATGQRVT LRCSPRSGDL SVYWYQQSLD QGLQFLIQYY NGEERAKGNI    60
LERFSAQQFP DLHSELNLSS LELGDSALYF CASSVVDIEQ YFGPGTRLTV TEDLKNVFPP   120
EVAVFEPSEA EISHTQKATL VCLATGFYPD HVELSWWVNG KEVHSGVCTD PQPLKEQPAL   180
NDSRYCLSSR LRVSATFWQN PRNHFRCQVQ FYGLSENDEW TQDRAKPVTQ IVSAEAWGRA   240
DCGFTSESYQ QGVLSATILY EILLGKATLY AVLVSALVLM AMVKRKDSR               289

SEQ ID NO: 149           moltype = AA   length = 289
FEATURE                  Location/Qualifiers
REGION                   1..289
                         note = Synthetic
source                   1..289
                         mol_type = protein
                         organism = synthetic construct
SEQUENCE: 149
DSGVTQTPKH LITATGQRVT LRCSPRSGNL SVYWYQQSLD QGLQFLIQYY NGEERAKGNI    60
LERFSAQQFP DLHSELNLSS LELGDSALYF CASSVVDGEQ TFGPGTRLTV TEDLKNVFPP   120
EVAVFEPSEA EISHTQKATL VCLATGFYPD HVELSWWVNG KEVHSGVCTD PQPLKEQPAL   180
NDSRYCLSSR LRVSATFWQN PRNHFRCQVQ FYGLSENDEW TQDRAKPVTQ IVSAEAWGRA   240
DCGFTSESYQ QGVLSATILY EILLGKATLY AVLVSALVLM AMVKRKDSR               289

SEQ ID NO: 150           moltype = AA   length = 289
FEATURE                  Location/Qualifiers
REGION                   1..289
                         note = Synthetic
source                   1..289
                         mol_type = protein
                         organism = synthetic construct
SEQUENCE: 150
DSGVTQTPKH LITATGQRVT LRCSPRSGDL SVYWYQQSLD QGLQFLIQYY NGEERAKGNI    60
LERFSAQQFP DLHSELNLSS LELGDSALYF CASLVVDGEQ TFGPGTRLTV TEDLKNVFPP   120
EVAVFEPSEA EISHTQKATL VCLATGFYPD HVELSWWVNG KEVHSGVCTD PQPLKEQPAL   180
NDSRYCLSSR LRVSATFWQN PRNHFRCQVQ FYGLSENDEW TQDRAKPVTQ IVSAEAWGRA   240
DCGFTSESYQ QGVLSATILY EILLGKATLY AVLVSALVLM AMVKRKDSR               289

SEQ ID NO: 151           moltype = AA   length = 289
FEATURE                  Location/Qualifiers
REGION                   1..289
                         note = Synthetic
source                   1..289
                         mol_type = protein
                         organism = synthetic construct
SEQUENCE: 151
DSGVTQTPKH LITATGQRVT LRCSPRSGLL SVYWYQQSLD QGLQFLIQYY NGEERAKGNI    60
LERFSAQQFP DLHSELNLSS LELGDSALYF CASSVVDGEQ YFGPGTRLTV TEDLKNVFPP   120
EVAVFEPSEA EISHTQKATL VCLATGFYPD HVELSWWVNG KEVHSGVCTD PQPLKEQPAL   180
NDSRYCLSSR LRVSATFWQN PRNHFRCQVQ FYGLSENDEW TQDRAKPVTQ IVSAEAWGRA   240
DCGFTSESYQ QGVLSATILY EILLGKATLY AVLVSALVLM AMVKRKDSR               289

SEQ ID NO: 152           moltype = AA   length = 289
FEATURE                  Location/Qualifiers
REGION                   1..289
```

-continued

```
                              note = Synthetic
source                        1..289
                              mol_type = protein
                              organism = synthetic construct
SEQUENCE: 152
DSGVTQTPKH LITATGQRVT LRCSPRSGSL SVYWYQQSLD QGLQFLIQYY NGEERAKGNI    60
LERFSAQQFP DLHSELNLSS LELGDSALYF CASSVVDGEQ YFGPGTRLTV TEDLKNVFPP   120
EVAVFEPSEA EISHTQKATL VCLATGFYPD HVELSWWVNG KEVHSGVCTD PQPLKEQPAL   180
NDSRYCLSSR LRVSATFWQN PRNHFRCQVQ FYGLSENDEW TQDRAKPVTQ IVSAEAWGRA   240
DCGFTSESYQ QGVLSATILY EILLGKATLY AVLVSALVLM AMVKRKDSR               289

SEQ ID NO: 153              moltype = AA  length = 289
FEATURE                    Location/Qualifiers
REGION                     1..289
                           note = Synthetic
source                     1..289
                           mol_type = protein
                           organism = synthetic construct
SEQUENCE: 153
DSGVTQTPKH LITATGQRVT LRCSPRTGDL SVYWYQQSLD QGLQFLIQYY NGEERAKGNI    60
LERFSAQQFP DLHSELNLSS LELGDSALYF CASSVVDGEQ YFGPGTRLTV TEDLKNVFPP   120
EVAVFEPSEA EISHTQKATL VCLATGFYPD HVELSWWVNG KEVHSGVCTD PQPLKEQPAL   180
NDSRYCLSSR LRVSATFWQN PRNHFRCQVQ FYGLSENDEW TQDRAKPVTQ IVSAEAWGRA   240
DCGFTSESYQ QGVLSATILY EILLGKATLY AVLVSALVLM AMVKRKDSR               289

SEQ ID NO: 154              moltype = AA  length = 289
FEATURE                    Location/Qualifiers
REGION                     1..289
                           note = Synthetic
source                     1..289
                           mol_type = protein
                           organism = synthetic construct
SEQUENCE: 154
DSGVTQTPKH LITATGQRVT LRCSPRSGDL SVYWYQQSLD QGLQFLIQYY NGEERAKGNI    60
LERFSAQQFP DLHSELNLSS LELGDSALYF CASSVVDDEQ YFGPGTRLTV TEDLKNVFPP   120
EVAVFEPSEA EISHTQKATL VCLATGFYPD HVELSWWVNG KEVHSGVCTD PQPLKEQPAL   180
NDSRYCLSSR LRVSATFWQN PRNHFRCQVQ FYGLSENDEW TQDRAKPVTQ IVSAEAWGRA   240
DCGFTSESYQ QGVLSATILY EILLGKATLY AVLVSALVLM AMVKRKDSR               289

SEQ ID NO: 155              moltype = AA  length = 289
FEATURE                    Location/Qualifiers
REGION                     1..289
                           note = Synthetic
source                     1..289
                           mol_type = protein
                           organism = synthetic construct
SEQUENCE: 155
DSGVTQTPKH LITATGQRVT LRCSPRSGDL SVYWYQQSLD QGLQFLIQYY NGEERAKGNI    60
LERFSAQQFP DLHSELNLSS LELGDSALYF CASSVVDYEQ YFGPGTRLTV TEDLKNVFPP   120
EVAVFEPSEA EISHTQKATL VCLATGFYPD HVELSWWVNG KEVHSGVCTD PQPLKEQPAL   180
NDSRYCLSSR LRVSATFWQN PRNHFRCQVQ FYGLSENDEW TQDRAKPVTQ IVSAEAWGRA   240
DCGFTSESYQ QGVLSATILY EILLGKATLY AVLVSALVLM AMVKRKDSR               289

SEQ ID NO: 156              moltype = AA  length = 289
FEATURE                    Location/Qualifiers
REGION                     1..289
                           note = Synthetic
source                     1..289
                           mol_type = protein
                           organism = synthetic construct
SEQUENCE: 156
DSGVTQTPKH LITATGQRVT LRCSPRSGDL SVYWYQQSLD QGLQFLIQYY NGEERAKGNI    60
LERFSAQQFP DLHSELNLSS LELGDSALYF CASSVVDGEQ YFGPGTRLTV TEDLKNVFPP   120
EVAVFEPSEA EISHTQKATL VCLATGFYPD HVELSWWVNG KEVHSGVCTD PQPLKEQPAL   180
NDSRYCLSSR LRVSATFWQN PRNHFRCQVQ FYGLSENDEW TQDRAKPVTQ IVSAEAWGRA   240
DCGFTSESYQ QGVLSATILY EILLGKATLY AVLVSALVLM AMVKRKDSR               289

SEQ ID NO: 157              moltype = AA  length = 289
FEATURE                    Location/Qualifiers
REGION                     1..289
                           note = Synthetic
source                     1..289
                           mol_type = protein
                           organism = synthetic construct
SEQUENCE: 157
DSGVTQTPKH LITATGQRVT LRCSPRSGNL SVYWYQQSLD QGLQFLIQYY NGEERAKGNI    60
LERFSAQQFP DLHSELNLSS LELGDSALYF CASSVVDDEQ YFGPGTRLTV TEDLKNVFPP   120
EVAVFEPSEA EISHTQKATL VCLATGFYPD HVELSWWVNG KEVHSGVCTD PQPLKEQPAL   180
NDSRYCLSSR LRVSATFWQN PRNHFRCQVQ FYGLSENDEW TQDRAKPVTQ IVSAEAWGRA   240
```

-continued

```
DCGFTSESYQ QGVLSATILY EILLGKATLY AVLVSALVLM AMVKRKDSR            289

SEQ ID NO: 158            moltype = AA  length = 289
FEATURE                   Location/Qualifiers
REGION                    1..289
                          note = Synthetic
source                    1..289
                          mol_type = protein
                          organism = synthetic construct
SEQUENCE: 158
DSGVTQTPKH LITATGQRVT LRCSPRSGDL SVYWYQQSLD QGLQFLIQYY NGEERAKGNI   60
LERFSAQQFP DLHSELNLSS LELGDSALYF CASAVVDGEQ YFGPGTRLTV TEDLKNVFPP  120
EVAVFEPSEA EISHTQKATL VCLATGFYPD HVELSWWVNG KEVHSGVCTD PQPLKEQPAL  180
NDSRYCLSSR LRVSATFWQN PRNHFRCQVQ FYGLSENDEW TQDRAKPVTQ IVSAEAWGRA  240
DCGFTSESYQ QGVLSATILY EILLGKATLY AVLVSALVLM AMVKRKDSR            289

SEQ ID NO: 159            moltype = AA  length = 289
FEATURE                   Location/Qualifiers
REGION                    1..289
                          note = Synthetic
source                    1..289
                          mol_type = protein
                          organism = synthetic construct
SEQUENCE: 159
DSGVTQTPKH LITATGQRVT LRCSPRSGDL SVYWYQQSLD QGLQFLIQYY NGEERAKGNI   60
LERFSAQQFP DLHSELNLSS LELGDSALYF CASNVVDGEQ YFGPGTRLTV TEDLKNVFPP  120
EVAVFEPSEA EISHTQKATL VCLATGFYPD HVELSWWVNG KEVHSGVCTD PQPLKEQPAL  180
NDSRYCLSSR LRVSATFWQN PRNHFRCQVQ FYGLSENDEW TQDRAKPVTQ IVSAEAWGRA  240
DCGFTSESYQ QGVLSATILY EILLGKATLY AVLVSALVLM AMVKRKDSR            289

SEQ ID NO: 160            moltype = AA  length = 289
FEATURE                   Location/Qualifiers
REGION                    1..289
                          note = Synthetic
source                    1..289
                          mol_type = protein
                          organism = synthetic construct
SEQUENCE: 160
DSGVTQTPKH LITATGQRVT LRCSPRMGDL SVYWYQQSLD QGLQFLIQYY NGEERAKGNI   60
LERFSAQQFP DLHSELNLSS LELGDSALYF CASSVVDGEQ YFGPGTRLTV TEDLKNVFPP  120
EVAVFEPSEA EISHTQKATL VCLATGFYPD HVELSWWVNG KEVHSGVCTD PQPLKEQPAL  180
NDSRYCLSSR LRVSATFWQN PRNHFRCQVQ FYGLSENDEW TQDRAKPVTQ IVSAEAWGRA  240
DCGFTSESYQ QGVLSATILY EILLGKATLY AVLVSALVLM AMVKRKDSR            289

SEQ ID NO: 161            moltype = AA  length = 289
FEATURE                   Location/Qualifiers
REGION                    1..289
                          note = Synthetic
source                    1..289
                          mol_type = protein
                          organism = synthetic construct
SEQUENCE: 161
DSGVTQTPKH LITATGQRVT LRCSPRSGDL SVYWYQQSLD QGLQFLIQYY NGEERAKGNI   60
LERFSAQQFP DLHSELNLSS LELGDSALYF CAWSVVDGEQ YFGPGTRLTV TEDLKNVFPP  120
EVAVFEPSEA EISHTQKATL VCLATGFYPD HVELSWWVNG KEVHSGVCTD PQPLKEQPAL  180
NDSRYCLSSR LRVSATFWQN PRNHFRCQVQ FYGLSENDEW TQDRAKPVTQ IVSAEAWGRA  240
DCGFTSESYQ QGVLSATILY EILLGKATLY AVLVSALVLM AMVKRKDSR            289

SEQ ID NO: 162            moltype = AA  length = 252
FEATURE                   Location/Qualifiers
REGION                    1..252
                          note = Synthetic
source                    1..252
                          mol_type = protein
                          organism = synthetic construct
SEQUENCE: 162
QKEVEQNSGP LSVPEGAIAS LNCTYSDRGS QSFFWYRQYS GKSPELIMFI YSNGDKEDGR   60
FTAQLNKASQ YVSLLIRDSQ PSDSATYLCA NMRAGGFKTI FGAGTRLFVK ANIQNPDPAV  120
YQLRDSKSSD KSVCLFTDFD SQTNVSQSKD SDVYITDKCV LDMRSMDFKS NSAVAWSNKS  180
DFACANAFNN SIIPEDTFFP SPESSCDVKL VEKSFETDTN LNFQNLSVIG FRILLLKVAG  240
FNLLMTLRLW SS                                                     252

SEQ ID NO: 163            moltype = AA  length = 289
FEATURE                   Location/Qualifiers
REGION                    1..289
                          note = Synthetic
source                    1..289
                          mol_type = protein
                          organism = synthetic construct
```

```
SEQUENCE: 163
DSGVTQTPKH LITATGQRVT LRCSPRSGDL SVYWYQQSLD QGLQFLIQYY NGEERAKGNI  60
LERFSAQQFP DLHSELNLSS LELGDSALYF CASSVVDGEQ YFGPGTRLTV TEDLKNVFPP  120
EVAVFEPSEA EISHTQKATL VCLATGFYPD HVELSWWVNG KEVHSGVCTD PQPLKEQPAL  180
NDSRYCLSSR LRVSATFWQN PRNHFRCQVQ FYGLSENDEW TQDRAKPVTQ IVSAEAWGRA  240
DCGFTSESYQ QGVLSATILY EILLGKATLY AVLVSALVLM AMVKRKDSR              289

SEQ ID NO: 164          moltype = AA  length = 252
FEATURE                 Location/Qualifiers
REGION                  1..252
                        note = Synthetic
source                  1..252
                        mol_type = protein
                        organism = synthetic construct
SEQUENCE: 164
QKEVEQNSGP LSVPEGAIAS LNCTYSDRGS QSFFWYRQYS GKSPELIMFI YSNGDKEDGR  60
FTAQLNKASQ YVSLLIRDSQ PSDSATYLCA VMRAQGFKTI FGAGTRLFVK ANIQNPDPAV  120
YQLRDSKSSD KSVCLFTDFD SQTNVSQSKD SDVYITDKCV LDMRSMDFKS NSAVAWSNKS  180
DFACANAFNN SIIPEDTFFP SPESSCDVKL VEKSFETDTN LNFQNLSVIG FRILLLKVAG  240
FNLLMTLRLW SS                                                     252

SEQ ID NO: 165          moltype = AA  length = 289
FEATURE                 Location/Qualifiers
REGION                  1..289
                        note = Synthetic
source                  1..289
                        mol_type = protein
                        organism = synthetic construct
SEQUENCE: 165
DSGVTQTPKH LITATGQRVT LRCSPRSGDL SVYWYQQSLD QGLQFLIQYY NGEERAKGNI  60
LERFSAQQFP DLHSELNLSS LELGDSALYF CASSVVDGEQ YFGPGTRLTV TEDLKNVFPP  120
EVAVFEPSEA EISHTQKATL VCLATGFYPD HVELSWWVNG KEVHSGVCTD PQPLKEQPAL  180
NDSRYCLSSR LRVSATFWQN PRNHFRCQVQ FYGLSENDEW TQDRAKPVTQ IVSAEAWGRA  240
DCGFTSESYQ QGVLSATILY EILLGKATLY AVLVSALVLM AMVKRKDSR              289

SEQ ID NO: 166          moltype = AA  length = 252
FEATURE                 Location/Qualifiers
REGION                  1..252
                        note = Synthetic
source                  1..252
                        mol_type = protein
                        organism = synthetic construct
SEQUENCE: 166
QKEVEQNSGP LSVPEGAIAS LNCTYSDRGS QSFFWYRQYS GKSPELIMFI YSNGDKEDGR  60
FTAQLNKASQ YVSLLIRDSQ PSDSATYLCA VMRAAGFKTI FGAGTRLFVK ANIQNPDPAV  120
YQLRDSKSSD KSVCLFTDFD SQTNVSQSKD SDVYITDKCV LDMRSMDFKS NSAVAWSNKS  180
DFACANAFNN SIIPEDTFFP SPESSCDVKL VEKSFETDTN LNFQNLSVIG FRILLLKVAG  240
FNLLMTLRLW SS                                                     252

SEQ ID NO: 167          moltype = AA  length = 289
FEATURE                 Location/Qualifiers
REGION                  1..289
                        note = Synthetic
source                  1..289
                        mol_type = protein
                        organism = synthetic construct
SEQUENCE: 167
DSGVTQTPKH LITATGQRVT LRCSPRSGDL SVYWYQQSLD QGLQFLIQYY NGEERAKGNI  60
LERFSAQQFP DLHSELNLSS LELGDSALYF CASSVVDGEQ YFGPGTRLTV TEDLKNVFPP  120
EVAVFEPSEA EISHTQKATL VCLATGFYPD HVELSWWVNG KEVHSGVCTD PQPLKEQPAL  180
NDSRYCLSSR LRVSATFWQN PRNHFRCQVQ FYGLSENDEW TQDRAKPVTQ IVSAEAWGRA  240
DCGFTSESYQ QGVLSATILY EILLGKATLY AVLVSALVLM AMVKRKDSR              289

SEQ ID NO: 168          moltype = AA  length = 252
FEATURE                 Location/Qualifiers
REGION                  1..252
                        note = Synthetic
source                  1..252
                        mol_type = protein
                        organism = synthetic construct
SEQUENCE: 168
QKEVEQNSGP LSVPEGAIAS LNCTYSDRGS QSFFWYRQYS GKSPELIMFI YSNGDKEDGR  60
FTAQLNKASQ YVSLLIRDSQ PSDSATYLCA VMFAGGFKTI FGAGTRLFVK ANIQNPDPAV  120
YQLRDSKSSD KSVCLFTDFD SQTNVSQSKD SDVYITDKCV LDMRSMDFKS NSAVAWSNKS  180
DFACANAFNN SIIPEDTFFP SPESSCDVKL VEKSFETDTN LNFQNLSVIG FRILLLKVAG  240
FNLLMTLRLW SS                                                     252

SEQ ID NO: 169          moltype = AA  length = 289
FEATURE                 Location/Qualifiers
```

```
REGION                    1..289
                          note = Synthetic
source                    1..289
                          mol_type = protein
                          organism = synthetic construct
SEQUENCE: 169
DSGVTQTPKH LITATGQRVT LRCSPRSGDL SVYWYQQSLD QGLQFLIQYY NGEERAKGNI    60
LERFSAQQFP DLHSELNLSS LELGDSALYF CASSVVDGEQ YFGPGTRLTV TEDLKNVFPP   120
EVAVFEPSEA EISHTQKATL VCLATGFYPD HVELSWWVNG KEVHSGVCTD PQPLKEQPAL   180
NDSRYCLSSR LRVSATFWQN PRNHFRCQVQ FYGLSENDEW TQDRAKPVTQ IVSAEAWGRA   240
DCGFTSESYQ QGVLSATILY EILLGKATLY AVLVSALVLM AMVKRKDSR               289

SEQ ID NO: 170          moltype = AA  length = 252
FEATURE                 Location/Qualifiers
REGION                    1..252
                          note = Synthetic
source                    1..252
                          mol_type = protein
                          organism = synthetic construct
SEQUENCE: 170
QKEVEQNSGP LSVPEGAIAS LNCTYSDRGS QSFFWYRQYS GKSPELIMFI YSNGDKEDGR    60
FTAQLNKASQ YVSLLIRDSQ PSDSATYLCA VMRAGGFKTA FGAGTRLFVK ANIQNPDPAV   120
YQLRDSKSSD KSVCLFTDFD SQTNVSQSKD SDVYITDKCV LDMRSMDFKS NSAVAWSNKS   180
DFACANAFNN SIIPEDTFFP SPESSCDVKL VEKSFETDTN LNFQNLSVIG FRILLLKVAG   240
FNLLMTLRLW SS                                                       252

SEQ ID NO: 171          moltype = AA  length = 289
FEATURE                 Location/Qualifiers
REGION                    1..289
                          note = Synthetic
source                    1..289
                          mol_type = protein
                          organism = synthetic construct
SEQUENCE: 171
DSGVTQTPKH LITATGQRVT LRCSPRSGDL SVYWYQQSLD QGLQFLIQYY NGEERAKGNI    60
LERFSAQQFP DLHSELNLSS LELGDSALYF CASSVVDGEQ YFGPGTRLTV TEDLKNVFPP   120
EVAVFEPSEA EISHTQKATL VCLATGFYPD HVELSWWVNG KEVHSGVCTD PQPLKEQPAL   180
NDSRYCLSSR LRVSATFWQN PRNHFRCQVQ FYGLSENDEW TQDRAKPVTQ IVSAEAWGRA   240
DCGFTSESYQ QGVLSATILY EILLGKATLY AVLVSALVLM AMVKRKDSR               289

SEQ ID NO: 172          moltype = AA  length = 252
FEATURE                 Location/Qualifiers
REGION                    1..252
                          note = Synthetic
source                    1..252
                          mol_type = protein
                          organism = synthetic construct
SEQUENCE: 172
QKEVEQNSGP LSVPEGAIAS LNCTYSDRGS QSFFWYRQYS GKSPELIMFI YSNGDKEDGR    60
FTAQLNKASQ YVSLLIRDSQ PSDSATYLCA VMRAVGFKTI FGAGTRLFVK ANIQNPDPAV   120
YQLRDSKSSD KSVCLFTDFD SQTNVSQSKD SDVYITDKCV LDMRSMDFKS NSAVAWSNKS   180
DFACANAFNN SIIPEDTFFP SPESSCDVKL VEKSFETDTN LNFQNLSVIG FRILLLKVAG   240
FNLLMTLRLW SS                                                       252

SEQ ID NO: 173          moltype = AA  length = 289
FEATURE                 Location/Qualifiers
REGION                    1..289
                          note = Synthetic
source                    1..289
                          mol_type = protein
                          organism = synthetic construct
SEQUENCE: 173
DSGVTQTPKH LITATGQRVT LRCSPRSGDL SVYWYQQSLD QGLQFLIQYY NGEERAKGNI    60
LERFSAQQFP DLHSELNLSS LELGDSALYF CASSVVDGEQ YFGPGTRLTV TEDLKNVFPP   120
EVAVFEPSEA EISHTQKATL VCLATGFYPD HVELSWWVNG KEVHSGVCTD PQPLKEQPAL   180
NDSRYCLSSR LRVSATFWQN PRNHFRCQVQ FYGLSENDEW TQDRAKPVTQ IVSAEAWGRA   240
DCGFTSESYQ QGVLSATILY EILLGKATLY AVLVSALVLM AMVKRKDSR               289

SEQ ID NO: 174          moltype = AA  length = 252
FEATURE                 Location/Qualifiers
REGION                    1..252
                          note = Synthetic
source                    1..252
                          mol_type = protein
                          organism = synthetic construct
SEQUENCE: 174
QKEVEQNSGP LSVPEGAIAS LNCTYSDRGS QSFFWYRQYS GKSPELIMFI YSNGDKEDGR    60
FTAQLNKASQ YVSLLIRDSQ PSDSATYLCA VMRAYGFKTI FGAGTRLFVK ANIQNPDPAV   120
YQLRDSKSSD KSVCLFTDFD SQTNVSQSKD SDVYITDKCV LDMRSMDFKS NSAVAWSNKS   180
```

-continued

```
DFACANAFNN SIIPEDTFFP SPESSCDVKL VEKSFETDTN LNFQNLSVIG FRILLLKVAG    240
FNLLMTLRLW SS                                                        252

SEQ ID NO: 175         moltype = AA  length = 289
FEATURE                Location/Qualifiers
REGION                 1..289
                       note = Synthetic
source                 1..289
                       mol_type = protein
                       organism = synthetic construct
SEQUENCE: 175
DSGVTQTPKH LITATGQRVT LRCSPRSGDL SVYWYQQSLD QGLQFLIQYY NGEERAKGNI    60
LERFSAQQFP DLHSELNLSS LELGDSALYF CASSVVDGEQ YFGPGTRLTV TEDLKNVFPP    120
EVAVFEPSEA EISHTQKATL VCLATGFYPD HVELSWWVNG KEVHSGVCTD PQPLKEQPAL    180
NDSRYCLSSR LRVSATFWQN PRNHFRCQVQ FYGLSENDEW TQDRAKPVTQ IVSAEAWGRA    240
DCGFTSESYQ QGVLSATILY EILLGKATLY AVLVSALVLM AMVKRKDSR               289

SEQ ID NO: 176         moltype = AA  length = 289
FEATURE                Location/Qualifiers
REGION                 1..289
                       note = Synthetic
source                 1..289
                       mol_type = protein
                       organism = synthetic construct
SEQUENCE: 176
DSGVTQTPKH LITATGQRVT LRCSPRSGDL SVYWYQQSLD QGLQFLIQYY NGEERAKGNI    60
LERFSAQQFP DLHSELNLSS LELGDSALYF CASSVVDGEQ YFGPGTRLTV TEDLKNVFPP    120
EVAVFEPSEA EISHTQKATL VCLATGFYPD HVELSWWVNG KEVHSGVCTD PQPLKEQPAL    180
NDSRYCLSSR LRVSATFWQN PRNHFRCQVQ FYGLSENDEW TQDRAKPVTQ IVSAEAWGRA    240
DCGFTSESYQ QGVLSATILY EILLGKATLY AVLVSALVLM AMVKRKDSR               289

SEQ ID NO: 177         moltype = AA  length = 252
FEATURE                Location/Qualifiers
REGION                 1..252
                       note = Synthetic
source                 1..252
                       mol_type = protein
                       organism = synthetic construct
SEQUENCE: 177
QKEVEQNSGP LSVPEGAIAS LNCTYSDRGS QSFFWYRQYS GKSPELIMFI YSNGDKEDGR    60
FTAQLNKASQ YVSLLIRDSQ PSDSATYLCA VMRASGFKTI FGAGTRLFVK ANIQNPDPAV    120
YQLRDSKSSD KSVCLFTDFD SQTNVSQSKD SDVYITDKCV LDMRSMDFKS NSAVAWSNKS    180
DFACANAFNN SIIPEDTFFP SPESSCDVKL VEKSFETDTN LNFQNLSVIG FRILLLKVAG    240
FNLLMTLRLW SS                                                        252

SEQ ID NO: 178         moltype = AA  length = 289
FEATURE                Location/Qualifiers
REGION                 1..289
                       note = Synthetic
source                 1..289
                       mol_type = protein
                       organism = synthetic construct
SEQUENCE: 178
DSGVTQTPKH LITATGQRVT LRCSPRSGDL SVYWYQQSLD QGLQFLIQYY NGEERAKGNI    60
LERFSAQQFP DLHSELNLSS LELGDSALYF CASSVVDGEQ YFGPGTRLTV TEDLKNVFPP    120
EVAVFEPSEA EISHTQKATL VCLATGFYPD HVELSWWVNG KEVHSGVCTD PQPLKEQPAL    180
NDSRYCLSSR LRVSATFWQN PRNHFRCQVQ FYGLSENDEW TQDRAKPVTQ IVSAEAWGRA    240
DCGFTSESYQ QGVLSATILY EILLGKATLY AVLVSALVLM AMVKRKDSR               289

SEQ ID NO: 179         moltype = AA  length = 252
FEATURE                Location/Qualifiers
REGION                 1..252
                       note = Synthetic
source                 1..252
                       mol_type = protein
                       organism = synthetic construct
SEQUENCE: 179
QKEVEQNSGP LSVPEGAIAS LNCTYSDRGS QSFFWYRQYS GKSPELIMFI YSNGDKEDGR    60
FTAQLNKASQ YVSLLIRDSQ PSDSATYLCA VMRALGFKTI FGAGTRLFVK ANIQNPDPAV    120
YQLRDSKSSD KSVCLFTDFD SQTNVSQSKD SDVYITDKCV LDMRSMDFKS NSAVAWSNKS    180
DFACANAFNN SIIPEDTFFP SPESSCDVKL VEKSFETDTN LNFQNLSVIG FRILLLKVAG    240
FNLLMTLRLW SS                                                        252

SEQ ID NO: 180         moltype = AA  length = 289
FEATURE                Location/Qualifiers
REGION                 1..289
                       note = Synthetic
source                 1..289
                       mol_type = protein
```

```
                              organism = synthetic construct
SEQUENCE: 180
DSGVTQTPKH LITATGQRVT LRCSPRSGDL SVYWYQQSLD QGLQFLIQYY NGEERAKGNI    60
LERFSAQQFP DLHSELNLSS LELGDSALYF CASSVVDGEQ YFGPGTRLTV TEDLKNVFPP   120
EVAVFEPSEA EISHTQKATL VCLATGFYPD HVELSWWVNG KEVHSGVCTD PQPLKEQPAL   180
NDSRYCLSSR LRVSATFWQN PRNHFRCQVQ FYGLSENDEW TQDRAKPVTQ IVSAEAWGRA   240
DCGFTSESYQ QGVLSATILY EILLGKATLY AVLVSALVLM AMVKRKDSR               289

SEQ ID NO: 181            moltype = AA   length = 252
FEATURE                   Location/Qualifiers
REGION                    1..252
                          note = Synthetic
source                    1..252
                          mol_type = protein
                          organism = synthetic construct
SEQUENCE: 181
QKEVEQNSGP LSVPEGAIAS LNCTYSDRGS QSFFWYRQYS GKSPELIMFI YSNGDKEDGR    60
FTAQLNKASQ YVSLLIRDSQ PSDSATYLCA VMRAGGFKTF FGAGTRLFVK ANIQNPDPAV   120
YQLRDSKSSD KSVCLFTDFD SQTNVSQSKD SDVYITDKCV LDMRSMDFKS NSAVAWSNKS   180
DFACANAFNN SIIPEDTFFP SPESSCDVKL VEKSFETDTN LNFQNLSVIG FRILLLKVAG   240
FNLLMTLRLW SS                                                       252

SEQ ID NO: 182            moltype = AA   length = 289
FEATURE                   Location/Qualifiers
REGION                    1..289
                          note = Synthetic
source                    1..289
                          mol_type = protein
                          organism = synthetic construct
SEQUENCE: 182
DSGVTQTPKH LITATGQRVT LRCSPRSGDL SVYWYQQSLD QGLQFLIQYY NGEERAKGNI    60
LERFSAQQFP DLHSELNLSS LELGDSALYF CASSVVDGEQ YFGPGTRLTV TEDLKNVFPP   120
EVAVFEPSEA EISHTQKATL VCLATGFYPD HVELSWWVNG KEVHSGVCTD PQPLKEQPAL   180
NDSRYCLSSR LRVSATFWQN PRNHFRCQVQ FYGLSENDEW TQDRAKPVTQ IVSAEAWGRA   240
DCGFTSESYQ QGVLSATILY EILLGKATLY AVLVSALVLM AMVKRKDSR               289

SEQ ID NO: 183            moltype = AA   length = 252
FEATURE                   Location/Qualifiers
REGION                    1..252
                          note = Synthetic
source                    1..252
                          mol_type = protein
                          organism = synthetic construct
SEQUENCE: 183
QKEVEQNSGP LSVPEGAIAS LNCTYSDRGS QSFFWYRQYS GKSPELIMFI YSNGDKEDGR    60
FTAQLNKASQ YVSLLIRDSQ PSDSATYLCA VMRAMGFKTI FGAGTRLFVK ANIQNPDPAV   120
YQLRDSKSSD KSVCLFTDFD SQTNVSQSKD SDVYITDKCV LDMRSMDFKS NSAVAWSNKS   180
DFACANAFNN SIIPEDTFFP SPESSCDVKL VEKSFETDTN LNFQNLSVIG FRILLLKVAG   240
FNLLMTLRLW SS                                                       252

SEQ ID NO: 184            moltype = AA   length = 289
FEATURE                   Location/Qualifiers
REGION                    1..289
                          note = Synthetic
source                    1..289
                          mol_type = protein
                          organism = synthetic construct
SEQUENCE: 184
DSGVTQTPKH LITATGQRVT LRCSPRSGDL SVYWYQQSLD QGLQFLIQYY NGEERAKGNI    60
LERFSAQQFP DLHSELNLSS LELGDSALYF CASSVVDGEQ YFGPGTRLTV TEDLKNVFPP   120
EVAVFEPSEA EISHTQKATL VCLATGFYPD HVELSWWVNG KEVHSGVCTD PQPLKEQPAL   180
NDSRYCLSSR LRVSATFWQN PRNHFRCQVQ FYGLSENDEW TQDRAKPVTQ IVSAEAWGRA   240
DCGFTSESYQ QGVLSATILY EILLGKATLY AVLVSALVLM AMVKRKDSR               289

SEQ ID NO: 185            moltype = AA   length = 252
FEATURE                   Location/Qualifiers
REGION                    1..252
                          note = Synthetic
source                    1..252
                          mol_type = protein
                          organism = synthetic construct
SEQUENCE: 185
QKEVEQNSGP LSVPEGAIAS LNCTYSQRGS QSFFWYRQYS GKSPELIMFI YSNGDKEDGR    60
FTAQLNKASQ YVSLLIRDSQ PSDSATYLCA VMRAGGFKTI FGAGTRLFVK ANIQNPDPAV   120
YQLRDSKSSD KSVCLFTDFD SQTNVSQSKD SDVYITDKCV LDMRSMDFKS NSAVAWSNKS   180
DFACANAFNN SIIPEDTFFP SPESSCDVKL VEKSFETDTN LNFQNLSVIG FRILLLKVAG   240
FNLLMTLRLW SS                                                       252

SEQ ID NO: 186            moltype = AA   length = 289
```

```
FEATURE                   Location/Qualifiers
REGION                    1..289
                          note = Synthetic
source                    1..289
                          mol_type = protein
                          organism = synthetic construct
SEQUENCE: 186
DSGVTQTPKH LITATGQRVT LRCSPRSGDL SVYWYQQSLD QGLQFLIQYY NGEERAKGNI   60
LERFSAQQFP DLHSELNLSS LELGDSALYF CASSVVDGEQ YFGPGTRLTV TEDLKNVFPP  120
EVAVFEPSEA EISHTQKATL VCLATGFYPD HVELSWWVNG KEVHSGVCTD PQPLKEQPAL  180
NDSRYCLSSR LRVSATFWQN PRNHFRCQVQ FYGLSENDEW TQDRAKPVTQ IVSAEAWGRA  240
DCGFTSESYQ QGVLSATILY EILLGKATLY AVLVSALVLM AMVKRKDSR               289

SEQ ID NO: 187           moltype = AA  length = 252
FEATURE                   Location/Qualifiers
REGION                    1..252
                          note = Synthetic
source                    1..252
                          mol_type = protein
                          organism = synthetic construct
SEQUENCE: 187
QKEVEQNSGP LSVPEGAIAS LNCTYSDRGN QSFFWYRQYS GKSPELIMFI YSNGDKEDGR   60
FTAQLNKASQ YVSLLIRDSQ PSDSATYLCA VMRAGGFKTI FGAGTRLFVK ANIQNPDPAV  120
YQLRDSKSSD KSVCLFTDFD SQTNVSQSKD SDVYITDKCV LDMRSMDFKS NSAVAWSNKS  180
DFACANAFNN SIIPEDTFFP SPESSCDVKL VEKSFETDTN LNFQNLSVIG FRILLLKVAG  240
FNLLMTLRLW SS                                                      252

SEQ ID NO: 188           moltype = AA  length = 289
FEATURE                   Location/Qualifiers
REGION                    1..289
                          note = Synthetic
source                    1..289
                          mol_type = protein
                          organism = synthetic construct
SEQUENCE: 188
DSGVTQTPKH LITATGQRVT LRCSPRSGDL SVYWYQQSLD QGLQFLIQYY NGEERAKGNI   60
LERFSAQQFP DLHSELNLSS LELGDSALYF CASSVVDGEQ YFGPGTRLTV TEDLKNVFPP  120
EVAVFEPSEA EISHTQKATL VCLATGFYPD HVELSWWVNG KEVHSGVCTD PQPLKEQPAL  180
NDSRYCLSSR LRVSATFWQN PRNHFRCQVQ FYGLSENDEW TQDRAKPVTQ IVSAEAWGRA  240
DCGFTSESYQ QGVLSATILY EILLGKATLY AVLVSALVLM AMVKRKDSR               289

SEQ ID NO: 189           moltype = AA  length = 289
FEATURE                   Location/Qualifiers
REGION                    1..289
                          note = Synthetic
source                    1..289
                          mol_type = protein
                          organism = synthetic construct
SEQUENCE: 189
DSGVTQTPKH LITATGQRVT LRCSPRGGDL SVYWYQQSLD QGLQFLIQYY NGEERAKGNI   60
LERFSAQQFP DLHSELNLSS LELGDSALYF CASSVVDGEQ YFGPGTRLTV TEDLKNVFPP  120
EVAVFEPSEA EISHTQKATL VCLATGFYPD HVELSWWVNG KEVHSGVCTD PQPLKEQPAL  180
NDSRYCLSSR LRVSATFWQN PRNHFRCQVQ FYGLSENDEW TQDRAKPVTQ IVSAEAWGRA  240
DCGFTSESYQ QGVLSATILY EILLGKATLY AVLVSALVLM AMVKRKDSR               289

SEQ ID NO: 190           moltype = AA  length = 289
FEATURE                   Location/Qualifiers
REGION                    1..289
                          note = Synthetic
source                    1..289
                          mol_type = protein
                          organism = synthetic construct
SEQUENCE: 190
DSGVTQTPKH LITATGQRVT LRCSPRSGDL SVYWYQQSLD QGLQFLIQYY NGEERAKGNI   60
LERFSAQQFP DLHSELNLSS LELGDSALYF CASSVVDGEM YFGPGTRLTV TEDLKNVFPP  120
EVAVFEPSEA EISHTQKATL VCLATGFYPD HVELSWWVNG KEVHSGVCTD PQPLKEQPAL  180
NDSRYCLSSR LRVSATFWQN PRNHFRCQVQ FYGLSENDEW TQDRAKPVTQ IVSAEAWGRA  240
DCGFTSESYQ QGVLSATILY EILLGKATLY AVLVSALVLM AMVKRKDSR               289

SEQ ID NO: 191           moltype = AA  length = 289
FEATURE                   Location/Qualifiers
REGION                    1..289
                          note = Synthetic
source                    1..289
                          mol_type = protein
                          organism = synthetic construct
SEQUENCE: 191
DSGVTQTPKH LITATGQRVT LRCSPRSGDL SVYWYQQSLD QGLQFLIQYY NGEERAKGNI   60
LERFSAQQFP DLHSELNLSS LELGDSALYF CASSVVDGEG YFGPGTRLTV TEDLKNVFPP  120
```

```
EVAVFEPSEA EISHTQKATL VCLATGFYPD HVELSWWVNG KEVHSGVCTD PQPLKEQPAL 180
NDSRYCLSSR LRVSATFWQN PRNHFRCQVQ FYGLSENDEW TQDRAKPVTQ IVSAEAWGRA 240
DCGFTSESYQ QGVLSATILY EILLGKATLY AVLVSALVLM AMVKRKDSR              289

SEQ ID NO: 192          moltype = AA  length = 289
FEATURE                 Location/Qualifiers
REGION                  1..289
                        note = Synthetic
source                  1..289
                        mol_type = protein
                        organism = synthetic construct
SEQUENCE: 192
DSGVTQTPKH LITATGQRVT LRCSPRSGDL SVYWYQQSLD QGLQFLIQYY NGEERAKGNI 60
LERFSAQQFP DLHSELNLSS LELGDSALYF CASSVVDGEN YFGPGTRLTV TEDLKNVFPP 120
EVAVFEPSEA EISHTQKATL VCLATGFYPD HVELSWWVNG KEVHSGVCTD PQPLKEQPAL 180
NDSRYCLSSR LRVSATFWQN PRNHFRCQVQ FYGLSENDEW TQDRAKPVTQ IVSAEAWGRA 240
DCGFTSESYQ QGVLSATILY EILLGKATLY AVLVSALVLM AMVKRKDSR              289

SEQ ID NO: 193          moltype = AA  length = 289
FEATURE                 Location/Qualifiers
REGION                  1..289
                        note = Synthetic
source                  1..289
                        mol_type = protein
                        organism = synthetic construct
SEQUENCE: 193
DSGVTQTPKH LITATGQRVT LRCSPRSGDL SVYWYQQSLD QGLQFLIQYY NGEERAKGNI 60
LERFSAQQFP DLHSELNLSS LELGDSALYF CASSVVDGEE YFGPGTRLTV TEDLKNVFPP 120
EVAVFEPSEA EISHTQKATL VCLATGFYPD HVELSWWVNG KEVHSGVCTD PQPLKEQPAL 180
NDSRYCLSSR LRVSATFWQN PRNHFRCQVQ FYGLSENDEW TQDRAKPVTQ IVSAEAWGRA 240
DCGFTSESYQ QGVLSATILY EILLGKATLY AVLVSALVLM AMVKRKDSR              289

SEQ ID NO: 194          moltype = AA  length = 289
FEATURE                 Location/Qualifiers
REGION                  1..289
                        note = Synthetic
source                  1..289
                        mol_type = protein
                        organism = synthetic construct
SEQUENCE: 194
DSGVTQTPKH LITATGQRVT LRCSPRSGDL SVYWYQQSLD QGLQFLIQYY NGEERAKGNI 60
LERFSAQQFP DLHSELNLSS LELGDSALYF CASSVVDGNQ YFGPGTRLTV TEDLKNVFPP 120
EVAVFEPSEA EISHTQKATL VCLATGFYPD HVELSWWVNG KEVHSGVCTD PQPLKEQPAL 180
NDSRYCLSSR LRVSATFWQN PRNHFRCQVQ FYGLSENDEW TQDRAKPVTQ IVSAEAWGRA 240
DCGFTSESYQ QGVLSATILY EILLGKATLY AVLVSALVLM AMVKRKDSR              289

SEQ ID NO: 195          moltype = AA  length = 252
FEATURE                 Location/Qualifiers
REGION                  1..252
                        note = Synthetic
source                  1..252
                        mol_type = protein
                        organism = synthetic construct
SEQUENCE: 195
QKEVEQNSGP LSVPEGAIAS LNCTYSDRGS QGFFWYRQYS GKSPELIMFI YSNGDKEDGR 60
FTAQLNKASQ YVSLLIRDSQ PSDSATYLCA VMRAGGFKTI FGAGTRLFVK ANIQNPDPAV 120
YQLRDSKSSD KSVCLFTDFD SQTNVSQSKD SDVYITDKCV LDMRSMDFKS NSAVAWSNKS 180
DFACANAFNN SIIPEDTFFP SPESSCDVKL VEKSFETDTN LNFQNLSVIG FRILLLKVAG 240
FNLLMTLRLW SS                                                     252

SEQ ID NO: 196          moltype = AA  length = 289
FEATURE                 Location/Qualifiers
REGION                  1..289
                        note = Synthetic
source                  1..289
                        mol_type = protein
                        organism = synthetic construct
SEQUENCE: 196
DSGVTQTPKH LITATGQRVT LRCSPRSGDL SVYWYQQSLD QGLQFLIQYY NGEERAKGNI 60
LERFSAQQFP DLHSELNLSS LELGDSALYF CASSVVDGEQ YFGPGTRLTV TEDLKNVFPP 120
EVAVFEPSEA EISHTQKATL VCLATGFYPD HVELSWWVNG KEVHSGVCTD PQPLKEQPAL 180
NDSRYCLSSR LRVSATFWQN PRNHFRCQVQ FYGLSENDEW TQDRAKPVTQ IVSAEAWGRA 240
DCGFTSESYQ QGVLSATILY EILLGKATLY AVLVSALVLM AMVKRKDSR              289

SEQ ID NO: 197          moltype = AA  length = 252
FEATURE                 Location/Qualifiers
REGION                  1..252
                        note = Synthetic
source                  1..252
```

```
                              mol_type = protein
                              organism = synthetic construct
SEQUENCE: 197
QKEVEQNSGP LSVPEGAIAS LNCTYSWRGS QSFFWYRQYS GKSPELIMFI YSNGDKEDGR    60
FTAQLNKASQ YVSLLIRDSQ PSDSATYLCA VMRAGGFKTI FGAGTRLFVK ANIQNPDPAV   120
YQLRDSKSSD KSVCLFTDFD SQTNVSQSKD SDVYITDKCV LDMRSMDFKS NSAVAWSNKS   180
DFACANAFNN SIIPEDTFFP SPESSCDVKL VEKSFETDTN LNFQNLSVIG FRILLLKVAG   240
FNLLMTLRLW SS                                                       252

SEQ ID NO: 198           moltype = AA   length = 289
FEATURE                  Location/Qualifiers
REGION                   1..289
                         note = Synthetic
source                   1..289
                         mol_type = protein
                         organism = synthetic construct
SEQUENCE: 198
DSGVTQTPKH LITATGQRVT LRCSPRSGDL SVYWYQQSLD QGLQFLIQYY NGEERAKGNI    60
LERFSAQQFP DLHSELNLSS LELGDSALYF CASSVVDGEQ YFGPGTRLTV TEDLKNVFPP   120
EVAVFEPSEA EISHTQKATL VCLATGFYPD HVELSWWVNG KEVHSGVCTD PQPLKEQPAL   180
NDSRYCLSSR LRVSATFWQN PRNHFRCQVQ FYGLSENDEW TQDRAKPVTQ IVSAEAWGRA   240
DCGFTSESYQ QGVLSATILY EILLGKATLY AVLVSALVLM AMVKRKDSR               289

SEQ ID NO: 199           moltype = AA   length = 252
FEATURE                  Location/Qualifiers
REGION                   1..252
                         note = Synthetic
source                   1..252
                         mol_type = protein
                         organism = synthetic construct
SEQUENCE: 199
QKEVEQNSGP LSVPEGAIAS LNCTYSDRGS QSFFWYRQYS GKSPELIMFI YSNGDKEDGR    60
FTAQLNKASQ YVSLLIRDSQ PSDSATYLCA VMRAGGFKTQ FGAGTRLFVK ANIQNPDPAV   120
YQLRDSKSSD KSVCLFTDFD SQTNVSQSKD SDVYITDKCV LDMRSMDFKS NSAVAWSNKS   180
DFACANAFNN SIIPEDTFFP SPESSCDVKL VEKSFETDTN LNFQNLSVIG FRILLLKVAG   240
FNLLMTLRLW SS                                                       252

SEQ ID NO: 200           moltype = AA   length = 289
FEATURE                  Location/Qualifiers
REGION                   1..289
                         note = Synthetic
source                   1..289
                         mol_type = protein
                         organism = synthetic construct
SEQUENCE: 200
DSGVTQTPKH LITATGQRVT LRCSPRSGDL SVYWYQQSLD QGLQFLIQYY NGEERAKGNI    60
LERFSAQQFP DLHSELNLSS LELGDSALYF CASSVVDGEQ YFGPGTRLTV TEDLKNVFPP   120
EVAVFEPSEA EISHTQKATL VCLATGFYPD HVELSWWVNG KEVHSGVCTD PQPLKEQPAL   180
NDSRYCLSSR LRVSATFWQN PRNHFRCQVQ FYGLSENDEW TQDRAKPVTQ IVSAEAWGRA   240
DCGFTSESYQ QGVLSATILY EILLGKATLY AVLVSALVLM AMVKRKDSR               289

SEQ ID NO: 201           moltype = AA   length = 252
FEATURE                  Location/Qualifiers
REGION                   1..252
                         note = Synthetic
source                   1..252
                         mol_type = protein
                         organism = synthetic construct
SEQUENCE: 201
QKEVEQNSGP LSVPEGAIAS LNCTYSDRGA QSFFWYRQYS GKSPELIMFI YSNGDKEDGR    60
FTAQLNKASQ YVSLLIRDSQ PSDSATYLCA VMRAGGFKTI FGAGTRLFVK ANIQNPDPAV   120
YQLRDSKSSD KSVCLFTDFD SQTNVSQSKD SDVYITDKCV LDMRSMDFKS NSAVAWSNKS   180
DFACANAFNN SIIPEDTFFP SPESSCDVKL VEKSFETDTN LNFQNLSVIG FRILLLKVAG   240
FNLLMTLRLW SS                                                       252

SEQ ID NO: 202           moltype = AA   length = 289
FEATURE                  Location/Qualifiers
REGION                   1..289
                         note = Synthetic
source                   1..289
                         mol_type = protein
                         organism = synthetic construct
SEQUENCE: 202
DSGVTQTPKH LITATGQRVT LRCSPRSGDL SVYWYQQSLD QGLQFLIQYY NGEERAKGNI    60
LERFSAQQFP DLHSELNLSS LELGDSALYF CASSVVDGEQ YFGPGTRLTV TEDLKNVFPP   120
EVAVFEPSEA EISHTQKATL VCLATGFYPD HVELSWWVNG KEVHSGVCTD PQPLKEQPAL   180
NDSRYCLSSR LRVSATFWQN PRNHFRCQVQ FYGLSENDEW TQDRAKPVTQ IVSAEAWGRA   240
DCGFTSESYQ QGVLSATILY EILLGKATLY AVLVSALVLM AMVKRKDSR               289
```

-continued

```
SEQ ID NO: 203          moltype = AA  length = 289
FEATURE                 Location/Qualifiers
REGION                  1..289
                        note = Synthetic
source                  1..289
                        mol_type = protein
                        organism = synthetic construct
SEQUENCE: 203
DSGVTQTPKH LITATGQRVT LRCSPRSGDL SVYWYQQSLD QGLQFLIQYY NGEERAKGNI  60
LERFSAQQFP DLHSELNLSS LELGDSALYF CASSVVDGEQ VFGPGTRLTV TEDLKNVFPP 120
EVAVFEPSEA EISHTQKATL VCLATGFYPD HVELSWWVNG KEVHSGVCTD PQPLKEQPAL 180
NDSRYCLSSR LRVSATFWQN PRNHFRCQVQ FYGLSENDEW TQDRAKPVTQ IVSAEAWGRA 240
DCGFTSESYQ QGVLSATILY EILLGKATLY AVLVSALVLM AMVKRKDSR            289

SEQ ID NO: 204          moltype = AA  length = 252
FEATURE                 Location/Qualifiers
REGION                  1..252
                        note = Synthetic
source                  1..252
                        mol_type = protein
                        organism = synthetic construct
SEQUENCE: 204
QKEVEQNSGP LSVPEGAIAS LNCTYSDRGS QSFFWYRQYS GKSPELIMFI YSNGDKEDGR  60
FTAQLNKASQ YVSLLIRDSQ PSDSATYLCA SMRAGGFKTI FGAGTRLFVK ANIQNPDPAV 120
YQLRDSKSSD KSVCLFTDFD SQTNVSQSKD SDVYITDKCV LDMRSMDFKS NSAVAWSNKS 180
DFACANAFNN SIIPEDTFFP SPESSCDVKL VEKSFETDTN LNFQNLSVIG FRILLLKVAG 240
FNLLMTLRLW SS                                                    252

SEQ ID NO: 205          moltype = AA  length = 289
FEATURE                 Location/Qualifiers
REGION                  1..289
                        note = Synthetic
source                  1..289
                        mol_type = protein
                        organism = synthetic construct
SEQUENCE: 205
DSGVTQTPKH LITATGQRVT LRCSPRSGDL SVYWYQQSLD QGLQFLIQYY NGEERAKGNI  60
LERFSAQQFP DLHSELNLSS LELGDSALYF CASSVVDGEQ YFGPGTRLTV TEDLKNVFPP 120
EVAVFEPSEA EISHTQKATL VCLATGFYPD HVELSWWVNG KEVHSGVCTD PQPLKEQPAL 180
NDSRYCLSSR LRVSATFWQN PRNHFRCQVQ FYGLSENDEW TQDRAKPVTQ IVSAEAWGRA 240
DCGFTSESYQ QGVLSATILY EILLGKATLY AVLVSALVLM AMVKRKDSR            289

SEQ ID NO: 206          moltype = AA  length = 252
FEATURE                 Location/Qualifiers
REGION                  1..252
                        note = Synthetic
source                  1..252
                        mol_type = protein
                        organism = synthetic construct
SEQUENCE: 206
QKEVEQNSGP LSVPEGAIAS LNCTYSDWGS QSFFWYRQYS GKSPELIMFI YSNGDKEDGR  60
FTAQLNKASQ YVSLLIRDSQ PSDSATYLCA VMRAGGFKTI FGAGTRLFVK ANIQNPDPAV 120
YQLRDSKSSD KSVCLFTDFD SQTNVSQSKD SDVYITDKCV LDMRSMDFKS NSAVAWSNKS 180
DFACANAFNN SIIPEDTFFP SPESSCDVKL VEKSFETDTN LNFQNLSVIG FRILLLKVAG 240
FNLLMTLRLW SS                                                    252

SEQ ID NO: 207          moltype = AA  length = 289
FEATURE                 Location/Qualifiers
REGION                  1..289
                        note = Synthetic
source                  1..289
                        mol_type = protein
                        organism = synthetic construct
SEQUENCE: 207
DSGVTQTPKH LITATGQRVT LRCSPRSGDL SVYWYQQSLD QGLQFLIQYY NGEERAKGNI  60
LERFSAQQFP DLHSELNLSS LELGDSALYF CASSVVDGEQ YFGPGTRLTV TEDLKNVFPP 120
EVAVFEPSEA EISHTQKATL VCLATGFYPD HVELSWWVNG KEVHSGVCTD PQPLKEQPAL 180
NDSRYCLSSR LRVSATFWQN PRNHFRCQVQ FYGLSENDEW TQDRAKPVTQ IVSAEAWGRA 240
DCGFTSESYQ QGVLSATILY EILLGKATLY AVLVSALVLM AMVKRKDSR            289

SEQ ID NO: 208          moltype = AA  length = 289
FEATURE                 Location/Qualifiers
REGION                  1..289
                        note = Synthetic
source                  1..289
                        mol_type = protein
                        organism = synthetic construct
SEQUENCE: 208
DSGVTQTPKH LITATGQRVT LRCSPRWGDL SVYWYQQSLD QGLQFLIQYY NGEERAKGNI  60
```

-continued

```
LERFSAQQFP DLHSELNLSS LELGDSALYF CASSVVDGEQ YFGPGTRLTV TEDLKNVFPP   120
EVAVFEPSEA EISHTQKATL VCLATGFYPD HVELSWWVNG KEVHSGVCTD PQPLKEQPAL   180
NDSRYCLSSR LRVSATFWQN PRNHFRCQVQ FYGLSENDEW TQDRAKPVTQ IVSAEAWGRA   240
DCGFTSESYQ QGVLSATILY EILLGKATLY AVLVSALVLM AMVKRKDSR               289

SEQ ID NO: 209              moltype = AA   length = 252
FEATURE                     Location/Qualifiers
REGION                      1..252
                            note = Synthetic
source                      1..252
                            mol_type = protein
                            organism = synthetic construct
SEQUENCE: 209
QKEVEQNSGP LSVPEGAIAS LNCTYSDGGS QSFFWYRQYS GKSPELIMFI YSNGDKEDGR   60
FTAQLNKASQ YVSLLIRDSQ PSDSATYLCA VMRAGGFKTI FGAGTRLFVK ANIQNPDPAV   120
YQLRDSKSSD KSVCLFTDFD SQTNVSQSKD SDVYITDKCV LDMRSMDFKS NSAVAWSNKS   180
DFACANAFNN SIIPEDTFFP SPESSCDVKL VEKSFETDTN LNFQNLSVIG FRILLLKVAG   240
FNLLMTLRLW SS                                                       252

SEQ ID NO: 210              moltype = AA   length = 289
FEATURE                     Location/Qualifiers
REGION                      1..289
                            note = Synthetic
source                      1..289
                            mol_type = protein
                            organism = synthetic construct
SEQUENCE: 210
DSGVTQTPKH LITATGQRVT LRCSPRSGDL SVYWYQQSLD QGLQFLIQYY NGEERAKGNI   60
LERFSAQQFP DLHSELNLSS LELGDSALYF CASSVVDGEQ YFGPGTRLTV TEDLKNVFPP   120
EVAVFEPSEA EISHTQKATL VCLATGFYPD HVELSWWVNG KEVHSGVCTD PQPLKEQPAL   180
NDSRYCLSSR LRVSATFWQN PRNHFRCQVQ FYGLSENDEW TQDRAKPVTQ IVSAEAWGRA   240
DCGFTSESYQ QGVLSATILY EILLGKATLY AVLVSALVLM AMVKRKDSR               289

SEQ ID NO: 211              moltype = AA   length = 252
FEATURE                     Location/Qualifiers
REGION                      1..252
                            note = Synthetic
source                      1..252
                            mol_type = protein
                            organism = synthetic construct
SEQUENCE: 211
QKEVEQNSGP LSVPEGAIAS LNCTYSDRPS QSFFWYRQYS GKSPELIMFI YSNGDKEDGR   60
FTAQLNKASQ YVSLLIRDSQ PSDSATYLCA VMRAGGFKTI FGAGTRLFVK ANIQNPDPAV   120
YQLRDSKSSD KSVCLFTDFD SQTNVSQSKD SDVYITDKCV LDMRSMDFKS NSAVAWSNKS   180
DFACANAFNN SIIPEDTFFP SPESSCDVKL VEKSFETDTN LNFQNLSVIG FRILLLKVAG   240
FNLLMTLRLW SS                                                       252

SEQ ID NO: 212              moltype = AA   length = 289
FEATURE                     Location/Qualifiers
REGION                      1..289
                            note = Synthetic
source                      1..289
                            mol_type = protein
                            organism = synthetic construct
SEQUENCE: 212
DSGVTQTPKH LITATGQRVT LRCSPRSGDL SVYWYQQSLD QGLQFLIQYY NGEERAKGNI   60
LERFSAQQFP DLHSELNLSS LELGDSALYF CASSVVDGEQ YFGPGTRLTV TEDLKNVFPP   120
EVAVFEPSEA EISHTQKATL VCLATGFYPD HVELSWWVNG KEVHSGVCTD PQPLKEQPAL   180
NDSRYCLSSR LRVSATFWQN PRNHFRCQVQ FYGLSENDEW TQDRAKPVTQ IVSAEAWGRA   240
DCGFTSESYQ QGVLSATILY EILLGKATLY AVLVSALVLM AMVKRKDSR               289

SEQ ID NO: 213              moltype = AA   length = 289
FEATURE                     Location/Qualifiers
REGION                      1..289
                            note = Synthetic
source                      1..289
                            mol_type = protein
                            organism = synthetic construct
SEQUENCE: 213
DSGVTQTPKH LITATGQRVT LRCSPRIGDL SVYWYQQSLD QGLQFLIQYY NGEERAKGNI   60
LERFSAQQFP DLHSELNLSS LELGDSALYF CASSVVDGEQ YFGPGTRLTV TEDLKNVFPP   120
EVAVFEPSEA EISHTQKATL VCLATGFYPD HVELSWWVNG KEVHSGVCTD PQPLKEQPAL   180
NDSRYCLSSR LRVSATFWQN PRNHFRCQVQ FYGLSENDEW TQDRAKPVTQ IVSAEAWGRA   240
DCGFTSESYQ QGVLSATILY EILLGKATLY AVLVSALVLM AMVKRKDSR               289

SEQ ID NO: 214              moltype = AA   length = 252
FEATURE                     Location/Qualifiers
REGION                      1..252
                            note = Synthetic
```

```
source                     1..252
                           mol_type = protein
                           organism = synthetic construct
SEQUENCE: 214
QKEVEQNSGP LSVPEGAIAS LNCTYSHRGS QSFFWYRQYS GKSPELIMFI YSNGDKEDGR   60
FTAQLNKASQ YVSLLIRDSQ PSDSATYLCA VMRAGGFKTI FGAGTRLFVK ANIQNPDPAV  120
YQLRDSKSSD KSVCLFTDFD SQTNVSQSKD SDVYITDKCV LDMRSMDFKS NSAVAWSNKS  180
DFACANAFNN SIIPEDTFFP SPESSCDVKL VEKSFETDTN LNFQNLSVIG FRILLLKVAG  240
FNLLMTLRLW SS                                                       252

SEQ ID NO: 215             moltype = AA   length = 289
FEATURE                    Location/Qualifiers
REGION                     1..289
                           note = Synthetic
source                     1..289
                           mol_type = protein
                           organism = synthetic construct
SEQUENCE: 215
DSGVTQTPKH LITATGQRVT LRCSPRSGDL SVYWYQQSLD QGLQFLIQYY NGEERAKGNI   60
LERFSAQQFP DLHSELNLSS LELGDSALYF CASSVVDGEQ YFGPGTRLTV TEDLKNVFPP  120
EVAVFEPSEA EISHTQKATL VCLATGFYPD HVELSWWVNG KEVHSGVCTD PQPLKEQPAL  180
NDSRYCLSSR LRVSATFWQN PRNHFRCQVQ FYGLSENDEW TQDRAKPVTQ IVSAEAWGRA  240
DCGFTSESYQ QGVLSATILY EILLGKATLY AVLVSALVLM AMVKRKDSR               289

SEQ ID NO: 216             moltype = AA   length = 252
FEATURE                    Location/Qualifiers
REGION                     1..252
                           note = Synthetic
source                     1..252
                           mol_type = protein
                           organism = synthetic construct
SEQUENCE: 216
QKEVEQNSGP LSVPEGAIAS LNCTYSDRSS QSFFWYRQYS GKSPELIMFI YSNGDKEDGR   60
FTAQLNKASQ YVSLLIRDSQ PSDSATYLCA VMRAGGFKTI FGAGTRLFVK ANIQNPDPAV  120
YQLRDSKSSD KSVCLFTDFD SQTNVSQSKD SDVYITDKCV LDMRSMDFKS NSAVAWSNKS  180
DFACANAFNN SIIPEDTFFP SPESSCDVKL VEKSFETDTN LNFQNLSVIG FRILLLKVAG  240
FNLLMTLRLW SS                                                       252

SEQ ID NO: 217             moltype = AA   length = 289
FEATURE                    Location/Qualifiers
REGION                     1..289
                           note = Synthetic
source                     1..289
                           mol_type = protein
                           organism = synthetic construct
SEQUENCE: 217
DSGVTQTPKH LITATGQRVT LRCSPRSGDL SVYWYQQSLD QGLQFLIQYY NGEERAKGNI   60
LERFSAQQFP DLHSELNLSS LELGDSALYF CASSVVDGEQ YFGPGTRLTV TEDLKNVFPP  120
EVAVFEPSEA EISHTQKATL VCLATGFYPD HVELSWWVNG KEVHSGVCTD PQPLKEQPAL  180
NDSRYCLSSR LRVSATFWQN PRNHFRCQVQ FYGLSENDEW TQDRAKPVTQ IVSAEAWGRA  240
DCGFTSESYQ QGVLSATILY EILLGKATLY AVLVSALVLM AMVKRKDSR               289

SEQ ID NO: 218             moltype = AA   length = 252
FEATURE                    Location/Qualifiers
REGION                     1..252
                           note = Synthetic
source                     1..252
                           mol_type = protein
                           organism = synthetic construct
SEQUENCE: 218
QKEVEQNSGP LSVPEGAIAS LNCTYSDRGS QSFFWYRQYS GKSPELIMFI YSNGDKEDGR   60
FTAQLNKASQ YVSLLIRDSQ PSDSATYLCL VMRAGGFKTI FGAGTRLFVK ANIQNPDPAV  120
YQLRDSKSSD KSVCLFTDFD SQTNVSQSKD SDVYITDKCV LDMRSMDFKS NSAVAWSNKS  180
DFACANAFNN SIIPEDTFFP SPESSCDVKL VEKSFETDTN LNFQNLSVIG FRILLLKVAG  240
FNLLMTLRLW SS                                                       252

SEQ ID NO: 219             moltype = AA   length = 289
FEATURE                    Location/Qualifiers
REGION                     1..289
                           note = Synthetic
source                     1..289
                           mol_type = protein
                           organism = synthetic construct
SEQUENCE: 219
DSGVTQTPKH LITATGQRVT LRCSPRSGDL SVYWYQQSLD QGLQFLIQYY NGEERAKGNI   60
LERFSAQQFP DLHSELNLSS LELGDSALYF CASSVVDGEQ YFGPGTRLTV TEDLKNVFPP  120
EVAVFEPSEA EISHTQKATL VCLATGFYPD HVELSWWVNG KEVHSGVCTD PQPLKEQPAL  180
NDSRYCLSSR LRVSATFWQN PRNHFRCQVQ FYGLSENDEW TQDRAKPVTQ IVSAEAWGRA  240
DCGFTSESYQ QGVLSATILY EILLGKATLY AVLVSALVLM AMVKRKDSR               289
```

-continued

```
SEQ ID NO: 220              moltype = AA   length = 289
FEATURE                     Location/Qualifiers
REGION                      1..289
                            note = Synthetic
source                      1..289
                            mol_type = protein
                            organism = synthetic construct
SEQUENCE: 220
DSGVTQTPKH LITATGQRVT LRCSPRQGDL SVYWYQQSLD QGLQFLIQYY NGEERAKGNI   60
LERFSAQQFP DLHSELNLSS LELGDSALYF CASSVVDGEQ YFGPGTRLTV TEDLKNVFPP  120
EVAVFEPSEA EISHTQKATL VCLATGFYPD HVELSWWVNG KEVHSGVCTD PQPLKEQPAL  180
NDSRYCLSSR LRVSATFWQN PRNHFRCQVQ FYGLSENDEW TQDRAKPVTQ IVSAEAWGRA  240
DCGFTSESYQ QGVLSATILY EILLGKATLY AVLVSALVLM AMVKRKDSR              289

SEQ ID NO: 221              moltype = AA   length = 252
FEATURE                     Location/Qualifiers
REGION                      1..252
                            note = Synthetic
source                      1..252
                            mol_type = protein
                            organism = synthetic construct
SEQUENCE: 221
QKEVEQNSGP LSVPEGAIAS LNCTYSDRGF QSFFWYRQYS GKSPELIMFI YSNGDKEDGR   60
FTAQLNKASQ YVSLLIRDSQ PSDSATYLCA VMRAGGFKTI FGAGTRLFVK ANIQNPDPAV  120
YQLRDSKSSD KSVCLFTDFD SQTNVSQSKD SDVYITDKCV LDMRSMDFKS NSAVAWSNKS  180
DFACANAFNN SIIPEDTFFP SPESSCDVKL VEKSFETDTN LNFQNLSVIG FRILLLKVAG  240
FNLLMTLRLW SS                                                     252

SEQ ID NO: 222              moltype = AA   length = 289
FEATURE                     Location/Qualifiers
REGION                      1..289
                            note = Synthetic
source                      1..289
                            mol_type = protein
                            organism = synthetic construct
SEQUENCE: 222
DSGVTQTPKH LITATGQRVT LRCSPRSGDL SVYWYQQSLD QGLQFLIQYY NGEERAKGNI   60
LERFSAQQFP DLHSELNLSS LELGDSALYF CASSVVDGEQ YFGPGTRLTV TEDLKNVFPP  120
EVAVFEPSEA EISHTQKATL VCLATGFYPD HVELSWWVNG KEVHSGVCTD PQPLKEQPAL  180
NDSRYCLSSR LRVSATFWQN PRNHFRCQVQ FYGLSENDEW TQDRAKPVTQ IVSAEAWGRA  240
DCGFTSESYQ QGVLSATILY EILLGKATLY AVLVSALVLM AMVKRKDSR              289

SEQ ID NO: 223              moltype = AA   length = 252
FEATURE                     Location/Qualifiers
REGION                      1..252
                            note = Synthetic
source                      1..252
                            mol_type = protein
                            organism = synthetic construct
SEQUENCE: 223
QKEVEQNSGP LSVPEGAIAS LNCTYSDRFS QSFFWYRQYS GKSPELIMFI YSNGDKEDGR   60
FTAQLNKASQ YVSLLIRDSQ PSDSATYLCA VVRAGGFKTI FGAGTRLFVK ANIQNPDPAV  120
YQLRDSKSSD KSVCLFTDFD SQTNVSQSKD SDVYITDKCV LDMRSMDFKS NSAVAWSNKS  180
DFACANAFNN SIIPEDTFFP SPESSCDVKL VEKSFETDTN LNFQNLSVIG FRILLLKVAG  240
FNLLMTLRLW SS                                                     252

SEQ ID NO: 224              moltype = AA   length = 289
FEATURE                     Location/Qualifiers
REGION                      1..289
                            note = Synthetic
source                      1..289
                            mol_type = protein
                            organism = synthetic construct
SEQUENCE: 224
DSGVTQTPKH LITATGQRVT LRCSPRSGDL SVYWYQQSLD QGLQFLIQYY NGEERAKGNI   60
LERFSAQQFP DLHSELNLSS LELGDSALYF CASSVVDGEQ YFGPGTRLTV TEDLKNVFPP  120
EVAVFEPSEA EISHTQKATL VCLATGFYPD HVELSWWVNG KEVHSGVCTD PQPLKEQPAL  180
NDSRYCLSSR LRVSATFWQN PRNHFRCQVQ FYGLSENDEW TQDRAKPVTQ IVSAEAWGRA  240
DCGFTSESYQ QGVLSATILY EILLGKATLY AVLVSALVLM AMVKRKDSR              289

SEQ ID NO: 225              moltype = AA   length = 252
FEATURE                     Location/Qualifiers
REGION                      1..252
                            note = Synthetic
source                      1..252
                            mol_type = protein
                            organism = synthetic construct
SEQUENCE: 225
```

```
QKEVEQNSGP LSVPEGAIAS LNCTYSDRFS QSFFWYRQYS GKSPELIMFI YSNGDKEDGR    60
FTAQLNKASQ YVSLLIRDSQ PSDSATYLCA VLRAGGFKTI FGAGTRLFVK ANIQNPDPAV   120
YQLRDSKSSD KSVCLFTDFD SQTNVSQSKD SDVYITDKCV LDMRSMDFKS NSAVAWSNKS   180
DFACANAFNN SIIPEDTFFP SPESSCDVKL VEKSFETDTN LNFQNLSVIG FRILLLKVAG   240
FNLLMTLRLW SS                                                       252
```

```
SEQ ID NO: 226         moltype = AA  length = 289
FEATURE                Location/Qualifiers
REGION                 1..289
                       note = Synthetic
source                 1..289
                       mol_type = protein
                       organism = synthetic construct
SEQUENCE: 226
DSGVTQTPKH LITATGQRVT LRCSPRSGDL SVYWYQQSLD QGLQFLIQYY NGEERAKGNI    60
LERFSAQQFP DLHSELNLSS LELGDSALYF CASSVVDGEQ YFGPGTRLTV TEDLKNVFPP   120
EVAVFEPSEA EISHTQKATL VCLATGFYPD HVELSWWVNG KEVHSGVCTD PQPLKEQPAL   180
NDSRYCLSSR LRVSATFWQN PRNHFRCQVQ FYGLSENDEW TQDRAKPVTQ IVSAEAWGRA   240
DCGFTSESYQ QGVLSATILY EILLGKATLY AVLVSALVLM AMVKRKDSR               289
```

```
SEQ ID NO: 227         moltype = AA  length = 252
FEATURE                Location/Qualifiers
REGION                 1..252
                       note = Synthetic
source                 1..252
                       mol_type = protein
                       organism = synthetic construct
SEQUENCE: 227
QKEVEQNSGP LSVPEGAIAS LNCTYSDRFS QSFFWYRQYS GKSPELIMFI YSNGDKEDGR    60
FTAQLNKASQ YVSLLIRDSQ PSDSATYLCA TMRAGGFKTI FGAGTRLFVK ANIQNPDPAV   120
YQLRDSKSSD KSVCLFTDFD SQTNVSQSKD SDVYITDKCV LDMRSMDFKS NSAVAWSNKS   180
DFACANAFNN SIIPEDTFFP SPESSCDVKL VEKSFETDTN LNFQNLSVIG FRILLLKVAG   240
FNLLMTLRLW SS                                                       252
```

```
SEQ ID NO: 228         moltype = AA  length = 289
FEATURE                Location/Qualifiers
REGION                 1..289
                       note = Synthetic
source                 1..289
                       mol_type = protein
                       organism = synthetic construct
SEQUENCE: 228
DSGVTQTPKH LITATGQRVT LRCSPRSGDL SVYWYQQSLD QGLQFLIQYY NGEERAKGNI    60
LERFSAQQFP DLHSELNLSS LELGDSALYF CASSVVDGEQ YFGPGTRLTV TEDLKNVFPP   120
EVAVFEPSEA EISHTQKATL VCLATGFYPD HVELSWWVNG KEVHSGVCTD PQPLKEQPAL   180
NDSRYCLSSR LRVSATFWQN PRNHFRCQVQ FYGLSENDEW TQDRAKPVTQ IVSAEAWGRA   240
DCGFTSESYQ QGVLSATILY EILLGKATLY AVLVSALVLM AMVKRKDSR               289
```

```
SEQ ID NO: 229         moltype = AA  length = 289
FEATURE                Location/Qualifiers
REGION                 1..289
                       note = Synthetic
source                 1..289
                       mol_type = protein
                       organism = synthetic construct
SEQUENCE: 229
DSGVTQTPKH LITATGQRVT LRCSPRSGDL SVYWYQQSLD QGLQFLIQYY NGEERAKGNI    60
LERFSAQQFP DLHSELNLSS LELGDSALYF CASSVVDGEQ FFGPGTRLTV TEDLKNVFPP   120
EVAVFEPSEA EISHTQKATL VCLATGFYPD HVELSWWVNG KEVHSGVCTD PQPLKEQPAL   180
NDSRYCLSSR LRVSATFWQN PRNHFRCQVQ FYGLSENDEW TQDRAKPVTQ IVSAEAWGRA   240
DCGFTSESYQ QGVLSATILY EILLGKATLY AVLVSALVLM AMVKRKDSR               289
```

```
SEQ ID NO: 230         moltype = AA  length = 289
FEATURE                Location/Qualifiers
REGION                 1..289
                       note = Synthetic
source                 1..289
                       mol_type = protein
                       organism = synthetic construct
SEQUENCE: 230
DSGVTQTPKH LITATGQRVT LRCSPRSGDL SVYWYQQSLD QGLQFLIQYY NGEERAKGNI    60
LERFSAQQFP DLHSELNLSS LELGDSALYF CASSVVDGEQ FFGPGTRLTV TEDLKNVFPP   120
EVAVFEPSEA EISHTQKATL VCLATGFYPD HVELSWWVNG KEVHSGVCTD PQPLKEQPAL   180
NDSRYCLSSR LRVSATFWQN PRNHFRCQVQ FYGLSENDEW TQDRAKPVTQ IVSAEAWGRA   240
DCGFTSESYQ QGVLSATILY EILLGKATLY AVLVSALVLM AMVKRKDSR               289
```

```
SEQ ID NO: 231         moltype = AA  length = 289
FEATURE                Location/Qualifiers
REGION                 1..289
```

-continued

```
                         note = Synthetic
source                   1..289
                         mol_type = protein
                         organism = synthetic construct
SEQUENCE: 231
DSGVTQTPKH LITATGQRVT LRCSPRSGDL SVYWYQQSLD QGLQFLIQYY NGEERAKGNI   60
LERFSAQQFP DLHSELNLSS LELGDSALYF CASSVVDGEQ FFGPGTRLTV TEDLKNVFPP  120
EVAVFEPSEA EISHTQKATL VCLATGFYPD HVELSWWVNG KEVHSGVCTD PQPLKEQPAL  180
NDSRYCLSSR LRVSATFWQN PRNHFRCQVQ FYGLSENDEW TQDRAKPVTQ IVSAEAWGRA  240
DCGFTSESYQ QGVLSATILY EILLGKATLY AVLVSALVLM AMVKRKDSR             289

SEQ ID NO: 232          moltype = AA   length = 289
FEATURE                 Location/Qualifiers
REGION                  1..289
                        note = Synthetic
source                  1..289
                        mol_type = protein
                        organism = synthetic construct
SEQUENCE: 232
DSGVTQTPKH LITATGQRVT LRCSPRTGDL SVYWYQQSLD QGLQFLIQYY NGEERAKGNI   60
LERFSAQQFP DLHSELNLSS LELGDSALYF CASSVVDGEQ YFGPGTRLTV TEDLKNVFPP  120
EVAVFEPSEA EISHTQKATL VCLATGFYPD HVELSWWVNG KEVHSGVCTD PQPLKEQPAL  180
NDSRYCLSSR LRVSATFWQN PRNHFRCQVQ FYGLSENDEW TQDRAKPVTQ IVSAEAWGRA  240
DCGFTSESYQ QGVLSATILY EILLGKATLY AVLVSALVLM AMVKRKDSR             289

SEQ ID NO: 233          moltype = AA   length = 289
FEATURE                 Location/Qualifiers
REGION                  1..289
                        note = Synthetic
source                  1..289
                        mol_type = protein
                        organism = synthetic construct
SEQUENCE: 233
DSGVTQTPKH LITATGQRVT LRCSPRTGDL SVYWYQQSLD QGLQFLIQYY NGEERAKGNI   60
LERFSAQQFP DLHSELNLSS LELGDSALYF CASSVVDGEQ YFGPGTRLTV TEDLKNVFPP  120
EVAVFEPSEA EISHTQKATL VCLATGFYPD HVELSWWVNG KEVHSGVCTD PQPLKEQPAL  180
NDSRYCLSSR LRVSATFWQN PRNHFRCQVQ FYGLSENDEW TQDRAKPVTQ IVSAEAWGRA  240
DCGFTSESYQ QGVLSATILY EILLGKATLY AVLVSALVLM AMVKRKDSR             289

SEQ ID NO: 234          moltype = AA   length = 289
FEATURE                 Location/Qualifiers
REGION                  1..289
                        note = Synthetic
source                  1..289
                        mol_type = protein
                        organism = synthetic construct
SEQUENCE: 234
DSGVTQTPKH LITATGQRVT LRCSPRTGDL SVYWYQQSLD QGLQFLIQYY NGEERAKGNI   60
LERFSAQQFP DLHSELNLSS LELGDSALYF CASSVVDGEQ YFGPGTRLTV TEDLKNVFPP  120
EVAVFEPSEA EISHTQKATL VCLATGFYPD HVELSWWVNG KEVHSGVCTD PQPLKEQPAL  180
NDSRYCLSSR LRVSATFWQN PRNHFRCQVQ FYGLSENDEW TQDRAKPVTQ IVSAEAWGRA  240
DCGFTSESYQ QGVLSATILY EILLGKATLY AVLVSALVLM AMVKRKDSR             289

SEQ ID NO: 235          moltype = AA   length = 289
FEATURE                 Location/Qualifiers
REGION                  1..289
                        note = Synthetic
source                  1..289
                        mol_type = protein
                        organism = synthetic construct
SEQUENCE: 235
DSGVTQTPKH LITATGQRVT LRCSPRSGDL SVYWYQQSLD QGLQFLIQYY NGEERAKGNI   60
LERFSAQQFP DLHSELNLSS LELGDSALYF CASSVVDGEQ FFGPGTRLTV TEDLKNVFPP  120
EVAVFEPSEA EISHTQKATL VCLATGFYPD HVELSWWVNG KEVHSGVCTD PQPLKEQPAL  180
NDSRYCLSSR LRVSATFWQN PRNHFRCQVQ FYGLSENDEW TQDRAKPVTQ IVSAEAWGRA  240
DCGFTSESYQ QGVLSATILY EILLGKATLY AVLVSALVLM AMVKRKDSR             289

SEQ ID NO: 236          moltype = AA   length = 289
FEATURE                 Location/Qualifiers
REGION                  1..289
                        note = Synthetic
source                  1..289
                        mol_type = protein
                        organism = synthetic construct
SEQUENCE: 236
DSGVTQTPKH LITATGQRVT LRCSPRTGDL SVYWYQQSLD QGLQFLIQYY NGEERAKGNI   60
LERFSAQQFP DLHSELNLSS LELGDSALYF CASSVVDGEQ YFGPGTRLTV TEDLKNVFPP  120
EVAVFEPSEA EISHTQKATL VCLATGFYPD HVELSWWVNG KEVHSGVCTD PQPLKEQPAL  180
NDSRYCLSSR LRVSATFWQN PRNHFRCQVQ FYGLSENDEW TQDRAKPVTQ IVSAEAWGRA  240
```

-continued

```
DCGFTSESYQ QGVLSATILY EILLGKATLY AVLVSALVLM AMVKRKDSR              289

SEQ ID NO: 237        moltype = AA  length = 289
FEATURE               Location/Qualifiers
REGION                1..289
                      note = Synthetic
source                1..289
                      mol_type = protein
                      organism = synthetic construct
SEQUENCE: 237
DSGVTQTPKH LITATGQRVT LRCSPRTGDL SVYWYQQSLD QGLQFLIQYY NGEERAKGNI  60
LERFSAQQFP DLHSELNLSS LELGDSALYF CASSVVDGEQ FFGPGTRLTV TEDLKNVFPP  120
EVAVFEPSEA EISHTQKATL VCLATGFYPD HVELSWWVNG KEVHSGVCTD PQPLKEQPAL  180
NDSRYCLSSR LRVSATFWQN PRNHFRCQVQ FYGLSENDEW TQDRAKPVTQ IVSAEAWGRA  240
DCGFTSESYQ QGVLSATILY EILLGKATLY AVLVSALVLM AMVKRKDSR              289

SEQ ID NO: 238        moltype = AA  length = 289
FEATURE               Location/Qualifiers
REGION                1..289
                      note = Synthetic
source                1..289
                      mol_type = protein
                      organism = synthetic construct
SEQUENCE: 238
DSGVTQTPKH LITATGQRVT LRCSPRTGDL SVYWYQQSLD QGLQFLIQYY NGEERAKGNI  60
LERFSAQQFP DLHSELNLSS LELGDSALYF CASSVVDGEQ YFGPGTRLTV TEDLKNVFPP  120
EVAVFEPSEA EISHTQKATL VCLATGFYPD HVELSWWVNG KEVHSGVCTD PQPLKEQPAL  180
NDSRYCLSSR LRVSATFWQN PRNHFRCQVQ FYGLSENDEW TQDRAKPVTQ IVSAEAWGRA  240
DCGFTSESYQ QGVLSATILY EILLGKATLY AVLVSALVLM AMVKRKDSR              289

SEQ ID NO: 239        moltype = AA  length = 289
FEATURE               Location/Qualifiers
REGION                1..289
                      note = Synthetic
source                1..289
                      mol_type = protein
                      organism = synthetic construct
SEQUENCE: 239
DSGVTQTPKH LITATGQRVT LRCSPRTGDL SVYWYQQSLD QGLQFLIQYY NGEERAKGNI  60
LERFSAQQFP DLHSELNLSS LELGDSALYF CASSVVDGEQ YFGPGTRLTV TEDLKNVFPP  120
EVAVFEPSEA EISHTQKATL VCLATGFYPD HVELSWWVNG KEVHSGVCTD PQPLKEQPAL  180
NDSRYCLSSR LRVSATFWQN PRNHFRCQVQ FYGLSENDEW TQDRAKPVTQ IVSAEAWGRA  240
DCGFTSESYQ QGVLSATILY EILLGKATLY AVLVSALVLM AMVKRKDSR              289

SEQ ID NO: 240        moltype = AA  length = 289
FEATURE               Location/Qualifiers
REGION                1..289
                      note = Synthetic
source                1..289
                      mol_type = protein
                      organism = synthetic construct
SEQUENCE: 240
DSGVTQTPKH LITATGQRVT LRCSPRTGDL SVYWYQQSLD QGLQFLIQYY NGEERAKGNI  60
LERFSAQQFP DLHSELNLSS LELGDSALYF CASSVVDGEQ YFGPGTRLTV TEDLKNVFPP  120
EVAVFEPSEA EISHTQKATL VCLATGFYPD HVELSWWVNG KEVHSGVCTD PQPLKEQPAL  180
NDSRYCLSSR LRVSATFWQN PRNHFRCQVQ FYGLSENDEW TQDRAKPVTQ IVSAEAWGRA  240
DCGFTSESYQ QGVLSATILY EILLGKATLY AVLVSALVLM AMVKRKDSR              289

SEQ ID NO: 241        moltype = AA  length = 289
FEATURE               Location/Qualifiers
REGION                1..289
                      note = Synthetic
source                1..289
                      mol_type = protein
                      organism = synthetic construct
SEQUENCE: 241
DSGVTQTPKH LITATGQRVT LRCSPRSGDL SVYWYQQSLD QGLQFLIQYY NGEERAKGNI  60
LERFSAQQFP DLHSELNLSS LELGDSALYF CASSVVDGEQ FFGPGTRLTV TEDLKNVFPP  120
EVAVFEPSEA EISHTQKATL VCLATGFYPD HVELSWWVNG KEVHSGVCTD PQPLKEQPAL  180
NDSRYCLSSR LRVSATFWQN PRNHFRCQVQ FYGLSENDEW TQDRAKPVTQ IVSAEAWGRA  240
DCGFTSESYQ QGVLSATILY EILLGKATLY AVLVSALVLM AMVKRKDSR              289

SEQ ID NO: 242        moltype = AA  length = 289
FEATURE               Location/Qualifiers
REGION                1..289
                      note = Synthetic
source                1..289
                      mol_type = protein
                      organism = synthetic construct
```

-continued

```
SEQUENCE: 242
DSGVTQTPKH LITATGQRVT LRCSPRSGDL SVYWYQQSLD QGLQFLIQYY NGEERAKGNI   60
LERFSAQQFP DLHSELNLSS LELGDSALYF CASSVVDGEQ FFGPGTRLTV TEDLKNVFPP  120
EVAVFEPSEA EISHTQKATL VCLATGFYPD HVELSWWVNG KEVHSGVCTD PQPLKEQPAL  180
NDSRYCLSSR LRVSATFWQN PRNHFRCQVQ FYGLSENDEW TQDRAKPVTQ IVSAEAWGRA  240
DCGFTSESYQ QGVLSATILY EILLGKATLY AVLVSALVLM AMVKRKDSR             289

SEQ ID NO: 243              moltype = AA   length = 289
FEATURE                    Location/Qualifiers
REGION                     1..289
                           note = Synthetic
source                     1..289
                           mol_type = protein
                           organism = synthetic construct
SEQUENCE: 243
DSGVTQTPKH LITATGQRVT LRCSPRSGDL SVYWYQQSLD QGLQFLIQYY NGEERAKGNI   60
LERFSAQQFP DLHSELNLSS LELGDSALYF CASSVVDGEQ FFGPGTRLTV TEDLKNVFPP  120
EVAVFEPSEA EISHTQKATL VCLATGFYPD HVELSWWVNG KEVHSGVCTD PQPLKEQPAL  180
NDSRYCLSSR LRVSATFWQN PRNHFRCQVQ FYGLSENDEW TQDRAKPVTQ IVSAEAWGRA  240
DCGFTSESYQ QGVLSATILY EILLGKATLY AVLVSALVLM AMVKRKDSR             289

SEQ ID NO: 244              moltype = AA   length = 289
FEATURE                    Location/Qualifiers
REGION                     1..289
                           note = Synthetic
source                     1..289
                           mol_type = protein
                           organism = synthetic construct
SEQUENCE: 244
DSGVTQTPKH LITATGQRVT LRCSPRTGDL SVYWYQQSLD QGLQFLIQYY NGEERAKGNI   60
LERFSAQQFP DLHSELNLSS LELGDSALYF CASSVVDGEQ FFGPGTRLTV TEDLKNVFPP  120
EVAVFEPSEA EISHTQKATL VCLATGFYPD HVELSWWVNG KEVHSGVCTD PQPLKEQPAL  180
NDSRYCLSSR LRVSATFWQN PRNHFRCQVQ FYGLSENDEW TQDRAKPVTQ IVSAEAWGRA  240
DCGFTSESYQ QGVLSATILY EILLGKATLY AVLVSALVLM AMVKRKDSR             289

SEQ ID NO: 245              moltype = AA   length = 289
FEATURE                    Location/Qualifiers
REGION                     1..289
                           note = Synthetic
source                     1..289
                           mol_type = protein
                           organism = synthetic construct
SEQUENCE: 245
DSGVTQTPKH LITATGQRVT LRCSPRTGDL SVYWYQQSLD QGLQFLIQYY NGEERAKGNI   60
LERFSAQQFP DLHSELNLSS LELGDSALYF CASSVVDGEQ FFGPGTRLTV TEDLKNVFPP  120
EVAVFEPSEA EISHTQKATL VCLATGFYPD HVELSWWVNG KEVHSGVCTD PQPLKEQPAL  180
NDSRYCLSSR LRVSATFWQN PRNHFRCQVQ FYGLSENDEW TQDRAKPVTQ IVSAEAWGRA  240
DCGFTSESYQ QGVLSATILY EILLGKATLY AVLVSALVLM AMVKRKDSR             289

SEQ ID NO: 246              moltype = AA   length = 289
FEATURE                    Location/Qualifiers
REGION                     1..289
                           note = Synthetic
source                     1..289
                           mol_type = protein
                           organism = synthetic construct
SEQUENCE: 246
DSGVTQTPKH LITATGQRVT LRCSPRTGDL SVYWYQQSLD QGLQFLIQYY NGEERAKGNI   60
LERFSAQQFP DLHSELNLSS LELGDSALYF CASSVVDGEQ FFGPGTRLTV TEDLKNVFPP  120
EVAVFEPSEA EISHTQKATL VCLATGFYPD HVELSWWVNG KEVHSGVCTD PQPLKEQPAL  180
NDSRYCLSSR LRVSATFWQN PRNHFRCQVQ FYGLSENDEW TQDRAKPVTQ IVSAEAWGRA  240
DCGFTSESYQ QGVLSATILY EILLGKATLY AVLVSALVLM AMVKRKDSR             289

SEQ ID NO: 247              moltype = AA   length = 289
FEATURE                    Location/Qualifiers
REGION                     1..289
                           note = Synthetic
source                     1..289
                           mol_type = protein
                           organism = synthetic construct
SEQUENCE: 247
DSGVTQTPKH LITATGQRVT LRCSPRTGDL SVYWYQQSLD QGLQFLIQYY NGEERAKGNI   60
LERFSAQQFP DLHSELNLSS LELGDSALYF CASSVVDGEQ FFGPGTRLTV TEDLKNVFPP  120
EVAVFEPSEA EISHTQKATL VCLATGFYPD HVELSWWVNG KEVHSGVCTD PQPLKEQPAL  180
NDSRYCLSSR LRVSATFWQN PRNHFRCQVQ FYGLSENDEW TQDRAKPVTQ IVSAEAWGRA  240
DCGFTSESYQ QGVLSATILY EILLGKATLY AVLVSALVLM AMVKRKDSR             289

SEQ ID NO: 248              moltype = AA   length = 289
FEATURE                    Location/Qualifiers
```

-continued

```
REGION                   1..289
                         note = Synthetic
source                   1..289
                         mol_type = protein
                         organism = synthetic construct
SEQUENCE: 248
DSGVTQTPKH LITATGQRVT LRCSPRTGDL SVYWYQQSLD QGLQFLIQYY NGEERAKGNI   60
LERFSAQQFP DLHSELNLSS LELGDSALYF CASSVVDGEQ FFGPGTRLTV TEDLKNVFPP  120
EVAVFEPSEA EISHTQKATL VCLATGFYPD HVELSWWVNG KEVHSGVCTD PQPLKEQPAL  180
NDSRYCLSSR LRVSATFWQN PRNHFRCQVQ FYGLSENDEW TQDRAKPVTQ IVSAEAWGRA  240
DCGFTSESYQ QGVLSATILY EILLGKATLY AVLVSALVLM AMVKRKDSR             289

SEQ ID NO: 249          moltype = AA   length = 289
FEATURE                 Location/Qualifiers
REGION                  1..289
                        note = Synthetic
source                  1..289
                        mol_type = protein
                        organism = synthetic construct
SEQUENCE: 249
DSGVTQTPKH LITATGQRVT LRCSPRTGDL SVYWYQQSLD QGLQFLIQYY NGEERAKGNI   60
LERFSAQQFP DLHSELNLSS LELGDSALYF CASSVVDGEQ FFGPGTRLTV TEDLKNVFPP  120
EVAVFEPSEA EISHTQKATL VCLATGFYPD HVELSWWVNG KEVHSGVCTD PQPLKEQPAL  180
NDSRYCLSSR LRVSATFWQN PRNHFRCQVQ FYGLSENDEW TQDRAKPVTQ IVSAEAWGRA  240
DCGFTSESYQ QGVLSATILY EILLGKATLY AVLVSALVLM AMVKRKDSR             289

SEQ ID NO: 250          moltype = AA   length = 252
FEATURE                 Location/Qualifiers
REGION                  1..252
                        note = Synthetic
source                  1..252
                        mol_type = protein
                        organism = synthetic construct
SEQUENCE: 250
QKEVEQNSGP LSVPEGAIAS LNCTYSDRGS QSFFWYRQYS GKSPELIMFI YSNGDKEDGR   60
FTAQLNKASQ YVSLLIRDSQ PSDSATYLCA TVRAGGFKTI FGAGTRLFVK ANIQNPDPAV  120
YQLRDSKSSD KSVCLFTDFD SQTNVSQSKD SDVYITDKCV LDMRSMDFKS NSAVAWSNKS  180
DFACANAFNN SIIPEDTFFP SPESSCDVKL VEKSFETDTN LNFQNLSVIG FRILLLKVAG  240
FNLLMTLRLW SS                                                     252

SEQ ID NO: 251          moltype = AA   length = 289
FEATURE                 Location/Qualifiers
REGION                  1..289
                        note = Synthetic
source                  1..289
                        mol_type = protein
                        organism = synthetic construct
SEQUENCE: 251
DSGVTQTPKH LITATGQRVT LRCSPRSGDL SVYWYQQSLD QGLQFLIQYY NGEERAKGNI   60
LERFSAQQFP DLHSELNLSS LELGDSALYF CASSVVDGEQ YFGPGTRLTV TEDLKNVFPP  120
EVAVFEPSEA EISHTQKATL VCLATGFYPD HVELSWWVNG KEVHSGVCTD PQPLKEQPAL  180
NDSRYCLSSR LRVSATFWQN PRNHFRCQVQ FYGLSENDEW TQDRAKPVTQ IVSAEAWGRA  240
DCGFTSESYQ QGVLSATILY EILLGKATLY AVLVSALVLM AMVKRKDSR             289

SEQ ID NO: 252          moltype = AA   length = 252
FEATURE                 Location/Qualifiers
REGION                  1..252
                        note = Synthetic
source                  1..252
                        mol_type = protein
                        organism = synthetic construct
SEQUENCE: 252
QKEVEQNSGP LSVPEGAIAS LNCTYSDRGS QSFFWYRQYS GKSPELIMFI YSNGDKEDGR   60
FTAQLNKASQ YVSLLIRDSQ PSDSATYLCA TLRAGGFKTI FGAGTRLFVK ANIQNPDPAV  120
YQLRDSKSSD KSVCLFTDFD SQTNVSQSKD SDVYITDKCV LDMRSMDFKS NSAVAWSNKS  180
DFACANAFNN SIIPEDTFFP SPESSCDVKL VEKSFETDTN LNFQNLSVIG FRILLLKVAG  240
FNLLMTLRLW SS                                                     252

SEQ ID NO: 253          moltype = AA   length = 289
FEATURE                 Location/Qualifiers
REGION                  1..289
                        note = Synthetic
source                  1..289
                        mol_type = protein
                        organism = synthetic construct
SEQUENCE: 253
DSGVTQTPKH LITATGQRVT LRCSPRSGDL SVYWYQQSLD QGLQFLIQYY NGEERAKGNI   60
LERFSAQQFP DLHSELNLSS LELGDSALYF CASSVVDGEQ YFGPGTRLTV TEDLKNVFPP  120
EVAVFEPSEA EISHTQKATL VCLATGFYPD HVELSWWVNG KEVHSGVCTD PQPLKEQPAL  180
```

```
NDSRYCLSSR LRVSATFWQN PRNHFRCQVQ FYGLSENDEW TQDRAKPVTQ IVSAEAWGRA    240
DCGFTSESYQ QGVLSATILY EILLGKATLY AVLVSALVLM AMVKRKDSR                289

SEQ ID NO: 254          moltype = AA   length = 252
FEATURE                 Location/Qualifiers
REGION                  1..252
                        note = Synthetic
source                  1..252
                        mol_type = protein
                        organism = synthetic construct
SEQUENCE: 254
QKEVEQNSGP LSVPEGAIAS LNCTYSDRFS QSFFWYRQYS GKSPELIMFI YSNGDKEDGR    60
FTAQLNKASQ YVSLLIRDSQ PSDSATYLCA TVRAGGFKTI FGAGTRLFVK ANIQNPDPAV    120
YQLRDSKSSD KSVCLFTDFD SQTNVSQSKD SDVYITDKCV LDMRSMDFKS NSAVAWSNKS    180
DFACANAFNN SIIPEDTFFP SPESSCDVKL VEKSFETDTN LNFQNLSVIG FRILLLKVAG    240
FNLLMTLRLW SS                                                        252

SEQ ID NO: 255          moltype = AA   length = 289
FEATURE                 Location/Qualifiers
REGION                  1..289
                        note = Synthetic
source                  1..289
                        mol_type = protein
                        organism = synthetic construct
SEQUENCE: 255
DSGVTQTPKH LITATGQRVT LRCSPRSGDL SVYWYQQSLD QGLQFLIQYY NGEERAKGNI    60
LERFSAQQFP DLHSELNLSS LELGDSALYF CASSVVDGEQ YFGPGTRLTV TEDLKNVFPP    120
EVAVFEPSEA EISHTQKATL VCLATGFYPD HVELSWWVNG KEVHSGVCTD PQPLKEQPAL    180
NDSRYCLSSR LRVSATFWQN PRNHFRCQVQ FYGLSENDEW TQDRAKPVTQ IVSAEAWGRA    240
DCGFTSESYQ QGVLSATILY EILLGKATLY AVLVSALVLM AMVKRKDSR                289

SEQ ID NO: 256          moltype = AA   length = 252
FEATURE                 Location/Qualifiers
REGION                  1..252
                        note = Synthetic
source                  1..252
                        mol_type = protein
                        organism = synthetic construct
SEQUENCE: 256
QKEVEQNSGP LSVPEGAIAS LNCTYSDRFS QSFFWYRQYS GKSPELIMFI YSNGDKEDGR    60
FTAQLNKASQ YVSLLIRDSQ PSDSATYLCA TLRAGGFKTI FGAGTRLFVK ANIQNPDPAV    120
YQLRDSKSSD KSVCLFTDFD SQTNVSQSKD SDVYITDKCV LDMRSMDFKS NSAVAWSNKS    180
DFACANAFNN SIIPEDTFFP SPESSCDVKL VEKSFETDTN LNFQNLSVIG FRILLLKVAG    240
FNLLMTLRLW SS                                                        252

SEQ ID NO: 257          moltype = AA   length = 289
FEATURE                 Location/Qualifiers
REGION                  1..289
                        note = Synthetic
source                  1..289
                        mol_type = protein
                        organism = synthetic construct
SEQUENCE: 257
DSGVTQTPKH LITATGQRVT LRCSPRSGDL SVYWYQQSLD QGLQFLIQYY NGEERAKGNI    60
LERFSAQQFP DLHSELNLSS LELGDSALYF CASSVVDGEQ YFGPGTRLTV TEDLKNVFPP    120
EVAVFEPSEA EISHTQKATL VCLATGFYPD HVELSWWVNG KEVHSGVCTD PQPLKEQPAL    180
NDSRYCLSSR LRVSATFWQN PRNHFRCQVQ FYGLSENDEW TQDRAKPVTQ IVSAEAWGRA    240
DCGFTSESYQ QGVLSATILY EILLGKATLY AVLVSALVLM AMVKRKDSR                289

SEQ ID NO: 258          moltype = AA   length = 11
FEATURE                 Location/Qualifiers
REGION                  1..11
                        note = Synthetic
source                  1..11
                        mol_type = protein
                        organism = synthetic construct
SEQUENCE: 258
AVMRAGGFKT I                                                         11

SEQ ID NO: 259          moltype = AA   length = 10
FEATURE                 Location/Qualifiers
REGION                  1..10
                        note = Synthetic
source                  1..10
                        mol_type = protein
                        organism = synthetic construct
SEQUENCE: 259
ASSVVDGEQY                                                           10
```

-continued

```
SEQ ID NO: 260        moltype = AA   length = 9
FEATURE               Location/Qualifiers
source                1..9
                      mol_type = protein
                      organism = synthetic construct
SEQUENCE: 260
SLLMWTTQC                                              9
```

The invention claimed is:

1. A method for isolating T-cells reactive to a target peptide, the method comprising:

obtaining peripheral mononuclear blood cells (PMBCs) from a subject, differentiating and maturing dendritic cells from a first portion of the PMBCs in a culture comprising the target peptide;

isolating naïve CD8+ T-cells from a second portion of the PMBCs;

co-culturing the CD8+ T-cells with the mature dendritic cells;

re-stimulating the cultured T cells with PBMCs from the subject that have been depleted of T cells and natural killer cells and incubated with the target peptide, between 5 and 15 days after co-culturing the CD8+ T-cells with the mature dendritic cells;

re-stimulating the cultured T cells with T2 cells that have been inactivated by mitomycin C and incubated with the target peptide, between 5 and 15 days after re-stimulating the cultured T cells with PBMCs depleted of T cells and natural killer cells; and isolating T-cells reactive to the peptide after re-stimulating the cultured T cells with T2 cells, wherein the step of isolating T-cells reactive to a target peptide comprises the step of sorting for IFN-γ secreting cells and expanding the sorted cells with phytohemagglutinin.

2. The method of claim 1, wherein the dendritic cells are matured from monocytes.

3. The method of claim 2, wherein the step of maturing the dendritic cells comprises maturing the dendritic cells in a culture comprising IFN-γ.

4. The method of claim 1, wherein the step of co-culturing the CD8+ T-cells with the mature dendritic cells comprises adding IL-21 to the culture.

5. The method of claim 1, wherein the step of isolating T-cells reactive to a target peptide comprises the step of sorting for IFN-γ secreting cells between 0 and 5 days after re-stimulating culture of T2 cells.

6. The method of claim 5, wherein the step of isolating T-cells reactive to a target peptide further comprises binding the TCR of the T-cell to an epitope of the target peptide.

7. The method of claim 6, wherein the step of isolating T-cells reactive to a target peptide comprises tetramer binding.

8. The method of claim 7, wherein the step of isolating T-cells reactive to a target peptide further comprises binding the T-cell receptor (TCR) of the T-cell to an epitope of the target peptide between 5 and 15 days after sorting for IFN-γ secreting cells.

9. The method of claim 8, wherein all of the steps of the method are completed between 15 and 40 days.

10. The method of claim 1, wherein the step of obtaining PBMCs comprises obtaining PMBCs from a subject with a cancer.

11. The method of claim 9, wherein the step of obtaining PMBCs comprises obtaining PMBCs from a subject previously treated with a checkpoint inhibitor.

12. The method of claim 1, wherein the step of obtaining PBMCs comprises obtaining PBMCs from a subject without cancer.

13. The method of claim 1, wherein the target peptide is NY-ESO-1.

14. A method for identifying T-cell receptors (TCRs) reactive to a target peptide, the method comprising:

obtaining peripheral mononuclear blood cells (PMBCs) from a subject, differentiating and maturing dendritic cells from a first portion of the PMBCs in a culture comprising the target peptide;

isolating naïve CD8+ T-cells from a second portion of the PMBCs;

co-culturing the CD8+ T-cells with the mature dendritic cells;

re-stimulating the cultured T cells with PBMCs from the subject that have been depleted of T cells and natural killer cells and incubated with the target peptide, between 5 and 15 days after co-culturing the CD8+ T-cells with the mature dendritic cells;

re-stimulating the cultured T cells with T2 cells that have been inactivated by mitomycin C and incubated with the target peptide, between 5 and 15 days after re-stimulating the cultured T cells with PBMCs depleted of T cells and natural killer cells;

isolating T-cells reactive to the peptide after re-stimulating the cultured T cells with T2 cells, wherein the step of isolating T-cells reactive to a target peptide comprises the step of sorting for IFN-γ secreting cells and expanding the sorted cells with phytohemagglutinin; and sequencing the TCRs of the isolated T-cells.

15. The method of claim 14, wherein the step of sequencing the TCRs comprises next generation sequencing (NGS).

16. The method of claim 14, wherein the dendritic cells are matured from monocytes.

17. The method of claim 16, wherein the step of maturing the dendritic cells comprises maturing the dendritic cells in a culture comprising IFN-γ.

18. The method of claim 16, wherein the step of co-culturing the CD8+ T-cells with the mature dendritic cells comprises adding IL-21 to the culture.

19. The method of claim 14, wherein the step of isolating T-cells reactive to a target peptide comprises the step of sorting for IFN-γ secreting cells between 0 and 5 days after re-stimulating culture of T2 cells.

20. The method of claim 19, wherein the step of isolating T-cells reactive to a target peptide further comprises binding the TCR of the T-cell to an epitope of the target peptide.

21. The method of claim 20, wherein the step of isolating T-cells reactive to a target peptide comprises tetramer binding.

22. The method of claim 21, wherein the step of isolating T-cells reactive to a target peptide further comprises binding the T-cell receptor (TCR) of the T-cell to an epitope of the target peptide between 5 and 15 days after sorting for IFN-$\gamma$ secreting cells.

23. The method of claim 22, wherein all of the steps of the method are completed between 15 and 40 days.

24. The method of claim 23, wherein the step of obtaining PMBCs comprises obtaining PMBCs from a subject with a cancer.

25. The method of claim 24, wherein the step of obtaining PMBCs comprises obtaining PMBCs from a subject previously treated with a checkpoint inhibitor.

26. The method of claim 23, wherein the step of obtaining PMBCs comprises obtaining PMBCs from a subject without cancer.

27. The method of claim 23, wherein the target peptide is NY-ESO-1.

* * * * *